US012252515B2

(12) United States Patent
Dong et al.

(10) Patent No.: US 12,252,515 B2
(45) Date of Patent: Mar. 18, 2025

(54) COMPOSITIONS AND METHODS FOR INHIBITING WNT SIGNALING

(71) Applicants: Children's Medical Center Corporation, Boston, MA (US); The Regents of the University of California, Oakland, CA (US)

(72) Inventors: Min Dong, Weatogue, CT (US); Liang Tao, Boston, MA (US); Rongsheng Jin, Irvine, CA (US); Peng Chen, Oakland, CA (US); Aina He, Boston, MA (US)

(73) Assignees: Children's Medical Center Corporation, Boston, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/962,338

(22) PCT Filed: Jan. 14, 2019

(86) PCT No.: PCT/US2019/013440
§ 371 (c)(1),
(2) Date: Jul. 15, 2020

(87) PCT Pub. No.: WO2019/143552
PCT Pub. Date: Jul. 25, 2019

(65) Prior Publication Data
US 2020/0339636 A1      Oct. 29, 2020

Related U.S. Application Data

(60) Provisional application No. 62/670,225, filed on May 11, 2018, provisional application No. 62/618,042, filed on Jan. 16, 2018.

(51) Int. Cl.
*C07K 14/33* (2006.01)
*A61K 38/00* (2006.01)
*A61P 35/00* (2006.01)

(52) U.S. Cl.
CPC .............. *C07K 14/33* (2013.01); *A61P 35/00* (2018.01); *A61K 38/00* (2013.01); *C07K 2319/21* (2013.01); *C07K 2319/30* (2013.01)

(58) Field of Classification Search
CPC ................ C07K 14/33; C07K 2319/21; C07K 2319/30; A61P 35/00; A61K 38/00
See application file for complete search history.

(56) References Cited

U.S. PATENT DOCUMENTS

| 10,913,786 B2 | 2/2021 | Dong et al. |
| 2004/0053366 A1 | 3/2004 | Lo et al. |
| 2006/0263368 A1 | 11/2006 | Rosenblum et al. |
| 2008/0241164 A1 | 10/2008 | Knopf et al. |
| 2008/0299136 A1 | 12/2008 | Ernst et al. |
| 2010/0104574 A1 | 4/2010 | Gurney et al. |
| 2015/0093389 A1 | 4/2015 | Shone et al. |
| 2015/0140070 A1 | 5/2015 | Heartlein et al. |

FOREIGN PATENT DOCUMENTS

| WO | WO 2013/150309 A1 | 10/2013 |
| WO | WO 2014/086787 A1 | 6/2014 |
| WO | WO 2017/165398 A1 | 9/2017 |
| WO | WO 2019/143552 A1 | 7/2019 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000, 10:398-400).*
Chen et al., Structural basis for recognition of frizzled proteins by Clostridium difficile toxin B. Science. May 11, 2018;360:664-669.
Debruine et al., Wnt5a promotes Frizzled-4 signalosome assembly by stabilizing cysteine-rich domain dimerization. Genes Dev. May 1, 2017;31(9):916-926.
Janda et al., Structural basis of Wnt recognition by Frizzled. Science. 2012;337(6090):59-64.
LaFrance et al., Identification of an epithelial cell receptor responsible for Clostridium difficile TcdB-induced cytotoxicity. Proc Natl Acad Sci U S A. 2015;112(22):7073-7078.
Nile et al., Unsaturated fatty acyl recognition by Frizzled receptors mediates dimerization upon Wnt ligand binding. Proc Natl Acad Sci U S A. 2017;114(16):4147-4152.
Salnikova et al., Physical characterization of clostridium difficile toxins and toxoids: effect of the formaldehyde crosslinking on thermal stability. J Pharm Sci. Sep. 2008. 97(9)3735-3552.
Takada et al., Monounsaturated fatty acid modification of Wnt protein: its role in Wnt secretion. Dev Cell. 2006;11(6):791-801.
Tao et al., Frizzled proteins are colonic epithelial receptors for C. difficile toxin B. Nature. Sep. 28, 2016;538(7625):350-355.
Willert et al., Wnt proteins are lipid-modified and can act as stem cell growth factors. Nature. 2003;423(6938):448-452.
Yuan et al., Chondroitin sulfate proteoglycan 4 functions as the cellular receptor for Clostridium difficile toxin B. Cell Res. 2015;25(2):157-168.

* cited by examiner

*Primary Examiner* — Robert A Zeman
(74) *Attorney, Agent, or Firm* — Wolf, Greenfield & Sacks, P.C.

(57) ABSTRACT

Provided herein are agents that bind to the lipid binding groove of Frizzled (FZD). In some embodiments, the agent is a fragment of TcdB corresponding to amino acids 1285-1804 of SEQ ID NO: 1. In some embodiments, binding of the agent to the lipid binding groove of FZD inhibits TcdB entry into cells, and/or inhibits Wnt signaling. Methods of treating *Clostridium difficile* infection (CDI) and methods of treating cancer are also provided.

9 Claims, 28 Drawing Sheets

Specification includes a Sequence Listing.

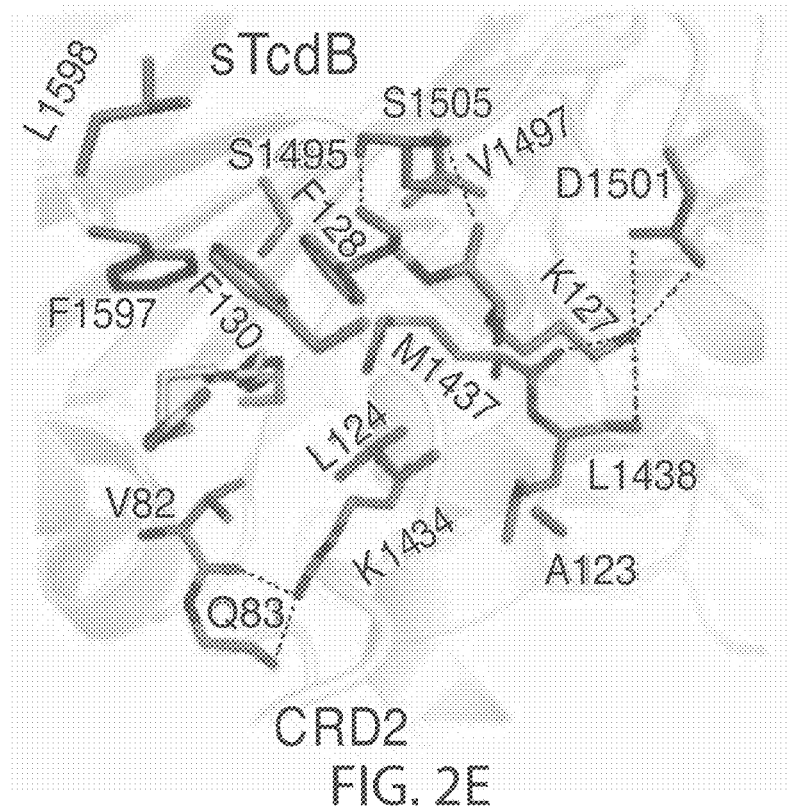

FIG. 2E

|  | 74 | 83 |  | 123 | 130 |  |
|---|---|---|---|---|---|---|
| FZD2 | H Q F Y P L | V K V Q | (SEQ ID NO: 115) | A L M N | K F G F | (SEQ ID NO: 103) |
| FZD7 | H Q F Y P L | V K V Q | (SEQ ID NO: 115) | A L M N | K F G F | (SEQ ID NO: 103) |
| FZD1 | H Q F Y P L | V K V Q | (SEQ ID NO: 115) | A L M N | K F G F | (SEQ ID NO: 103) |
| FZD5 | H Q F W P L | V E I Q | (SEQ ID NO: 97) | P L M R | Q Y G F | (SEQ ID NO: 104) |
| FZD8 | H Q F W P L | V E I Q | (SEQ ID NO: 97) | P L M R | Q Y G F | (SEQ ID NO: 104) |
| FZD9 | A E F A P L | V Q Y G | (SEQ ID NO: 98) | P I M E | Q F N F | (SEQ ID NO: 105) |
| FZD10 | H E F A P L | V E Y G | (SEQ ID NO: 99) | P I M E | Q F N F | (SEQ ID NO: 105) |
| FZD4 | T T F T P L | I Q Y G | (SEQ ID NO: 100) | P V L K | E F G F | (SEQ ID NO: 106) |
| FZD3 | E P F H P M | V N L D | (SEQ ID NO: 101) | K L M E | M F G V | (SEQ ID NO: 107) |
| FZD6 | E H F L P L | A N L E | (SEQ ID NO: 102) | K L I D | T E G I | (SEQ ID NO: 108) |
| FZD2 | H Q F Y P L | V K V Q | (SEQ ID NO: 115) | A L M N | K F G F | (SEQ ID NO: 103) |

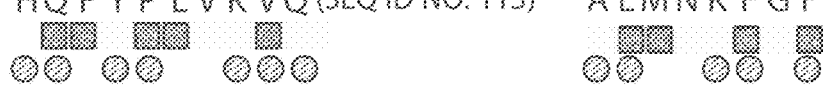

FIG. 2F

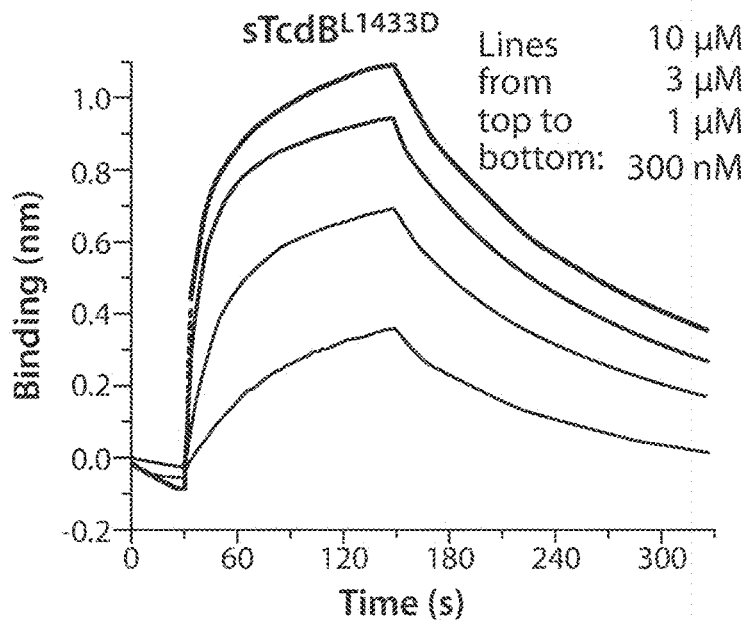

FIG. 5E

| sTcdB variants | $k_{on}$(1/Ms) | $k_{on}$ error | $k_{off}$ (1/s) | $k_{off}$ error | $K_D$ (μM) |
|---|---|---|---|---|---|
| WT | $1.14 \times 10^5$ | $1.69 \times 10^3$ | $1.50 \times 10^{-3}$ | $3.59 \times 10^{-5}$ | 0.013±0.002 |
| D1501A | $1.99 \times 10^4$ | $4.26 \times 10^2$ | $1.06 \times 10^{-2}$ | $1.21 \times 10^{-4}$ | 0.53±0.06 |
| Y1509A/N1511A | $2.34 \times 10^4$ | $7.52 \times 10^2$ | $2.80 \times 10^{-2}$ | $3.24 \times 10^{-4}$ | 1.26±0.26 |
| F1597G | NA | NA | NA | NA | >10 |
| F1597D | NA | NA | NA | NA | >10 |
| V1595NFLQS => GEF | NA | NA | NA | NA | >10 |
| Y1509A/Q1599A | $1.66 \times 10^4$ | $9.29 \times 10^2$ | $3.02 \times 10^{-2}$ | $6.08 \times 10^{-4}$ | 1.79±0.13 |
| M1437D/L1493A | NA | NA | NA | NA | >10 |
| L1433D/M1437D/L1493A | NA | NA | NA | NA | >10 |
| L1433D | $2.10 \times 10^4$ | $9.86 \times 10^2$ | $7.30 \times 10^{-3}$ | $2.29 \times 10^{-4}$ | 0.48±0.11 |

FIG. 5F

```
                          SEQUENCE LISTING

<160> NUMBER OF SEQ ID NOS: 115

<210> SEQ ID NO 1
    <211> LENGTH: 2366
    <212> TYPE: PRT
    <213> ORGANISM: Clostridium difficile

<400> SEQUENCE: 1

Met Ser Leu Val Asn Arg Lys Gln Leu Glu Lys Met Ala Asn Val Arg
    1               5                   10                  15

Phe Arg Thr Gln Glu Asp Glu Tyr Val Ala Ile Leu Asp Ala Leu Glu
                    20                  25                  30

Glu Tyr His Asn Met Ser Glu Asn Thr Val Val Glu Lys Tyr Leu Lys
                35                  40                  45

Leu Lys Asp Ile Asn Ser Leu Thr Asp Ile Tyr Ile Asp Thr Tyr Lys
            50                  55                  60

Lys Ser Gly Arg Asn Lys Ala Leu Lys Lys Phe Lys Glu Tyr Leu Val
    65                  70                  75                  80

Thr Glu Val Leu Glu Leu Lys Asn Asn Asn Leu Thr Pro Val Glu Lys
                    85                  90                  95

Asn Leu His Phe Val Trp Ile Gly Gly Gln Ile Asn Asp Thr Ala Ile
                100                 105                 110

Asn Tyr Ile Asn Gln Trp Lys Asp Val Asn Ser Asp Tyr Asn Val Asn
                115                 120                 125

Val Phe Tyr Asp Ser Asn Ala Phe Leu Ile Asn Thr Leu Lys Lys Thr
            130                 135                 140

Val Val Glu Ser Ala Ile Asn Asp Thr Leu Glu Ser Phe Arg Glu Asn
    145                 150                 155                 160

Leu Asn Asp Pro Arg Phe Asp Tyr Asn Lys Phe Phe Arg Lys Arg Met
                    165                 170                 175
```

```
Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
```

```
                595                 600                 605
    Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                    645                 650                 655

Glu Phe Asn Thr Asp Ile Phe Ala Gly Phe Asp Val Asp Ser Leu Ser
                    660                 665                 670

Thr Glu Ile Glu Ala Ala Ile Asp Leu Ala Lys Glu Asp Ile Ser Pro
                    675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Lys Val Lys
    705                 710                 715                 720

Asp Lys Ile Ser Glu Leu Met Pro Ser Ile Ser Gln Asp Ser Ile Ile
                    725                 730                 735

Val Ser Ala Asn Gln Tyr Glu Val Arg Ile Asn Ser Glu Gly Arg Arg
                    740                 745                 750

Glu Leu Leu Asp His Ser Gly Glu Trp Ile Asn Lys Glu Ser Ile
                    755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
    785                 790                 795                 800

Leu Gln Glu Ile Arg Asn Asn Ser Asn Ser Ser Asp Ile Glu Leu Glu
                    805                 810                 815

Glu Lys Val Met Leu Thr Glu Cys Glu Ile Asn Val Ile Ser Asn Ile
                    820                 825                 830

Asp Thr Gln Ile Val Glu Glu Arg Ile Glu Glu Ala Lys Asn Leu Thr
                    835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                    885                 890                 895

Ser Ile Arg Phe Ile Asn Lys Glu Thr Gly Glu Ser Ile Phe Val Glu
                    900                 905                 910

Thr Glu Lys Thr Ile Phe Ser Glu Tyr Ala Asn His Ile Thr Glu Glu
                    915                 920                 925

Ile Ser Lys Ile Lys Gly Thr Ile Phe Asp Thr Val Asn Gly Lys Leu
                    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                    965                 970                 975

Ser Leu Ser Asn Leu Ser Val Ala Met Lys Val Gln Tyr Ala Gln
                    980                 985                 990

Leu Phe Ser Thr Gly Leu Asn Thr  Ile Thr Asp Ala Ala  Lys Val Val
                    995                 1000                1005

Glu Leu  Val Ser Thr Ala Leu  Asp Glu Thr Ile Asp  Leu Leu Pro
                1010                1015                1020
```

```
Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Thr Ala Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Val Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290

Asn Thr Arg Ser Phe Ile Val Pro Ile Ile Thr Thr Glu Tyr Ile
    1295                1300                1305

Arg Glu Lys Leu Ser Tyr Ser Phe Tyr Gly Ser Gly Gly Thr Tyr
    1310                1315                1320

Ala Leu Ser Leu Ser Gln Tyr Asn Met Gly Ile Asn Ile Glu Leu
    1325                1330                1335

Ser Glu Ser Asp Val Trp Ile Ile Asp Val Asp Asn Val Val Arg
    1340                1345                1350

Asp Val Thr Ile Glu Ser Asp Lys Ile Lys Lys Gly Asp Leu Ile
    1355                1360                1365

Glu Gly Ile Leu Ser Thr Leu Ser Ile Glu Glu Asn Lys Ile Ile
    1370                1375                1380

Leu Asn Ser His Glu Ile Asn Phe Ser Gly Glu Val Asn Gly Ser
    1385                1390                1395

Asn Gly Phe Val Ser Leu Thr Phe Ser Ile Leu Glu Gly Ile Asn
    1400                1405                1410
```

```
Ala Ile Ile Glu Val Asp Leu Leu Ser Lys Ser Tyr Lys Leu Leu
1415                1420                1425

Ile Ser Gly Glu Leu Lys Ile Leu Met Leu Asn Ser Asn His Ile
1430                1435                1440

Gln Gln Lys Ile Asp Tyr Ile Gly Phe Asn Ser Glu Leu Gln Lys
1445                1450                1455

Asn Ile Pro Tyr Ser Phe Val Asp Ser Glu Gly Lys Glu Asn Gly
1460                1465                1470

Phe Ile Asn Gly Ser Thr Lys Glu Gly Leu Phe Val Ser Glu Leu
1475                1480                1485

Pro Asp Val Val Leu Ile Ser Lys Val Tyr Met Asp Asp Ser Lys
1490                1495                1500

Pro Ser Phe Gly Tyr Tyr Ser Asn Asn Leu Lys Asp Val Lys Val
1505                1510                1515

Ile Thr Lys Asp Asn Val Asn Ile Leu Thr Gly Tyr Tyr Leu Lys
1520                1525                1530

Asp Asp Ile Lys Ile Ser Leu Ser Leu Thr Leu Gln Asp Glu Lys
1535                1540                1545

Thr Ile Lys Leu Asn Ser Val His Leu Asp Glu Ser Gly Val Ala
1550                1555                1560

Glu Ile Leu Lys Phe Met Asn Arg Lys Gly Asn Thr Asn Thr Ser
1565                1570                1575

Asp Ser Leu Met Ser Phe Leu Glu Ser Met Asn Ile Lys Ser Ile
1580                1585                1590

Phe Val Asn Phe Leu Gln Ser Asn Ile Lys Phe Ile Leu Asp Ala
1595                1600                1605

Asn Phe Ile Ile Ser Gly Thr Thr Ser Ile Gly Gln Phe Glu Phe
1610                1615                1620

Ile Cys Asp Glu Asn Asp Asn Ile Gln Pro Tyr Phe Ile Lys Phe
1625                1630                1635

Asn Thr Leu Glu Thr Asn Tyr Thr Leu Tyr Val Gly Asn Arg Gln
1640                1645                1650

Asn Met Ile Val Glu Pro Asn Tyr Asp Leu Asp Asp Ser Gly Asp
1655                1660                1665

Ile Ser Ser Thr Val Ile Asn Phe Ser Gln Lys Tyr Leu Tyr Gly
1670                1675                1680

Ile Asp Ser Cys Val Asn Lys Val Val Ile Ser Pro Asn Ile Tyr
1685                1690                1695

Thr Asp Glu Ile Asn Ile Thr Pro Val Tyr Glu Thr Asn Asn Thr
1700                1705                1710

Tyr Pro Glu Val Ile Val Leu Asp Ala Asn Tyr Ile Asn Glu Lys
1715                1720                1725

Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
1745                1750                1755

Lys Val Ser Gln Val Lys Ile Arg Phe Val Asn Val Phe Lys Asp
1760                1765                1770

Lys Thr Leu Ala Asn Lys Leu Ser Phe Asn Phe Ser Asp Lys Gln
1775                1780                1785

Asp Val Pro Val Ser Glu Ile Ile Leu Ser Phe Thr Pro Ser Tyr
1790                1795                1800

Tyr Glu Asp Gly Leu Ile Gly Tyr Asp Leu Gly Leu Val Ser Leu
```

```
            1805                1810                1815
Tyr Asn Glu Lys Phe Tyr Ile Asn Asn Phe Gly Met Met Val Ser
            1820                1825                1830

Gly Leu Ile Tyr Ile Asn Asp Ser Leu Tyr Tyr Phe Lys Pro Pro
            1835                1840                1845

Val Asn Asn Leu Ile Thr Gly Phe Val Thr Val Gly Asp Asp Lys
            1850                1855                1860

Tyr Tyr Phe Asn Pro Ile Asn Gly Gly Ala Ala Ser Ile Gly Glu
            1865                1870                1875

Thr Ile Ile Asp Asp Lys Asn Tyr Tyr Phe Asn Gln Ser Gly Val
            1880                1885                1890

Leu Gln Thr Gly Val Phe Ser Thr Glu Asp Gly Phe Lys Tyr Phe
            1895                1900                1905

Ala Pro Ala Asn Thr Leu Asp Glu Asn Leu Glu Gly Glu Ala Ile
            1910                1915                1920

Asp Phe Thr Gly Lys Leu Ile Ile Asp Glu Asn Ile Tyr Tyr Phe
            1925                1930                1935

Asp Asp Asn Tyr Arg Gly Ala Val Glu Trp Lys Glu Leu Asp Gly
            1940                1945                1950

Glu Met His Tyr Phe Ser Pro Glu Thr Gly Lys Ala Phe Lys Gly
            1955                1960                1965

Leu Asn Gln Ile Gly Asp Tyr Lys Tyr Tyr Phe Asn Ser Asp Gly
            1970                1975                1980

Val Met Gln Lys Gly Phe Val Ser Ile Asn Asp Asn Lys His Tyr
            1985                1990                1995

Phe Asp Asp Ser Gly Val Met Lys Val Gly Tyr Thr Glu Ile Asp
            2000                2005                2010

Gly Lys His Phe Tyr Phe Ala Glu Asn Gly Glu Met Gln Ile Gly
            2015                2020                2025

Val Phe Asn Thr Glu Asp Gly Phe Lys Tyr Phe Ala His His Asn
            2030                2035                2040

Glu Asp Leu Gly Asn Glu Glu Gly Glu Glu Ile Ser Tyr Ser Gly
            2045                2050                2055

Ile Leu Asn Phe Asn Asn Lys Ile Tyr Tyr Phe Asp Asp Ser Phe
            2060                2065                2070

Thr Ala Val Val Gly Trp Lys Asp Leu Glu Asp Gly Ser Lys Tyr
            2075                2080                2085

Tyr Phe Asp Glu Asp Thr Ala Glu Ala Tyr Ile Gly Leu Ser Leu
            2090                2095                2100

Ile Asn Asp Gly Gln Tyr Tyr Phe Asn Asp Asp Gly Ile Met Gln
            2105                2110                2115

Val Gly Phe Val Thr Ile Asn Asp Lys Val Phe Tyr Phe Ser Asp
            2120                2125                2130

Ser Gly Ile Ile Glu Ser Gly Val Gln Asn Ile Asp Asp Asn Tyr
            2135                2140                2145

Phe Tyr Ile Asp Asp Asn Gly Ile Val Gln Ile Gly Val Phe Asp
            2150                2155                2160

Thr Ser Asp Gly Tyr Lys Tyr Phe Ala Pro Ala Asn Thr Val Asn
            2165                2170                2175

Asp Asn Ile Tyr Gly Gln Ala Val Glu Tyr Ser Gly Leu Val Arg
            2180                2185                2190

Val Gly Glu Asp Val Tyr Tyr Phe Gly Glu Thr Tyr Thr Ile Glu
            2195                2200                2205
```

```
Thr Gly Trp Ile Tyr Asp Met Glu Asn Glu Ser Asp Lys Tyr Tyr
           2210                2215                2220

Phe Asn Pro Glu Thr Lys Lys Ala Cys Lys Gly Ile Asn Leu Ile
    2225                2230                2235

Asp Asp Ile Lys Tyr Tyr Phe Asp Glu Lys Gly Ile Met Arg Thr
    2240                2245                2250

Gly Leu Ile Ser Phe Glu Asn Asn Tyr Tyr Phe Asn Glu Asn
    2255                2260                2265

Gly Glu Met Gln Phe Gly Tyr Ile Asn Ile Glu Asp Lys Met Phe
    2270                2275                2280

Tyr Phe Gly Glu Asp Gly Val Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365

<210> SEQ ID NO 2
<211> LENGTH: 520
<212> TYPE: PRT
<213> ORGANISM: Clostridium difficile

<400> SEQUENCE: 2

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
```

```
                195                 200                 205
Leu Ile Ser Lys Val Tyr Met Asp Asp Ser Lys Pro Ser Phe Gly Tyr
        210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Ile Lys Ile Ser Leu
                245                 250                 255

Ser Leu Thr Leu Gln Asp Glu Lys Thr Ile Lys Leu Asn Ser Val His
        260                 265                 270

Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
        290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr
        515                 520

<210> SEQ ID NO 3
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 3

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
```

Val His Gln Phe Tyr Pro Leu Val Lys Val Gln Cys Ser Ala Glu Leu
 50                  55                  60

Lys Phe Phe Leu Cys Ser Met Tyr Ala Pro Val Cys Thr Val Leu Glu
65                   70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
                100                 105                 110

Lys Cys Glu Lys Phe Pro Val His Gly Ala Gly Glu Leu Cys Val Gly
                115                 120                 125

Gln Asn Thr Ser Asp Lys
            130

<210> SEQ ID NO 4
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 4

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
 50                  55                  60

Lys Phe Phe Leu Cys Ser Met Tyr Ala Pro Val Cys Thr Val Leu Glu
65                   70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
                100                 105                 110

Lys Cys Glu Lys Phe Pro Val His Gly Ala Gly Glu Leu Cys Val Gly
                115                 120                 125

Gln Asn Thr Ser Asp Lys
            130

<210> SEQ ID NO 5
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 5

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
 50                  55                  60

```
Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys
    130

<210> SEQ ID NO 6
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 6

Ala Lys Glu Leu Ala Cys Gln Glu Ile Thr Val Pro Leu Cys Lys Gly
  1               5                  10                  15

Ile Gly Tyr Asn Tyr Thr Tyr Met Pro Asn Gln Phe Asn His Asp Thr
                 20                  25                  30

Gln Asp Glu Ala Gly Leu Glu Val His Gln Phe Trp Pro Leu Val Glu
             35                  40                  45

Ile Gln Cys Ser Pro Asp Leu Lys Phe Phe Leu Cys Ser Met Tyr Thr
 50                  55                  60

Pro Ile Cys Leu Glu Asp Tyr Lys Lys Pro Leu Pro Pro Cys Arg Ser
 65                  70                  75                  80

Val Cys Glu Arg Ala Lys Ala Gly Cys Ala Pro Leu Met Arg Gln Tyr
                 85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr
        115                 120

<210> SEQ ID NO 7
<211> LENGTH: 225
<212> TYPE: PRT
<213> ORGANISM: Artificial Sequence
<220> FEATURE:
<223> OTHER INFORMATION: Synthetic polypeptide

<400> SEQUENCE: 7

Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
                 20                  25                  30

Arg Thr Pro Glu Val Thr Cys Val Val Val Asp Val Ser His Glu Asp
             35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Val Pro Ile Glu Lys
            100                 105                 110
```

```
Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 8
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 8

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Asn Asn Leu Lys Asp Val Lys Val Ile Thr Lys Asp Asn Val
225                 230                 235                 240
```

```
Asn Ile Leu Thr Gly Tyr Tyr Leu Lys Asp Ile Lys Ile Ser Leu
            245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
            290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
            325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
            370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
            405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Gly Asn Lys Val Ser Gln Val Lys
465                 470                 475                 480

Ile Arg Phe Val Asn Val Phe Lys Asp Lys Thr Leu Ala Asn Lys Leu
            485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Thr His Thr Cys Pro Cys Pro
            515                 520                 525

Ala Pro Glu Leu Leu Gly Gly Pro Ser Val Phe Leu Phe Pro Pro Lys
            530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
            565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
            610                 615                 620

Ala Leu Pro Val Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
            645                 650                 655
```

```
Thr Lys Asn Gln Val Ser Leu Thr Cys Leu Val Lys Gly Phe Tyr Pro
                660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Pro Phe Phe Leu
        690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
                740                 745

<210> SEQ ID NO 9
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 9

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
            210                 215                 220

Lys Thr Asn Ile Arg Ile Asn Leu Asp Ser Asn Thr Arg Ser Phe Ile
225                 230                 235                 240

Val Pro Ile Ile Thr Thr Glu Tyr Ile Arg Glu Lys Leu Ser Tyr Ser
                245                 250                 255

Phe Tyr Gly Ser Gly Gly Thr Tyr Ala Leu Ser Leu Ser Gln Tyr Asn
            260                 265                 270
```

```
Met Gly Ile Asn Ile Glu Leu Ser Glu Ser Asp Val Trp Ile Ile Asp
            275                 280                 285
Val Asp Asn Val Val Arg Asp Val Thr Ile Glu Ser Asp Lys Ile Lys
            290                 295                 300
Lys Gly Asp Leu Ile Glu Gly Ile Leu Ser Thr Leu Ser Ile Glu Glu
305                 310                 315                 320
Asn Lys Ile Ile Leu Asn Ser His Glu Ile Asn Phe Ser Gly Glu Val
                325                 330                 335
Asn Gly Ser Asn Gly Phe Val Ser Leu Thr Phe Ser Ile Leu Glu Gly
            340                 345                 350
Ile Asn Ala Ile Ile Glu Val Asp Leu Leu Ser Lys Ser Tyr Lys Leu
            355                 360                 365
Leu Ile Ser Gly Glu Leu Lys Ile Leu Met Leu Asn Ser Asn His Ile
            370                 375                 380
Gln Gln Lys Ile Asp Tyr Ile Gly Phe Asn Ser Glu Leu Gln Lys Asn
385                 390                 395                 400
Ile Pro Tyr Ser Phe Val Asp Ser Glu Gly Lys Glu Asn Gly Phe Ile
                405                 410                 415
Asn Gly Ser Thr Lys Glu Gly Leu Phe Val Ser Glu Leu Pro Asp Val
            420                 425                 430
Val Leu Ile Ser Lys Val Tyr Met Asp Asp Ser Lys Pro Ser Phe Gly
            435                 440                 445
Tyr Tyr Ser Asn Asn Leu Lys Asp Val Lys Val Ile Thr Lys Asp Asn
            450                 455                 460
Val Asn Ile Leu Thr Gly Tyr Tyr Leu Lys Asp Ile Lys Ile Ser
465                 470                 475                 480
Leu Ser Leu Thr Leu Gln Asp Glu Lys Thr Ile Lys Leu Asn Ser Val
                485                 490                 495
His Leu Asp Glu Ser Gly Val Ala Glu Ile Leu Lys Phe Met Asn Arg
            500                 505                 510
Lys Gly Asn Thr Asn Thr Ser Asp Ser Leu Met Ser Phe Leu Glu Ser
            515                 520                 525
Met Asn Ile Lys Ser Ile Phe Val Asn Phe Leu Gln Ser Asn Ile Lys
            530                 535                 540
Phe Ile Leu Asp Ala Asn Phe Ile Ile Ser Gly Thr Thr Ser Ile Gly
545                 550                 555                 560
Gln Phe Glu Phe Ile Cys Asp Glu Asn Asp Asn Ile Gln Pro Tyr Phe
                565                 570                 575
Ile Lys Phe Asn Thr Leu Glu Thr Asn Tyr Thr Leu Tyr Val Gly Asn
            580                 585                 590
Arg Gln Asn Met Ile Val Glu Pro Asn Tyr Asp Leu Asp Asp Ser Gly
            595                 600                 605
Asp Ile Ser Ser Thr Val Ile Asn Phe Ser Gln Lys Tyr Leu Tyr Gly
            610                 615                 620
Ile Asp Ser Cys Val Asn Lys Val Val Ile Ser Pro Asn Ile Tyr Thr
625                 630                 635                 640
Asp Glu Ile Asn Ile Thr Pro Val Tyr Glu Thr Asn Asn Thr Tyr Pro
                645                 650                 655
Glu Val Ile Val Leu Asp Ala Asn Tyr Ile Asn Glu Lys Ile Asn Val
            660                 665                 670
Asn Ile Asn Asp Leu Ser Ile Arg Tyr Val Trp Ser Asn Asp Gly Asn
            675                 680                 685
Asp Phe Ile Leu Met Ser Thr Ser Glu Glu Asn Lys Val Ser Gln Val
```

```
            690             695             700
Lys Ile Arg Phe Val Asn Val Phe Lys Asp Lys Thr Leu Ala Asn Lys
705             710             715             720

Leu Ser Phe Asn Phe Ser Asp Lys Gln Asp Val Pro Val Ser Glu Ile
                725             730             735

Ile Leu Ser Phe Thr Pro Ser Tyr Tyr
                740             745
```

<210> SEQ ID NO 10
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 10

```
Tyr Asn Gly Glu Arg Gly Ile Ser Val Pro Asp His Gly Tyr Cys Gln
1               5               10              15

Pro Ile Ser Ile Pro Leu Cys Thr Asp Ile Ala Tyr Asn Gln Thr Ile
                20              25              30

Met Pro Asn Leu Leu Gly His Thr Asn Gln Glu Asp Ala Gly Leu Glu
            35              40              45

Val His Gln Phe Tyr Pro Leu Val Lys Val Gln Cys Ser Ala Glu Leu
50              55              60

Lys Phe Phe Leu Cys Ser Met Tyr Ala Pro Val Cys Thr Val Leu Glu
65              70              75              80

Gln Ala Leu Pro Pro Cys Arg Ser Leu Cys Glu Arg Ala Arg Gln Gly
                85              90              95

Cys Glu Ala Leu Met Asn Lys Phe Gly Phe Gln Trp Pro Asp Thr Leu
            100             105             110

Lys Cys Glu Lys Phe Pro Val His Gly Ala Gly Glu Leu Cys Val Gly
        115             120             125

Gln Asn Thr Ser Asp Lys Thr Asn Ile Arg Ile Asn Leu Asp Ser Asn
    130             135             140

Thr Arg Ser Phe Ile Val Pro Ile Ile Thr Thr Glu Tyr Ile Arg Glu
145             150             155             160

Lys Leu Ser Tyr Ser Phe Tyr Gly Ser Gly Gly Thr Tyr Ala Leu Ser
                165             170             175

Leu Ser Gln Tyr Asn Met Gly Ile Asn Ile Glu Leu Ser Glu Ser Asp
            180             185             190

Val Trp Ile Ile Asp Val Asp Asn Val Val Arg Asp Val Thr Ile Glu
        195             200             205

Ser Asp Lys Ile Lys Lys Gly Asp Leu Ile Glu Gly Ile Leu Ser Thr
    210             215             220

Leu Ser Ile Glu Glu Asn Lys Ile Ile Leu Asn Ser His Glu Ile Asn
225             230             235             240

Phe Ser Gly Glu Val Asn Gly Ser Asn Gly Phe Val Ser Leu Thr Phe
                245             250             255

Ser Ile Leu Glu Gly Ile Asn Ala Ile Ile Glu Val Asp Leu Leu Ser
            260             265             270

Lys Ser Tyr Lys Leu Leu Ile Ser Gly Glu Leu Lys Ile Leu Met Leu
        275             280             285

Asn Ser Asn His Ile Gln Gln Lys Ile Asp Tyr Ile Gly Phe Asn Ser
    290             295             300

Glu Leu Gln Lys Asn Ile Pro Tyr Ser Phe Val Asp Ser Glu Gly Lys
```

```
            305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
                340                 345                 350

Lys Pro Ser Phe Gly Tyr Tyr Ser Asn Asn Leu Lys Asp Val Lys Val
                355                 360                 365

Ile Thr Lys Asp Asn Val Asn Ile Leu Thr Gly Tyr Tyr Leu Lys Asp
                370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
                420                 425                 430

Ser Phe Leu Glu Ser Met Asn Ile Lys Ser Ile Phe Val Asn Phe Leu
                435                 440                 445

Gln Ser Asn Ile Lys Phe Ile Leu Asp Ala Asn Phe Ile Ile Ser Gly
                450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
                500                 505                 510

Leu Asp Asp Ser Gly Asp Ile Ser Ser Thr Val Ile Asn Phe Ser Gln
                515                 520                 525

Lys Tyr Leu Tyr Gly Ile Asp Ser Cys Val Asn Lys Val Val Ile Ser
                530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
                580                 585                 590

Ser Asn Asp Gly Asn Asp Phe Ile Leu Met Ser Thr Ser Glu Glu Asn
                595                 600                 605

Lys Val Ser Gln Val Lys Ile Arg Phe Val Asn Val Phe Lys Asp Lys
                610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650
```

<210> SEQ ID NO 11
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 11

```
Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
```

```
                 20                  25                  30
Met Pro Asn Leu Leu Gly His Thr Asn Gln Glu Asp Ala Gly Leu Glu
             35                  40                  45

Val His Gln Phe Tyr Pro Leu Val Lys Val Gln Cys Ser Ala Glu Leu
         50                  55                  60

Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
            115                 120                 125

Gln Asn Thr Ser Asp Lys Thr Asn Ile Arg Ile Asn Leu Asp Ser Asn
            130                 135                 140

Thr Arg Ser Phe Ile Val Pro Ile Ile Thr Glu Tyr Ile Arg Glu
145                 150                 155                 160

Lys Leu Ser Tyr Ser Phe Tyr Gly Ser Gly Thr Tyr Ala Leu Ser
            165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
            195                 200                 205

Ser Asp Lys Ile Lys Lys Gly Asp Leu Ile Glu Gly Ile Leu Ser Thr
            210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
            245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
            275                 280                 285

Asn Ser Asn His Ile Gln Gln Lys Ile Asp Tyr Ile Gly Phe Asn Ser
            290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
            325                 330                 335

Glu Leu Pro Asp Val Val Leu Ile Ser Lys Val Tyr Met Asp Asp Ser
            340                 345                 350

Lys Pro Ser Phe Gly Tyr Tyr Ser Asn Asn Leu Lys Asp Val Lys Val
            355                 360                 365

Ile Thr Lys Asp Asn Val Asn Ile Leu Thr Gly Tyr Tyr Leu Lys Asp
            370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
            405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
            435                 440                 445
```

-continued

```
Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650
```

<210> SEQ ID NO 12
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 12

```
Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
    115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160
```

-continued

```
Lys Leu Ser Tyr Ser Phe Tyr Gly Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
                195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
                260                 265                 270

Lys Ser Tyr Lys Leu Leu Ile Ser Gly Glu Leu Lys Ile Leu Met Leu
    275                 280                 285

Asn Ser Asn His Ile Gln Gln Lys Ile Asp Tyr Ile Gly Phe Asn Ser
290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
                340                 345                 350

Lys Pro Ser Phe Gly Tyr Tyr Ser Asn Asn Leu Lys Asp Val Lys Val
                355                 360                 365

Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Ser Ser Leu Met
                420                 425                 430

Ser Phe Leu Glu Ser Met Asn Ile Lys Ser Ile Phe Val Asn Phe Leu
    435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
                500                 505                 510

Leu Asp Asp Ser Gly Asp Ile Ser Ser Thr Val Ile Asn Phe Ser Gln
    515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575
```

```
Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
        610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650
```

<210> SEQ ID NO 13
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 13

```
Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
            20                  25                  30

Gln Asp Glu Ala Gly Leu Glu Val His Gln Phe Trp Pro Leu Val Glu
        35                  40                  45

Ile Gln Cys Ser Pro Asp Leu Lys Phe Phe Leu Cys Ser Met Tyr Thr
    50                  55                  60

Pro Ile Cys Leu Glu Asp Tyr Lys Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
        115                 120                 125

Leu Asp Ser Asn Thr Arg Ser Phe Ile Val Pro Ile Ile Thr Thr Glu
    130                 135                 140

Tyr Ile Arg Glu Lys Leu Ser Tyr Ser Phe Tyr Gly Ser Gly Thr
145                 150                 155                 160

Tyr Ala Leu Ser Leu Ser Gln Tyr Asn Met Gly Ile Asn Ile Glu Leu
                165                 170                 175

Ser Glu Ser Asp Val Trp Ile Ile Asp Val Asp Asn Val Val Arg Asp
            180                 185                 190

Val Thr Ile Glu Ser Asp Lys Ile Lys Lys Gly Asp Leu Ile Glu Gly
        195                 200                 205

Ile Leu Ser Thr Leu Ser Ile Glu Glu Asn Lys Ile Ile Leu Asn Ser
    210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
                245                 250                 255

Asp Leu Leu Ser Lys Ser Tyr Lys Leu Leu Ile Ser Gly Glu Leu Lys
            260                 265                 270

Ile Leu Met Leu Asn Ser Asn His Ile Gln Gln Lys Ile Asp Tyr Ile
        275                 280                 285
```

-continued

```
Gly Phe Asn Ser Glu Leu Gln Lys Asn Ile Pro Tyr Ser Phe Val Asp
    290                 295                 300

Ser Glu Gly Lys Glu Asn Gly Phe Ile Asn Gly Ser Thr Lys Glu Gly
305                 310                 315                 320

Leu Phe Val Ser Glu Leu Pro Asp Val Val Leu Ile Ser Lys Val Tyr
                325                 330                 335

Met Asp Asp Ser Lys Pro Ser Phe Gly Tyr Tyr Ser Asn Asn Leu Lys
            340                 345                 350

Asp Val Lys Val Ile Thr Lys Asp Asn Val Asn Ile Leu Thr Gly Tyr
        355                 360                 365

Tyr Leu Lys Asp Asp Ile Lys Ile Ser Leu Ser Leu Thr Leu Gln Asp
    370                 375                 380

Glu Lys Thr Ile Lys Leu Asn Ser Val His Leu Asp Glu Ser Gly Val
385                 390                 395                 400

Ala Glu Ile Leu Lys Phe Met Asn Arg Lys Gly Asn Thr Asn Thr Ser
                405                 410                 415

Asp Ser Leu Met Ser Phe Leu Glu Ser Met Asn Ile Lys Ser Ile Phe
            420                 425                 430

Val Asn Phe Leu Gln Ser Asn Ile Lys Phe Ile Leu Asp Ala Asn Phe
        435                 440                 445

Ile Ile Ser Gly Thr Thr Ser Ile Gly Gln Phe Glu Phe Ile Cys Asp
    450                 455                 460

Glu Asn Asp Asn Ile Gln Pro Tyr Phe Ile Lys Phe Asn Thr Leu Glu
465                 470                 475                 480

Thr Asn Tyr Thr Leu Tyr Val Gly Asn Arg Gln Asn Met Ile Val Glu
                485                 490                 495

Pro Asn Tyr Asp Leu Asp Asp Ser Gly Asp Ile Ser Ser Thr Val Ile
            500                 505                 510

Asn Phe Ser Gln Lys Tyr Leu Tyr Gly Ile Asp Ser Cys Val Asn Lys
        515                 520                 525

Val Val Ile Ser Pro Asn Ile Tyr Thr Asp Glu Ile Asn Ile Thr Pro
    530                 535                 540

Val Tyr Glu Thr Asn Asn Thr Tyr Pro Glu Val Ile Val Leu Asp Ala
545                 550                 555                 560

Asn Tyr Ile Asn Glu Lys Ile Asn Val Asn Ile Asn Asp Leu Ser Ile
                565                 570                 575

Arg Tyr Val Trp Ser Asn Asp Gly Asn Asp Phe Ile Leu Met Ser Thr
            580                 585                 590

Ser Glu Glu Asn Lys Val Ser Gln Val Lys Ile Arg Phe Val Asn Val
        595                 600                 605

Phe Lys Asp Lys Thr Leu Ala Asn Lys Leu Ser Phe Asn Phe Ser Asp
    610                 615                 620

Lys Gln Asp Val Pro Val Ser Glu Ile Ile Leu Ser Phe Thr Pro Ser
625                 630                 635                 640

Tyr Tyr
```

<210> SEQ ID NO 14
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 14

Thr Asn Ile Arg Ile Asn Leu Asp Ser Asn Thr Arg Ser Phe Ile Val

-continued

```
1               5                   10                  15
Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
                35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
                115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
                180                 185                 190

Gly Ser Thr Lys Glu Gly Leu Phe Val Ser Glu Leu Pro Asp Val Val
                195                 200                 205

Leu Ile Ser Lys Val Tyr Met Asp Asp Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
                260                 265                 270

Leu Asp Glu Ser Gly Val Ala Glu Ile Leu Lys Phe Met Asn Arg Lys
                275                 280                 285

Gly Asn Thr Asn Thr Ser Asp Ser Leu Met Ser Phe Leu Glu Ser Met
                290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
                340                 345                 350

Lys Phe Asn Thr Leu Glu Thr Asn Tyr Thr Leu Tyr Val Gly Asn Arg
                355                 360                 365

Gln Asn Met Ile Val Glu Pro Asn Tyr Asp Leu Asp Asp Ser Gly Asp
                370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
                420                 425                 430
```

```
Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr Tyr Asn Gly Glu Arg Gly Ile Ser
            515                 520                 525

Val Pro Asp His Gly Tyr Cys Gln Pro Ile Ser Ile Pro Leu Cys Thr
        530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
        595                 600                 605

Leu Cys Glu Arg Ala Arg Gln Gly Cys Glu Ala Leu Met Asn Lys Phe
    610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 15
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 15

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Gly Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
        130                 135                 140
```

-continued

```
Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
        515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560
```

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
        595                 600                 605

Leu Cys Glu Arg Ala Arg Gln Gly Cys Glu Ala Leu Met Asn Lys Phe
    610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 16
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 16

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

```
Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
            325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
            405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
            485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
            515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
            565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
            595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 17
<211> LENGTH: 642
<212> TYPE: PRT
<213> ORGANISM: Artificial Sequence
<220> FEATURE:
<223> OTHER INFORMATION: Synthetic polypeptide
```

<400> SEQUENCE: 17

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
```

-continued

```
                    405                 410                 415
Glu Ile Asn Ile Thr Pro Val Tyr Glu Thr Asn Asn Thr Tyr Pro Glu
                420                 425                 430
Val Ile Val Leu Asp Ala Asn Tyr Ile Asn Glu Lys Ile Asn Val Asn
                435                 440                 445
Ile Asn Asp Leu Ser Ile Arg Tyr Val Trp Ser Asn Asp Gly Asn Asp
            450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
Ser Phe Asn Phe Ser Asp Lys Gln Asp Val Pro Val Ser Glu Ile Ile
                500                 505                 510
Leu Ser Phe Thr Pro Ser Tyr Tyr Ala Lys Glu Leu Ala Cys Gln Glu
                515                 520                 525
Ile Thr Val Pro Leu Cys Lys Gly Ile Gly Tyr Asn Tyr Thr Tyr Met
                530                 535                 540
Pro Asn Gln Phe Asn His Asp Thr Gln Asp Glu Ala Gly Leu Glu Val
545                 550                 555                 560
His Gln Phe Trp Pro Leu Val Glu Ile Gln Cys Ser Pro Asp Leu Lys
                565                 570                 575
Phe Phe Leu Cys Ser Met Tyr Thr Pro Ile Cys Leu Glu Asp Tyr Lys
                580                 585                 590
Lys Pro Leu Pro Pro Cys Arg Ser Val Cys Glu Arg Ala Lys Ala Gly
                595                 600                 605
Cys Ala Pro Leu Met Arg Gln Tyr Gly Phe Ala Trp Pro Asp Arg Met
610                 615                 620
Arg Cys Asp Arg Leu Pro Glu Gln Gly Asn Pro Asp Thr Leu Cys Met
625                 630                 635                 640
Asp Tyr

<210> SEQ ID NO 18
<211> LENGTH: 20
<212> TYPE: PRT
<213> ORGANISM: Homo sapiens

<400> SEQUENCE: 18

Met Tyr Arg Met Gln Leu Leu Ser Cys Ile Ala Leu Ser Leu Ala Leu
1               5                   10                  15
Val Thr Asn Ser
            20

<210> SEQ ID NO 19
<211> LENGTH: 520
<212> TYPE: PRT
<213> ORGANISM: Artificial Sequence
<220> FEATURE:
<223> OTHER INFORMATION: Synthetic polypeptide

<400> SEQUENCE: 19

Thr Asn Ile Arg Ile Asn Leu Asp Ser Asn Thr Arg Ser Phe Ile Val
1               5                   10                  15
Pro Ile Ile Thr Thr Glu Tyr Ile Arg Glu Lys Leu Ser Tyr Ser Phe
                20                  25                  30
Tyr Gly Ser Gly Gly Thr Tyr Ala Leu Ser Leu Ser Gln Tyr Asn Met
            35                  40                  45
```

```
Gly Ile Asn Ile Glu Leu Ser Glu Ser Asp Val Trp Ile Ile Asp Val
    50                  55                  60
Asp Asn Val Val Arg Asp Val Thr Ile Glu Ser Asp Lys Ile Lys Lys
65                  70                  75                  80
Gly Asp Leu Ile Glu Gly Ile Leu Ser Thr Leu Ser Ile Glu Glu Asn
                85                  90                  95
Lys Ile Ile Leu Asn Ser His Glu Ile Asn Phe Ser Gly Glu Val Asn
                100                 105                 110
Gly Ser Asn Gly Phe Val Ser Leu Thr Phe Ser Ile Leu Glu Gly Ile
            115                 120                 125
Asn Ala Ile Ile Glu Val Asp Leu Leu Ser Lys Ser Tyr Lys Leu Leu
130                 135                 140
Ile Ser Gly Glu Leu Lys Ile Leu Met Leu Asn Ser Asn His Ile Gln
145                 150                 155                 160
Gln Lys Ile Asp Tyr Ile Gly Phe Asn Ser Glu Leu Gln Lys Asn Ile
                165                 170                 175
Pro Tyr Ser Phe Val Asp Ser Glu Gly Lys Glu Asn Gly Phe Ile Asn
            180                 185                 190
Gly Ser Thr Lys Glu Gly Leu Phe Val Ser Glu Leu Pro Asp Val Val
        195                 200                 205
Leu Ile Ser Lys Val Tyr Met Asp Ala Ser Lys Pro Ser Phe Gly Tyr
    210                 215                 220
Tyr Ser Asn Asn Leu Lys Asp Val Lys Val Ile Thr Lys Asp Asn Val
225                 230                 235                 240
Asn Ile Leu Thr Gly Tyr Tyr Leu Lys Asp Asp Ile Lys Ile Ser Leu
                245                 250                 255
Ser Leu Thr Leu Gln Asp Glu Lys Thr Ile Lys Leu Asn Ser Val His
            260                 265                 270
Leu Asp Glu Ser Gly Val Ala Glu Ile Leu Lys Phe Met Asn Arg Lys
        275                 280                 285
Gly Asn Thr Asn Thr Ser Asp Ser Leu Met Ser Phe Leu Glu Ser Met
    290                 295                 300
Asn Ile Lys Ser Ile Phe Val Asn Phe Leu Gln Ser Asn Ile Lys Phe
305                 310                 315                 320
Ile Leu Asp Ala Asn Phe Ile Ile Ser Gly Thr Thr Ser Ile Gly Gln
                325                 330                 335
Phe Glu Phe Ile Cys Asp Glu Asn Asp Asn Ile Gln Pro Tyr Phe Ile
            340                 345                 350
Lys Phe Asn Thr Leu Glu Thr Asn Tyr Thr Leu Tyr Val Gly Asn Arg
        355                 360                 365
Gln Asn Met Ile Val Glu Pro Asn Tyr Asp Leu Asp Asp Ser Gly Asp
    370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                405                 410                 415
Glu Ile Asn Ile Thr Pro Val Tyr Glu Thr Asn Asn Thr Tyr Pro Glu
            420                 425                 430
Val Ile Val Leu Asp Ala Asn Tyr Ile Asn Glu Lys Ile Asn Val Asn
        435                 440                 445
Ile Asn Asp Leu Ser Ile Arg Tyr Val Trp Ser Asn Asp Gly Asn Asp
    450                 455                 460
Phe Ile Leu Met Ser Thr Ser Glu Glu Asn Lys Val Ser Gln Val Lys
```

```
                465                 470                 475                 480
Ile Arg Phe Val Asn Val Phe Lys Asp Lys Thr Leu Ala Asn Lys Leu
                    485                 490                 495

Ser Phe Asn Phe Ser Asp Lys Gln Asp Val Pro Val Ser Glu Ile Ile
                    500                 505                 510

Leu Ser Phe Thr Pro Ser Tyr Tyr
                    515                 520

<210> SEQ ID NO 20
<211> LENGTH: 520
<212> TYPE: PRT
<213> ORGANISM: Artificial Sequence
<220> FEATURE:
<223> OTHER INFORMATION: Synthetic polypeptide

<400> SEQUENCE: 20

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
```

```
305                 310                 315                 320
Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
                340                 345                 350

Lys Phe Asn Thr Leu Glu Thr Asn Tyr Thr Leu Tyr Val Gly Asn Arg
                355                 360                 365

Gln Asn Met Ile Val Glu Pro Asn Tyr Asp Leu Asp Asp Ser Gly Asp
            370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
                420                 425                 430

Val Ile Val Leu Asp Ala Asn Tyr Ile Asn Glu Lys Ile Asn Val Asn
                435                 440                 445

Ile Asn Asp Leu Ser Ile Arg Tyr Val Trp Ser Asn Asp Gly Asn Asp
            450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr
            515                 520

<210> SEQ ID NO 21
<211> LENGTH: 520
<212> TYPE: PRT
<213> ORGANISM: Artificial Sequence
<220> FEATURE:
<223> OTHER INFORMATION: Synthetic polypeptide

<400> SEQUENCE: 21

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
        130                 135                 140

Ile Ser Gly Glu Leu Lys Ile Leu Met Leu Asn Ser Asn His Ile Gln
```

```
                145                 150                 155                 160
        Gln Lys Ile Asp Tyr Ile Gly Phe Asn Ser Glu Leu Gln Lys Asn Ile
                        165                 170                 175

Pro Tyr Ser Phe Val Asp Ser Glu Gly Lys Glu Asn Gly Phe Ile Asn
                        180                 185                 190

Gly Ser Thr Lys Glu Gly Leu Phe Val Ser Glu Leu Pro Asp Val Val
                        195                 200                 205

Leu Ile Ser Lys Val Tyr Met Asp Asp Ser Lys Pro Ser Phe Gly Tyr
                        210                 215                 220

Tyr Ser Ala Asn Leu Lys Asp Val Lys Val Ile Thr Lys Asp Asn Val
        225                 230                 235                 240

Asn Ile Leu Thr Gly Tyr Tyr Leu Lys Asp Ile Lys Ile Ser Leu
                        245                 250                 255

Ser Leu Thr Leu Gln Asp Glu Lys Thr Ile Lys Leu Asn Ser Val His
                        260                 265                 270

Leu Asp Glu Ser Gly Val Ala Glu Ile Leu Lys Phe Met Asn Arg Lys
                        275                 280                 285

Gly Asn Thr Asn Thr Ser Asp Ser Leu Met Ser Phe Leu Glu Ser Met
                        290                 295                 300

Asn Ile Lys Ser Ile Phe Val Asn Phe Leu Gln Ser Asn Ile Lys Phe
        305                 310                 315                 320

Ile Leu Asp Ala Asn Phe Ile Ile Ser Gly Thr Thr Ser Ile Gly Gln
                        325                 330                 335

Phe Glu Phe Ile Cys Asp Glu Asn Asp Asn Ile Gln Pro Tyr Phe Ile
                        340                 345                 350

Lys Phe Asn Thr Leu Glu Thr Asn Tyr Thr Leu Tyr Val Gly Asn Arg
                        355                 360                 365

Gln Asn Met Ile Val Glu Pro Asn Tyr Asp Leu Asp Asp Ser Gly Asp
                        370                 375                 380

Ile Ser Ser Thr Val Ile Asn Phe Ser Gln Lys Tyr Leu Tyr Gly Ile
        385                 390                 395                 400

Asp Ser Cys Val Asn Lys Val Val Ile Ser Pro Asn Ile Tyr Thr Asp
                        405                 410                 415

Glu Ile Asn Ile Thr Pro Val Tyr Glu Thr Asn Asn Thr Tyr Pro Glu
                        420                 425                 430

Val Ile Val Leu Asp Ala Asn Tyr Ile Asn Glu Lys Ile Asn Val Asn
                        435                 440                 445

Ile Asn Asp Leu Ser Ile Arg Tyr Val Trp Ser Asn Asp Gly Asn Asp
        450                 455                 460

Phe Ile Leu Met Ser Thr Ser Glu Glu Asn Lys Val Ser Gln Val Lys
        465                 470                 475                 480

Ile Arg Phe Val Asn Val Phe Lys Asp Lys Thr Leu Ala Asn Lys Leu
                        485                 490                 495

Ser Phe Asn Phe Ser Asp Lys Gln Asp Val Pro Val Ser Glu Ile Ile
                        500                 505                 510

Leu Ser Phe Thr Pro Ser Tyr Tyr
                        515                 520

<210> SEQ ID NO 22
<211> LENGTH: 520
<212> TYPE: PRT
<213> ORGANISM: Artificial Sequence
<220> FEATURE:
<223> OTHER INFORMATION: Synthetic polypeptide
```

-continued

```
<400> SEQUENCE: 22

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415
```

-continued

```
Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
            450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr
            515                 520

<210> SEQ ID NO 23
<211> LENGTH: 520
<212> TYPE: PRT
<213> ORGANISM: Artificial Sequence
<220> FEATURE:
<223> OTHER INFORMATION: Synthetic polypeptide

<400> SEQUENCE: 23

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255
```

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Ser Ile Gly Gln
                325                 330                 335

Phe Glu Phe Ile Cys Asp Glu Asn Asp Asn Ile Gln Pro Tyr Phe Ile
                340                 345                 350

Lys Phe Asn Thr Leu Glu Thr Asn Tyr Thr Leu Tyr Val Gly Asn Arg
                355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
                420                 425                 430

Val Ile Val Leu Asp Ala Asn Tyr Ile Asn Glu Lys Ile Asn Val Asn
                435                 440                 445

Ile Asn Asp Leu Ser Ile Arg Tyr Val Trp Ser Asp Gly Asn Asp
                450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr
            515                 520

<210> SEQ ID NO 24
<211> LENGTH: 520
<212> TYPE: PRT
<213> ORGANISM: Artificial Sequence
<220> FEATURE:
<223> OTHER INFORMATION: Synthetic polypeptide

<400> SEQUENCE: 24

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

-continued

```
Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510
```

```
Leu Ser Phe Thr Pro Ser Tyr Tyr
        515                 520

<210> SEQ ID NO 25
<211> LENGTH: 520
<212> TYPE: PRT
<213> ORGANISM: Artificial Sequence
<220> FEATURE:
<223> OTHER INFORMATION: Synthetic polypeptide

<400> SEQUENCE: 25

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Asp Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350
```

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
        370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Thr Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
        450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr
        515                 520

<210> SEQ ID NO 26
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 26

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

```
Gly Ser Thr Lys Glu Gly Leu Phe Val Ser Glu Leu Pro Asp Val Val
            195                 200                 205

Leu Ile Ser Lys Val Tyr Met Asp Ala Ser Lys Pro Ser Phe Gly Tyr
            210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
            290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
            370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Thr His Thr Cys Pro Pro Cys Pro
            515                 520                 525

Ala Pro Glu Leu Leu Gly Gly Pro Ser Val Phe Leu Phe Pro Pro Lys
            530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
```

```
            610                 615                 620
Ala Leu Pro Val Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Pro Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 27
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 27

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Asn Asn Leu Lys Asp Val Lys Val Ile Thr Lys Asp Asn Val
```

```
                225                 230                 235                 240
Asn Ile Leu Thr Gly Tyr Tyr Leu Lys Asp Asp Ile Lys Ile Ser Leu
                    245                 250                 255

Ser Leu Thr Leu Gln Asp Glu Lys Thr Ile Lys Leu Asn Ser Val His
                260                 265                 270

Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
        290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
                340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
        370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Thr His Thr Cys Pro Pro Cys Pro
        515                 520                 525

Ala Pro Glu Leu Leu Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
610                 615                 620

Ala Leu Pro Val Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
                645                 650                 655
```

```
Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Pro Phe Phe Leu
            690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 28
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 28

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
            85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
            130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
            195                 200                 205

Leu Ile Ser Lys Val Tyr Met Asp Asp Ser Lys Pro Ser Phe Gly Tyr
            210                 215                 220

Tyr Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270
```

```
Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
            290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
            325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
            370                 375                 380

Ile Ser Ser Thr Val Ile Asn Phe Ser Gln Lys Tyr Leu Tyr Gly Ile
385                 390                 395                 400

Asp Ser Cys Val Asn Lys Val Ile Ser Pro Asn Ile Tyr Thr Asp
            405                 410                 415

Glu Ile Asn Ile Thr Pro Val Tyr Glu Thr Asn Asn Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
            485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Thr His Thr Cys Pro Pro Cys Pro
            515                 520                 525

Ala Pro Glu Leu Leu Gly Gly Pro Ser Val Phe Leu Phe Pro Pro Lys
            530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
            565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
610                 615                 620

Ala Leu Pro Val Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
            645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685
```

```
Tyr Lys Thr Thr Pro Pro Val Leu Asp Ser Asp Gly Pro Phe Phe Leu
    690             695                 700

Tyr Ser Lys Leu Thr Val Asp Lys Ser Arg Trp Gln Gln Gly Asn Val
705             710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 29
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 29

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65              70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300
```

```
Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
            325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
            405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
            485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Thr His Thr Cys Pro Pro Cys Pro
            515                 520                 525

Ala Pro Glu Leu Leu Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
            565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
610                 615                 620

Ala Leu Pro Val Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
            645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Pro Phe Phe Leu
            690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
```

```
              725                 730                 735
Lys Ser Leu Ser Leu Ser Pro Gly Lys
            740                 745

<210> SEQ ID NO 30
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 30

Thr Asn Ile Arg Ile Asn Leu Asp Ser Asn Thr Arg Ser Phe Ile Val
1               5                  10                 15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
```

```
                340               345               350
Lys Phe Asn Thr Leu Glu Thr Asn Tyr Thr Leu Tyr Val Gly Asn Arg
            355               360               365

Gln Asn Met Ile Val Glu Pro Asn Tyr Asp Leu Asp Asp Ser Gly Asp
        370               375               380

Ile Ser Ser Thr Val Ile Asn Phe Ser Gln Lys Tyr Leu Tyr Gly Ile
385               390               395               400

Asp Ser Cys Val Asn Lys Val Val Ile Ser Pro Asn Ile Tyr Thr Asp
                405               410               415

Glu Ile Asn Ile Thr Pro Val Tyr Glu Thr Asn Asn Thr Tyr Pro Glu
            420               425               430

Val Ile Val Leu Asp Ala Asn Tyr Ile Asn Glu Lys Ile Asn Val Asn
        435               440               445

Ile Asn Asp Leu Ser Ile Arg Tyr Val Trp Ser Asn Asp Gly Asn Asp
450               455               460

Phe Ile Leu Met Ser Thr Ser Glu Glu Asn Lys Val Ser Gln Val Lys
465               470               475               480

Ile Arg Phe Val Asn Val Phe Lys Asp Lys Thr Leu Ala Asn Lys Leu
                485               490               495

Ser Phe Asn Phe Ser Asp Lys Gln Asp Val Pro Val Ser Glu Ile Ile
            500               505               510

Leu Ser Phe Thr Pro Ser Tyr Tyr Thr His Thr Cys Pro Cys Pro
        515               520               525

Ala Pro Glu Leu Leu Gly Gly Pro Ser Val Phe Leu Phe Pro Pro Lys
        530               535               540

Pro Lys Asp Thr Leu Met Ile Ser Arg Thr Pro Glu Val Thr Cys Val
545               550               555               560

Val Val Asp Val Ser His Glu Asp Pro Glu Val Lys Phe Asn Trp Tyr
                565               570               575

Val Asp Gly Val Glu Val His Asn Ala Lys Thr Lys Pro Arg Glu Glu
            580               585               590

Gln Tyr Asn Ser Thr Tyr Arg Val Val Ser Val Leu Thr Val Leu His
        595               600               605

Gln Asp Trp Leu Asn Gly Lys Glu Tyr Lys Cys Lys Val Ser Asn Lys
    610               615               620

Ala Leu Pro Val Pro Ile Glu Lys Thr Ile Ser Lys Ala Lys Gly Gln
625               630               635               640

Pro Arg Glu Pro Gln Val Tyr Thr Leu Pro Pro Ser Arg Glu Glu Met
                645               650               655

Thr Lys Asn Gln Val Ser Leu Thr Cys Leu Val Lys Gly Phe Tyr Pro
            660               665               670

Ser Asp Ile Ala Val Glu Trp Glu Ser Asn Gly Gln Pro Glu Asn Asn
        675               680               685

Tyr Lys Thr Thr Pro Pro Val Leu Asp Ser Asp Gly Pro Phe Phe Leu
    690               695               700

Tyr Ser Lys Leu Thr Val Asp Lys Ser Arg Trp Gln Gln Gly Asn Val
705               710               715               720

Phe Ser Cys Ser Val Met His Glu Ala Leu His Asn His Tyr Thr Gln
                725               730               735

Lys Ser Leu Ser Leu Ser Pro Gly Lys
            740               745

<210> SEQ ID NO 31
```

```
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 31
```

| | | | | | | | | | | | | | | |
|---|---|---|---|---|---|---|---|---|---|---|---|---|---|---|
| Thr | Asn | Ile | Arg | Ile | Asn | Leu | Asp | Ser | Asn | Thr | Arg | Ser | Phe | Ile | Val |
| 1 | | | | 5 | | | | | 10 | | | | | 15 |
| Pro | Ile | Ile | Thr | Thr | Glu | Tyr | Ile | Arg | Glu | Lys | Leu | Ser | Tyr | Ser | Phe |
| | | | 20 | | | | | 25 | | | | | 30 | |
| Tyr | Gly | Ser | Gly | Gly | Thr | Tyr | Ala | Leu | Ser | Leu | Ser | Gln | Tyr | Asn | Met |
| | | 35 | | | | | 40 | | | | | 45 | | |
| Gly | Ile | Asn | Ile | Glu | Leu | Ser | Glu | Ser | Asp | Val | Trp | Ile | Ile | Asp | Val |
| | 50 | | | | | 55 | | | | | 60 | | | | |
| Asp | Asn | Val | Val | Arg | Asp | Val | Thr | Ile | Glu | Ser | Asp | Lys | Ile | Lys | Lys |
| 65 | | | | | 70 | | | | | 75 | | | | | 80 |
| Gly | Asp | Leu | Ile | Glu | Gly | Ile | Leu | Ser | Thr | Leu | Ser | Ile | Glu | Glu | Asn |
| | | | | 85 | | | | | 90 | | | | | 95 | |
| Lys | Ile | Ile | Leu | Asn | Ser | His | Glu | Ile | Asn | Phe | Ser | Gly | Glu | Val | Asn |
| | | | | 100 | | | | | 105 | | | | | 110 | |
| Gly | Ser | Asn | Gly | Phe | Val | Ser | Leu | Thr | Phe | Ser | Ile | Leu | Glu | Gly | Ile |
| | | | 115 | | | | | 120 | | | | | 125 | | |
| Asn | Ala | Ile | Ile | Glu | Val | Asp | Leu | Leu | Ser | Lys | Ser | Tyr | Lys | Leu | Leu |
| | | | 130 | | | | | 135 | | | | | 140 | | |
| Ile | Ser | Gly | Glu | Leu | Lys | Ile | Leu | Met | Leu | Asn | Ser | Asn | His | Ile | Gln |
| 145 | | | | | 150 | | | | | 155 | | | | | 160 |
| Gln | Lys | Ile | Asp | Tyr | Ile | Gly | Phe | Asn | Ser | Glu | Leu | Gln | Lys | Asn | Ile |
| | | | | 165 | | | | | 170 | | | | | 175 | |
| Pro | Tyr | Ser | Phe | Val | Asp | Ser | Glu | Gly | Lys | Glu | Asn | Gly | Phe | Ile | Asn |
| | | | 180 | | | | | 185 | | | | | 190 | | |
| Gly | Ser | Thr | Lys | Glu | Gly | Leu | Phe | Val | Ser | Glu | Leu | Pro | Asp | Val | Val |
| | | | 195 | | | | | 200 | | | | | 205 | | |
| Leu | Ile | Ser | Lys | Val | Tyr | Met | Asp | Asp | Ser | Lys | Pro | Ser | Phe | Gly | Tyr |
| | 210 | | | | | 215 | | | | | 220 | | | | |
| Ala | Ser | Asn | Asn | Leu | Lys | Asp | Val | Lys | Val | Ile | Thr | Lys | Asp | Asn | Val |
| 225 | | | | | 230 | | | | | 235 | | | | | 240 |
| Asn | Ile | Leu | Thr | Gly | Tyr | Tyr | Leu | Lys | Asp | Asp | Ile | Lys | Ile | Ser | Leu |
| | | | | 245 | | | | | 250 | | | | | 255 | |
| Ser | Leu | Thr | Leu | Gln | Asp | Glu | Lys | Thr | Ile | Lys | Leu | Asn | Ser | Val | His |
| | | | 260 | | | | | 265 | | | | | 270 | | |
| Leu | Asp | Glu | Ser | Gly | Val | Ala | Glu | Ile | Leu | Lys | Phe | Met | Asn | Arg | Lys |
| | | 275 | | | | | 280 | | | | | 285 | | | |
| Gly | Asn | Thr | Asn | Thr | Ser | Asp | Ser | Leu | Met | Ser | Phe | Leu | Glu | Ser | Met |
| | 290 | | | | | 295 | | | | | 300 | | | | |
| Asn | Ile | Lys | Ser | Ile | Phe | Val | Asn | Phe | Leu | Ala | Ser | Asn | Ile | Lys | Phe |
| 305 | | | | | 310 | | | | | 315 | | | | | 320 |
| Ile | Leu | Asp | Ala | Asn | Phe | Ile | Ile | Ser | Gly | Thr | Thr | Ser | Ile | Gly | Gln |
| | | | | 325 | | | | | 330 | | | | | 335 | |
| Phe | Glu | Phe | Ile | Cys | Asp | Glu | Asn | Asp | Asn | Ile | Gln | Pro | Tyr | Phe | Ile |
| | | | 340 | | | | | 345 | | | | | 350 | | |
| Lys | Phe | Asn | Thr | Leu | Glu | Thr | Asn | Tyr | Thr | Leu | Tyr | Val | Gly | Asn | Arg |
| | | 355 | | | | | 360 | | | | | 365 | | | |
| Gln | Asn | Met | Ile | Val | Glu | Pro | Asn | Tyr | Asp | Leu | Asp | Asp | Ser | Gly | Asp |
| | 370 | | | | | 375 | | | | | 380 | | | | |

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
            405                 410                 415

Glu Ile Asn Ile Thr Pro Val Tyr Glu Thr Asn Asn Tyr Pro Glu
        420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr Thr His Thr Cys Pro Pro Cys Pro
        515                 520                 525

Ala Pro Glu Leu Leu Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
610                 615                 620

Ala Leu Pro Val Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Pro Phe Phe Leu
690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 32
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 32

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35              40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Asp Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415
```

```
Glu Ile Asn Ile Thr Pro Val Tyr Glu Thr Asn Thr Tyr Pro Glu
            420                 425                 430

Val Ile Val Leu Asp Ala Asn Tyr Ile Asn Glu Lys Ile Asn Val Asn
435                 440                 445

Ile Asn Asp Leu Ser Ile Arg Tyr Val Trp Ser Asn Asp Gly Asn Asp
            450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Thr His Thr Cys Pro Pro Cys Pro
            515                 520                 525

Ala Pro Glu Leu Leu Gly Gly Pro Ser Val Phe Leu Phe Pro Pro Lys
            530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
610                 615                 620

Ala Leu Pro Val Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Pro Phe Phe Leu
690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 33
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 33

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30
```

```
Arg Thr Pro Glu Val Thr Cys Val Val Asp Val Ser His Glu Asp
         35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
210                 215                 220

Lys Thr Asn Ile Arg Ile Asn Leu Asp Ser Asn Thr Arg Ser Phe Ile
225                 230                 235                 240

Val Pro Ile Ile Thr Thr Glu Tyr Ile Arg Glu Lys Leu Ser Tyr Ser
                245                 250                 255

Phe Tyr Gly Ser Gly Gly Thr Tyr Ala Leu Ser Leu Ser Gln Tyr Asn
            260                 265                 270

Met Gly Ile Asn Ile Glu Leu Ser Glu Ser Asp Val Trp Ile Ile Asp
        275                 280                 285

Val Asp Asn Val Val Arg Asp Val Thr Ile Glu Ser Asp Lys Ile Lys
290                 295                 300

Lys Gly Asp Leu Ile Glu Gly Ile Leu Ser Thr Leu Ser Ile Glu Glu
305                 310                 315                 320

Asn Lys Ile Ile Leu Asn Ser His Glu Ile Asn Phe Ser Gly Glu Val
                325                 330                 335

Asn Gly Ser Asn Gly Phe Val Ser Leu Thr Phe Ser Ile Leu Glu Gly
            340                 345                 350

Ile Asn Ala Ile Ile Glu Val Asp Leu Leu Ser Lys Ser Tyr Lys Leu
        355                 360                 365

Leu Ile Ser Gly Glu Leu Lys Ile Leu Met Leu Asn Ser Asn His Ile
370                 375                 380

Gln Gln Lys Ile Asp Tyr Ile Gly Phe Asn Ser Glu Leu Gln Lys Asn
385                 390                 395                 400

Ile Pro Tyr Ser Phe Val Asp Ser Glu Gly Lys Glu Asn Gly Phe Ile
                405                 410                 415

Asn Gly Ser Thr Lys Glu Gly Leu Phe Val Ser Glu Leu Pro Asp Val
            420                 425                 430

Val Leu Ile Ser Lys Val Tyr Met Asp Ala Ser Lys Pro Ser Phe Gly
        435                 440                 445

Tyr Tyr Ser Asn Asn Leu Lys Asp Val Lys Val Ile Thr Lys Asp Asn
```

```
                450             455             460
Val Asn Ile Leu Thr Gly Tyr Tyr Leu Lys Asp Asp Ile Lys Ile Ser
465                 470                 475                 480

Leu Ser Leu Thr Leu Gln Asp Glu Lys Thr Ile Lys Leu Asn Ser Val
                485                 490                 495

His Leu Asp Glu Ser Gly Val Ala Glu Ile Leu Lys Phe Met Asn Arg
            500                 505                 510

Lys Gly Asn Thr Asn Thr Ser Asp Ser Leu Met Ser Phe Leu Glu Ser
            515                 520                 525

Met Asn Ile Lys Ser Ile Phe Val Asn Phe Leu Gln Ser Asn Ile Lys
        530                 535                 540

Phe Ile Leu Asp Ala Asn Phe Ile Ile Ser Gly Thr Thr Ser Ile Gly
545                 550                 555                 560

Gln Phe Glu Phe Ile Cys Asp Glu Asn Asp Asn Ile Gln Pro Tyr Phe
                565                 570                 575

Ile Lys Phe Asn Thr Leu Glu Thr Asn Tyr Thr Leu Tyr Val Gly Asn
                580                 585                 590

Arg Gln Asn Met Ile Val Glu Pro Asn Tyr Asp Leu Asp Asp Ser Gly
            595                 600                 605

Asp Ile Ser Ser Thr Val Ile Asn Phe Ser Gln Lys Tyr Leu Tyr Gly
            610                 615                 620

Ile Asp Ser Cys Val Asn Lys Val Val Ile Ser Pro Asn Ile Tyr Thr
625                 630                 635                 640

Asp Glu Ile Asn Ile Thr Pro Val Tyr Glu Thr Asn Asn Thr Tyr Pro
                645                 650                 655

Glu Val Ile Val Leu Asp Ala Asn Tyr Ile Asn Glu Lys Ile Asn Val
                660                 665                 670

Asn Ile Asn Asp Leu Ser Ile Arg Tyr Val Trp Ser Asn Asp Gly Asn
            675                 680                 685

Asp Phe Ile Leu Met Ser Thr Ser Glu Glu Asn Lys Val Ser Gln Val
            690                 695                 700

Lys Ile Arg Phe Val Asn Val Phe Lys Asp Lys Thr Leu Ala Asn Lys
705                 710                 715                 720

Leu Ser Phe Asn Phe Ser Asp Lys Gln Asp Val Pro Val Ser Glu Ile
                725                 730                 735

Ile Leu Ser Phe Thr Pro Ser Tyr Tyr
            740                 745

<210> SEQ ID NO 34
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 34

Thr His Thr Cys Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
```

```
                65                  70                  75                  80
Val Ser Val Leu Thr Val Leu His Gln Asp Trp Leu Asn Gly Lys Glu
                        85                  90                  95

Tyr Lys Cys Lys Val Ser Asn Lys Ala Leu Pro Val Pro Ile Glu Lys
                       100                 105                 110

Thr Ile Ser Lys Ala Lys Gly Gln Pro Arg Glu Pro Gln Val Tyr Thr
                       115                 120                 125

Leu Pro Pro Ser Arg Glu Glu Met Thr Lys Asn Gln Val Ser Leu Thr
            130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
                195                 200                 205

Ala Leu His Asn His Tyr Thr Gln Lys Ser Leu Ser Leu Ser Pro Gly
            210                 215                 220

Lys Thr Asn Ile Arg Ile Asn Leu Asp Ser Asn Thr Arg Ser Phe Ile
225                 230                 235                 240

Val Pro Ile Ile Thr Thr Glu Tyr Ile Arg Glu Lys Leu Ser Tyr Ser
                245                 250                 255

Phe Tyr Gly Ser Gly Gly Thr Tyr Ala Leu Ser Leu Ser Gln Tyr Asn
                260                 265                 270

Met Gly Ile Asn Ile Glu Leu Ser Glu Ser Asp Val Trp Ile Ile Asp
            275                 280                 285

Val Asp Asn Val Val Arg Asp Val Thr Ile Glu Ser Lys Ile Lys
            290                 295                 300

Lys Gly Asp Leu Ile Glu Gly Ile Leu Ser Thr Leu Ser Ile Glu Glu
305                 310                 315                 320

Asn Lys Ile Ile Leu Asn Ser His Glu Ile Asn Phe Ser Gly Glu Val
                325                 330                 335

Asn Gly Ser Asn Gly Phe Val Ser Leu Thr Phe Ser Ile Leu Glu Gly
            340                 345                 350

Ile Asn Ala Ile Ile Glu Val Asp Leu Leu Ser Lys Ser Tyr Lys Leu
            355                 360                 365

Leu Ile Ser Gly Glu Leu Lys Ile Leu Met Leu Asn Ser Asn His Ile
            370                 375                 380

Gln Gln Lys Ile Asp Tyr Ile Gly Phe Asn Ser Glu Leu Gln Lys Asn
385                 390                 395                 400

Ile Pro Tyr Ser Phe Val Asp Ser Glu Gly Lys Glu Asn Gly Phe Ile
                405                 410                 415

Asn Gly Ser Thr Lys Glu Gly Leu Phe Val Ser Glu Leu Pro Asp Val
            420                 425                 430

Val Leu Ile Ser Lys Val Tyr Met Asp Asp Ser Lys Pro Ser Phe Gly
            435                 440                 445

Tyr Ala Ser Asn Asn Leu Lys Asp Val Lys Val Ile Thr Lys Asp Asn
450                 455                 460

Val Asn Ile Leu Thr Gly Tyr Tyr Leu Lys Asp Asp Ile Lys Ile Ser
465                 470                 475                 480

Leu Ser Leu Thr Leu Gln Asp Glu Lys Thr Ile Lys Leu Asn Ser Val
            485                 490                 495
```

```
His Leu Asp Glu Ser Gly Val Ala Glu Ile Leu Lys Phe Met Asn Arg
                500                 505                 510

Lys Gly Asn Thr Asn Thr Ser Asp Ser Leu Met Ser Phe Leu Glu Ser
            515                 520                 525

Met Asn Ile Lys Ser Ile Phe Val Asn Phe Leu Gln Ser Asn Ile Lys
530                 535                 540

Phe Ile Leu Asp Ala Asn Phe Ile Ile Ser Gly Thr Thr Ser Ile Gly
545                 550                 555                 560

Gln Phe Glu Phe Ile Cys Asp Glu Asn Asp Asn Ile Gln Pro Tyr Phe
                565                 570                 575

Ile Lys Phe Asn Thr Leu Glu Thr Asn Tyr Thr Leu Tyr Val Gly Asn
            580                 585                 590

Arg Gln Asn Met Ile Val Glu Pro Asn Tyr Asp Leu Asp Asp Ser Gly
            595                 600                 605

Asp Ile Ser Ser Thr Val Ile Asn Phe Ser Gln Lys Tyr Leu Tyr Gly
        610                 615                 620

Ile Asp Ser Cys Val Asn Lys Val Val Ile Ser Pro Asn Ile Tyr Thr
625                 630                 635                 640

Asp Glu Ile Asn Ile Thr Pro Val Tyr Glu Thr Asn Asn Thr Tyr Pro
                645                 650                 655

Glu Val Ile Val Leu Asp Ala Asn Tyr Ile Asn Glu Lys Ile Asn Val
            660                 665                 670

Asn Ile Asn Asp Leu Ser Ile Arg Tyr Val Trp Ser Asn Asp Gly Asn
            675                 680                 685

Asp Phe Ile Leu Met Ser Thr Ser Glu Glu Asn Lys Val Ser Gln Val
        690                 695                 700

Lys Ile Arg Phe Val Asn Val Phe Lys Asp Lys Thr Leu Ala Asn Lys
705                 710                 715                 720

Leu Ser Phe Asn Phe Ser Asp Lys Gln Asp Val Pro Val Ser Glu Ile
                725                 730                 735

Ile Leu Ser Phe Thr Pro Ser Tyr Tyr
            740                 745

<210> SEQ ID NO 35
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 35

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110
```

```
Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Thr Asn Ile Arg Ile Asn Leu Asp Ser Asn Thr Arg Ser Phe Ile
225                 230                 235                 240

Val Pro Ile Ile Thr Thr Glu Tyr Ile Arg Glu Lys Leu Ser Tyr Ser
                245                 250                 255

Phe Tyr Gly Ser Gly Thr Tyr Ala Leu Ser Leu Ser Gln Tyr Asn
            260                 265                 270

Met Gly Ile Asn Ile Glu Leu Ser Glu Ser Asp Val Trp Ile Ile Asp
        275                 280                 285

Val Asp Asn Val Val Arg Asp Val Thr Ile Glu Ser Asp Lys Ile Lys
    290                 295                 300

Lys Gly Asp Leu Ile Glu Gly Ile Leu Ser Thr Leu Ser Ile Glu Glu
305                 310                 315                 320

Asn Lys Ile Ile Leu Asn Ser His Glu Ile Asn Phe Ser Gly Glu Val
                325                 330                 335

Asn Gly Ser Asn Gly Phe Val Ser Leu Thr Phe Ser Ile Leu Glu Gly
            340                 345                 350

Ile Asn Ala Ile Ile Glu Val Asp Leu Leu Ser Lys Ser Tyr Lys Leu
        355                 360                 365

Leu Ile Ser Gly Glu Leu Lys Ile Leu Met Leu Asn Ser Asn His Ile
    370                 375                 380

Gln Gln Lys Ile Asp Tyr Ile Gly Phe Asn Ser Glu Leu Gln Lys Asn
385                 390                 395                 400

Ile Pro Tyr Ser Phe Val Asp Ser Glu Gly Lys Glu Asn Gly Phe Ile
                405                 410                 415

Asn Gly Ser Thr Lys Glu Gly Leu Phe Val Ser Glu Leu Pro Asp Val
            420                 425                 430

Val Leu Ile Ser Lys Val Tyr Met Asp Asp Ser Lys Pro Ser Phe Gly
        435                 440                 445

Tyr Tyr Ser Ala Asn Leu Lys Asp Val Lys Val Ile Thr Lys Asp Asn
    450                 455                 460

Val Asn Ile Leu Thr Gly Tyr Tyr Leu Lys Asp Asp Ile Lys Ile Ser
465                 470                 475                 480

Leu Ser Leu Thr Leu Gln Asp Glu Lys Thr Ile Lys Leu Asn Ser Val
                485                 490                 495

His Leu Asp Glu Ser Gly Val Ala Glu Ile Leu Lys Phe Met Asn Arg
            500                 505                 510

Lys Gly Asn Thr Asn Thr Ser Asp Ser Leu Met Ser Phe Leu Glu Ser
        515                 520                 525
```

```
Met Asn Ile Lys Ser Ile Phe Val Asn Phe Leu Gln Ser Asn Ile Lys
            530                 535                 540

Phe Ile Leu Asp Ala Asn Phe Ile Ile Ser Gly Thr Thr Ser Ile Gly
545                 550                 555                 560

Gln Phe Glu Phe Ile Cys Asp Glu Asn Asp Asn Ile Gln Pro Tyr Phe
                565                 570                 575

Ile Lys Phe Asn Thr Leu Glu Thr Asn Tyr Thr Leu Tyr Val Gly Asn
            580                 585                 590

Arg Gln Asn Met Ile Val Glu Pro Asn Tyr Asp Leu Asp Ser Gly
            595                 600                 605

Asp Ile Ser Ser Thr Val Ile Asn Phe Ser Gln Lys Tyr Leu Tyr Gly
610                 615                 620

Ile Asp Ser Cys Val Asn Lys Val Val Ile Ser Pro Asn Ile Tyr Thr
625                 630                 635                 640

Asp Glu Ile Asn Ile Thr Pro Val Tyr Glu Thr Asn Thr Tyr Pro
                645                 650                 655

Glu Val Ile Val Leu Asp Ala Asn Tyr Ile Asn Glu Lys Ile Asn Val
            660                 665                 670

Asn Ile Asn Asp Leu Ser Ile Arg Tyr Val Trp Ser Asn Asp Gly Asn
            675                 680                 685

Asp Phe Ile Leu Met Ser Thr Ser Glu Glu Asn Lys Val Ser Gln Val
690                 695                 700

Lys Ile Arg Phe Val Asn Val Phe Lys Asp Lys Thr Leu Ala Asn Lys
705                 710                 715                 720

Leu Ser Phe Asn Phe Ser Asp Lys Gln Asp Val Pro Val Ser Glu Ile
                725                 730                 735

Ile Leu Ser Phe Thr Pro Ser Tyr Tyr
                740                 745

<210> SEQ ID NO 36
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 36

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140
```

```
Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Thr Asn Ile Arg Ile Asn Leu Asp Ser Asn Thr Arg Ser Phe Ile
225                 230                 235                 240

Val Pro Ile Ile Thr Thr Glu Tyr Ile Arg Glu Lys Leu Ser Tyr Ser
                245                 250                 255

Phe Tyr Gly Ser Gly Gly Thr Tyr Ala Leu Ser Leu Ser Gln Tyr Asn
            260                 265                 270

Met Gly Ile Asn Ile Glu Leu Ser Glu Ser Asp Val Trp Ile Ile Asp
            275                 280                 285

Val Asp Asn Val Val Arg Asp Val Thr Ile Glu Ser Asp Lys Ile Lys
290                 295                 300

Lys Gly Asp Leu Ile Glu Gly Ile Leu Ser Thr Leu Ser Ile Glu Glu
305                 310                 315                 320

Asn Lys Ile Ile Leu Asn Ser His Glu Ile Asn Phe Ser Gly Glu Val
                325                 330                 335

Asn Gly Ser Asn Gly Phe Val Ser Leu Thr Phe Ser Ile Leu Glu Gly
            340                 345                 350

Ile Asn Ala Ile Ile Glu Val Asp Leu Leu Ser Lys Ser Tyr Lys Leu
            355                 360                 365

Leu Ile Ser Gly Glu Leu Lys Ile Leu Met Leu Asn Ser Asn His Ile
    370                 375                 380

Gln Gln Lys Ile Asp Tyr Ile Gly Phe Asn Ser Glu Leu Gln Lys Asn
385                 390                 395                 400

Ile Pro Tyr Ser Phe Val Asp Ser Glu Gly Lys Glu Asn Gly Phe Ile
                405                 410                 415

Asn Gly Ser Thr Lys Glu Gly Leu Phe Val Ser Glu Leu Pro Asp Val
            420                 425                 430

Val Leu Ile Ser Lys Val Tyr Met Asp Asp Ser Lys Pro Ser Phe Gly
    435                 440                 445

Tyr Tyr Ser Asn Asn Leu Lys Asp Val Lys Val Ile Thr Lys Asp Asn
450                 455                 460

Val Asn Ile Leu Thr Gly Tyr Tyr Leu Lys Asp Asp Ile Lys Ile Ser
465                 470                 475                 480

Leu Ser Leu Thr Leu Gln Asp Glu Lys Thr Ile Lys Leu Asn Ser Val
                485                 490                 495

His Leu Asp Glu Ser Gly Val Ala Glu Ile Leu Lys Phe Met Asn Arg
            500                 505                 510

Lys Gly Asn Thr Asn Thr Ser Asp Ser Leu Met Ser Phe Leu Glu Ser
            515                 520                 525

Met Asn Ile Lys Ser Ile Phe Val Asn Phe Leu Ala Ser Asn Ile Lys
            530                 535                 540

Phe Ile Leu Asp Ala Asn Phe Ile Ile Ser Gly Thr Thr Ser Ile Gly
545                 550                 555                 560

Gln Phe Glu Phe Ile Cys Asp Glu Asn Asp Asn Ile Gln Pro Tyr Phe
```

```
                        565                 570                 575

Ile Lys Phe Asn Thr Leu Glu Thr Asn Tyr Thr Leu Tyr Val Gly Asn
                580                 585                 590

Arg Gln Asn Met Ile Val Glu Pro Asn Tyr Asp Leu Asp Asp Ser Gly
            595                 600                 605

Asp Ile Ser Ser Thr Val Ile Asn Phe Ser Gln Lys Tyr Leu Tyr Gly
        610                 615                 620

Ile Asp Ser Cys Val Asn Lys Val Val Ile Ser Pro Asn Ile Tyr Thr
625                 630                 635                 640

Asp Glu Ile Asn Ile Thr Pro Val Tyr Glu Thr Asn Asn Thr Tyr Pro
                645                 650                 655

Glu Val Ile Val Leu Asp Ala Asn Tyr Ile Asn Glu Lys Ile Asn Val
            660                 665                 670

Asn Ile Asn Asp Leu Ser Ile Arg Tyr Val Trp Ser Asn Asp Gly Asn
        675                 680                 685

Asp Phe Ile Leu Met Ser Thr Ser Glu Glu Asn Lys Val Ser Gln Val
    690                 695                 700

Lys Ile Arg Phe Val Asn Val Phe Lys Asp Lys Thr Leu Ala Asn Lys
705                 710                 715                 720

Leu Ser Phe Asn Phe Ser Asp Lys Gln Asp Val Pro Val Ser Glu Ile
                725                 730                 735

Ile Leu Ser Phe Thr Pro Ser Tyr Tyr
            740                 745

<210> SEQ ID NO 37
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 37

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
```

```
            180                 185                 190
Ser Arg Trp Gln Gln Gly Asn Val Phe Ser Cys Ser Val Met His Glu
            195                 200                 205
Ala Leu His Asn His Tyr Thr Gln Lys Ser Leu Ser Leu Ser Pro Gly
            210                 215                 220
Lys Thr Asn Ile Arg Ile Asn Leu Asp Ser Asn Thr Arg Ser Phe Ile
225                 230                 235                 240
Val Pro Ile Ile Thr Thr Glu Tyr Ile Arg Glu Lys Leu Ser Tyr Ser
                245                 250                 255
Phe Tyr Gly Ser Gly Thr Tyr Ala Leu Ser Leu Ser Gln Tyr Asn
                260                 265                 270
Met Gly Ile Asn Ile Glu Leu Ser Glu Ser Asp Val Trp Ile Ile Asp
                275                 280                 285
Val Asp Asn Val Val Arg Asp Val Thr Ile Glu Ser Asp Lys Ile Lys
            290                 295                 300
Lys Gly Asp Leu Ile Glu Gly Ile Leu Ser Thr Leu Ser Ile Glu Glu
305                 310                 315                 320
Asn Lys Ile Ile Leu Asn Ser His Glu Ile Asn Phe Ser Gly Glu Val
                325                 330                 335
Asn Gly Ser Asn Gly Phe Val Ser Leu Thr Phe Ser Ile Leu Glu Gly
                340                 345                 350
Ile Asn Ala Ile Ile Glu Val Asp Leu Leu Ser Lys Ser Tyr Lys Leu
                355                 360                 365
Leu Ile Ser Gly Glu Leu Lys Ile Leu Met Leu Asn Ser Asn His Ile
            370                 375                 380
Gln Gln Lys Ile Asp Tyr Ile Gly Phe Asn Ser Glu Leu Gln Lys Asn
385                 390                 395                 400
Ile Pro Tyr Ser Phe Val Asp Ser Glu Gly Lys Glu Asn Gly Phe Ile
                405                 410                 415
Asn Gly Ser Thr Lys Glu Gly Leu Phe Val Ser Glu Leu Pro Asp Val
                420                 425                 430
Val Leu Ile Ser Lys Val Tyr Met Asp Asp Ser Lys Pro Ser Phe Gly
                435                 440                 445
Tyr Ala Ser Ala Asn Leu Lys Asp Val Lys Val Ile Thr Lys Asp Asn
            450                 455                 460
Val Asn Ile Leu Thr Gly Tyr Tyr Leu Lys Asp Asp Ile Lys Ile Ser
465                 470                 475                 480
Leu Ser Leu Thr Leu Gln Asp Glu Lys Thr Ile Lys Leu Asn Ser Val
                485                 490                 495
His Leu Asp Glu Ser Gly Val Ala Glu Ile Leu Lys Phe Met Asn Arg
                500                 505                 510
Lys Gly Asn Thr Asn Thr Ser Asp Ser Leu Met Ser Phe Leu Glu Ser
                515                 520                 525
Met Asn Ile Lys Ser Ile Phe Val Asn Phe Leu Gln Ser Asn Ile Lys
            530                 535                 540
Phe Ile Leu Asp Ala Asn Phe Ile Ile Ser Gly Thr Thr Ser Ile Gly
545                 550                 555                 560
Gln Phe Glu Phe Ile Cys Asp Glu Asn Asp Ile Gln Pro Tyr Phe
                565                 570                 575
Ile Lys Phe Asn Thr Leu Glu Thr Asn Tyr Thr Leu Tyr Val Gly Asn
                580                 585                 590
Arg Gln Asn Met Ile Val Glu Pro Asn Tyr Asp Leu Asp Asp Ser Gly
                595                 600                 605
```

```
Asp Ile Ser Ser Thr Val Ile Asn Phe Ser Gln Lys Tyr Leu Tyr Gly
        610                 615                 620

Ile Asp Ser Cys Val Asn Lys Val Val Ile Ser Pro Asn Ile Tyr Thr
625                 630                 635                 640

Asp Glu Ile Asn Ile Thr Pro Val Tyr Glu Thr Asn Asn Thr Tyr Pro
                645                 650                 655

Glu Val Ile Val Leu Asp Ala Asn Tyr Ile Asn Glu Lys Ile Asn Val
                660                 665                 670

Asn Ile Asn Asp Leu Ser Ile Arg Tyr Val Trp Ser Asn Asp Gly Asn
        675                 680                 685

Asp Phe Ile Leu Met Ser Thr Ser Glu Glu Asn Lys Val Ser Gln Val
        690                 695                 700

Lys Ile Arg Phe Val Asn Val Phe Lys Asp Lys Thr Leu Ala Asn Lys
705                 710                 715                 720

Leu Ser Phe Asn Phe Ser Asp Lys Gln Asp Val Pro Val Ser Glu Ile
                725                 730                 735

Ile Leu Ser Phe Thr Pro Ser Tyr Tyr
                740                 745

<210> SEQ ID NO 38
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 38

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220
```

```
Lys Thr Asn Ile Arg Ile Asn Leu Asp Ser Asn Thr Arg Ser Phe Ile
225                 230                 235                 240

Val Pro Ile Ile Thr Thr Glu Tyr Ile Arg Glu Lys Leu Ser Tyr Ser
            245                 250                 255

Phe Tyr Gly Ser Gly Gly Thr Tyr Ala Leu Ser Leu Ser Gln Tyr Asn
        260                 265                 270

Met Gly Ile Asn Ile Glu Leu Ser Glu Ser Asp Val Trp Ile Ile Asp
        275                 280                 285

Val Asp Asn Val Val Arg Asp Val Thr Ile Glu Ser Asp Lys Ile Lys
    290                 295                 300

Lys Gly Asp Leu Ile Glu Gly Ile Leu Ser Thr Leu Ser Ile Glu Glu
305                 310                 315                 320

Asn Lys Ile Ile Leu Asn Ser His Glu Ile Asn Phe Ser Gly Glu Val
                325                 330                 335

Asn Gly Ser Asn Gly Phe Val Ser Leu Thr Phe Ser Ile Leu Glu Gly
            340                 345                 350

Ile Asn Ala Ile Ile Glu Val Asp Leu Leu Ser Lys Ser Tyr Lys Leu
        355                 360                 365

Leu Ile Ser Gly Glu Leu Lys Ile Leu Met Leu Asn Ser Asn His Ile
370                 375                 380

Gln Gln Lys Ile Asp Tyr Ile Gly Phe Asn Ser Glu Leu Gln Lys Asn
385                 390                 395                 400

Ile Pro Tyr Ser Phe Val Asp Ser Glu Gly Lys Glu Asn Gly Phe Ile
                405                 410                 415

Asn Gly Ser Thr Lys Glu Gly Leu Phe Val Ser Glu Leu Pro Asp Val
            420                 425                 430

Val Leu Ile Ser Lys Val Tyr Met Asp Asp Ser Lys Pro Ser Phe Gly
        435                 440                 445

Tyr Ala Ser Asn Asn Leu Lys Asp Val Lys Val Ile Thr Lys Asp Asn
    450                 455                 460

Val Asn Ile Leu Thr Gly Tyr Tyr Leu Lys Asp Asp Ile Lys Ile Ser
465                 470                 475                 480

Leu Ser Leu Thr Leu Gln Asp Glu Lys Thr Ile Lys Leu Asn Ser Val
                485                 490                 495

His Leu Asp Glu Ser Gly Val Ala Glu Ile Leu Lys Phe Met Asn Arg
            500                 505                 510

Lys Gly Asn Thr Asn Thr Ser Asp Ser Leu Met Ser Phe Leu Glu Ser
        515                 520                 525

Met Asn Ile Lys Ser Ile Phe Val Asn Phe Leu Ala Ser Asn Ile Lys
    530                 535                 540

Phe Ile Leu Asp Ala Asn Phe Ile Ile Ser Gly Thr Thr Ser Ile Gly
545                 550                 555                 560

Gln Phe Glu Phe Ile Cys Asp Glu Asn Asp Asn Ile Gln Pro Tyr Phe
                565                 570                 575

Ile Lys Phe Asn Thr Leu Glu Thr Asn Tyr Thr Leu Tyr Val Gly Asn
            580                 585                 590

Arg Gln Asn Met Ile Val Glu Pro Asn Tyr Asp Leu Asp Asp Ser Gly
        595                 600                 605

Asp Ile Ser Ser Thr Val Ile Asn Phe Ser Gln Lys Tyr Leu Tyr Gly
    610                 615                 620

Ile Asp Ser Cys Val Asn Lys Val Val Ile Ser Pro Asn Ile Tyr Thr
625                 630                 635                 640
```

```
Asp Glu Ile Asn Ile Thr Pro Val Tyr Glu Thr Asn Thr Tyr Pro
                    645                 650                 655

Glu Val Ile Val Leu Asp Ala Asn Tyr Ile Asn Glu Lys Ile Asn Val
            660                 665                 670

Asn Ile Asn Asp Leu Ser Ile Arg Tyr Val Trp Ser Asn Asp Gly Asn
            675                 680                 685

Asp Phe Ile Leu Met Ser Thr Ser Glu Glu Asn Lys Val Ser Gln Val
            690                 695                 700

Lys Ile Arg Phe Val Asn Val Phe Lys Asp Lys Thr Leu Ala Asn Lys
705                 710                 715                 720

Leu Ser Phe Asn Phe Ser Asp Lys Gln Asp Val Pro Val Ser Glu Ile
            725                 730                 735

Ile Leu Ser Phe Thr Pro Ser Tyr Tyr
            740                 745

<210> SEQ ID NO 39
<211> LENGTH: 745
<212> TYPE: PRT
<213> ORGANISM: Artificial Sequence
<220> FEATURE:
<223> OTHER INFORMATION: Synthetic polypeptide

<400> SEQUENCE: 39

Thr His Thr Cys Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
            35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Val Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
    210                 215                 220

Lys Thr Asn Ile Arg Ile Asn Leu Asp Ser Asn Thr Arg Ser Phe Ile
225                 230                 235                 240

Val Pro Ile Ile Thr Thr Glu Tyr Ile Arg Glu Lys Leu Ser Tyr Ser
            245                 250                 255
```

-continued

```
Phe Tyr Gly Ser Gly Gly Thr Tyr Ala Leu Ser Leu Ser Gln Tyr Asn
            260                 265                 270

Met Gly Ile Asn Ile Glu Leu Ser Glu Ser Asp Val Trp Ile Ile Asp
            275                 280                 285

Val Asp Asn Val Val Arg Asp Val Thr Ile Glu Ser Asp Lys Ile Lys
            290                 295                 300

Lys Gly Asp Leu Ile Glu Gly Ile Leu Ser Thr Leu Ser Ile Glu Glu
305                 310                 315                 320

Asn Lys Ile Ile Leu Asn Ser His Glu Ile Asn Phe Ser Gly Glu Val
                325                 330                 335

Asn Gly Ser Asn Gly Phe Val Ser Leu Thr Phe Ser Ile Leu Glu Gly
            340                 345                 350

Ile Asn Ala Ile Ile Glu Val Asp Leu Leu Ser Lys Ser Tyr Lys Leu
            355                 360                 365

Leu Ile Ser Gly Glu Asp Lys Ile Leu Met Leu Asn Ser Asn His Ile
            370                 375                 380

Gln Gln Lys Ile Asp Tyr Ile Gly Phe Asn Ser Glu Leu Gln Lys Asn
385                 390                 395                 400

Ile Pro Tyr Ser Phe Val Asp Ser Glu Gly Lys Glu Asn Gly Phe Ile
                405                 410                 415

Asn Gly Ser Thr Lys Glu Gly Leu Phe Val Ser Glu Leu Pro Asp Val
            420                 425                 430

Val Leu Ile Ser Lys Val Tyr Met Asp Asp Ser Lys Pro Ser Phe Gly
            435                 440                 445

Tyr Tyr Ser Asn Asn Leu Lys Asp Val Lys Val Ile Thr Lys Asp Asn
            450                 455                 460

Val Asn Ile Leu Thr Gly Tyr Tyr Leu Lys Asp Ile Lys Ile Ser
465                 470                 475                 480

Leu Ser Leu Thr Leu Gln Asp Glu Lys Thr Ile Lys Leu Asn Ser Val
                485                 490                 495

His Leu Asp Glu Ser Gly Val Ala Glu Ile Leu Lys Phe Met Asn Arg
            500                 505                 510

Lys Gly Asn Thr Asn Thr Ser Asp Ser Leu Met Ser Phe Leu Glu Ser
            515                 520                 525

Met Asn Ile Lys Ser Ile Phe Val Asn Phe Leu Gln Ser Asn Ile Lys
            530                 535                 540

Phe Ile Leu Asp Ala Asn Phe Ile Ile Ser Gly Thr Thr Ser Ile Gly
545                 550                 555                 560

Gln Phe Glu Phe Ile Cys Asp Glu Asn Asp Asn Ile Gln Pro Tyr Phe
                565                 570                 575

Ile Lys Phe Asn Thr Leu Glu Thr Asn Tyr Thr Leu Tyr Val Gly Asn
            580                 585                 590

Arg Gln Asn Met Ile Val Glu Pro Asn Tyr Asp Leu Asp Asp Ser Gly
            595                 600                 605

Asp Ile Ser Ser Thr Val Ile Asn Phe Ser Gln Lys Tyr Leu Tyr Gly
            610                 615                 620

Ile Asp Ser Cys Val Asn Lys Val Ile Ser Pro Asn Ile Tyr Thr
625                 630                 635                 640

Asp Glu Ile Asn Ile Thr Pro Val Tyr Glu Thr Asn Asn Thr Tyr Pro
                645                 650                 655

Glu Val Ile Val Leu Asp Ala Asn Tyr Ile Asn Glu Lys Ile Asn Val
            660                 665                 670

Asn Ile Asn Asp Leu Ser Ile Arg Tyr Val Trp Ser Asn Asp Gly Asn
```

```
            675                 680                 685
Asp Phe Ile Leu Met Ser Thr Ser Glu Glu Asn Lys Val Ser Gln Val
    690                 695                 700

Lys Ile Arg Phe Val Asn Val Phe Lys Asp Lys Thr Leu Ala Asn Lys
705                 710                 715                 720

Leu Ser Phe Asn Phe Ser Asp Lys Gln Asp Val Pro Val Ser Glu Ile
                725                 730                 735

Ile Leu Ser Phe Thr Pro Ser Tyr Tyr
                740                 745
```

<210> SEQ ID NO 40
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 40

```
Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
        50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
```

```
            290                 295                 300
Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
            325                 330                 335

Glu Leu Pro Asp Val Val Leu Ile Ser Lys Val Tyr Met Asp Ala Ser
            340                 345                 350

Lys Pro Ser Phe Gly Tyr Tyr Ser Asn Asn Leu Lys Asp Val Lys Val
            355                 360                 365

Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
            405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
            435                 440                 445

Gln Ser Asn Ile Lys Phe Ile Leu Asp Ala Asn Phe Ile Ile Ser Gly
            450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
            485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
            515                 520                 525

Lys Tyr Leu Tyr Gly Ile Asp Ser Cys Val Asn Lys Val Val Ile Ser
            530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
            565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
            595                 600                 605

Lys Val Ser Gln Val Lys Ile Arg Phe Val Asn Val Phe Lys Asp Lys
            610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
            645                 650

<210> SEQ ID NO 41
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 41

Tyr Asn Gly Glu Arg Gly Ile Ser Val Pro Asp His Gly Tyr Cys Gln
```

```
1               5                   10                  15
Pro Ile Ser Ile Pro Leu Cys Thr Asp Ile Ala Tyr Asn Gln Thr Ile
             20                  25                  30

Met Pro Asn Leu Leu Gly His Thr Asn Gln Glu Asp Ala Gly Leu Glu
             35                  40                  45

Val His Gln Phe Tyr Pro Leu Val Lys Val Gln Cys Ser Ala Glu Leu
             50                  55                  60

Lys Phe Phe Leu Cys Ser Met Tyr Ala Pro Val Cys Thr Val Leu Glu
65                   70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
             100                 105                 110

Lys Cys Glu Lys Phe Pro Val His Gly Ala Gly Glu Leu Cys Val Gly
             115                 120                 125

Gln Asn Thr Ser Asp Lys Thr Asn Ile Arg Ile Asn Leu Asp Ser Asn
             130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                 165                 170                 175

Leu Ser Gln Tyr Asn Met Gly Ile Asn Ile Glu Leu Ser Glu Ser Asp
             180                 185                 190

Val Trp Ile Ile Asp Val Asp Asn Val Val Arg Asp Val Thr Ile Glu
             195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                 245                 250                 255

Ser Ile Leu Glu Gly Ile Asn Ala Ile Ile Glu Val Asp Leu Leu Ser
             260                 265                 270

Lys Ser Tyr Lys Leu Leu Ile Ser Gly Glu Leu Lys Ile Leu Met Leu
             275                 280                 285

Asn Ser Asn His Ile Gln Gln Lys Ile Asp Tyr Ile Gly Phe Asn Ser
             290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                 325                 330                 335

Glu Leu Pro Asp Val Val Leu Ile Ser Lys Val Tyr Met Asp Asp Ser
             340                 345                 350

Lys Pro Ser Phe Gly Tyr Ala Ser Asn Asn Leu Lys Asp Val Lys Val
             355                 360                 365

Ile Thr Lys Asp Asn Val Asn Ile Leu Thr Gly Tyr Tyr Leu Lys Asp
             370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                 405                 410                 415

Lys Phe Met Asn Arg Lys Gly Asn Thr Asn Thr Ser Asp Ser Leu Met
             420                 425                 430
```

```
Ser Phe Leu Glu Ser Met Asn Ile Lys Ser Ile Phe Val Asn Phe Leu
        435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
            485                 490                 495

Leu Tyr Val Gly Asn Arg Gln Asn Met Ile Val Glu Pro Asn Tyr Asp
        500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
            565                 570                 575

Glu Lys Ile Asn Val Asn Ile Asn Asp Leu Ser Ile Arg Tyr Val Trp
        580                 585                 590

Ser Asn Asp Gly Asn Asp Phe Ile Leu Met Ser Thr Ser Glu Glu Asn
    595                 600                 605

Lys Val Ser Gln Val Lys Ile Arg Phe Val Asn Val Phe Lys Asp Lys
610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
            645                 650

<210> SEQ ID NO 42
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 42

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
            85                  90                  95

Cys Glu Ala Leu Met Asn Lys Phe Gly Phe Gln Trp Pro Asp Thr Leu
        100                 105                 110

Lys Cys Glu Lys Phe Pro Val His Gly Ala Gly Glu Leu Cys Val Gly
    115                 120                 125

Gln Asn Thr Ser Asp Lys Thr Asn Ile Arg Ile Asn Leu Asp Ser Asn
130                 135                 140
```

-continued

```
Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Tyr Ser Ala Asn Leu Lys Asp Val Lys Val
        355                 360                 365

Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Gln Ser Asn Ile Lys Phe Ile Leu Asp Ala Asn Phe Ile Ile Ser Gly
450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
530                 535                 540

Pro Asn Ile Tyr Thr Asp Glu Ile Asn Ile Thr Pro Val Tyr Glu Thr
545                 550                 555                 560
```

```
Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
            595                 600             605

Lys Val Ser Gln Val Lys Ile Arg Phe Val Asn Val Phe Lys Asp Lys
        610                 615             620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650
```

<210> SEQ ID NO 43
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 43

```
Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
    130                 135                 140

Thr Arg Ser Phe Ile Val Pro Ile Ile Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270
```

```
Lys Ser Tyr Lys Leu Leu Ile Ser Gly Glu Leu Lys Ile Leu Met Leu
                275                 280                 285

Asn Ser Asn His Ile Gln Gln Lys Ile Asp Tyr Ile Gly Phe Asn Ser
            290                 295                 300

Glu Leu Gln Lys Asn Ile Pro Tyr Ser Phe Val Asp Ser Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
                340                 345                 350

Lys Pro Ser Phe Gly Tyr Tyr Ser Asn Asn Leu Lys Asp Val Lys Val
            355                 360                 365

Ile Thr Lys Asp Asn Val Asn Ile Leu Thr Gly Tyr Tyr Leu Lys Asp
        370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Ala Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650
```

<210> SEQ ID NO 44
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 44

```
Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
    290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Ala Ser Ala Asn Leu Lys Asp Val Lys Val
        355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
```

```
            405                 410                 415
Lys Phe Met Asn Arg Lys Gly Asn Thr Asn Thr Ser Asp Ser Leu Met
                420                 425                 430

Ser Phe Leu Glu Ser Met Asn Ile Lys Ser Ile Phe Val Asn Phe Leu
            435                 440                 445

Gln Ser Asn Ile Lys Phe Ile Leu Asp Ala Asn Phe Ile Ile Ser Gly
        450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 45
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 45

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
        50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
```

```
              115                 120                 125
Gln Asn Thr Ser Asp Lys Thr Asn Ile Arg Ile Asn Leu Asp Ser Asn
    130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
                180                 185                 190

Val Trp Ile Ile Asp Val Asp Asn Val Val Arg Asp Val Thr Ile Glu
            195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
                260                 265                 270

Lys Ser Tyr Lys Leu Leu Ile Ser Gly Glu Leu Lys Ile Leu Met Leu
            275                 280                 285

Asn Ser Asn His Ile Gln Gln Lys Ile Asp Tyr Ile Gly Phe Asn Ser
    290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
                340                 345                 350

Lys Pro Ser Phe Gly Tyr Ala Ser Asn Asn Leu Lys Asp Val Lys Val
            355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
                420                 425                 430

Ser Phe Leu Glu Ser Met Asn Ile Lys Ser Ile Phe Val Asn Phe Leu
            435                 440                 445

Ala Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
                500                 505                 510

Leu Asp Asp Ser Gly Asp Ile Ser Ser Thr Val Ile Asn Phe Ser Gln
            515                 520                 525

Lys Tyr Leu Tyr Gly Ile Asp Ser Cys Val Asn Lys Val Val Ile Ser
    530                 535                 540
```

```
Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650
```

<210> SEQ ID NO 46
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 46

```
Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
    130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255
```

Ser Ile Leu Glu Gly Ile Asn Ala Ile Ile Glu Val Asp Leu Leu Ser
           260                 265                 270

Lys Ser Tyr Lys Leu Leu Ile Ser Gly Glu Asp Lys Ile Leu Met Leu
           275                 280                 285

Asn Ser Asn His Ile Gln Gln Lys Ile Asp Tyr Ile Gly Phe Asn Ser
           290                 295                 300

Glu Leu Gln Lys Asn Ile Pro Tyr Ser Phe Val Asp Ser Gly Lys
305                 310                 315                 320

Glu Asn Gly Phe Ile Asn Gly Ser Thr Lys Glu Gly Leu Phe Val Ser
                    325                 330                 335

Glu Leu Pro Asp Val Val Leu Ile Ser Lys Val Tyr Met Asp Asp Ser
               340                 345                 350

Lys Pro Ser Phe Gly Tyr Tyr Ser Asn Asn Leu Lys Asp Val Lys Val
               355                 360                 365

Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                    405                 410                 415

Lys Phe Met Asn Arg Lys Gly Asn Thr Asn Thr Ser Asp Ser Leu Met
               420                 425                 430

Ser Phe Leu Glu Ser Met Asn Ile Lys Ser Ile Phe Val Asn Phe Leu
           435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                    485                 490                 495

Leu Tyr Val Gly Asn Arg Gln Asn Met Ile Val Glu Pro Asn Tyr Asp
               500                 505                 510

Leu Asp Asp Ser Gly Asp Ile Ser Ser Thr Val Ile Asn Phe Ser Gln
               515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                    565                 570                 575

Glu Lys Ile Asn Val Asn Ile Asn Asp Leu Ser Ile Arg Tyr Val Trp
               580                 585                 590

Ser Asn Asp Gly Asn Asp Phe Ile Leu Met Ser Thr Ser Glu Glu Asn
           595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                    645                 650

<210> SEQ ID NO 47
<211> LENGTH: 654

```
<212> TYPE: PRT
<213> ORGANISM: Artificial Sequence
<220> FEATURE:
<223> OTHER INFORMATION: Synthetic polypeptide

<400> SEQUENCE: 47

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
                35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
                115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
                180                 185                 190

Gly Ser Thr Lys Glu Gly Leu Phe Val Ser Glu Leu Pro Asp Val Val
                195                 200                 205

Leu Ile Ser Lys Val Tyr Met Asp Ala Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
                260                 265                 270

Leu Asp Glu Ser Gly Val Ala Glu Ile Leu Lys Phe Met Asn Arg Lys
                275                 280                 285

Gly Asn Thr Asn Thr Ser Asp Ser Leu Met Ser Phe Leu Glu Ser Met
                290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Ser Ile Gly Gln
                325                 330                 335

Phe Glu Phe Ile Cys Asp Glu Asn Asp Asn Ile Gln Pro Tyr Phe Ile
                340                 345                 350

Lys Phe Asn Thr Leu Glu Thr Asn Tyr Thr Leu Tyr Val Gly Asn Arg
                355                 360                 365

Gln Asn Met Ile Val Glu Pro Asn Tyr Asp Leu Asp Asp Ser Gly Asp
                370                 375                 380
```

```
Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
            405                 410                 415

Glu Ile Asn Ile Thr Pro Val Tyr Glu Thr Asn Asn Thr Tyr Pro Glu
        420                 425                 430

Val Ile Val Leu Asp Ala Asn Tyr Ile Asn Glu Lys Ile Asn Val Asn
                435                 440                 445

Ile Asn Asp Leu Ser Ile Arg Tyr Val Trp Ser Asn Asp Gly Asn Asp
        450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
        515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
        595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 48
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 48

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95
```

```
Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
```

```
            515                 520                 525
Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
                580                 585                 590

Ala Pro Val Cys Thr Val Leu Glu Gln Ala Leu Pro Pro Cys Arg Ser
                595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 49
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 49

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
                35                  40                  45

Gly Ile Asn Ile Glu Leu Ser Glu Ser Asp Val Trp Ile Ile Asp Val
                50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
                115                 120                 125

Asn Ala Ile Ile Glu Val Asp Leu Leu Ser Lys Ser Tyr Lys Leu Leu
                130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
                180                 185                 190

Gly Ser Thr Lys Glu Gly Leu Phe Val Ser Glu Leu Pro Asp Val Val
                195                 200                 205

Leu Ile Ser Lys Val Tyr Met Asp Asp Ser Lys Pro Ser Phe Gly Tyr
                210                 215                 220

Tyr Ser Ala Asn Leu Lys Asp Val Lys Val Ile Thr Lys Asp Asn Val
```

```
            225                 230                 235                 240

Asn Ile Leu Thr Gly Tyr Tyr Leu Lys Asp Asp Ile Lys Ile Ser Leu
            245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
            290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
            325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
            370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
            405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
            450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
            485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
            515                 520                 525

Val Pro Asp His Gly Tyr Cys Gln Pro Ile Ser Ile Pro Leu Cys Thr
            530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
            565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
            595                 600                 605

Leu Cys Glu Arg Ala Arg Gln Gly Cys Glu Ala Leu Met Asn Lys Phe
            610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
            645                 650
```

<210> SEQ ID NO 50
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 50

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365
```

```
Gln Asn Met Ile Val Glu Pro Asn Tyr Asp Leu Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
                435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
    515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
    595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 51
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 51

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80
```

-continued

```
Gly Asp Leu Ile Glu Gly Ile Leu Ser Thr Leu Ser Ile Glu Glu Asn
                 85                  90                  95
Lys Ile Ile Leu Asn Ser His Glu Ile Asn Phe Ser Gly Glu Val Asn
            100                 105                 110
Gly Ser Asn Gly Phe Val Ser Leu Thr Phe Ser Ile Leu Glu Gly Ile
        115                 120                 125
Asn Ala Ile Ile Glu Val Asp Leu Leu Ser Lys Ser Tyr Lys Leu Leu
130                 135                 140
Ile Ser Gly Glu Leu Lys Ile Leu Met Leu Asn Ser Asn His Ile Gln
145                 150                 155                 160
Gln Lys Ile Asp Tyr Ile Gly Phe Asn Ser Glu Leu Gln Lys Asn Ile
                165                 170                 175
Pro Tyr Ser Phe Val Asp Ser Glu Gly Lys Glu Asn Gly Phe Ile Asn
            180                 185                 190
Gly Ser Thr Lys Glu Gly Leu Phe Val Ser Glu Leu Pro Asp Val Val
        195                 200                 205
Leu Ile Ser Lys Val Tyr Met Asp Asp Ser Lys Pro Ser Phe Gly Tyr
210                 215                 220
Ala Ser Ala Asn Leu Lys Asp Val Lys Val Ile Thr Lys Asp Asn Val
225                 230                 235                 240
Asn Ile Leu Thr Gly Tyr Tyr Leu Lys Asp Asp Ile Lys Ile Ser Leu
                245                 250                 255
Ser Leu Thr Leu Gln Asp Glu Lys Thr Ile Lys Leu Asn Ser Val His
            260                 265                 270
Leu Asp Glu Ser Gly Val Ala Glu Ile Leu Lys Phe Met Asn Arg Lys
        275                 280                 285
Gly Asn Thr Asn Thr Ser Asp Ser Leu Met Ser Phe Leu Glu Ser Met
290                 295                 300
Asn Ile Lys Ser Ile Phe Val Asn Phe Leu Gln Ser Asn Ile Lys Phe
305                 310                 315                 320
Ile Leu Asp Ala Asn Phe Ile Ile Ser Gly Thr Thr Ser Ile Gly Gln
                325                 330                 335
Phe Glu Phe Ile Cys Asp Glu Asn Asp Asn Ile Gln Pro Tyr Phe Ile
            340                 345                 350
Lys Phe Asn Thr Leu Glu Thr Asn Tyr Thr Leu Tyr Val Gly Asn Arg
        355                 360                 365
Gln Asn Met Ile Val Glu Pro Asn Tyr Asp Leu Asp Asp Ser Gly Asp
370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                405                 410                 415
Glu Ile Asn Ile Thr Pro Val Tyr Glu Thr Asn Asn Thr Tyr Pro Glu
            420                 425                 430
Val Ile Val Leu Asp Ala Asn Tyr Ile Asn Glu Lys Ile Asn Val Asn
        435                 440                 445
Ile Asn Asp Leu Ser Ile Arg Tyr Val Trp Ser Asn Asp Gly Asn Asp
450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
```

-continued

```
Ser Phe Asn Phe Ser Asp Lys Gln Asp Val Pro Val Ser Glu Ile Ile
                500                 505                 510

Leu Ser Phe Thr Pro Ser Tyr Tyr Tyr Asn Gly Glu Arg Gly Ile Ser
            515                 520                 525

Val Pro Asp His Gly Tyr Cys Gln Pro Ile Ser Ile Pro Leu Cys Thr
        530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
        595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 52
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 52

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
        130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205
```

```
Leu Ile Ser Lys Val Tyr Met Asp Asp Ser Lys Pro Ser Phe Gly Tyr
    210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
        515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
        595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
```

```
                625                 630                 635                 640
Gly Ala Gly Glu Leu Cys Val Gly Gln Asn Thr Ser Asp Lys
                    645                 650

<210> SEQ ID NO 53
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 53

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
        130                 135                 140

Ile Ser Gly Glu Asp Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
                180                 185                 190

Gly Ser Thr Lys Glu Gly Leu Phe Val Ser Glu Leu Pro Asp Val Val
            195                 200                 205

Leu Ile Ser Lys Val Tyr Met Asp Asp Ser Lys Pro Ser Phe Gly Tyr
        210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
                260                 265                 270

Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
        290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
```

```
                    340                 345                 350
Lys Phe Asn Thr Leu Glu Thr Asn Tyr Thr Leu Tyr Val Gly Asn Arg
                355                 360                 365
Gln Asn Met Ile Val Glu Pro Asn Tyr Asp Leu Asp Asp Ser Gly Asp
            370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                405                 410                 415
Glu Ile Asn Ile Thr Pro Val Tyr Glu Thr Asn Asn Thr Tyr Pro Glu
            420                 425                 430
Val Ile Val Leu Asp Ala Asn Tyr Ile Asn Glu Lys Ile Asn Val Asn
                435                 440                 445
Ile Asn Asp Leu Ser Ile Arg Tyr Val Trp Ser Asn Asp Gly Asn Asp
            450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
Ser Phe Asn Phe Ser Asp Lys Gln Asp Val Pro Val Ser Glu Ile Ile
                500                 505                 510
Leu Ser Phe Thr Pro Ser Tyr Tyr Tyr Asn Gly Glu Arg Gly Ile Ser
            515                 520                 525
Val Pro Asp His Gly Tyr Cys Gln Pro Ile Ser Ile Pro Leu Cys Thr
        530                 535                 540
Asp Ile Ala Tyr Asn Gln Thr Ile Met Pro Asn Leu Leu Gly His Thr
545                 550                 555                 560
Asn Gln Glu Asp Ala Gly Leu Glu Val His Gln Phe Tyr Pro Leu Val
                565                 570                 575
Lys Val Gln Cys Ser Ala Glu Leu Lys Phe Phe Leu Cys Ser Met Tyr
            580                 585                 590
Ala Pro Val Cys Thr Val Leu Glu Gln Ala Leu Pro Pro Cys Arg Ser
        595                 600                 605
Leu Cys Glu Arg Ala Arg Gln Gly Cys Glu Ala Leu Met Asn Lys Phe
    610                 615                 620
Gly Phe Gln Trp Pro Asp Thr Leu Lys Cys Glu Lys Phe Pro Val His
625                 630                 635                 640
Gly Ala Gly Glu Leu Cys Val Gly Gln Asn Thr Ser Asp Lys
                645                 650

<210> SEQ ID NO 54
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 54

Tyr Asn Gly Glu Arg Gly Ile Ser Val Pro Asp His Gly Tyr Cys Gln
1               5                   10                  15
Pro Ile Ser Ile Pro Leu Cys Thr Asp Ile Ala Tyr Asn Gln Thr Ile
            20                  25                  30
Met Pro Asn Leu Leu Gly His Thr Asn Gln Glu Asp Ala Gly Leu Glu
        35                  40                  45
Val His Gln Phe Tyr Pro Leu Val Lys Val Gln Cys Ser Ala Glu Leu
```

```
            50                  55                  60
Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                     85                  90                  95

Cys Glu Ala Leu Met Asn Lys Phe Gly Phe Gln Trp Pro Asp Thr Leu
                100                 105                 110

Lys Cys Glu Lys Phe Pro Val His Gly Ala Gly Glu Leu Cys Val Gly
                115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
                180                 185                 190

Val Trp Ile Ile Asp Val Asp Asn Val Val Arg Asp Val Thr Ile Glu
                195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
                260                 265                 270

Lys Ser Tyr Lys Leu Leu Ile Ser Gly Glu Leu Lys Ile Leu Met Leu
                275                 280                 285

Asn Ser Asn His Ile Gln Gln Lys Ile Asp Tyr Ile Gly Phe Asn Ser
                290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Ala Ser
                340                 345                 350

Lys Pro Ser Phe Gly Tyr Tyr Ser Asn Asn Leu Lys Asp Val Lys Val
                355                 360                 365

Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
                420                 425                 430

Ser Phe Leu Glu Ser Met Asn Ile Lys Ser Ile Phe Val Asn Phe Leu
                435                 440                 445

Gln Ser Asn Ile Lys Phe Ile Leu Asp Ala Asn Phe Ile Ile Ser Gly
                450                 455                 460

Thr Thr Ser Ile Gly Gln Phe Glu Phe Ile Cys Asp Glu Asn Asp Asn
465                 470                 475                 480
```

```
Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 55
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 55

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
    130                 135                 140

Thr Arg Ser Phe Ile Val Pro Ile Ile Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190
```

```
Val Trp Ile Ile Asp Val Asp Asn Val Val Arg Asp Val Thr Ile Glu
            195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
    290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Ala Ser Asn Asn Leu Lys Asp Val Lys Val
        355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605
```

-continued

```
Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 56
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 56

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
        50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
290                 295                 300

Glu Leu Gln Lys Asn Ile Pro Tyr Ser Phe Val Asp Ser Glu Gly Lys
305                 310                 315                 320
```

-continued

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Tyr Ser Ala Asn Leu Lys Asp Val Lys Val
        355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 57
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 57

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

-continued

```
Met Pro Asn Leu Leu Gly His Thr Asn Gln Glu Asp Ala Gly Leu Glu
         35                  40                  45

Val His Gln Phe Tyr Pro Leu Val Lys Val Gln Cys Ser Ala Glu Leu
 50                  55                  60

Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
    130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
    290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Tyr Ser Asn Asn Leu Lys Asp Val Lys Val
        355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Ala Ser Asn Ile Lys Phe Ile Leu Asp Ala Asn Phe Ile Ile Ser Gly
```

```
                    450                 455                 460
Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                    485                 490                 495

Leu Tyr Val Gly Asn Arg Gln Asn Met Ile Val Glu Pro Asn Tyr Asp
                500                 505                 510

Leu Asp Asp Ser Gly Asp Ile Ser Ser Thr Val Ile Asn Phe Ser Gln
                515                 520                 525

Lys Tyr Leu Tyr Gly Ile Asp Ser Cys Val Asn Lys Val Val Ile Ser
                530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
                580                 585                 590

Ser Asn Asp Gly Asn Asp Phe Ile Leu Met Ser Thr Ser Glu Glu Asn
                595                 600                 605

Lys Val Ser Gln Val Lys Ile Arg Phe Val Asn Val Phe Lys Asp Lys
                610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 58
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 58

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
                115                 120                 125

Gln Asn Thr Ser Asp Lys Thr Asn Ile Arg Ile Asn Leu Asp Ser Asn
            130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Gly Thr Tyr Ala Leu Ser
```

```
                165                 170                 175
Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
    290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Ala Ser Ala Asn Leu Lys Asp Val Lys Val
        355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590
```

```
Ser Asn Asp Gly Asn Asp Phe Ile Leu Met Ser Thr Ser Glu Glu Asn
            595                 600                 605

Lys Val Ser Gln Val Lys Ile Arg Phe Val Asn Val Phe Lys Asp Lys
610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
            645                 650

<210> SEQ ID NO 59
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 59

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
    130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
    290                 295                 300
```

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
            325                 330                 335

Glu Leu Pro Asp Val Val Leu Ile Ser Lys Val Tyr Met Asp Asp Ser
        340                 345                 350

Lys Pro Ser Phe Gly Tyr Ala Ser Asn Asn Leu Lys Asp Val Lys Val
    355                 360                 365

Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
            405                 410                 415

Lys Phe Met Asn Arg Lys Gly Asn Thr Asn Thr Ser Asp Ser Leu Met
        420                 425                 430

Ser Phe Leu Glu Ser Met Asn Ile Lys Ser Ile Phe Val Asn Phe Leu
    435                 440                 445

Ala Ser Asn Ile Lys Phe Ile Leu Asp Ala Asn Phe Ile Ile Ser Gly
450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
            485                 490                 495

Leu Tyr Val Gly Asn Arg Gln Asn Met Ile Val Glu Pro Asn Tyr Asp
        500                 505                 510

Leu Asp Asp Ser Gly Asp Ile Ser Ser Thr Val Ile Asn Phe Ser Gln
    515                 520                 525

Lys Tyr Leu Tyr Gly Ile Asp Ser Cys Val Asn Lys Val Val Ile Ser
530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
            565                 570                 575

Glu Lys Ile Asn Val Asn Ile Asn Asp Leu Ser Ile Arg Tyr Val Trp
        580                 585                 590

Ser Asn Asp Gly Asn Asp Phe Ile Leu Met Ser Thr Ser Glu Glu Asn
    595                 600                 605

Lys Val Ser Gln Val Lys Ile Arg Phe Val Asn Val Phe Lys Asp Lys
            610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
            645                 650

<210> SEQ ID NO 60
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 60

Tyr Asn Gly Glu Arg Gly Ile Ser Val Pro Asp His Gly Tyr Cys Gln
1               5                   10                  15

```
Pro Ile Ser Ile Pro Leu Cys Thr Asp Ile Ala Tyr Asn Gln Thr Ile
             20                  25                  30

Met Pro Asn Leu Leu Gly His Thr Asn Gln Glu Asp Ala Gly Leu Glu
         35                  40                  45

Val His Gln Phe Tyr Pro Leu Val Lys Val Gln Cys Ser Ala Glu Leu
 50                  55                  60

Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
            115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Thr Tyr Ala Leu Ser
                165                 170                 175

Leu Ser Gln Tyr Asn Met Gly Ile Asn Ile Glu Leu Ser Glu Ser Asp
                180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
        210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
                260                 265                 270

Lys Ser Tyr Lys Leu Leu Ile Ser Gly Glu Asp Lys Ile Leu Met Leu
        275                 280                 285

Asn Ser Asn His Ile Gln Gln Lys Ile Asp Tyr Ile Gly Phe Asn Ser
        290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
                340                 345                 350

Lys Pro Ser Phe Gly Tyr Tyr Ser Asn Asn Leu Lys Asp Val Lys Val
        355                 360                 365

Ile Thr Lys Asp Asn Val Asn Ile Leu Thr Gly Tyr Tyr Leu Lys Asp
        370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
        420                 425                 430
```

```
Ser Phe Leu Glu Ser Met Asn Ile Lys Ser Ile Phe Val Asn Phe Leu
            435                 440                 445

Gln Ser Asn Ile Lys Phe Ile Leu Asp Ala Asn Phe Ile Ile Ser Gly
        450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 61
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 61

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140
```

-continued

```
Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Ala Ser Lys Pro Ser Phe Gly Tyr
    210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Asn Gly Glu Arg Gly Ile Ser
        515                 520                 525

Val Pro Asp His Gly Tyr Cys Gln Pro Ile Ser Ile Pro Leu Cys Thr
    530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
```

```
            565                 570                 575
Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
            595                 600                 605

Leu Cys Glu Arg Ala Arg Gln Gly Cys Glu Ala Leu Met Asn Lys Phe
    610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 62
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 62

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
```

```
                275                 280                 285
Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
                340                 345                 350

Lys Phe Asn Thr Leu Glu Thr Asn Tyr Thr Leu Tyr Val Gly Asn Arg
                355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
                420                 425                 430

Val Ile Val Leu Asp Ala Asn Tyr Ile Asn Glu Lys Ile Asn Val Asn
                435                 440                 445

Ile Asn Asp Leu Ser Ile Arg Tyr Val Trp Ser Asn Asp Gly Asn Asp
450                 455                 460

Phe Ile Leu Met Ser Thr Ser Glu Gly Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr Tyr Asn Gly Glu Arg Gly Ile Ser
                515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
                580                 585                 590

Ala Pro Val Cys Thr Val Leu Glu Gln Ala Leu Pro Pro Cys Arg Ser
                595                 600                 605

Leu Cys Glu Arg Ala Arg Gln Gly Cys Glu Ala Leu Met Asn Lys Phe
                610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 63
<211> LENGTH: 654
<212> TYPE: PRT
<213> ORGANISM: Artificial Sequence
<220> FEATURE:
<223> OTHER INFORMATION: Synthetic polypeptide
```

```
<400> SEQUENCE: 63

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Tyr Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415
```

```
Glu Ile Asn Ile Thr Pro Val Tyr Glu Thr Asn Asn Thr Tyr Pro Glu
                420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr Tyr Asn Gly Glu Arg Gly Ile Ser
            515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
            595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 64
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 64

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125
```

-continued

```
Asn Ala Ile Ile Glu Val Asp Leu Leu Ser Lys Ser Tyr Lys Leu Leu
130                 135                 140
Ile Ser Gly Glu Leu Lys Ile Leu Met Leu Asn Ser Asn His Ile Gln
145                 150                 155                 160
Gln Lys Ile Asp Tyr Ile Gly Phe Asn Ser Glu Leu Gln Lys Asn Ile
                165                 170                 175
Pro Tyr Ser Phe Val Asp Ser Glu Gly Lys Glu Asn Gly Phe Ile Asn
                180                 185                 190
Gly Ser Thr Lys Glu Gly Leu Phe Val Ser Glu Leu Pro Asp Val Val
                195                 200                 205
Leu Ile Ser Lys Val Tyr Met Asp Asp Ser Lys Pro Ser Phe Gly Tyr
210                 215                 220
Tyr Ser Asn Asn Leu Lys Asp Val Lys Val Ile Thr Lys Asp Asn Val
225                 230                 235                 240
Asn Ile Leu Thr Gly Tyr Tyr Leu Lys Asp Asp Ile Lys Ile Ser Leu
                245                 250                 255
Ser Leu Thr Leu Gln Asp Glu Lys Thr Ile Lys Leu Asn Ser Val His
                260                 265                 270
Leu Asp Glu Ser Gly Val Ala Glu Ile Leu Lys Phe Met Asn Arg Lys
                275                 280                 285
Gly Asn Thr Asn Thr Ser Asp Ser Leu Met Ser Phe Leu Glu Ser Met
290                 295                 300
Asn Ile Lys Ser Ile Phe Val Asn Phe Leu Ala Ser Asn Ile Lys Phe
305                 310                 315                 320
Ile Leu Asp Ala Asn Phe Ile Ile Ser Gly Thr Thr Ser Ile Gly Gln
                325                 330                 335
Phe Glu Phe Ile Cys Asp Glu Asn Asp Asn Ile Gln Pro Tyr Phe Ile
                340                 345                 350
Lys Phe Asn Thr Leu Glu Thr Asn Tyr Thr Leu Tyr Val Gly Asn Arg
                355                 360                 365
Gln Asn Met Ile Val Glu Pro Asn Tyr Asp Leu Asp Asp Ser Gly Asp
370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                405                 410                 415
Glu Ile Asn Ile Thr Pro Val Tyr Glu Thr Asn Asn Thr Tyr Pro Glu
                420                 425                 430
Val Ile Val Leu Asp Ala Asn Tyr Ile Asn Glu Lys Ile Asn Val Asn
                435                 440                 445
Ile Asn Asp Leu Ser Ile Arg Tyr Val Trp Ser Asn Asp Gly Asn Asp
450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
Ser Phe Asn Phe Ser Asp Lys Gln Asp Val Pro Val Ser Glu Ile Ile
                500                 505                 510
Leu Ser Phe Thr Pro Ser Tyr Tyr Asn Gly Glu Arg Gly Ile Ser
                515                 520                 525
Val Pro Asp His Gly Tyr Cys Gln Pro Ile Ser Ile Pro Leu Cys Thr
530                 535                 540
```

```
Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
            565                 570                 575

Lys Val Gln Cys Ser Ala Glu Leu Lys Phe Phe Leu Cys Ser Met Tyr
        580                 585                 590

Ala Pro Val Cys Thr Val Leu Glu Gln Ala Leu Pro Pro Cys Arg Ser
    595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 65
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 65

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255
```

-continued

Ser Leu Thr Leu Gln Asp Glu Lys Thr Ile Lys Leu Asn Ser Val His
           260                 265                 270

Leu Asp Glu Ser Gly Val Ala Glu Ile Leu Lys Phe Met Asn Arg Lys
       275                 280                 285

Gly Asn Thr Asn Thr Ser Asp Ser Leu Met Ser Phe Leu Glu Ser Met
   290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
               325                 330                 335

Phe Glu Phe Ile Cys Asp Glu Asn Asp Asn Ile Gln Pro Tyr Phe Ile
           340                 345                 350

Lys Phe Asn Thr Leu Glu Thr Asn Tyr Thr Leu Tyr Val Gly Asn Arg
       355                 360                 365

Gln Asn Met Ile Val Glu Pro Asn Tyr Asp Leu Asp Asp Ser Gly Asp
   370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
               405                 410                 415

Glu Ile Asn Ile Thr Pro Val Tyr Glu Thr Asn Asn Thr Tyr Pro Glu
           420                 425                 430

Val Ile Val Leu Asp Ala Asn Tyr Ile Asn Glu Lys Ile Asn Val Asn
       435                 440                 445

Ile Asn Asp Leu Ser Ile Arg Tyr Val Trp Ser Asn Asp Gly Asn Asp
   450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
               485                 490                 495

Ser Phe Asn Phe Ser Asp Lys Gln Asp Val Pro Val Ser Glu Ile Ile
           500                 505                 510

Leu Ser Phe Thr Pro Ser Tyr Tyr Tyr Asn Gly Glu Arg Gly Ile Ser
       515                 520                 525

Val Pro Asp His Gly Tyr Cys Gln Pro Ile Ser Ile Pro Leu Cys Thr
   530                 535                 540

Asp Ile Ala Tyr Asn Gln Thr Ile Met Pro Asn Leu Leu Gly His Thr
545                 550                 555                 560

Asn Gln Glu Asp Ala Gly Leu Gly Val His Gln Phe Tyr Pro Leu Val
               565                 570                 575

Lys Val Gln Cys Ser Ala Glu Leu Lys Phe Phe Leu Cys Ser Met Tyr
           580                 585                 590

Ala Pro Val Cys Thr Val Leu Glu Gln Ala Leu Pro Pro Cys Arg Ser
       595                 600                 605

Leu Cys Glu Arg Ala Arg Gln Gly Cys Glu Ala Leu Met Asn Lys Phe
   610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
               645                 650

<210> SEQ ID NO 66
<211> LENGTH: 654
<212> TYPE: PRT

<213> ORGANISM: Artificial Sequence
<220> FEATURE:
<223> OTHER INFORMATION: Synthetic polypeptide

<400> SEQUENCE: 66

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
```

```
                385                 390                 395                 400
Asp Ser Cys Val Asn Lys Val Val Ile Ser Pro Asn Ile Tyr Thr Asp
                    405                 410                 415

Glu Ile Asn Ile Thr Pro Val Tyr Glu Thr Asn Asn Thr Tyr Pro Glu
                420                 425                 430

Val Ile Val Leu Asp Ala Asn Tyr Ile Asn Glu Lys Ile Asn Val Asn
                435                 440                 445

Ile Asn Asp Leu Ser Ile Arg Tyr Val Trp Ser Asn Asp Gly Asn Asp
450                 455                 460

Phe Ile Leu Met Ser Thr Ser Glu Gly Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr Tyr Asn Gly Glu Arg Gly Ile Ser
                515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
                580                 585                 590

Ala Pro Val Cys Thr Val Leu Glu Gln Ala Leu Pro Pro Cys Arg Ser
                595                 600                 605

Leu Cys Glu Arg Ala Arg Gln Gly Cys Glu Ala Leu Met Asn Lys Phe
                610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 67
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 67

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
```

```
                100             105                 110
Gly Ser Asn Gly Phe Val Ser Leu Thr Phe Ser Ile Leu Glu Gly Ile
            115                 120                 125
Asn Ala Ile Ile Glu Val Asp Leu Leu Ser Lys Ser Tyr Lys Leu Leu
        130                 135                 140
Ile Ser Gly Glu Asp Lys Ile Leu Met Leu Asn Ser Asn His Ile Gln
145                 150                 155                 160
Gln Lys Ile Asp Tyr Ile Gly Phe Asn Ser Glu Leu Gln Lys Asn Ile
                165                 170                 175
Pro Tyr Ser Phe Val Asp Ser Glu Gly Lys Glu Asn Gly Phe Ile Asn
            180                 185                 190
Gly Ser Thr Lys Glu Gly Leu Phe Val Ser Glu Leu Pro Asp Val Val
        195                 200                 205
Leu Ile Ser Lys Val Tyr Met Asp Asp Ser Lys Pro Ser Phe Gly Tyr
    210                 215                 220
Tyr Ser Asn Asn Leu Lys Asp Val Lys Val Ile Thr Lys Asp Asn Val
225                 230                 235                 240
Asn Ile Leu Thr Gly Tyr Tyr Leu Lys Asp Asp Ile Lys Ile Ser Leu
                245                 250                 255
Ser Leu Thr Leu Gln Asp Glu Lys Thr Ile Lys Leu Asn Ser Val His
            260                 265                 270
Leu Asp Glu Ser Gly Val Ala Glu Ile Leu Lys Phe Met Asn Arg Lys
        275                 280                 285
Gly Asn Thr Asn Thr Ser Asp Ser Leu Met Ser Phe Leu Glu Ser Met
    290                 295                 300
Asn Ile Lys Ser Ile Phe Val Asn Phe Leu Gln Ser Asn Ile Lys Phe
305                 310                 315                 320
Ile Leu Asp Ala Asn Phe Ile Ile Ser Gly Thr Thr Ser Ile Gly Gln
                325                 330                 335
Phe Glu Phe Ile Cys Asp Glu Asn Asp Asn Ile Gln Pro Tyr Phe Ile
            340                 345                 350
Lys Phe Asn Thr Leu Glu Thr Asn Tyr Thr Leu Tyr Val Gly Asn Arg
        355                 360                 365
Gln Asn Met Ile Val Glu Pro Asn Tyr Asp Leu Asp Asp Ser Gly Asp
    370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                405                 410                 415
Glu Ile Asn Ile Thr Pro Val Tyr Glu Thr Asn Asn Thr Tyr Pro Glu
            420                 425                 430
Val Ile Val Leu Asp Ala Asn Tyr Ile Asn Glu Lys Ile Asn Val Asn
        435                 440                 445
Ile Asn Asp Leu Ser Ile Arg Tyr Val Trp Ser Asn Asp Gly Asn Asp
    450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
Ser Phe Asn Phe Ser Asp Lys Gln Asp Val Pro Val Ser Glu Ile Ile
            500                 505                 510
Leu Ser Phe Thr Pro Ser Tyr Tyr Tyr Asn Gly Glu Arg Gly Ile Ser
        515                 520                 525
```

```
Val Pro Asp His Gly Tyr Cys Gln Pro Ile Ser Ile Pro Leu Cys Thr
    530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
                580                 585                 590

Ala Pro Val Cys Thr Val Leu Glu Gln Ala Leu Pro Pro Cys Arg Ser
            595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 68
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 68

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
        50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
    130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240
```

```
Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
    290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Ala Ser
            340                 345                 350

Lys Pro Ser Phe Gly Tyr Tyr Ser Asn Asn Leu Lys Asp Val Lys Val
        355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650
```

<210> SEQ ID NO 69
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 69

```
Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
    130                 135                 140

Thr Arg Ser Phe Ile Val Pro Ile Ile Thr Glu Tyr Ile Arg Glu
145                 150                 155                 160

Lys Leu Ser Tyr Ser Phe Tyr Gly Ser Gly Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
    210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
    290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Ala Ser Asn Asn Leu Lys Asp Val Lys Val
        355                 360                 365
```

```
Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Gln Ser Asn Ile Lys Phe Ile Leu Asp Ala Asn Phe Ile Ile Ser Gly
450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 70
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 70

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
        50                  55                  60

Lys Phe Phe Leu Cys Ser Met Tyr Ala Pro Val Cys Thr Val Leu Glu
65                  70                  75                  80
```

```
Gln Ala Leu Pro Pro Cys Arg Ser Leu Cys Glu Arg Ala Arg Gln Gly
                85                  90                  95
Cys Glu Ala Leu Met Asn Lys Phe Gly Phe Gln Trp Pro Asp Thr Leu
            100                 105                 110
Lys Cys Glu Lys Phe Pro Val His Gly Ala Gly Glu Leu Cys Val Gly
        115                 120                 125
Gln Asn Thr Ser Asp Lys Thr Asn Ile Arg Ile Asn Leu Asp Ser Asn
    130                 135                 140
Thr Arg Ser Phe Ile Val Pro Ile Ile Thr Thr Glu Tyr Ile Arg Glu
145                 150                 155                 160
Lys Leu Ser Tyr Ser Phe Tyr Gly Ser Gly Gly Thr Tyr Ala Leu Ser
                165                 170                 175
Leu Ser Gln Tyr Asn Met Gly Ile Asn Ile Glu Leu Ser Glu Ser Asp
            180                 185                 190
Val Trp Ile Ile Asp Val Asp Asn Val Val Arg Asp Val Thr Ile Glu
        195                 200                 205
Ser Asp Lys Ile Lys Lys Gly Asp Leu Ile Glu Gly Ile Leu Ser Thr
    210                 215                 220
Leu Ser Ile Glu Glu Asn Lys Ile Ile Leu Asn Ser His Glu Ile Asn
225                 230                 235                 240
Phe Ser Gly Glu Val Asn Gly Ser Asn Gly Phe Val Ser Leu Thr Phe
                245                 250                 255
Ser Ile Leu Glu Gly Ile Asn Ala Ile Ile Glu Val Asp Leu Leu Ser
            260                 265                 270
Lys Ser Tyr Lys Leu Leu Ile Ser Gly Glu Leu Lys Ile Leu Met Leu
        275                 280                 285
Asn Ser Asn His Ile Gln Gln Lys Ile Asp Tyr Ile Gly Phe Asn Ser
    290                 295                 300
Glu Leu Gln Lys Asn Ile Pro Tyr Ser Phe Val Asp Ser Glu Gly Lys
305                 310                 315                 320
Glu Asn Gly Phe Ile Asn Gly Ser Thr Lys Glu Gly Leu Phe Val Ser
                325                 330                 335
Glu Leu Pro Asp Val Val Leu Ile Ser Lys Val Tyr Met Asp Asp Ser
            340                 345                 350
Lys Pro Ser Phe Gly Tyr Tyr Ser Ala Asn Leu Lys Asp Val Lys Val
        355                 360                 365
Ile Thr Lys Asp Asn Val Asn Ile Leu Thr Gly Tyr Tyr Leu Lys Asp
    370                 375                 380
Asp Ile Lys Ile Ser Leu Ser Leu Thr Leu Gln Asp Glu Lys Thr Ile
385                 390                 395                 400
Lys Leu Asn Ser Val His Leu Asp Glu Ser Gly Val Ala Glu Ile Leu
                405                 410                 415
Lys Phe Met Asn Arg Lys Gly Asn Thr Asn Thr Ser Asp Ser Leu Met
            420                 425                 430
Ser Phe Leu Glu Ser Met Asn Ile Lys Ser Ile Phe Val Asn Phe Leu
        435                 440                 445
Gln Ser Asn Ile Lys Phe Ile Leu Asp Ala Asn Phe Ile Ile Ser Gly
    450                 455                 460
Thr Thr Ser Ile Gly Gln Phe Glu Phe Ile Cys Asp Glu Asn Asp Asn
465                 470                 475                 480
Ile Gln Pro Tyr Phe Ile Lys Phe Asn Thr Leu Glu Thr Asn Tyr Thr
                485                 490                 495
Leu Tyr Val Gly Asn Arg Gln Asn Met Ile Val Glu Pro Asn Tyr Asp
```

```
                500                 505                 510
Leu Asp Asp Ser Gly Asp Ile Ser Ser Thr Val Ile Asn Phe Ser Gln
            515                 520                 525

Lys Tyr Leu Tyr Gly Ile Asp Ser Cys Val Asn Lys Val Val Ile Ser
        530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
            565                 570                 575

Glu Lys Ile Asn Val Asn Ile Asn Asp Leu Ser Ile Arg Tyr Val Trp
        580                 585                 590

Ser Asn Asp Gly Asn Asp Phe Ile Leu Met Ser Thr Ser Glu Glu Asn
            595                 600                 605

Lys Val Ser Gln Val Lys Ile Arg Phe Val Asn Val Phe Lys Asp Lys
        610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
            645                 650

<210> SEQ ID NO 71
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 71

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
            85                  90                  95

Cys Glu Ala Leu Met Asn Lys Phe Gly Phe Gln Trp Pro Asp Thr Leu
        100                 105                 110

Lys Cys Glu Lys Phe Pro Val His Gly Ala Gly Glu Leu Cys Val Gly
    115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Gly Thr Tyr Ala Leu Ser
            165                 170                 175

Leu Ser Gln Tyr Asn Met Gly Ile Asn Ile Glu Leu Ser Glu Ser Asp
        180                 185                 190

Val Trp Ile Ile Asp Val Asp Asn Val Val Arg Asp Val Thr Ile Glu
    195                 200                 205

Ser Asp Lys Ile Lys Lys Gly Asp Leu Ile Glu Gly Ile Leu Ser Thr
```

```
              210                 215                 220
Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                    245                 250                 255

Ser Ile Leu Glu Gly Ile Asn Ala Ile Ile Glu Val Asp Leu Leu Ser
                260                 265                 270

Lys Ser Tyr Lys Leu Leu Ile Ser Gly Glu Leu Lys Ile Leu Met Leu
            275                 280                 285

Asn Ser Asn His Ile Gln Gln Lys Ile Asp Tyr Ile Gly Phe Asn Ser
290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                    325                 330                 335

Glu Leu Pro Asp Val Val Leu Ile Ser Lys Val Tyr Met Asp Asp Ser
                340                 345                 350

Lys Pro Ser Phe Gly Tyr Tyr Ser Asn Asn Leu Lys Asp Val Lys Val
            355                 360                 365

Ile Thr Lys Asp Asn Val Asn Ile Leu Thr Gly Tyr Tyr Leu Lys Asp
        370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                    405                 410                 415

Lys Phe Met Asn Arg Lys Gly Asn Thr Asn Thr Ser Asp Ser Leu Met
                420                 425                 430

Ser Phe Leu Glu Ser Met Asn Ile Lys Ser Ile Phe Val Asn Phe Leu
            435                 440                 445

Ala Ser Asn Ile Lys Phe Ile Leu Asp Ala Asn Phe Ile Ile Ser Gly
        450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                    485                 490                 495

Leu Tyr Val Gly Asn Arg Gln Asn Met Ile Val Glu Pro Asn Tyr Asp
                500                 505                 510

Leu Asp Asp Ser Gly Asp Ile Ser Ser Thr Val Ile Asn Phe Ser Gln
            515                 520                 525

Lys Tyr Leu Tyr Gly Ile Asp Ser Cys Val Asn Lys Val Val Ile Ser
        530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                    565                 570                 575

Glu Lys Ile Asn Val Asn Ile Asn Asp Leu Ser Ile Arg Tyr Val Trp
                580                 585                 590

Ser Asn Asp Gly Asn Asp Phe Ile Leu Met Ser Thr Ser Glu Glu Asn
            595                 600                 605

Lys Val Ser Gln Val Lys Ile Arg Phe Val Asn Val Phe Lys Asp Lys
        610                 615                 620

Thr Leu Ala Asn Lys Leu Ser Phe Asn Phe Ser Asp Lys Gln Asp Val
625                 630                 635                 640
```

```
Pro Val Ser Glu Ile Ile Leu Ser Phe Thr Pro Ser Tyr Tyr
            645                 650

<210> SEQ ID NO 72
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 72

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Asp Ala Gly Leu Glu
            35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350
```

-continued

Lys Pro Ser Phe Gly Tyr Ala Ser Ala Asn Leu Lys Asp Val Lys Val
            355                 360                 365

Ile Thr Lys Asp Asn Val Asn Ile Leu Thr Gly Tyr Tyr Leu Lys Asp
    370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
            405                 410                 415

Lys Phe Met Asn Arg Lys Gly Asn Thr Asn Thr Ser Asp Ser Leu Met
        420                 425                 430

Ser Phe Leu Glu Ser Met Asn Ile Lys Ser Ile Phe Val Asn Phe Leu
            435                 440                 445

Gln Ser Asn Ile Lys Phe Ile Leu Asp Ala Asn Phe Ile Ile Ser Gly
    450                 455                 460

Thr Thr Ser Ile Gly Gln Phe Glu Phe Ile Cys Asp Glu Asn Asp Asn
465                 470                 475                 480

Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
        515                 520                 525

Lys Tyr Leu Tyr Gly Ile Asp Ser Cys Val Asn Lys Val Val Ile Ser
    530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
        595                 600                 605

Lys Val Ser Gln Val Lys Ile Arg Phe Val Asn Val Phe Lys Asp Lys
    610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 73
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 73

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

```
Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys Thr Asn Ile Arg Ile Asn Leu Asp Ser Asn
130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Gly Thr Tyr Ala Leu Ser
                165                 170                 175

Leu Ser Gln Tyr Asn Met Gly Ile Asn Ile Glu Leu Ser Glu Ser Asp
            180                 185                 190

Val Trp Ile Ile Asp Val Asp Asn Val Val Arg Asp Val Thr Ile Glu
        195                 200                 205

Ser Asp Lys Ile Lys Lys Gly Asp Leu Ile Glu Gly Ile Leu Ser Thr
210                 215                 220

Leu Ser Ile Glu Glu Asn Lys Ile Ile Leu Asn Ser His Glu Ile Asn
225                 230                 235                 240

Phe Ser Gly Glu Val Asn Gly Ser Asn Gly Phe Val Ser Leu Thr Phe
                245                 250                 255

Ser Ile Leu Glu Gly Ile Asn Ala Ile Ile Glu Val Asp Leu Leu Ser
            260                 265                 270

Lys Ser Tyr Lys Leu Leu Ile Ser Gly Glu Leu Lys Ile Leu Met Leu
        275                 280                 285

Asn Ser Asn His Ile Gln Gln Lys Ile Asp Tyr Ile Gly Phe Asn Ser
290                 295                 300

Glu Leu Gln Lys Asn Ile Pro Tyr Ser Phe Val Asp Ser Glu Gly Lys
305                 310                 315                 320

Glu Asn Gly Phe Ile Asn Gly Ser Thr Lys Glu Gly Leu Phe Val Ser
                325                 330                 335

Glu Leu Pro Asp Val Val Leu Ile Ser Lys Val Tyr Met Asp Asp Ser
            340                 345                 350

Lys Pro Ser Phe Gly Tyr Ala Ser Asn Asn Leu Lys Asp Val Lys Val
        355                 360                 365

Ile Thr Lys Asp Asn Val Asn Ile Leu Thr Gly Tyr Tyr Leu Lys Asp
370                 375                 380

Asp Ile Lys Ile Ser Leu Ser Leu Thr Leu Gln Asp Glu Lys Thr Ile
385                 390                 395                 400

Lys Leu Asn Ser Val His Leu Asp Glu Ser Gly Val Ala Glu Ile Leu
                405                 410                 415

Lys Phe Met Asn Arg Lys Gly Asn Thr Asn Thr Ser Asp Ser Leu Met
            420                 425                 430

Ser Phe Leu Glu Ser Met Asn Ile Lys Ser Ile Phe Val Asn Phe Leu
        435                 440                 445

Ala Ser Asn Ile Lys Phe Ile Leu Asp Ala Asn Phe Ile Ile Ser Gly
450                 455                 460

Thr Thr Ser Ile Gly Gln Phe Glu Phe Ile Cys Asp Glu Asn Asp Asn
465                 470                 475                 480
```

```
Ile Gln Pro Tyr Phe Ile Lys Phe Asn Thr Leu Glu Thr Asn Tyr Thr
                485                 490                 495

Leu Tyr Val Gly Asn Arg Gln Asn Met Ile Val Glu Pro Asn Tyr Asp
            500                 505                 510

Leu Asp Asp Ser Gly Asp Ile Ser Ser Thr Val Ile Asn Phe Ser Gln
            515                 520                 525

Lys Tyr Leu Tyr Gly Ile Asp Ser Cys Val Asn Lys Val Val Ile Ser
            530                 535                 540

Pro Asn Ile Tyr Thr Asp Glu Ile Asn Ile Thr Pro Val Tyr Glu Thr
545                 550                 555                 560

Asn Asn Thr Tyr Pro Glu Val Ile Val Leu Asp Ala Asn Tyr Ile Asn
                565                 570                 575

Glu Lys Ile Asn Val Asn Ile Asn Asp Leu Ser Ile Arg Tyr Val Trp
            580                 585                 590

Ser Asn Asp Gly Asn Asp Phe Ile Leu Met Ser Thr Ser Glu Glu Asn
            595                 600                 605

Lys Val Ser Gln Val Lys Ile Arg Phe Val Asn Val Phe Lys Asp Lys
            610                 615                 620

Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 74
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 74

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
                20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
            115                 120                 125

Gln Asn Thr Ser Asp Lys Thr Asn Ile Arg Ile Asn Leu Asp Ser Asn
            130                 135                 140

Thr Arg Ser Phe Ile Val Pro Ile Ile Thr Thr Glu Tyr Ile Arg Glu
145                 150                 155                 160

Lys Leu Ser Tyr Ser Phe Tyr Gly Ser Gly Gly Thr Tyr Ala Leu Ser
                165                 170                 175

Leu Ser Gln Tyr Asn Met Gly Ile Asn Ile Glu Leu Ser Glu Ser Asp
            180                 185                 190
```

-continued

```
Val Trp Ile Ile Asp Val Asp Asn Val Val Arg Asp Val Thr Ile Glu
            195                 200                 205
Ser Asp Lys Ile Lys Lys Gly Asp Leu Ile Glu Gly Ile Leu Ser Thr
210                 215                 220
Leu Ser Ile Glu Glu Asn Lys Ile Ile Leu Asn Ser His Glu Ile Asn
225                 230                 235                 240
Phe Ser Gly Glu Val Asn Gly Ser Asn Gly Phe Val Ser Leu Thr Phe
                245                 250                 255
Ser Ile Leu Glu Gly Ile Asn Ala Ile Glu Val Asp Leu Leu Ser
                260                 265                 270
Lys Ser Tyr Lys Leu Leu Ile Ser Gly Glu Asp Lys Ile Leu Met Leu
            275                 280                 285
Asn Ser Asn His Ile Gln Gln Lys Ile Asp Tyr Ile Gly Phe Asn Ser
290                 295                 300
Glu Leu Gln Lys Asn Ile Pro Tyr Ser Phe Val Asp Ser Glu Gly Lys
305                 310                 315                 320
Glu Asn Gly Phe Ile Asn Gly Ser Thr Lys Glu Gly Leu Phe Val Ser
                325                 330                 335
Glu Leu Pro Asp Val Val Leu Ile Ser Lys Val Tyr Met Asp Asp Ser
                340                 345                 350
Lys Pro Ser Phe Gly Tyr Tyr Ser Asn Asn Leu Lys Asp Val Lys Val
            355                 360                 365
Ile Thr Lys Asp Asn Val Asn Ile Leu Thr Gly Tyr Tyr Leu Lys Asp
            370                 375                 380
Asp Ile Lys Ile Ser Leu Ser Leu Thr Leu Gln Asp Glu Lys Thr Ile
385                 390                 395                 400
Lys Leu Asn Ser Val His Leu Asp Glu Ser Gly Val Ala Glu Ile Leu
                405                 410                 415
Lys Phe Met Asn Arg Lys Gly Asn Thr Asn Thr Ser Asp Ser Leu Met
            420                 425                 430
Ser Phe Leu Glu Ser Met Asn Ile Lys Ser Ile Phe Val Asn Phe Leu
            435                 440                 445
Gln Ser Asn Ile Lys Phe Ile Leu Asp Ala Asn Phe Ile Ile Ser Gly
        450                 455                 460
Thr Thr Ser Ile Gly Gln Phe Glu Phe Ile Cys Asp Glu Asn Asp Asn
465                 470                 475                 480
Ile Gln Pro Tyr Phe Ile Lys Phe Asn Thr Leu Glu Thr Asn Tyr Thr
                485                 490                 495
Leu Tyr Val Gly Asn Arg Gln Asn Met Ile Val Glu Pro Asn Tyr Asp
                500                 505                 510
Leu Asp Asp Ser Gly Asp Ile Ser Ser Thr Val Ile Asn Phe Ser Gln
            515                 520                 525
Lys Tyr Leu Tyr Gly Ile Asp Ser Cys Val Asn Lys Val Val Ile Ser
            530                 535                 540
Pro Asn Ile Tyr Thr Asp Glu Ile Asn Ile Thr Pro Val Tyr Glu Thr
545                 550                 555                 560
Asn Asn Thr Tyr Pro Glu Val Ile Val Leu Asp Ala Asn Tyr Ile Asn
                565                 570                 575
Glu Lys Ile Asn Val Asn Ile Asn Asp Leu Ser Ile Arg Tyr Val Trp
            580                 585                 590
Ser Asn Asp Gly Asn Asp Phe Ile Leu Met Ser Thr Ser Glu Glu Asn
            595                 600                 605
Lys Val Ser Gln Val Lys Ile Arg Phe Val Asn Val Phe Lys Asp Lys
```

```
               610                 615                 620
Thr Leu Ala Asn Lys Leu Ser Phe Asn Phe Ser Asp Lys Gln Asp Val
625                 630                 635                 640

Pro Val Ser Glu Ile Ile Leu Ser Phe Thr Pro Ser Tyr Tyr
                645                 650

<210> SEQ ID NO 75
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 75

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Ala Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
```

```
                325                 330                 335
Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
            405                 410                 415

Glu Ile Asn Ile Thr Pro Val Tyr Glu Thr Asn Asn Thr Tyr Pro Glu
        420                 425                 430

Val Ile Val Leu Asp Ala Asn Tyr Ile Asn Glu Lys Ile Asn Val Asn
    435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
            485                 490                 495

Ser Phe Asn Phe Ser Asp Lys Gln Asp Val Pro Val Ser Glu Ile Ile
        500                 505                 510

Leu Ser Phe Thr Pro Ser Tyr Tyr Tyr Asn Gly Glu Arg Gly Ile Ser
    515                 520                 525

Val Pro Asp His Gly Tyr Cys Gln Pro Ile Ser Ile Pro Leu Cys Thr
530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
            565                 570                 575

Lys Val Gln Cys Ser Ala Glu Leu Lys Phe Phe Leu Cys Ser Met Tyr
        580                 585                 590

Ala Pro Val Cys Thr Val Leu Glu Gln Ala Leu Pro Pro Cys Arg Ser
    595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
            645                 650
```

<210> SEQ ID NO 76
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 76

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
```

```
            35                  40                  45
Gly Ile Asn Ile Glu Leu Ser Glu Ser Asp Val Trp Ile Ile Asp Val
 50                  55                  60
Asp Asn Val Val Arg Asp Val Thr Ile Glu Ser Asp Lys Ile Lys Lys
 65                  70                  75                  80
Gly Asp Leu Ile Glu Gly Ile Leu Ser Thr Leu Ser Ile Glu Glu Asn
                 85                  90                  95
Lys Ile Ile Leu Asn Ser His Glu Ile Asn Phe Ser Gly Glu Val Asn
            100                 105                 110
Gly Ser Asn Gly Phe Val Ser Leu Thr Phe Ser Ile Leu Glu Gly Ile
            115                 120                 125
Asn Ala Ile Ile Glu Val Asp Leu Leu Ser Lys Ser Tyr Lys Leu Leu
            130                 135                 140
Ile Ser Gly Glu Leu Lys Ile Leu Met Leu Asn Ser Asn His Ile Gln
145                 150                 155                 160
Gln Lys Ile Asp Tyr Ile Gly Phe Asn Ser Glu Leu Gln Lys Asn Ile
            165                 170                 175
Pro Tyr Ser Phe Val Asp Ser Glu Gly Lys Glu Asn Gly Phe Ile Asn
            180                 185                 190
Gly Ser Thr Lys Glu Gly Leu Phe Val Ser Glu Leu Pro Asp Val Val
            195                 200                 205
Leu Ile Ser Lys Val Tyr Met Asp Asp Ser Lys Pro Ser Phe Gly Tyr
210                 215                 220
Ala Ser Asn Asn Leu Lys Asp Val Lys Val Ile Thr Lys Asp Asn Val
225                 230                 235                 240
Asn Ile Leu Thr Gly Tyr Tyr Leu Lys Asp Asp Ile Lys Ile Ser Leu
            245                 250                 255
Ser Leu Thr Leu Gln Asp Glu Lys Thr Ile Lys Leu Asn Ser Val His
            260                 265                 270
Leu Asp Glu Ser Gly Val Ala Glu Ile Leu Lys Phe Met Asn Arg Lys
            275                 280                 285
Gly Asn Thr Asn Thr Ser Asp Ser Leu Met Ser Phe Leu Glu Ser Met
            290                 295                 300
Asn Ile Lys Ser Ile Phe Val Asn Phe Leu Gln Ser Asn Ile Lys Phe
305                 310                 315                 320
Ile Leu Asp Ala Asn Phe Ile Ile Ser Gly Thr Thr Ser Ile Gly Gln
            325                 330                 335
Phe Glu Phe Ile Cys Asp Glu Asn Asp Asn Ile Gln Pro Tyr Phe Ile
            340                 345                 350
Lys Phe Asn Thr Leu Glu Thr Asn Tyr Thr Leu Tyr Val Gly Asn Arg
            355                 360                 365
Gln Asn Met Ile Val Glu Pro Asn Tyr Asp Leu Asp Asp Ser Gly Asp
            370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
            405                 410                 415
Glu Ile Asn Ile Thr Pro Val Tyr Glu Thr Asn Asn Thr Tyr Pro Glu
            420                 425                 430
Val Ile Val Leu Asp Ala Asn Tyr Ile Asn Glu Lys Ile Asn Val Asn
            435                 440                 445
Ile Asn Asp Leu Ser Ile Arg Tyr Val Trp Ser Asn Asp Gly Asn Asp
            450                 455                 460
```

```
Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
        515                 520                 525

Val Pro Asp His Gly Tyr Cys Gln Pro Ile Ser Ile Pro Leu Cys Thr
    530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
        595                 600                 605

Leu Cys Glu Arg Ala Arg Gln Gly Cys Glu Ala Leu Met Asn Lys Phe
    610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 77
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 77

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
        130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175
```

```
Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Asn Gly Glu Arg Gly Ile Ser
        515                 520                 525

Val Pro Asp His Gly Tyr Cys Gln Pro Ile Ser Ile Pro Leu Cys Thr
    530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590
```

```
Ala Pro Val Cys Thr Val Leu Glu Gln Ala Leu Pro Pro Cys Arg Ser
            595                 600                 605

Leu Cys Glu Arg Ala Arg Gln Gly Cys Glu Ala Leu Met Asn Lys Phe
        610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 78
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 78

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300
```

```
Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
        515                 520                 525

Val Pro Asp His Gly Tyr Cys Gln Pro Ile Ser Ile Pro Leu Cys Thr
    530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
        595                 600                 605

Leu Cys Glu Arg Ala Arg Gln Gly Cys Glu Ala Leu Met Asn Lys Phe
    610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 79
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 79

Thr Asn Ile Arg Ile Asn Leu Asp Ser Asn Thr Arg Ser Phe Ile Val
1               5                   10                  15
```

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Ala Ser Ala Asn Leu Lys Asp Val Lys Val Ile Thr Lys Asp Asn Val
225                 230                 235                 240

Asn Ile Leu Thr Gly Tyr Tyr Leu Lys Asp Ile Lys Ile Ser Leu
                245                 250                 255

Ser Leu Thr Leu Gln Asp Glu Lys Thr Ile Lys Leu Asn Ser Val His
        260                 265                 270

Leu Asp Glu Ser Gly Val Ala Glu Ile Leu Lys Phe Met Asn Arg Lys
    275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn

```
                435                 440                 445
Ile Asn Asp Leu Ser Ile Arg Tyr Val Trp Ser Asn Asp Gly Asn Asp
450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
Ser Phe Asn Phe Ser Asp Lys Gln Asp Val Pro Val Ser Glu Ile Ile
                500                 505                 510
Leu Ser Phe Thr Pro Ser Tyr Tyr Tyr Asn Gly Glu Arg Gly Ile Ser
                515                 520                 525
Val Pro Asp His Gly Tyr Cys Gln Pro Ile Ser Ile Pro Leu Cys Thr
                530                 535                 540
Asp Ile Ala Tyr Asn Gln Thr Ile Met Pro Asn Leu Leu Gly His Thr
545                 550                 555                 560
Asn Gln Glu Asp Ala Gly Leu Glu Val His Gln Phe Tyr Pro Leu Val
                565                 570                 575
Lys Val Gln Cys Ser Ala Glu Leu Lys Phe Phe Leu Cys Ser Met Tyr
                580                 585                 590
Ala Pro Val Cys Thr Val Leu Glu Gln Ala Leu Pro Pro Cys Arg Ser
                595                 600                 605
Leu Cys Glu Arg Ala Arg Gln Gly Cys Glu Ala Leu Met Asn Lys Phe
610                 615                 620
Gly Phe Gln Trp Pro Asp Thr Leu Lys Cys Glu Lys Phe Pro Val His
625                 630                 635                 640
Gly Ala Gly Glu Leu Cys Val Gly Gln Asn Thr Ser Asp Lys
                645                 650

<210> SEQ ID NO 80
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 80

Thr Asn Ile Arg Ile Asn Leu Asp Ser Asn Thr Arg Ser Phe Ile Val
1               5                   10                  15
Pro Ile Ile Thr Thr Glu Tyr Ile Arg Glu Lys Leu Ser Tyr Ser Phe
                20                  25                  30
Tyr Gly Ser Gly Gly Thr Tyr Ala Leu Ser Leu Ser Gln Tyr Asn Met
            35                  40                  45
Gly Ile Asn Ile Glu Leu Ser Glu Ser Asp Val Trp Ile Ile Asp Val
        50                  55                  60
Asp Asn Val Val Arg Asp Val Thr Ile Glu Ser Asp Lys Ile Lys Lys
65                  70                  75                  80
Gly Asp Leu Ile Glu Gly Ile Leu Ser Thr Leu Ser Ile Glu Glu Asn
                85                  90                  95
Lys Ile Ile Leu Asn Ser His Glu Ile Asn Phe Ser Gly Glu Val Asn
                100                 105                 110
Gly Ser Asn Gly Phe Val Ser Leu Thr Phe Ser Ile Leu Glu Gly Ile
            115                 120                 125
Asn Ala Ile Ile Glu Val Asp Leu Leu Ser Lys Ser Tyr Lys Leu Leu
        130                 135                 140
Ile Ser Gly Glu Leu Lys Ile Leu Met Leu Asn Ser Asn His Ile Gln
```

```
            145                 150                 155                 160
Gln Lys Ile Asp Tyr Ile Gly Phe Asn Ser Glu Leu Gln Lys Asn Ile
                    165                 170                 175
Pro Tyr Ser Phe Val Asp Ser Glu Gly Lys Glu Asn Gly Phe Ile Asn
                    180                 185                 190
Gly Ser Thr Lys Glu Gly Leu Phe Val Ser Glu Leu Pro Asp Val Val
                    195                 200                 205
Leu Ile Ser Lys Val Tyr Met Asp Asp Ser Lys Pro Ser Phe Gly Tyr
210                 215                 220
Ala Ser Asn Asn Leu Lys Asp Val Lys Val Ile Thr Lys Asp Asn Val
225                 230                 235                 240
Asn Ile Leu Thr Gly Tyr Tyr Leu Lys Asp Ile Lys Ile Ser Leu
                    245                 250                 255
Ser Leu Thr Leu Gln Asp Glu Lys Thr Ile Lys Leu Asn Ser Val His
                    260                 265                 270
Leu Asp Glu Ser Gly Val Ala Glu Ile Leu Lys Phe Met Asn Arg Lys
                    275                 280                 285
Gly Asn Thr Asn Thr Ser Asp Ser Leu Met Ser Phe Leu Glu Ser Met
                    290                 295                 300
Asn Ile Lys Ser Ile Phe Val Asn Phe Leu Ala Ser Asn Ile Lys Phe
305                 310                 315                 320
Ile Leu Asp Ala Asn Phe Ile Ile Ser Gly Thr Thr Ser Ile Gly Gln
                    325                 330                 335
Phe Glu Phe Ile Cys Asp Glu Asn Asp Asn Ile Gln Pro Tyr Phe Ile
                    340                 345                 350
Lys Phe Asn Thr Leu Glu Thr Asn Tyr Thr Leu Tyr Val Gly Asn Arg
                    355                 360                 365
Gln Asn Met Ile Val Glu Pro Asn Tyr Asp Leu Asp Asp Ser Gly Asp
                    370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                    405                 410                 415
Glu Ile Asn Ile Thr Pro Val Tyr Glu Thr Asn Asn Thr Tyr Pro Glu
                    420                 425                 430
Val Ile Val Leu Asp Ala Asn Tyr Ile Asn Glu Lys Ile Asn Val Asn
                    435                 440                 445
Ile Asn Asp Leu Ser Ile Arg Tyr Val Trp Ser Asn Asp Gly Asn Asp
450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                    485                 490                 495
Ser Phe Asn Phe Ser Asp Lys Gln Asp Val Pro Val Ser Glu Ile Ile
                    500                 505                 510
Leu Ser Phe Thr Pro Ser Tyr Tyr Tyr Asn Gly Glu Arg Gly Ile Ser
                    515                 520                 525
Val Pro Asp His Gly Tyr Cys Gln Pro Ile Ser Ile Pro Leu Cys Thr
                    530                 535                 540
Asp Ile Ala Tyr Asn Gln Thr Ile Met Pro Asn Leu Leu Gly His Thr
545                 550                 555                 560
Asn Gln Glu Asp Ala Gly Leu Glu Val His Gln Phe Tyr Pro Leu Val
                    565                 570                 575
```

```
Lys Val Gln Cys Ser Ala Glu Leu Lys Phe Phe Leu Cys Ser Met Tyr
                580                 585                 590

Ala Pro Val Cys Thr Val Leu Glu Gln Ala Leu Pro Pro Cys Arg Ser
                595                 600                 605

Leu Cys Glu Arg Ala Arg Gln Gly Cys Glu Ala Leu Met Asn Lys Phe
610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 81
<211> LENGTH: 654
<212> TYPE: PRT
<213> ORGANISM: Artificial Sequence
<220> FEATURE:
<223> OTHER INFORMATION: Synthetic polypeptide

<400> SEQUENCE: 81

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
                35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
130                 135                 140

Ile Ser Gly Glu Asp Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
                180                 185                 190

Gly Ser Thr Lys Glu Gly Leu Phe Val Ser Glu Leu Pro Asp Val Val
            195                 200                 205

Leu Ile Ser Lys Val Tyr Met Asp Asp Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
                260                 265                 270

Leu Asp Glu Ser Gly Val Ala Glu Ile Leu Lys Phe Met Asn Arg Lys
            275                 280                 285
```

Gly Asn Thr Asn Thr Ser Asp Ser Leu Met Ser Phe Leu Glu Ser Met
            290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
                355                 360                 365

Gln Asn Met Ile Val Glu Pro Asn Tyr Asp Leu Asp Asp Ser Gly Asp
            370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
                435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Tyr Asn Gly Glu Arg Gly Ile Ser
                515                 520                 525

Val Pro Asp His Gly Tyr Cys Gln Pro Ile Ser Ile Pro Leu Cys Thr
            530                 535                 540

Asp Ile Ala Tyr Asn Gln Thr Ile Met Pro Asn Leu Leu Gly His Thr
545                 550                 555                 560

Asn Gln Glu Asp Ala Gly Leu Glu Val His Gln Phe Tyr Pro Leu Val
                565                 570                 575

Lys Val Gln Cys Ser Ala Glu Leu Lys Phe Phe Leu Cys Ser Met Tyr
            580                 585                 590

Ala Pro Val Cys Thr Val Leu Glu Gln Ala Leu Pro Pro Cys Arg Ser
                595                 600                 605

Leu Cys Glu Arg Ala Arg Gln Gly Cys Glu Ala Leu Met Asn Lys Phe
            610                 615                 620

Gly Phe Gln Trp Pro Asp Thr Leu Lys Cys Glu Lys Phe Pro Val His
625                 630                 635                 640

Gly Ala Gly Glu Leu Cys Val Gly Gln Asn Thr Ser Asp Lys
                645                 650

<210> SEQ ID NO 82
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 82

-continued

```
Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
            20                  25                  30

Gln Asp Glu Ala Gly Leu Glu Val His Gln Phe Trp Pro Leu Val Glu
        35                  40                  45

Ile Gln Cys Ser Pro Asp Leu Lys Phe Phe Leu Cys Ser Met Tyr Thr
    50                  55                  60

Pro Ile Cys Leu Glu Asp Tyr Lys Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
            115                 120                 125

Leu Asp Ser Asn Thr Arg Ser Phe Ile Val Pro Ile Ile Thr Thr Glu
130                 135                 140

Tyr Ile Arg Glu Lys Leu Ser Tyr Ser Phe Tyr Gly Ser Gly Gly Thr
145                 150                 155                 160

Tyr Ala Leu Ser Leu Ser Gln Tyr Asn Met Gly Ile Asn Ile Glu Leu
            165                 170                 175

Ser Glu Ser Asp Val Trp Ile Ile Asp Val Asp Asn Val Val Arg Asp
            180                 185                 190

Val Thr Ile Glu Ser Asp Lys Ile Lys Lys Gly Asp Leu Ile Glu Gly
            195                 200                 205

Ile Leu Ser Thr Leu Ser Ile Glu Gln Asn Lys Ile Ile Leu Asn Ser
            210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
            245                 250                 255

Asp Leu Leu Ser Lys Ser Tyr Lys Leu Leu Ile Ser Gly Glu Leu Lys
            260                 265                 270

Ile Leu Met Leu Asn Ser Asn His Ile Gln Gln Lys Ile Asp Tyr Ile
            275                 280                 285

Gly Phe Asn Ser Glu Leu Gln Lys Asn Ile Pro Tyr Ser Phe Val Asp
            290                 295                 300

Ser Glu Gly Lys Glu Asn Gly Phe Ile Asn Gly Ser Thr Lys Glu Gly
305                 310                 315                 320

Leu Phe Val Ser Glu Leu Pro Asp Val Val Leu Ile Ser Lys Val Tyr
            325                 330                 335

Met Asp Ala Ser Lys Pro Ser Phe Gly Tyr Tyr Ser Asn Asn Leu Lys
            340                 345                 350

Asp Val Lys Val Ile Thr Lys Asp Asn Val Asn Ile Leu Thr Gly Tyr
            355                 360                 365

Tyr Leu Lys Asp Asp Ile Lys Ile Ser Leu Ser Leu Thr Leu Gln Asp
            370                 375                 380

Glu Lys Thr Ile Lys Leu Asn Ser Val His Leu Asp Glu Ser Gly Val
385                 390                 395                 400

Ala Glu Ile Leu Lys Phe Met Asn Arg Lys Gly Asn Thr Asn Thr Ser
            405                 410                 415
```

-continued

```
Asp Ser Leu Met Ser Phe Leu Glu Ser Met Asn Ile Lys Ser Ile Phe
            420                 425                 430

Val Asn Phe Leu Gln Ser Asn Ile Lys Phe Ile Leu Asp Ala Asn Phe
                435                 440                 445

Ile Ile Ser Gly Thr Thr Ser Ile Gly Gln Phe Glu Phe Ile Cys Asp
            450                 455                 460

Glu Asn Asp Asn Ile Gln Pro Tyr Phe Ile Lys Phe Asn Thr Leu Glu
465                 470                 475                 480

Thr Asn Tyr Thr Leu Tyr Val Gly Asn Arg Gln Asn Met Ile Val Glu
                485                 490                 495

Pro Asn Tyr Asp Leu Asp Asp Ser Gly Asp Ile Ser Ser Thr Val Ile
            500                 505                 510

Asn Phe Ser Gln Lys Tyr Leu Tyr Gly Ile Asp Ser Cys Val Asn Lys
            515                 520                 525

Val Val Ile Ser Pro Asn Ile Tyr Thr Asp Glu Ile Asn Ile Thr Pro
            530                 535                 540

Val Tyr Glu Thr Asn Asn Thr Tyr Pro Glu Val Ile Val Leu Asp Ala
545                 550                 555                 560

Asn Tyr Ile Asn Glu Lys Ile Asn Val Asn Ile Asn Asp Leu Ser Ile
                565                 570                 575

Arg Tyr Val Trp Ser Asn Asp Gly Asn Asp Phe Ile Leu Met Ser Thr
            580                 585                 590

Ser Glu Glu Asn Lys Val Ser Gln Val Lys Ile Arg Phe Val Asn Val
            595                 600                 605

Phe Lys Asp Lys Thr Leu Ala Asn Lys Leu Ser Phe Asn Phe Ser Asp
            610                 615                 620

Lys Gln Asp Val Pro Val Ser Glu Ile Ile Leu Ser Phe Thr Pro Ser
625                 630                 635                 640

Tyr Tyr

<210> SEQ ID NO 83
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 83

Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
                20                  25                  30

Gln Asp Glu Ala Gly Leu Glu Val His Gln Phe Trp Pro Leu Val Glu
            35                  40                  45

Ile Gln Cys Ser Pro Asp Leu Lys Phe Phe Leu Cys Ser Met Tyr Thr
        50                  55                  60

Pro Ile Cys Leu Glu Asp Tyr Lys Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
            115                 120                 125

Leu Asp Ser Asn Thr Arg Ser Phe Ile Val Pro Ile Ile Thr Thr Glu
```

```
                130                 135                 140
Tyr Ile Arg Glu Lys Leu Ser Tyr Ser Phe Tyr Gly Ser Gly Gly Thr
145                 150                 155                 160

Tyr Ala Leu Ser Leu Ser Gln Tyr Asn Met Gly Ile Asn Ile Glu Leu
                165                 170                 175

Ser Glu Ser Asp Val Trp Ile Ile Asp Val Asp Asn Val Val Arg Asp
                180                 185                 190

Val Thr Ile Glu Ser Asp Lys Ile Lys Lys Gly Asp Leu Ile Glu Gly
                195                 200                 205

Ile Leu Ser Thr Leu Ser Ile Glu Glu Asn Lys Ile Ile Leu Asn Ser
                210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
                245                 250                 255

Asp Leu Leu Ser Lys Ser Tyr Lys Leu Leu Ile Ser Gly Glu Leu Lys
                260                 265                 270

Ile Leu Met Leu Asn Ser Asn His Ile Gln Gln Lys Ile Asp Tyr Ile
                275                 280                 285

Gly Phe Asn Ser Glu Leu Gln Lys Asn Ile Pro Tyr Ser Phe Val Asp
                290                 295                 300

Ser Glu Gly Lys Glu Asn Gly Phe Ile Asn Gly Ser Thr Lys Glu Gly
305                 310                 315                 320

Leu Phe Val Ser Glu Leu Pro Asp Val Val Leu Ile Ser Lys Val Tyr
                325                 330                 335

Met Asp Asp Ser Lys Pro Ser Phe Gly Tyr Ala Ser Asn Asn Leu Lys
                340                 345                 350

Asp Val Lys Val Ile Thr Lys Asp Asn Val Asn Ile Leu Thr Gly Tyr
                355                 360                 365

Tyr Leu Lys Asp Asp Ile Lys Ile Ser Leu Ser Leu Thr Leu Gln Asp
                370                 375                 380

Glu Lys Thr Ile Lys Leu Asn Ser Val His Leu Asp Glu Ser Gly Val
385                 390                 395                 400

Ala Glu Ile Leu Lys Phe Met Asn Arg Lys Gly Asn Thr Asn Thr Ser
                405                 410                 415

Asp Ser Leu Met Ser Phe Leu Glu Ser Met Asn Ile Lys Ser Ile Phe
                420                 425                 430

Val Asn Phe Leu Gln Ser Asn Ile Lys Phe Ile Leu Asp Ala Asn Phe
                435                 440                 445

Ile Ile Ser Gly Thr Thr Ser Ile Gly Gln Phe Glu Phe Ile Cys Asp
450                 455                 460

Glu Asn Asp Asn Ile Gln Pro Tyr Phe Ile Lys Phe Asn Thr Leu Glu
465                 470                 475                 480

Thr Asn Tyr Thr Leu Tyr Val Gly Asn Arg Gln Asn Met Ile Val Glu
                485                 490                 495

Pro Asn Tyr Asp Leu Asp Asp Ser Gly Asp Ile Ser Ser Thr Val Ile
                500                 505                 510

Asn Phe Ser Gln Lys Tyr Leu Tyr Gly Ile Asp Ser Cys Val Asn Lys
                515                 520                 525

Val Val Ile Ser Pro Asn Ile Tyr Thr Asp Glu Ile Asn Ile Thr Pro
                530                 535                 540

Val Tyr Glu Thr Asn Asn Thr Tyr Pro Glu Val Ile Val Leu Asp Ala
545                 550                 555                 560
```

```
Asn Tyr Ile Asn Glu Lys Ile Asn Val Asn Ile Asn Asp Leu Ser Ile
                565                 570                 575

Arg Tyr Val Trp Ser Asn Asp Gly Asn Asp Phe Ile Leu Met Ser Thr
            580                 585                 590

Ser Glu Glu Asn Lys Val Ser Gln Val Lys Ile Arg Phe Val Asn Val
        595                 600                 605

Phe Lys Asp Lys Thr Leu Ala Asn Lys Leu Ser Phe Asn Phe Ser Asp
    610                 615                 620

Lys Gln Asp Val Pro Val Ser Glu Ile Ile Leu Ser Phe Thr Pro Ser
625                 630                 635                 640

Tyr Tyr

<210> SEQ ID NO 84
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 84

Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
            20                  25                  30

Gln Asp Glu Ala Gly Leu Glu Val His Gln Phe Trp Pro Leu Val Glu
        35                  40                  45

Ile Gln Cys Ser Pro Asp Leu Lys Phe Phe Leu Cys Ser Met Tyr Thr
    50                  55                  60

Pro Ile Cys Leu Glu Asp Tyr Lys Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
        115                 120                 125

Leu Asp Ser Asn Thr Arg Ser Phe Ile Val Pro Ile Ile Thr Thr Glu
130                 135                 140

Tyr Ile Arg Glu Lys Leu Ser Tyr Ser Phe Tyr Gly Ser Gly Gly Thr
145                 150                 155                 160

Tyr Ala Leu Ser Leu Ser Gln Tyr Asn Met Gly Ile Asn Ile Glu Leu
                165                 170                 175

Ser Glu Ser Asp Val Trp Ile Ile Asp Val Asp Asn Val Val Arg Asp
            180                 185                 190

Val Thr Ile Glu Ser Asp Lys Ile Lys Lys Gly Asp Leu Ile Glu Gly
        195                 200                 205

Ile Leu Ser Thr Leu Ser Ile Glu Glu Asn Lys Ile Ile Leu Asn Ser
    210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
                245                 250                 255

Asp Leu Leu Ser Lys Ser Tyr Lys Leu Leu Ile Ser Gly Glu Leu Lys
            260                 265                 270
```

```
Ile Leu Met Leu Asn Ser Asn His Ile Gln Gln Lys Ile Asp Tyr Ile
            275                 280                 285

Gly Phe Asn Ser Glu Leu Gln Lys Asn Ile Pro Tyr Ser Phe Val Asp
290                 295                 300

Ser Glu Gly Lys Glu Asn Gly Phe Ile Asn Gly Ser Thr Lys Glu Gly
305                 310                 315                 320

Leu Phe Val Ser Glu Leu Pro Asp Val Val Leu Ile Ser Lys Val Tyr
                325                 330                 335

Met Asp Asp Ser Lys Pro Ser Phe Gly Tyr Tyr Ser Ala Asn Leu Lys
            340                 345                 350

Asp Val Lys Val Ile Thr Lys Asp Asn Val Asn Ile Leu Thr Gly Tyr
        355                 360                 365

Tyr Leu Lys Asp Asp Ile Lys Ile Ser Leu Ser Leu Thr Leu Gln Asp
    370                 375                 380

Glu Lys Thr Ile Lys Leu Asn Ser Val His Leu Asp Glu Ser Gly Val
385                 390                 395                 400

Ala Glu Ile Leu Lys Phe Met Asn Arg Lys Gly Asn Thr Asn Thr Ser
                405                 410                 415

Asp Ser Leu Met Ser Phe Leu Glu Ser Met Asn Ile Lys Ser Ile Phe
            420                 425                 430

Val Asn Phe Leu Gln Ser Asn Ile Lys Phe Ile Leu Asp Ala Asn Phe
        435                 440                 445

Ile Ile Ser Gly Thr Thr Ser Ile Gly Gln Phe Glu Phe Ile Cys Asp
    450                 455                 460

Glu Asn Asp Asn Ile Gln Pro Tyr Phe Ile Lys Phe Asn Thr Leu Glu
465                 470                 475                 480

Thr Asn Tyr Thr Leu Tyr Val Gly Asn Arg Gln Asn Met Ile Val Glu
                485                 490                 495

Pro Asn Tyr Asp Leu Asp Asp Ser Gly Asp Ile Ser Ser Thr Val Ile
            500                 505                 510

Asn Phe Ser Gln Lys Tyr Leu Tyr Gly Ile Asp Ser Cys Val Asn Lys
        515                 520                 525

Val Val Ile Ser Pro Asn Ile Tyr Thr Asp Glu Ile Asn Ile Thr Pro
    530                 535                 540

Val Tyr Glu Thr Asn Asn Thr Tyr Pro Glu Val Ile Val Leu Asp Ala
545                 550                 555                 560

Asn Tyr Ile Asn Glu Lys Ile Asn Val Asn Ile Asn Asp Leu Ser Ile
                565                 570                 575

Arg Tyr Val Trp Ser Asn Asp Gly Asn Asp Phe Ile Leu Met Ser Thr
            580                 585                 590

Ser Glu Glu Asn Lys Val Ser Gln Val Lys Ile Arg Phe Val Asn Val
        595                 600                 605

Phe Lys Asp Lys Thr Leu Ala Asn Lys Leu Ser Phe Asn Phe Ser Asp
    610                 615                 620

Lys Gln Asp Val Pro Val Ser Glu Ile Ile Leu Ser Phe Thr Pro Ser
625                 630                 635                 640

Tyr Tyr
```

<210> SEQ ID NO 85
<211> LENGTH: 642
<212> TYPE: PRT
<213> ORGANISM: Artificial Sequence
<220> FEATURE:
<223> OTHER INFORMATION: Synthetic polypeptide

```
<400> SEQUENCE: 85

Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
            20                  25                  30

Gln Asp Glu Ala Gly Leu Glu Val His Gln Phe Trp Pro Leu Val Glu
        35                  40                  45

Ile Gln Cys Ser Pro Asp Leu Lys Phe Phe Leu Cys Ser Met Tyr Thr
    50                  55                  60

Pro Ile Cys Leu Glu Asp Tyr Lys Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
        115                 120                 125

Leu Asp Ser Asn Thr Arg Ser Phe Ile Val Pro Ile Ile Thr Thr Glu
    130                 135                 140

Tyr Ile Arg Glu Lys Leu Ser Tyr Ser Phe Tyr Gly Ser Gly Gly Thr
145                 150                 155                 160

Tyr Ala Leu Ser Leu Ser Gln Tyr Asn Met Gly Ile Asn Ile Glu Leu
                165                 170                 175

Ser Glu Ser Asp Val Trp Ile Ile Asp Val Asp Asn Val Val Arg Asp
            180                 185                 190

Val Thr Ile Glu Ser Asp Lys Ile Lys Lys Gly Asp Leu Ile Glu Gly
        195                 200                 205

Ile Leu Ser Thr Leu Ser Ile Glu Glu Asn Lys Ile Ile Leu Asn Ser
    210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
                245                 250                 255

Asp Leu Leu Ser Lys Ser Tyr Lys Leu Leu Ile Ser Gly Glu Leu Lys
            260                 265                 270

Ile Leu Met Leu Asn Ser Asn His Ile Gln Gln Lys Ile Asp Tyr Ile
        275                 280                 285

Gly Phe Asn Ser Glu Leu Gln Lys Asn Ile Pro Tyr Ser Phe Val Asp
    290                 295                 300

Ser Glu Gly Lys Glu Asn Gly Phe Ile Asn Gly Ser Thr Lys Glu Gly
305                 310                 315                 320

Leu Phe Val Ser Glu Leu Pro Asp Val Val Leu Ile Ser Lys Val Tyr
                325                 330                 335

Met Asp Asp Ser Lys Pro Ser Phe Gly Tyr Tyr Ser Asn Asn Leu Lys
            340                 345                 350

Asp Val Lys Val Ile Thr Lys Asp Asn Val Asn Ile Leu Thr Gly Tyr
        355                 360                 365

Tyr Leu Lys Asp Asp Ile Lys Ile Ser Leu Ser Leu Thr Leu Gln Asp
    370                 375                 380

Glu Lys Thr Ile Lys Leu Asn Ser Val His Leu Asp Glu Ser Gly Val
385                 390                 395                 400

Ala Glu Ile Leu Lys Phe Met Asn Arg Lys Gly Asn Thr Asn Thr Ser
                405                 410                 415
```

```
Asp Ser Leu Met Ser Phe Leu Glu Ser Met Asn Ile Lys Ser Ile Phe
            420                 425                 430

Val Asn Phe Leu Ala Ser Asn Ile Lys Phe Ile Leu Asp Ala Asn Phe
            435                 440                 445

Ile Ile Ser Gly Thr Thr Ser Ile Gly Gln Phe Glu Phe Ile Cys Asp
        450                 455                 460

Glu Asn Asp Asn Ile Gln Pro Tyr Phe Ile Lys Phe Asn Thr Leu Glu
465                 470                 475                 480

Thr Asn Tyr Thr Leu Tyr Val Gly Asn Arg Gln Asn Met Ile Val Glu
                485                 490                 495

Pro Asn Tyr Asp Leu Asp Asp Ser Gly Asp Ile Ser Ser Thr Val Ile
            500                 505                 510

Asn Phe Ser Gln Lys Tyr Leu Tyr Gly Ile Asp Ser Cys Val Asn Lys
            515                 520                 525

Val Val Ile Ser Pro Asn Ile Tyr Thr Asp Glu Ile Asn Ile Thr Pro
530                 535                 540

Val Tyr Glu Thr Asn Asn Thr Tyr Pro Glu Val Ile Val Leu Asp Ala
545                 550                 555                 560

Asn Tyr Ile Asn Glu Lys Ile Asn Val Asn Ile Asn Asp Leu Ser Ile
                565                 570                 575

Arg Tyr Val Trp Ser Asn Asp Gly Asn Asp Phe Ile Leu Met Ser Thr
            580                 585                 590

Ser Glu Glu Asn Lys Val Ser Gln Val Lys Ile Arg Phe Val Asn Val
            595                 600                 605

Phe Lys Asp Lys Thr Leu Ala Asn Lys Leu Ser Phe Asn Phe Ser Asp
            610                 615                 620

Lys Gln Asp Val Pro Val Ser Glu Ile Ile Leu Ser Phe Thr Pro Ser
625                 630                 635                 640

Tyr Tyr

<210> SEQ ID NO 86
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 86

Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
            20                  25                  30

Gln Asp Glu Ala Gly Leu Glu Val His Gln Phe Trp Pro Leu Val Glu
        35                  40                  45

Ile Gln Cys Ser Pro Asp Leu Lys Phe Phe Leu Cys Ser Met Tyr Thr
    50                  55                  60

Pro Ile Cys Leu Glu Asp Tyr Lys Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
        115                 120                 125
```

-continued

Leu Asp Ser Asn Thr Arg Ser Phe Ile Val Pro Ile Ile Thr Thr Glu
130                 135                 140

Tyr Ile Arg Glu Lys Leu Ser Tyr Ser Phe Tyr Gly Ser Gly Gly Thr
145                 150                 155                 160

Tyr Ala Leu Ser Leu Ser Gln Tyr Asn Met Gly Ile Asn Ile Glu Leu
                165                 170                 175

Ser Glu Ser Asp Val Trp Ile Ile Asp Val Asp Asn Val Val Arg Asp
                180                 185                 190

Val Thr Ile Glu Ser Asp Lys Ile Lys Lys Gly Asp Leu Ile Glu Gly
                195                 200                 205

Ile Leu Ser Thr Leu Ser Ile Glu Glu Asn Lys Ile Ile Leu Asn Ser
210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
                245                 250                 255

Asp Leu Leu Ser Lys Ser Tyr Lys Leu Leu Ile Ser Gly Glu Leu Lys
                260                 265                 270

Ile Leu Met Leu Asn Ser Asn His Ile Gln Gln Lys Ile Asp Tyr Ile
                275                 280                 285

Gly Phe Asn Ser Glu Leu Gln Lys Asn Ile Pro Tyr Ser Phe Val Asp
290                 295                 300

Ser Glu Gly Lys Glu Asn Gly Phe Ile Asn Gly Ser Thr Lys Glu Gly
305                 310                 315                 320

Leu Phe Val Ser Glu Leu Pro Asp Val Val Leu Ile Ser Lys Val Tyr
                325                 330                 335

Met Asp Asp Ser Lys Pro Ser Phe Gly Tyr Ala Ser Ala Asn Leu Lys
                340                 345                 350

Asp Val Lys Val Ile Thr Lys Asp Asn Val Asn Ile Leu Thr Gly Tyr
                355                 360                 365

Tyr Leu Lys Asp Asp Ile Lys Ile Ser Leu Ser Leu Thr Leu Gln Asp
                370                 375                 380

Glu Lys Thr Ile Lys Leu Asn Ser Val His Leu Asp Glu Ser Gly Val
385                 390                 395                 400

Ala Glu Ile Leu Lys Phe Met Asn Arg Lys Gly Asn Thr Asn Thr Ser
                405                 410                 415

Asp Ser Leu Met Ser Phe Leu Glu Ser Met Asn Ile Lys Ser Ile Phe
                420                 425                 430

Val Asn Phe Leu Gln Ser Asn Ile Lys Phe Ile Leu Asp Ala Asn Phe
                435                 440                 445

Ile Ile Ser Gly Thr Thr Ser Ile Gly Gln Phe Glu Phe Ile Cys Asp
450                 455                 460

Glu Asn Asp Asn Ile Gln Pro Tyr Phe Ile Lys Phe Asn Thr Leu Glu
465                 470                 475                 480

Thr Asn Tyr Thr Leu Tyr Val Gly Asn Arg Gln Asn Met Ile Val Glu
                485                 490                 495

Pro Asn Tyr Asp Leu Asp Asp Ser Gly Asp Ile Ser Ser Thr Val Ile
                500                 505                 510

Asn Phe Ser Gln Lys Tyr Leu Tyr Gly Ile Asp Ser Cys Val Asn Lys
                515                 520                 525

Val Val Ile Ser Pro Asn Ile Tyr Thr Asp Glu Ile Asn Ile Thr Pro
530                 535                 540

Val Tyr Glu Thr Asn Asn Thr Tyr Pro Glu Val Ile Val Leu Asp Ala

```
                545                 550                 555                 560
Asn Tyr Ile Asn Glu Lys Ile Asn Val Asn Ile Asn Asp Leu Ser Ile
            565                 570                 575

Arg Tyr Val Trp Ser Asn Asp Gly Asn Asp Phe Ile Leu Met Ser Thr
            580                 585                 590

Ser Glu Glu Asn Lys Val Ser Gln Val Lys Ile Arg Phe Val Asn Val
            595                 600                 605

Phe Lys Asp Lys Thr Leu Ala Asn Lys Leu Ser Phe Asn Phe Ser Asp
            610                 615                 620

Lys Gln Asp Val Pro Val Ser Glu Ile Ile Leu Ser Phe Thr Pro Ser
625                 630                 635                 640

Tyr Tyr

<210> SEQ ID NO 87
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 87

Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
            20                  25                  30

Gln Asp Glu Ala Gly Leu Glu Val His Gln Phe Trp Pro Leu Val Glu
        35                  40                  45

Ile Gln Cys Ser Pro Asp Leu Lys Phe Phe Leu Cys Ser Met Tyr Thr
    50                  55                  60

Pro Ile Cys Leu Glu Asp Tyr Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
        115                 120                 125

Leu Asp Ser Asn Thr Arg Ser Phe Ile Val Pro Ile Ile Thr Thr Glu
    130                 135                 140

Tyr Ile Arg Glu Lys Leu Ser Tyr Ser Phe Tyr Gly Ser Gly Gly Thr
145                 150                 155                 160

Tyr Ala Leu Ser Leu Ser Gln Tyr Asn Met Gly Ile Asn Ile Glu Leu
                165                 170                 175

Ser Glu Ser Asp Val Trp Ile Ile Asp Val Asp Asn Val Val Arg Asp
            180                 185                 190

Val Thr Ile Glu Ser Asp Lys Ile Lys Lys Gly Asp Leu Ile Glu Gly
        195                 200                 205

Ile Leu Ser Thr Leu Ser Ile Glu Glu Asn Lys Ile Ile Leu Asn Ser
    210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
                245                 250                 255

Asp Leu Leu Ser Lys Ser Tyr Lys Leu Leu Ile Ser Gly Glu Leu Lys
            260                 265                 270
```

```
Ile Leu Met Leu Asn Ser Asn His Ile Gln Gln Lys Ile Asp Tyr Ile
            275                 280                 285
Gly Phe Asn Ser Glu Leu Gln Lys Asn Ile Pro Tyr Ser Phe Val Asp
    290                 295                 300
Ser Glu Gly Lys Glu Asn Gly Phe Ile Asn Gly Ser Thr Lys Glu Gly
305                 310                 315                 320
Leu Phe Val Ser Glu Leu Pro Asp Val Val Leu Ile Ser Lys Val Tyr
                325                 330                 335
Met Asp Asp Ser Lys Pro Ser Phe Gly Tyr Ala Ser Asn Asn Leu Lys
            340                 345                 350
Asp Val Lys Val Ile Thr Lys Asp Asn Val Asn Ile Leu Thr Gly Tyr
        355                 360                 365
Tyr Leu Lys Asp Asp Ile Lys Ile Ser Leu Ser Leu Thr Leu Gln Asp
    370                 375                 380
Glu Lys Thr Ile Lys Leu Asn Ser Val His Leu Asp Glu Ser Gly Val
385                 390                 395                 400
Ala Glu Ile Leu Lys Phe Met Asn Arg Lys Gly Asn Thr Asn Thr Ser
                405                 410                 415
Asp Ser Leu Met Ser Phe Leu Glu Ser Met Asn Ile Lys Ser Ile Phe
            420                 425                 430
Val Asn Phe Leu Ala Ser Asn Ile Lys Phe Ile Leu Asp Ala Asn Phe
        435                 440                 445
Ile Ile Ser Gly Thr Thr Ser Ile Gly Gln Phe Glu Phe Ile Cys Asp
    450                 455                 460
Glu Asn Asp Asn Ile Gln Pro Tyr Phe Ile Lys Phe Asn Thr Leu Glu
465                 470                 475                 480
Thr Asn Tyr Thr Leu Tyr Val Gly Asn Arg Gln Asn Met Ile Val Glu
                485                 490                 495
Pro Asn Tyr Asp Leu Asp Asp Ser Gly Asp Ile Ser Ser Thr Val Ile
            500                 505                 510
Asn Phe Ser Gln Lys Tyr Leu Tyr Gly Ile Asp Ser Cys Val Asn Lys
        515                 520                 525
Val Val Ile Ser Pro Asn Ile Tyr Thr Asp Glu Ile Asn Ile Thr Pro
    530                 535                 540
Val Tyr Glu Thr Asn Asn Thr Tyr Pro Glu Val Ile Val Leu Asp Ala
545                 550                 555                 560
Asn Tyr Ile Asn Glu Lys Ile Asn Val Asn Ile Asn Asp Leu Ser Ile
                565                 570                 575
Arg Tyr Val Trp Ser Asn Asp Gly Asn Asp Phe Ile Leu Met Ser Thr
            580                 585                 590
Ser Glu Glu Asn Lys Val Ser Gln Val Lys Ile Arg Phe Val Asn Val
        595                 600                 605
Phe Lys Asp Lys Thr Leu Ala Asn Lys Leu Ser Phe Asn Phe Ser Asp
    610                 615                 620
Lys Gln Asp Val Pro Val Ser Glu Ile Ile Leu Ser Phe Thr Pro Ser
625                 630                 635                 640

Tyr Tyr

<210> SEQ ID NO 88
<211> LENGTH: 642
<212> TYPE: PRT
<213> ORGANISM: Artificial Sequence
<220> FEATURE:
<223> OTHER INFORMATION: Synthetic polypeptide
```

<400> SEQUENCE: 88

```
Ala Lys Glu Leu Ala Cys Gln Glu Ile Thr Val Pro Leu Cys Lys Gly
1               5                   10                  15

Ile Gly Tyr Asn Tyr Thr Tyr Met Pro Asn Gln Phe Asn His Asp Thr
            20                  25                  30

Gln Asp Glu Ala Gly Leu Glu Val His Gln Phe Trp Pro Leu Val Glu
        35                  40                  45

Ile Gln Cys Ser Pro Asp Leu Lys Phe Phe Leu Cys Ser Met Tyr Thr
    50                  55                  60

Pro Ile Cys Leu Glu Asp Tyr Lys Lys Pro Leu Pro Pro Cys Arg Ser
65                  70                  75                  80

Val Cys Glu Arg Ala Lys Ala Gly Cys Ala Pro Leu Met Arg Gln Tyr
                85                  90                  95

Gly Phe Ala Trp Pro Asp Arg Met Arg Cys Asp Arg Leu Pro Glu Gln
            100                 105                 110

Gly Asn Pro Asp Thr Leu Cys Met Asp Tyr Thr Asn Ile Arg Ile Asn
        115                 120                 125

Leu Asp Ser Asn Thr Arg Ser Phe Ile Val Pro Ile Ile Thr Thr Glu
130                 135                 140

Tyr Ile Arg Glu Lys Leu Ser Tyr Ser Phe Tyr Gly Ser Gly Gly Thr
145                 150                 155                 160

Tyr Ala Leu Ser Leu Ser Gln Tyr Asn Met Gly Ile Asn Ile Glu Leu
                165                 170                 175

Ser Glu Ser Asp Val Trp Ile Ile Asp Val Asp Asn Val Val Arg Asp
            180                 185                 190

Val Thr Ile Glu Ser Asp Lys Ile Lys Lys Gly Asp Leu Ile Glu Gly
        195                 200                 205

Ile Leu Ser Thr Leu Ser Ile Glu Glu Asn Lys Ile Ile Leu Asn Ser
210                 215                 220

His Glu Ile Asn Phe Ser Gly Glu Val Asn Gly Ser Asn Gly Phe Val
225                 230                 235                 240

Ser Leu Thr Phe Ser Ile Leu Glu Gly Ile Asn Ala Ile Ile Glu Val
                245                 250                 255

Asp Leu Leu Ser Lys Ser Tyr Lys Leu Leu Ile Ser Gly Glu Asp Lys
            260                 265                 270

Ile Leu Met Leu Asn Ser Asn His Ile Gln Gln Lys Ile Asp Tyr Ile
        275                 280                 285

Gly Phe Asn Ser Glu Leu Gln Lys Asn Ile Pro Tyr Ser Phe Val Asp
290                 295                 300

Ser Glu Gly Lys Glu Asn Gly Phe Ile Asn Gly Ser Thr Lys Glu Gly
305                 310                 315                 320

Leu Phe Val Ser Glu Leu Pro Asp Val Val Leu Ile Ser Lys Val Tyr
                325                 330                 335

Met Asp Asp Ser Lys Pro Ser Phe Gly Tyr Tyr Ser Asn Asn Leu Lys
            340                 345                 350

Asp Val Lys Val Ile Thr Lys Asp Asn Val Asn Ile Leu Thr Gly Tyr
        355                 360                 365

Tyr Leu Lys Asp Asp Ile Lys Ile Ser Leu Ser Thr Leu Gln Asp
370                 375                 380

Glu Lys Thr Ile Lys Leu Asn Ser Val His Leu Asp Glu Ser Gly Val
385                 390                 395                 400

Ala Glu Ile Leu Lys Phe Met Asn Arg Lys Gly Asn Thr Asn Thr Ser
```

```
                      405                 410                 415

Asp Ser Leu Met Ser Phe Leu Glu Ser Met Asn Ile Lys Ser Ile Phe
            420                 425                 430

Val Asn Phe Leu Gln Ser Asn Ile Lys Phe Ile Leu Asp Ala Asn Phe
            435                 440                 445

Ile Ile Ser Gly Thr Thr Ser Ile Gly Gln Phe Glu Phe Ile Cys Asp
450                 455                 460

Glu Asn Asp Asn Ile Gln Pro Tyr Phe Ile Lys Phe Asn Thr Leu Glu
465                 470                 475                 480

Thr Asn Tyr Thr Leu Tyr Val Gly Asn Arg Gln Asn Met Ile Val Glu
                485                 490                 495

Pro Asn Tyr Asp Leu Asp Asp Ser Gly Asp Ile Ser Ser Thr Val Ile
                500                 505                 510

Asn Phe Ser Gln Lys Tyr Leu Tyr Gly Ile Asp Ser Cys Val Asn Lys
            515                 520                 525

Val Val Ile Ser Pro Asn Ile Tyr Thr Asp Glu Ile Asn Ile Thr Pro
530                 535                 540

Val Tyr Glu Thr Asn Asn Thr Tyr Pro Glu Val Ile Val Leu Asp Ala
545                 550                 555                 560

Asn Tyr Ile Asn Glu Lys Ile Asn Val Asn Ile Asn Asp Leu Ser Ile
                565                 570                 575

Arg Tyr Val Trp Ser Asn Asp Gly Asn Asp Phe Ile Leu Met Ser Thr
            580                 585                 590

Ser Glu Glu Asn Lys Val Ser Gln Val Lys Ile Arg Phe Val Asn Val
                595                 600                 605

Phe Lys Asp Lys Thr Leu Ala Asn Lys Leu Ser Phe Asn Phe Ser Asp
            610                 615                 620

Lys Gln Asp Val Pro Val Ser Glu Ile Ile Leu Ser Phe Thr Pro Ser
625                 630                 635                 640

Tyr Tyr

<210> SEQ ID NO 89
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 89

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125
```

```
Asn Ala Ile Ile Glu Val Asp Leu Leu Ser Lys Ser Tyr Lys Leu Leu
130                 135                 140
Ile Ser Gly Glu Leu Lys Ile Leu Met Leu Asn Ser Asn His Ile Gln
145                 150                 155                 160
Gln Lys Ile Asp Tyr Ile Gly Phe Asn Ser Glu Leu Gln Lys Asn Ile
                165                 170                 175
Pro Tyr Ser Phe Val Asp Ser Glu Gly Lys Glu Asn Gly Phe Ile Asn
                180                 185                 190
Gly Ser Thr Lys Glu Gly Leu Phe Val Ser Glu Leu Pro Asp Val Val
                195                 200                 205
Leu Ile Ser Lys Val Tyr Met Asp Ala Ser Lys Pro Ser Phe Gly Tyr
210                 215                 220
Tyr Ser Asn Asn Leu Lys Asp Val Lys Val Ile Thr Lys Asp Asn Val
225                 230                 235                 240
Asn Ile Leu Thr Gly Tyr Tyr Leu Lys Asp Asp Ile Lys Ile Ser Leu
                245                 250                 255
Ser Leu Thr Leu Gln Asp Glu Lys Thr Ile Lys Leu Asn Ser Val His
                260                 265                 270
Leu Asp Glu Ser Gly Val Ala Glu Ile Leu Lys Phe Met Asn Arg Lys
                275                 280                 285
Gly Asn Thr Asn Thr Ser Asp Ser Leu Met Ser Phe Leu Glu Ser Met
290                 295                 300
Asn Ile Lys Ser Ile Phe Val Asn Phe Leu Gln Ser Asn Ile Lys Phe
305                 310                 315                 320
Ile Leu Asp Ala Asn Phe Ile Ile Ser Gly Thr Thr Ser Ile Gly Gln
                325                 330                 335
Phe Glu Phe Ile Cys Asp Glu Asn Asp Asn Ile Gln Pro Tyr Phe Ile
                340                 345                 350
Lys Phe Asn Thr Leu Glu Thr Asn Tyr Thr Leu Tyr Val Gly Asn Arg
                355                 360                 365
Gln Asn Met Ile Val Glu Pro Asn Tyr Asp Leu Asp Asp Ser Gly Asp
370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                405                 410                 415
Glu Ile Asn Ile Thr Pro Val Tyr Glu Thr Asn Asn Thr Tyr Pro Glu
                420                 425                 430
Val Ile Val Leu Asp Ala Asn Tyr Ile Asn Glu Lys Ile Asn Val Asn
                435                 440                 445
Ile Asn Asp Leu Ser Ile Arg Tyr Val Trp Ser Asn Asp Gly Asn Asp
450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
Ser Phe Asn Phe Ser Asp Lys Gln Asp Val Pro Val Ser Glu Ile Ile
                500                 505                 510
Leu Ser Phe Thr Pro Ser Tyr Tyr Ala Lys Glu Leu Ala Cys Gln Glu
                515                 520                 525
Ile Thr Val Pro Leu Cys Lys Gly Ile Gly Tyr Asn Tyr Thr Tyr Met
530                 535                 540
```

-continued

```
Pro Asn Gln Phe Asn His Asp Thr Gln Asp Glu Ala Gly Leu Glu Val
545                 550                 555                 560

His Gln Phe Trp Pro Leu Val Glu Ile Gln Cys Ser Pro Asp Leu Lys
            565                 570                 575

Phe Phe Leu Cys Ser Met Tyr Thr Pro Ile Cys Leu Glu Asp Tyr Lys
        580                 585                 590

Lys Pro Leu Pro Pro Cys Arg Ser Val Cys Glu Arg Ala Lys Ala Gly
    595                 600                 605

Cys Ala Pro Leu Met Arg Gln Tyr Gly Phe Ala Trp Pro Asp Arg Met
610                 615                 620

Arg Cys Asp Arg Leu Pro Glu Gln Gly Asn Pro Asp Thr Leu Cys Met
625                 630                 635                 640

Asp Tyr

<210> SEQ ID NO 90
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 90

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
            85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
            165                 170                 175

Pro Tyr Ser Phe Val Asp Ser Glu Gly Lys Glu Asn Gly Phe Ile Asn
        180                 185                 190

Gly Ser Thr Lys Glu Gly Leu Phe Val Ser Glu Leu Pro Asp Val Val
    195                 200                 205

Leu Ile Ser Lys Val Tyr Met Asp Asp Ser Lys Pro Ser Phe Gly Tyr
210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
            245                 250                 255

Ser Leu Thr Leu Gln Asp Glu Lys Thr Ile Lys Leu Asn Ser Val His
```

```
                    260                 265                 270
Leu Asp Glu Ser Gly Val Ala Glu Ile Leu Lys Phe Met Asn Arg Lys
            275                 280                 285
Gly Asn Thr Asn Thr Ser Asp Ser Leu Met Ser Phe Leu Glu Ser Met
        290                 295                 300
Asn Ile Lys Ser Ile Phe Val Asn Phe Leu Gln Ser Asn Ile Lys Phe
305                 310                 315                 320
Ile Leu Asp Ala Asn Phe Ile Ile Ser Gly Thr Thr Ser Ile Gly Gln
                325                 330                 335
Phe Glu Phe Ile Cys Asp Glu Asn Asp Asn Ile Gln Pro Tyr Phe Ile
            340                 345                 350
Lys Phe Asn Thr Leu Glu Thr Asn Tyr Thr Leu Tyr Val Gly Asn Arg
        355                 360                 365
Gln Asn Met Ile Val Glu Pro Asn Tyr Asp Leu Asp Asp Ser Gly Asp
    370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
                405                 410                 415
Glu Ile Asn Ile Thr Pro Val Tyr Glu Thr Asn Asn Thr Tyr Pro Glu
            420                 425                 430
Val Ile Val Leu Asp Ala Asn Tyr Ile Asn Glu Lys Ile Asn Val Asn
        435                 440                 445
Ile Asn Asp Leu Ser Ile Arg Tyr Val Trp Ser Asn Asp Gly Asn Asp
    450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
                485                 490                 495
Ser Phe Asn Phe Ser Asp Lys Gln Asp Val Pro Val Ser Glu Ile Ile
            500                 505                 510
Leu Ser Phe Thr Pro Ser Tyr Tyr Ala Lys Glu Leu Ala Cys Gln Glu
        515                 520                 525
Ile Thr Val Pro Leu Cys Lys Gly Ile Gly Tyr Asn Tyr Thr Tyr Met
    530                 535                 540
Pro Asn Gln Phe Asn His Asp Thr Gln Asp Glu Ala Gly Leu Glu Val
545                 550                 555                 560
His Gln Phe Trp Pro Leu Val Glu Ile Gln Cys Ser Pro Asp Leu Lys
                565                 570                 575
Phe Phe Leu Cys Ser Met Tyr Thr Pro Ile Cys Leu Glu Asp Tyr Lys
            580                 585                 590
Lys Pro Leu Pro Pro Cys Arg Ser Val Cys Glu Arg Ala Lys Ala Gly
        595                 600                 605
Cys Ala Pro Leu Met Arg Gln Tyr Gly Phe Ala Trp Pro Asp Arg Met
    610                 615                 620
Arg Cys Asp Arg Leu Pro Glu Gln Gly Asn Pro Asp Thr Leu Cys Met
625                 630                 635                 640
Asp Tyr

<210> SEQ ID NO 91
<211> LENGTH: 642
<212> TYPE: PRT
<213> ORGANISM: Artificial Sequence
<220> FEATURE:
```

<223> OTHER INFORMATION: Synthetic polypeptide

<400> SEQUENCE: 91

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Tyr Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ile Ser Ile Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Thr Val Ile Asn Phe Ser Gln Lys Tyr Leu Tyr Gly Ile
385                 390                 395                 400
```

```
Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Tyr Pro Glu
            420                 425                 430

Val Ile Val Leu Asp Ala Asn Tyr Ile Asn Glu Lys Ile Asn Val Asn
            435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr Ala Lys Glu Leu Ala Cys Gln Glu
            515                 520                 525

Ile Thr Val Pro Leu Cys Lys Gly Ile Gly Tyr Asn Tyr Thr Tyr Met
            530                 535                 540

Pro Asn Gln Phe Asn His Asp Thr Gln Asp Glu Ala Gly Leu Glu Val
545                 550                 555                 560

His Gln Phe Trp Pro Leu Val Glu Ile Gln Cys Ser Pro Asp Leu Lys
                565                 570                 575

Phe Phe Leu Cys Ser Met Tyr Thr Pro Ile Cys Leu Glu Asp Tyr Lys
                580                 585                 590

Lys Pro Leu Pro Pro Cys Arg Ser Val Cys Glu Arg Ala Lys Ala Gly
            595                 600                 605

Cys Ala Pro Leu Met Arg Gln Tyr Gly Phe Ala Trp Pro Asp Arg Met
610                 615                 620

Arg Cys Asp Arg Leu Pro Glu Gln Gly Asn Pro Asp Thr Leu Cys Met
625                 630                 635                 640

Asp Tyr

<210> SEQ ID NO 92
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 92

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
```

```
            115                 120                 125
Asn Ala Ile Ile Glu Val Asp Leu Leu Ser Lys Ser Tyr Lys Leu Leu
            130                 135                 140
Ile Ser Gly Glu Leu Lys Ile Leu Met Leu Asn Ser Asn His Ile Gln
145                 150                 155                 160
Gln Lys Ile Asp Tyr Ile Gly Phe Asn Ser Glu Leu Gln Lys Asn Ile
            165                 170                 175
Pro Tyr Ser Phe Val Asp Ser Glu Gly Lys Glu Asn Gly Phe Ile Asn
            180                 185                 190
Gly Ser Thr Lys Glu Gly Leu Phe Val Ser Glu Leu Pro Asp Val Val
            195                 200                 205
Leu Ile Ser Lys Val Tyr Met Asp Asp Ser Lys Pro Ser Phe Gly Tyr
            210                 215                 220
Tyr Ser Asn Asn Leu Lys Asp Val Lys Val Ile Thr Lys Asp Asn Val
225                 230                 235                 240
Asn Ile Leu Thr Gly Tyr Tyr Leu Lys Asp Asp Ile Lys Ile Ser Leu
            245                 250                 255
Ser Leu Thr Leu Gln Asp Glu Lys Thr Ile Lys Leu Asn Ser Val His
            260                 265                 270
Leu Asp Glu Ser Gly Val Ala Glu Ile Leu Lys Phe Met Asn Arg Lys
            275                 280                 285
Gly Asn Thr Asn Thr Ser Asp Ser Leu Met Ser Phe Leu Glu Ser Met
290                 295                 300
Asn Ile Lys Ser Ile Phe Val Asn Phe Leu Ala Ser Asn Ile Lys Phe
305                 310                 315                 320
Ile Leu Asp Ala Asn Phe Ile Ile Ser Gly Thr Thr Ser Ile Gly Gln
            325                 330                 335
Phe Glu Phe Ile Cys Asp Glu Asn Asp Asn Ile Gln Pro Tyr Phe Ile
            340                 345                 350
Lys Phe Asn Thr Leu Glu Thr Asn Tyr Thr Leu Tyr Val Gly Asn Arg
            355                 360                 365
Gln Asn Met Ile Val Glu Pro Asn Tyr Asp Leu Asp Asp Ser Gly Asp
            370                 375                 380
Ile Ser Ser Thr Val Ile Asn Phe Ser Gln Lys Tyr Leu Tyr Gly Ile
385                 390                 395                 400
Asp Ser Cys Val Asn Lys Val Val Ile Ser Pro Asn Ile Tyr Thr Asp
            405                 410                 415
Glu Ile Asn Ile Thr Pro Val Tyr Glu Thr Asn Asn Thr Tyr Pro Glu
            420                 425                 430
Val Ile Val Leu Asp Ala Asn Tyr Ile Asn Glu Lys Ile Asn Val Asn
            435                 440                 445
Ile Asn Asp Leu Ser Ile Arg Tyr Val Trp Ser Asn Asp Gly Asn Asp
            450                 455                 460
Phe Ile Leu Met Ser Thr Ser Glu Glu Asn Lys Val Ser Gln Val Lys
465                 470                 475                 480
Ile Arg Phe Val Asn Val Phe Lys Asp Lys Thr Leu Ala Asn Lys Leu
            485                 490                 495
Ser Phe Asn Phe Ser Asp Lys Gln Asp Val Pro Val Ser Glu Ile Ile
            500                 505                 510
Leu Ser Phe Thr Pro Ser Tyr Tyr Ala Lys Glu Leu Ala Cys Gln Glu
            515                 520                 525
Ile Thr Val Pro Leu Cys Lys Gly Ile Gly Tyr Asn Tyr Thr Tyr Met
            530                 535                 540
```

-continued

```
Pro Asn Gln Phe Asn His Asp Thr Gln Asp Glu Ala Gly Leu Glu Val
545                 550                 555                 560

His Gln Phe Trp Pro Leu Val Glu Ile Gln Cys Ser Pro Asp Leu Lys
            565                 570                 575

Phe Phe Leu Cys Ser Met Tyr Thr Pro Ile Cys Leu Glu Asp Tyr Lys
        580                 585                 590

Lys Pro Leu Pro Pro Cys Arg Ser Val Cys Glu Arg Ala Lys Ala Gly
        595                 600                 605

Cys Ala Pro Leu Met Arg Gln Tyr Gly Phe Ala Trp Pro Asp Arg Met
    610                 615                 620

Arg Cys Asp Arg Leu Pro Glu Gln Gly Asn Pro Asp Thr Leu Cys Met
625                 630                 635                 640

Asp Tyr
```

<210> SEQ ID NO 93
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 93

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
    50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
            100                 105                 110

Gly Ser Asn Gly Phe Val Ser Leu Thr Phe Ser Ile Leu Glu Gly Ile
        115                 120                 125

Asn Ala Ile Ile Glu Val Asp Leu Leu Ser Lys Ser Tyr Lys Leu Leu
    130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
    210                 215                 220

Ala Ser Ala Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255
```

```
Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
    290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
    370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
    450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Ala Lys Glu Leu Ala Cys Gln Glu
        515                 520                 525

Ile Thr Val Pro Leu Cys Lys Gly Ile Gly Tyr Asn Tyr Thr Tyr Met
    530                 535                 540

Pro Asn Gln Phe Asn His Asp Thr Gln Asp Glu Ala Gly Leu Glu Val
545                 550                 555                 560

His Gln Phe Trp Pro Leu Val Glu Ile Gln Cys Ser Pro Asp Leu Lys
                565                 570                 575

Phe Phe Leu Cys Ser Met Tyr Thr Pro Ile Cys Leu Glu Asp Tyr Lys
            580                 585                 590

Lys Pro Leu Pro Pro Cys Arg Ser Val Cys Glu Arg Ala Lys Ala Gly
        595                 600                 605

Cys Ala Pro Leu Met Arg Gln Tyr Gly Phe Ala Trp Pro Asp Arg Met
    610                 615                 620

Arg Cys Asp Arg Leu Pro Glu Gln Gly Asn Pro Asp Thr Leu Cys Met
625                 630                 635                 640

Asp Tyr

<210> SEQ ID NO 94
<211> LENGTH: 642
<212> TYPE: PRT
<213> ORGANISM: Artificial Sequence
```

<220> FEATURE:
<223> OTHER INFORMATION: Synthetic polypeptide

<400> SEQUENCE: 94

```
Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
            20                  25                  30

Tyr Gly Ser Gly Gly Thr Tyr Ala Leu Ser Leu Ser Gln Tyr Asn Met
        35                  40                  45

Gly Ile Asn Ile Glu Leu Ser Glu Ser Asp Val Trp Ile Ile Asp Val
50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Glu Ile Asn Phe Ser Gly Glu Val Asn
                100                 105                 110

Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
            130                 135                 140

Ile Ser Gly Glu Leu Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
                180                 185                 190

Gly Ser Thr Lys Glu Gly Leu Phe Val Ser Glu Leu Pro Asp Val Val
            195                 200                 205

Leu Ile Ser Lys Val Tyr Met Asp Asp Ser Lys Pro Ser Phe Gly Tyr
210                 215                 220

Ala Ser Asn Asn Leu Lys Asp Val Lys Val Ile Thr Lys Asp Asn Val
225                 230                 235                 240

Asn Ile Leu Thr Gly Tyr Tyr Leu Lys Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
            275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Ala Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
                340                 345                 350

Lys Phe Asn Thr Leu Glu Thr Asn Tyr Thr Leu Tyr Val Gly Asn Arg
            355                 360                 365

Gln Asn Met Ile Val Glu Pro Asn Tyr Asp Leu Asp Asp Ser Gly Asp
            370                 375                 380

Ile Ser Ser Thr Val Ile Asn Phe Ser Gln Lys Tyr Leu Tyr Gly Ile
385                 390                 395                 400
```

```
Asp Ser Cys Val Asn Lys Val Ile Ser Pro Asn Ile Tyr Thr Asp
            405                 410                 415

Glu Ile Asn Ile Thr Pro Val Tyr Glu Thr Asn Thr Tyr Pro Glu
        420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
                500                 505                 510

Leu Ser Phe Thr Pro Ser Tyr Tyr Ala Lys Glu Leu Ala Cys Gln Glu
            515                 520                 525

Ile Thr Val Pro Leu Cys Lys Gly Ile Gly Tyr Asn Tyr Thr Tyr Met
            530                 535                 540

Pro Asn Gln Phe Asn His Asp Thr Gln Asp Glu Ala Gly Leu Glu Val
545                 550                 555                 560

His Gln Phe Trp Pro Leu Val Glu Ile Gln Cys Ser Pro Asp Leu Lys
                565                 570                 575

Phe Phe Leu Cys Ser Met Tyr Thr Pro Ile Cys Leu Glu Asp Tyr Lys
                580                 585                 590

Lys Pro Leu Pro Pro Cys Arg Ser Val Cys Glu Arg Ala Lys Ala Gly
            595                 600                 605

Cys Ala Pro Leu Met Arg Gln Tyr Gly Phe Ala Trp Pro Asp Arg Met
610                 615                 620

Arg Cys Asp Arg Leu Pro Glu Gln Gly Asn Pro Asp Thr Leu Cys Met
625                 630                 635                 640

Asp Tyr

<210> SEQ ID NO 95
<211> LENGTH: 642
<212> TYPE: PRT
<213> ORGANISM: Artificial Sequence
<220> FEATURE:
<223> OTHER INFORMATION: Synthetic polypeptide

<400> SEQUENCE: 95

Thr Asn Ile Arg Ile Asn Leu Asp Ser Asn Thr Arg Ser Phe Ile Val
1               5                   10                  15

Pro Ile Ile Thr Thr Glu Tyr Ile Arg Glu Lys Leu Ser Tyr Ser Phe
                20                  25                  30

Tyr Gly Ser Gly Gly Thr Tyr Ala Leu Ser Leu Ser Gln Tyr Asn Met
            35                  40                  45

Gly Ile Asn Ile Glu Leu Ser Glu Ser Asp Val Trp Ile Ile Asp Val
        50                  55                  60

Asp Asn Val Val Arg Asp Val Thr Ile Glu Ser Asp Lys Ile Lys Lys
65                  70                  75                  80

Gly Asp Leu Ile Glu Gly Ile Leu Ser Thr Leu Ser Ile Glu Glu Asn
                85                  90                  95

Lys Ile Ile Leu Asn Ser His Gly Ile Asn Phe Ser Gly Glu Val Asn
                100                 105                 110
```

-continued

```
Gly Ser Asn Gly Phe Val Ser Leu Thr Phe Ser Ile Leu Glu Gly Ile
            115                 120                 125

Asn Ala Ile Ile Glu Val Asp Leu Leu Ser Lys Ser Tyr Lys Leu Leu
130                 135                 140

Ile Ser Gly Glu Asp Lys Ile Leu Met Leu Asn Ser Asn His Ile Gln
145                 150                 155                 160

Gln Lys Ile Asp Tyr Ile Gly Phe Asn Ser Glu Leu Gln Lys Asn Ile
                165                 170                 175

Pro Tyr Ser Phe Val Asp Ser Glu Gly Lys Glu Asn Gly Phe Ile Asn
            180                 185                 190

Gly Ser Thr Lys Glu Gly Leu Phe Val Ser Glu Leu Pro Asp Val Val
        195                 200                 205

Leu Ile Ser Lys Val Tyr Met Asp Asp Ser Lys Pro Ser Phe Gly Tyr
210                 215                 220

Tyr Ser Asn Asn Leu Lys Asp Val Lys Val Ile Thr Lys Asp Asn Val
225                 230                 235                 240

Asn Ile Leu Thr Gly Tyr Tyr Leu Lys Asp Asp Ile Lys Ile Ser Leu
                245                 250                 255

Ser Leu Thr Leu Gln Asp Glu Lys Thr Ile Lys Leu Asn Ser Val His
            260                 265                 270

Leu Asp Glu Ser Gly Val Ala Glu Ile Leu Lys Phe Met Asn Arg Lys
        275                 280                 285

Gly Asn Thr Asn Thr Ser Asp Ser Leu Met Ser Phe Leu Glu Ser Met
290                 295                 300

Asn Ile Lys Ser Ile Phe Val Asn Phe Leu Gln Ser Asn Ile Lys Phe
305                 310                 315                 320

Ile Leu Asp Ala Asn Phe Ile Ile Ser Gly Thr Thr Ser Ile Gly Gln
                325                 330                 335

Phe Glu Phe Ile Cys Asp Glu Asn Asp Asn Ile Gln Pro Tyr Phe Ile
            340                 345                 350

Lys Phe Asn Thr Leu Glu Thr Asn Tyr Thr Leu Tyr Val Gly Asn Arg
        355                 360                 365

Gln Asn Met Ile Val Glu Pro Asn Tyr Asp Leu Asp Asp Ser Gly Asp
370                 375                 380

Ile Ser Ser Thr Val Ile Asn Phe Ser Gln Lys Tyr Leu Tyr Gly Ile
385                 390                 395                 400

Asp Ser Cys Val Asn Lys Val Val Ile Ser Pro Asn Ile Tyr Thr Asp
                405                 410                 415

Glu Ile Asn Ile Thr Pro Val Tyr Glu Thr Asn Asn Thr Tyr Pro Glu
            420                 425                 430

Val Ile Val Leu Asp Ala Asn Tyr Ile Asn Glu Lys Ile Asn Val Asn
        435                 440                 445

Ile Asn Asp Leu Ser Ile Arg Tyr Val Trp Ser Asn Asp Gly Asn Asp
450                 455                 460

Phe Ile Leu Met Ser Thr Ser Glu Glu Asn Lys Val Ser Gln Val Lys
465                 470                 475                 480

Ile Arg Phe Val Asn Val Phe Lys Asp Lys Thr Leu Ala Asn Lys Leu
                485                 490                 495

Ser Phe Asn Phe Ser Asp Lys Gln Asp Val Pro Val Ser Glu Ile Ile
            500                 505                 510

Leu Ser Phe Thr Pro Ser Tyr Tyr Ala Lys Glu Leu Ala Cys Gln Glu
        515                 520                 525

Ile Thr Val Pro Leu Cys Lys Gly Ile Gly Tyr Asn Tyr Thr Tyr Met
```

```
                530             535             540
Pro Asn Gln Phe Asn His Asp Thr Gln Asp Glu Ala Gly Leu Glu Val
545                 550                 555                 560

His Gln Phe Trp Pro Leu Val Glu Ile Gln Cys Ser Pro Asp Leu Lys
                565                 570                 575

Phe Phe Leu Cys Ser Met Tyr Thr Pro Ile Cys Leu Glu Asp Tyr Lys
                580                 585                 590

Lys Pro Leu Pro Pro Cys Arg Ser Val Cys Glu Arg Ala Lys Ala Gly
                595                 600                 605

Cys Ala Pro Leu Met Arg Gln Tyr Gly Phe Ala Trp Pro Asp Arg Met
                610                 615                 620

Arg Cys Asp Arg Leu Pro Glu Gln Gly Asn Pro Asp Thr Leu Cys Met
625                 630                 635                 640

Asp Tyr

<210> SEQ ID NO 96
<211> LENGTH: 10
<212> TYPE: PRT
<213> ORGANISM: homo sapiens

<400> SEQUENCE: 96

His Gln Phe Tyr Pro Leu Val Lys Lys Gln
1               5                   10

<210> SEQ ID NO 97
<211> LENGTH: 10
<212> TYPE: PRT
<213> ORGANISM: homo sapiens

<400> SEQUENCE: 97

His Gln Phe Trp Pro Leu Val Glu Ile Gln
1               5                   10

<210> SEQ ID NO 98
<211> LENGTH: 10
<212> TYPE: PRT
<213> ORGANISM: homo sapiens

<400> SEQUENCE: 98

Ala Glu Phe Ala Pro Leu Val Gln Tyr Gly
1               5                   10

<210> SEQ ID NO 99
<211> LENGTH: 10
<212> TYPE: PRT
<213> ORGANISM: homo sapiens

<400> SEQUENCE: 99

His Glu Phe Ala Pro Leu Val Glu Tyr Gly
1               5                   10

<210> SEQ ID NO 100
<211> LENGTH: 10
<212> TYPE: PRT
<213> ORGANISM: homo sapiens

<400> SEQUENCE: 100

Thr Thr Phe Thr Pro Leu Ile Gln Tyr Gly
1               5                   10

<210> SEQ ID NO 101
```

```
<211> LENGTH: 10
<212> TYPE: PRT
<213> ORGANISM: homo sapiens

<400> SEQUENCE: 101

Glu Pro Phe His Pro Met Val Asn Leu Asp
1               5                   10

<210> SEQ ID NO 102
<211> LENGTH: 10
<212> TYPE: PRT
<213> ORGANISM: homo sapiens

<400> SEQUENCE: 102

Glu His Phe Leu Pro Leu Ala Asn Leu Glu
1               5                   10

<210> SEQ ID NO 103
<211> LENGTH: 8
<212> TYPE: PRT
<213> ORGANISM: homo sapiens

<400> SEQUENCE: 103

Ala Leu Met Asn Lys Phe Gly Phe
1               5

<210> SEQ ID NO 104
<211> LENGTH: 8
<212> TYPE: PRT
<213> ORGANISM: homo sapiens

<400> SEQUENCE: 104

Pro Leu Met Arg Gln Tyr Gly Phe
1               5

<210> SEQ ID NO 105
<211> LENGTH: 8
<212> TYPE: PRT
<213> ORGANISM: homo sapiens

<400> SEQUENCE: 105

Pro Ile Met Glu Gln Phe Asn Phe
1               5

<210> SEQ ID NO 106
<211> LENGTH: 8
<212> TYPE: PRT
<213> ORGANISM: homo sapiens

<400> SEQUENCE: 106

Pro Val Leu Lys Glu Phe Gly Phe
1               5

<210> SEQ ID NO 107
<211> LENGTH: 8
<212> TYPE: PRT
<213> ORGANISM: homo sapiens

<400> SEQUENCE: 107

Lys Leu Met Glu Met Phe Gly Val
1               5

<210> SEQ ID NO 108
<211> LENGTH: 8
<212> TYPE: PRT
```

<213> ORGANISM: homo sapiens

<400> SEQUENCE: 108

Lys Leu Ile Asp Thr Phe Gly Ile
1               5

<210> SEQ ID NO 109
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 109

Lys Ser Tyr Lys Leu Ile Ser Gly Glu Leu Lys Ile Leu Met Leu
1               5                   10                  15

Asn Ser Asn His Ile Gln Gln Lys Ile Asp Tyr Ile Gly Phe Asn Ser
                20                  25                  30

Glu Leu Gln Lys Asn Ile Pro Tyr Ser Phe Val Asp Ser Glu Gly Lys
            35                  40                  45

Glu Asn Gly Phe Ile Asn Gly Ser Thr Lys Glu Gly Leu Phe Val Ser
        50                  55                  60

Glu Leu Pro Asp Val Val
65                  70

<210> SEQ ID NO 110
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 110

Lys Ser Tyr Ser Leu Leu Ser Gly Asp Lys Asn Tyr Leu Ile Ser
1               5                   10                  15

Asn Leu Ser Asn Thr Ile Glu Lys Ile Asn Thr Leu Gly Leu Asp Ser
                20                  25                  30

Lys Asn Ile Ala Tyr Asn Tyr Thr Asp Glu Ser Asn Asn Lys Tyr Phe
            35                  40                  45

Gly Ala Ile Ser Lys Thr Ser Gln Lys Ser Ile Ile His Tyr Lys Lys
        50                  55                  60

Asp Ser Lys
65

<210> SEQ ID NO 111
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 111

Leu Ile Ser Lys Val Tyr Met Asp Asp Ser Lys Pro Ser Phe Gly Tyr
1               5                   10                  15

Tyr Ser Asn Asn Leu Lys Asp Val Lys Val Ile Thr Lys Asp Asn Val
                20                  25                  30

Asn Ile Leu Thr Gly Tyr Tyr Leu Lys Asp Asp Ile Lys Ile Ser Leu
            35                  40                  45

Ser Leu Thr Leu Gln Asp Glu Lys Thr Ile Lys Leu Asn Ser Val His
        50                  55                  60

Leu Asp Glu
65

<210> SEQ ID NO 112
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 112

Asn Ile Leu Glu Phe Tyr Asn Asp Ser Thr Leu Glu Phe Asn Ser Lys
1               5                   10                  15

Asp Phe Ile Ala Glu Asp Ile Asn Val Phe Met Lys Asp Ile Asn
            20                  25                  30

Thr Ile Thr Gly Lys Tyr Tyr Val Asp Asn Asn Thr Asp Lys Ser Ile
        35                  40                  45

Asp Phe Ser Ile Ser Leu Val Ser Lys Asn Gln Val Lys Val Asn Gly
    50                  55                  60

Leu Tyr Leu Asn Glu
65

<210> SEQ ID NO 113
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 113

Ser Gly Val Ala Glu Ile Leu Lys Phe Met Asn Arg Lys Gly Asn Thr
1               5                   10                  15

Asn Thr Ser Asp Ser Leu Met Ser Phe Leu Glu Ser Met Asn Ile Lys
            20                  25                  30

Ser Ile Phe Val Asn Phe Leu Gln Ser Asn Ile Lys Phe Ile Leu Asp
        35                  40                  45

Ala Asn Phe Ile Ile Ser Gly Thr Thr Ser Ile Gly Gln Phe Glu Phe
    50                  55                  60

Ile Cys Asp Glu Asn
65

<210> SEQ ID NO 114
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 114

Ser Val Tyr Ser Ser Tyr Leu Asp Phe Val Lys Asn Ser Asp Gly His
1               5                   10                  15

His Asn Thr Ser Asn Phe Met Asn Leu Phe Leu Asp Asn Ile Ser Phe
            20                  25                  30

Trp Lys Leu Phe Gly Phe Glu Asn Ile Asn Phe Val Ile Asp Lys Tyr
        35                  40                  45

Phe Thr Leu Val Gly Lys Thr Asn Leu Gly Tyr Val Glu Phe Ile Cys
    50                  55                  60

Asp Asn Asn
65

```
<210> SEQ ID NO 115
<211> LENGTH: 10
<212> TYPE: PRT
<213> ORGANISM: homo sapiens

<400> SEQUENCE: 115

His Gln Phe Tyr Pro Leu Val Lys Val Gln
1               5                   10
```

COMPOSITIONS AND METHODS FOR INHIBITING WNT SIGNALING

RELATED APPLICATIONS

This application is a National Stage Filing under 35 U.S.C. § 371 of International Application No. PCT/US2019/013440, filed Jan. 14, 2019, which claims the benefit under 35 U.S.C. § 119(e) to U.S. Provisional Application No. 62/618,042, filed Jan. 16, 2018, entitled "COMPOSITIONS AND METHODS FOR INHIBITING WNT SIGNALING," and U.S. Provisional Application No. 62/670,225, filed May 11, 2018, entitled "COMPOSITIONS AND METHODS FOR INHIBITING WNT SIGNALING," the entire contents of each of which are incorporated herein by reference.

GOVERNMENT SUPPORT

This disclosure was made with government support under grant numbers R01 AI091823, R01 AI125704, R21AI123920, R01 NS080833, and R01 AI132387, awarded by the National Institutes of Health. The government has certain rights in this invention.

REFERENCE TO A SEQUENCE LISTING SUBMITTED AS A TEXT FILE VIA EFS-WEB RELATED APPLICATIONS

The present application contains a Sequence Listing which has been submitted in ASCII format via EFS-Web and is hereby incorporated by reference in its entirety. Said ASCII copy, created on Jun. 15, 2022, 2022, is named C123370130US02-SEQ-ARM and is 536,135 bytes in size.

BACKGROUND

*Clostridium difficile* is an opportunistic pathogen that colonizes the colon in humans when the normal gut microbiome is disrupted. *Clostridium difficile* infection (CDI) leads to disruption of the colonic epithelial barrier, resulting in diarrhea and pseudomembranous colitis. The diseases associated with CDI are caused by two homologous exotoxins, *C. difficile* toxin A (TcdA) and toxin B (TcdB). Of the two toxins, TcdB alone is capable of causing the full-spectrum of diseases in humans. TcdB's entry into colonic epithelial cells is mediated by its binding to Frizzled (FZD). FZD is a family of transmembrane receptors for lipid-modified morphogen Wnt. Binding of TcdB to FZD inhibits Wnt signaling.

SUMMARY

The present disclosure, in some aspects, relate to the co-crystal structure of a TcdB fragment containing the FZD-binding region (sTcdB) in complex with human FZD2 cysteine rich region (CRD2). It was unexpectedly found from the co-crystal structure that an endogenous free fatty acid was buried in a hydrophobic groove in CRD2 and was simultaneously bound by TcdB. The lipid-binding groove is conserved among FZDs and accommodates the palmitoleic acid (PAM) lipid modification of Wnt. TcdB binding to FZD is enhanced when CRD is bound with an endogenous fatty acid or a pre-loaded exogenous PAM. On the other hand, TcdB impedes Wnt binding to CRD by hampering docking of the Wnt PAM, instead of directly competing with Wnt for protein-protein interactions.

Described herein are agents that bind to the lipid binding grove of FZD, e.g., artificial proteins, antibodies small molecules, or TcdB fragments. In some embodiments, such agents block the binding of TcdB to Frizzled. In some embodiments, such agents block the entry of TcdB into epithelial cells. In some embodiments, such agents block the binding of Wnt to FZD. Compositions and methods for treating various diseases (e.g., CDI or cancer) are also provided.

Some aspects of the present disclosure provide isolated polypeptides comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to the amino acid sequence of any one of SEQ ID NOs: 2 and 19-25. In some embodiments, the isolated polypeptide comprises 1-50 conservative amino acid substitution in any one of SEQ ID NOs: 2 and 19-25. In some embodiments, the isolated polypeptide comprises the amino acid sequence of any one of SEQ ID NOs: 2 and 19-25. In some embodiments, the isolated polypeptide consists of the amino acid sequence of any one of SEQ ID NOs: 2 and 19-25.

In some embodiments, the polypeptide is cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combinations thereof. In some embodiments, the isolated polypeptide comprises a modification at the C-terminus or at the N-terminus.

In some embodiments, the isolated polypeptide further comprises a fusion domain. In some embodiments, the fusion domain is selected from the group consisting of polyhistidine, Glu-Glu, glutathione S transferase (GST), thioredoxin, protein A, protein G, an immunoglobulin heavy chain constant region (Fc), maltose binding protein (MBP), or human serum albumin. In some embodiments, the fusion domain is an Fc portion of human IgG1. In some embodiments, the Fc portion of human IgG1 comprises the amino acid sequence of SEQ ID NO: 7. In some embodiments, the isolated polypeptide comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to the amino acid sequence of any one of SEQ ID NOs: 8, 9, and 26-39. In some embodiments, the isolated polypeptide comprises the amino acid sequence of any one of SEQ ID NOs: 8, 9, and 26-39. In some embodiments, the isolated polypeptide consists of the amino acid sequence of any one of SEQ ID NOs: 8, 9, and 26-39.

In some embodiments, the fusion domain comprises a cysteine-rich domain (CRD) of Frizzled. In some embodiments, the CRD comprises the amino acid sequence of any one of SEQ ID NO: 3-6. In some embodiments, the isolated polypeptide comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to the amino acid sequence of any one of SEQ ID NO: 10-17 and 40-95. In some embodiments, the isolated polypeptide comprises the amino acid sequence of any one of SEQ ID NO: 10-17 and 39-95. In some embodiments, the isolated polypeptide consists of the amino acid sequence of any one of SEQ ID NO: 10-17 and 40-95.

In some embodiments, the fusion domain comprises a therapeutic agent. In some embodiments, the therapeutic agent is an anti-bacterial agent or an antibody for a Frizzled co-receptor. In some embodiments, the anti-bacterial agent is an antibiotic. In some embodiments, the Frizzled co-receptor is lipoprotein receptor-related protein (LRP)-5/6, receptor tyrosine kinase (RTK), or tyrosine-protein kinase transmembrane receptor (ROR2).

In some embodiments, the isolated polypeptide is attached to a polymer. In some embodiments, the polymer prolongs the serum half-life of the isolated polypeptide. In some embodiments, the polymer prolongs the shelf-life of the isolated polypeptide.

In some embodiments, the polypeptide binds to Frizzled. In some embodiments, the polypeptide reduces Wnt signaling.

Other aspects of the present disclosure provide nucleic acid molecules comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity of any one of SEQ ID NO: 2 and 8-95. Vectors comprising such nucleic acids are provided. Cells comprising such nucleic acid molecules or vectors are also provided.

Other aspects of the present disclosure provide methods of producing the isolated polypeptide the method comprising the steps of culturing the cells described herein under conditions wherein said polypeptide is produced. In some embodiments, the method further comprises recovering the polypeptide from the culture.

Further provided herein are agents that binds to a lipid-binding groove of Frizzled. In some embodiments, the agent is an artificial protein. In some embodiments, the agent is an antibody. In some embodiments, the agent is a small molecule. In some embodiments, the agent comprises a polypeptide comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to the amino acid sequence of any one of SEQ ID NOs: 2 and 19-25. In some embodiments, the agent comprises a polypeptide comprising the amino acid sequence of SEQ ID NOs: 2 and 19-25. In some embodiments, the agent blocks binding of TcdB to Frizzled. In some embodiments, the agent blocks binding of Wnt to Frizzled.

Other aspects of the present disclosure provide compositions comprising the isolated polypeptide or the agent described herein. In some embodiments, the composition is a pharmaceutical composition. In some embodiments, the composition further comprises a pharmaceutically acceptable carrier.

Other aspects of the present disclosure provide methods of treating *Clostridium difficile* infection (CDI), the method comprising administering to a subject in need thereof, a therapeutically effective amount of the isolated polypeptide, the agent, or the pharmaceutical composition described herein. In some embodiments, the method further comprises administering to the subject an effective amount of a second agent that induces Wnt signaling downstream of Frizzled in a cell. In some embodiments, the second agent is a GSK-3 inhibitor. In some embodiments, the GSK-3 inhibitor is Lithium (LiCl), CHIR99021, SB 216763, BIO, TCS 2002, TC-G 24, TWS 119, SB 415286, A 1070722, AR-A 014418, L803-mts, or combination thereof. In some embodiments, the method further comprises administering to the subject an effective amount of a third agent that inhibits the cysteine protease activity of TcdB in a cell. In some embodiments, the third agent is ebselen. In some embodiments, the method further comprises administering to the subject a Frizzled antibody.

Further provided herein are methods of treating cancer, the method comprising administering to a subject in need thereof, a therapeutically effective amount of the isolated polypeptide, the agent, or the pharmaceutical composition described herein. In some embodiments, the method further comprises administering to the subject an effective amount of a second agent that blocks Wnt signaling. In some embodiments, the second agent is a Dkk family protein, a Secreted Frizzled Related Protein (sFRP), Draxin, IGFBP-4, SOST/Sclerostin, USAG1, WIF-1, or a Frizzled antibody.

In some embodiments, the cancer is metastatic cancer. In some embodiments, the cancer is osteosarcoma. In some embodiments, the cancer is breast cancer, stomach cancer, pancreatic cancer, or prostate cancer. In some embodiments, the breast cancer is triple negative breast cancer. In some embodiments, the method further comprises administering to the subject a therapeutically effective amount of an anti-cancer agent.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 1A) Schematic diagrams showing the domain structures of TcdB and FZD2, as well as the two interacting fragments used in this study. GTD: glucosyltransferase domain; CPD: cysteine protease domain; Delivery/RBD: delivery and receptor-binding domain; CROPs: combined repetitive oligopeptides domain; CRD: cysteine-rich domain; 7TMs: 7 transmembrane helices. (FIG. 1B) Cartoon representation of the complex of sTcdB and CRD2, and PAM in a grey sphere model. An N-acetyl glucosamine (NAG) due to N-linked glycosylation on CRD2-N53 is shown as sticks. (FIG. 1C) Superimposed structures of the sTcdB-CRD2 and the Wnt8-CRD8 complexes. The two distinct interfaces between Wnt8 and CRD8 are highlighted in circles (site 1 & 2). (FIG. 1D) Electron density of the PAM bound between sTcdB and CRD2. An omit electron density map contoured at 2.5 σ was overlaid with the final refined model. (FIG. 1E) A close-up view of the lipid-binding grooves. The PAM molecules bound in the sTcdB-CRD2 and the Wnt8-CRD8 complexes are shown as dark grey and light grey sticks, respectively.

FIGS. 2A to 2F. sTcdB recognizes CRD2 through combined fatty acid- and peptide-mediated interactions. (FIG. 2A) An open-book view of the sTcdB-CRD2 interface. Residues that participate in protein-protein, protein-lipid, or both are dark grey. (FIGS. 2B, 2C) A PAM molecule simultaneously interacts with CRD2 (FIG. 2B) and sTcdB (FIG. 2C). Key PAM-binding residues and PAM are shown as stick models. (FIGS. 2D, 2E) Two neighboring protein-mediated interfaces between sTcdB and CRD2, which surround the lipid-binding groove in CRD2. (FIG. 2F) Amino acid sequence alignment among the ten human FZDs within the sTcdB-interacting region. Invariable residues are shaded grey. CRD2 residues that bind to PAM and sTcdB are labeled as cubes and ovals, respectively.

(FIG. 3A) Mutations in sTcdB that disrupt its interactions with PAM and/or CRD2 impaired sTcdB (50 nM) binding to HeLa cells overexpressing FZD2. (FIG. 3B) When expressed in HeLa cells, the wild type (WT) but not the mutant forms of FZD2 mediated robust binding of full-length TcdB (10 nM) on cell surfaces. K127A, K127E, and Y77A are mutations in CRD2 that disrupt protein-mediated interactions with TcdB. F76A, F76D, and L79D are mutations that are in the core lipid-binding groove in CRD2. F130D and F128D are mutations in the two surface residues that partly interact with PAM and TcdB. Proper glycosylation of FZD2 was not detected in the four mutations that have disrupted lipid-binding groove (highlighted in an orange box). (FIG. 3C) These FZD2 mutants failed to reach cell surfaces as examined by detecting biotinylated FZD2 on cell surfaces. (FIG. 3D) FZD2-K127A/E mutants were capable of mediating Wnt signaling to a lever similar to the WT. (FIG. 3E) The WT sTcdB, but not the mutants (F1597G, M1437D/L1493A), inhibited signaling by Wnt3A CM in HEK293T cells as measured by TOPFLASH reporter assay. Data are mean±s.d., n=6, *p<0.001, t-test. (FIG. 3F) The sensitivity of FZD1/2/7 triple knockout HeLa cells and CSPG4 KO HeLa cells to full length WT TcdB and TcdB$^{GFE}$ was determined by cell-rounding assays. $CR_{50}$ is defined as the toxin concentration that induces 50% of cells to become round in 24 hours.

(FIGS. 4A, 4B) Pre-loading FZD5-CRD with palmitoleic acid (FIG. 4A) or Wnt3A (FIG. 4B) enhanced its binding to sTcdB based on pull-down assays. (FIG. 4C) Pre-loading Wnt3A to FZD5-CRD enhanced its binding to sTcdB based on BLI assays. The enhancement was minimal for sTcdB-F1597G. Sequential loading of different proteins to the biosensor and binding dissociation are shown. (FIG. 4D) Pre-loading Wnt3A to CRD2 did not interfere with subsequent binding of sTcdB. (FIG. 4E) Pre-loading CRD2 with sTcdB impeded subsequent binding of Wnt3A. (FIG. 4F) Two different configurations of CRD dimers that are proposed to be involved in Wnt activation are superimposed to the sTcdB-CRD2 complex. Either of the proposed CRD dimer assemblies is incompatible with the sTcdB-CRD2 complex due to steric competition. (FIG. 4G) A proposed model for Wnt signaling inhibition by TcdB. (FIG. 4H) Superimposed structures of the TcdB-FBD-CRD2 and the Wnt8-CRD8 complexes. The two distinct interfaces between Wnt8 and CRD8 are highlighted in circles (site 1 & 2).

FIGS. 5A to 5F. Binding of sTcdB variants to CRD2. Representative binding curves of sTcdB variants to recombinant Fc-tagged CRD2 examined by BLI assays. (FIG. 5A) the WT sTcdB bound to CRD2 with a high affinity. Four sTcdB mutants tested in this study displayed significantly weakened binding to CRD2: sTcdB-D1501A (FIG. 5B), sTcdB-Y1509A/N1511A (FIG. 5C), sTcdB-Y1509A/Q1599A (FIG. 5D), and sTcdB-L1433D (FIG. 5E). All other mutants tested did not show detectable binding to CRD2. The concentrations of sTcdB variants were labeled in FIGS. 5A to 5F. Kinetic analysis results are summarized in (FIG. 5F).

(FIGS. 6A, 6B) The L-shape sTcdB could be divided into two subdomains composed of residues 1285-1509 and 1510-1804, respectively. These two subdomains of TcdB (light grey) and TcdA (dark grey) form slightly different angles. The root-mean-square deviations are ~1.26 Å, ~1.18 Å, and ~3.28 Å when the two subdomains are aligned separately (FIG. 6A) or as a whole (FIG. 6B). (FIG. 6C) Amino acid sequence alignment between sTcdB and TcdA in the CRD2-binding area. The secondary structures of sTcdB are shown on the top. Residues of sTcdB that bind to PAM and CRD2 are labeled as cubes and ovals, respectively.

(FIG. 8A) FZD7CRD-Myc-GPI was stably expressed in the HeLa/FZD7CRD-GPI cell line as detected by the anti-Myc antibody. (FIG. 8B) sTcdB variants (~50 nM) that carry mutations to disrupt its interactions with PAM and/or CRD2 failed to bind HeLa/FZD7CRD-GPI cells when compared to the WT sTcdB. Cell lysates were harvested and subjected to immunoblot analysis c, The binding of sTcdB variants (~1.5 µM) to the immobilized His-tagged CRD2 was examined using pull-down assays. Samples were analyzed by SDS-PAGE and Coomassie Blue staining. The pull-down assays (FIG. 8C) and the BLI assays (FIG. 5A to 5F) were more sensitive than the cell-based assays (FIG. 3A, FIG. 8B) in detecting weak interactions between CRD2 and sTcdB mutants. This is likely due to the relatively low concentration of FZD2/5 expressed on the cell surface, while the pull-down and BLI assays were using higher concentration of highly purified CRD2 that was immobilized on the matrix.

(FIG. 9A) DVL2 phosphorylation induced by Wnt3A CM in WT and FZD1/2/7 triple KO HeLa cells. Asteroids (*) indicate the phosphorylated DVL2. (FIG. 9B) DVL2 phosphorylation induced by Wnt3A CM in FZD1/2/7 triple KO cells expressing WT FZD2 or the K127A/E mutants. (FIG. 9C) sTcdB (40 nM) was able to inhibit the phosphorylation of DVL2 induced by Wnt3A CM in HEK293T cells. (FIG. 9D) Wnt-induced DVL2 phosphorylation was inhibited by WT sTcdB, but not the F1597G or M1437D/L1493A mutants.

(FIG. 10A) Binding of full-length TcdB to CRD5 was enhanced by pre-loading Wnt3A to CRD5 in BLI assays. CRD5-Fc and Wnt3A were pre-mixed and loaded to the biosensor, followed by sequential exposure to 1 µM TcdB. Binding of sTcdB to CRDs of FZD4 (FIG. 10B), FZD8 (FIG. 10C), and FZD9 (FIG. 10D) was enhanced by pre-loading Wnt3A to CRDs in BLI assays. CRDs-Fc and Wnt3A were pre-mixed and loaded to the biosensor, followed by sequential exposure to 5 µM sTcdB.

(FIG. 14A) WT TcdB, TcdB$^{GFE}$, or the saline control was injected into the cecum of WT mice in vivo. The cecum tissues were harvested 12 hours later. The representative cecum tissues were shown, and the weight of each cecum was measured and plotted. (Boxes represent mean±standard error of the mean (s.e.m.), and the bars represent s.d., Mann-Whitney). (FIGS. 14B and 14C) Cecum tissue sections were subjected to hematoxylin and eosin (H&E) staining. The representative images were shown in panel B. The histological scores (panel C) were assessed based on disruption of the epithelia, hemorrhagic congestion, mucosal edema, and inflammatory cell infiltration. (Data are mean±s.d., Mann-Whitney). Scale bar, 100 µm. (FIG. 14D) Immunofluorescent staining of epithelial cell junction marker Claudin-3 in ceca from mice injected with saline, TcdB, or TcdB$^{GFE}$.Scale bar, 50 µm.

(FIG. 15A) Two different configurations of CRD dimers are proposed to be involved in Wnt activation. (FIG. 15B) These two proposed CRD dimer assemblies are superimposed to the TcdB-FBD-CRD2 complex. Both are incompatible with the TcdB-FBD-CRD2 complex due to steric competition.

DETAILED DESCRIPTION OF CERTAIN EMBODIMENTS

Figure 1A:
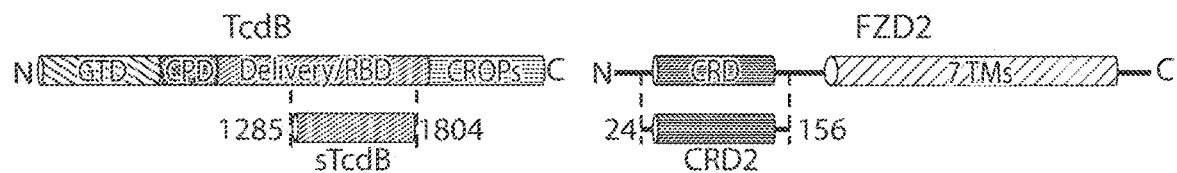
FIGS. 1A to 1E. Overall structure of sTcdB in complex with CRD2.

*Clostridium difficile* infection (CDI) is the most common cause of antibiotic-associated diarrhea and gastroenteritis-associated death across developed countries[1-6]. *C. difficile* toxin B (TcdB) is a major virulent factor responsible for diseases associated with CDI. TcdB enters cells via receptor-mediated endocytosis and inactivates small GTPases by glucosylation of a key residue, resulting in actin cytoskeleton disruption and cell death[3,7-9].

The Wnt receptor frizzled family (FZDs) are major receptors for TcdB in the colonic epithelium[10]. TcdB binds to the conserved Wnt-binding region of FZDs known as the cysteine-rich domain (CRD), with the highest affinity toward FZD1, 2, and 7. The co-crystal structure of a TcdB fragment containing the FZD-binding region in complex with human FZD2-CRD (CRD2) is presented in the present disclosure.

Unexpectedly, an endogenous free fatty acid was found to be buried in a hydrophobic groove in CRD2 and simultaneously bound by TcdB. A network of hydrophobic interactions between TcdB and the fatty acid, combined with the direct TcdB-CRD2 interactions, form the basis for high affinity and specificity binding of TcdB to CDR2. This lipid-binding groove in CRD is largely conserved among FZDs, which accommodates the palmitoleic acid (PAM) lipid modification of Wnt[11-13]. TcdB binding to FZD is enhanced when CRD is bound with an endogenous fatty acid or a pre-loaded exogenous PAM. Moreover, multiple FZDs when pre-bound with Wnt show elevated binding of TcdB, suggesting that the Wnt PAM docked into the lipid-binding groove of FZDs can be used by TcdB to strengthen binding. On the other hand, TcdB impedes Wnt binding to CRD by hampering docking of the Wnt PAM, instead of directly competing with Wnt for protein-protein interactions. These findings establish the molecular mechanism by which TcdB exploits a conserved lipid-binding function of FZD-CRDs that is crucial for Wnt signaling for host recognition.

Some aspects of the present disclosure provide agents that bind to the lipid binding grove of Frizzled (FZD). "Frizzled (FZD)" refers a family of trans-membrane protein receptors involved in Wnt signaling. These receptors span the plasma membrane seven times and constitute a distinct family of G-protein coupled receptors (GPCRs). FZDs play key roles in governing cell polarity, embryonic development, formation of neural synapses, cell proliferation, and many other processes in developing and adult organisms, many of which relate to the Wnt signaling pathways.

The Wnt signaling pathways are a group of signal transduction pathways comprising proteins that pass signals into a cell through cell surface receptors. Three Wnt signaling pathways have been characterized: the canonical Wnt pathway, the noncanonical planar cell polarity pathway, and the noncanonical Wnt/calcium pathway. All three pathways are activated by binding a Wnt-protein ligand to a Frizzled family receptor, which passes the biological signal to proteins inside the cell. The canonical Wnt pathway leads to regulation of gene transcription. The noncanonical planar cell polarity pathway regulates the cytoskeleton that is responsible for the shape of the cell. The noncanonical Wnt/calcium pathway regulates calcium inside the cell. Wnt signaling pathways use either nearby cell-cell communication (paracrine) or same-cell communication (autocrine).

Wnt signaling was first identified for its role in carcinogenesis, then for its function in embryonic development. Wnt signaling also controls tissue regeneration in adult bone marrow, skin and intestine. For example, Wnt signaling is essential for maintaining colonic stem cells in vivo, which continuously give rise to new epithelial cells. The health of stem cells is critical for maintaining and repairing the epithelium, which turns over at an extraordinary rate: the entire colonic epithelium undergoes complete replacement every 5-7 days. Thus, as illustrated in the present disclosure, during *Clostridium difficile* infection, inhibition of Wnt signaling pathway led to depletion of colonic stem cells and greatly amplified the damage to the epithelium.

It was previously demonstrated that TcdB binds to FZD in a cysteine-rich domain (CRD) and the binding mediates the entry of TcdB into cells (e.g., Tao et al., Nature 538(7625): 350-355, 2016, incorporated herein by reference). Both TcdB and Wnt bind to an N-terminal extracellular cysteine-rich domain of FZDs (FZD-CRD). The amino acid sequences of the CRDs of FZD 1, 2, 7 and 8 are provided herein in Table 4.

A "lipid binding groove" in a FZD protein, as described herein, comprises at lease residues corresponding to Q75, F76, M125, F130, P78, L79, V82, L124 and F128 of FZD2 (SEQ ID NO: 4). Without wishing to be bound by scientific theory, as demonstrated in FIG. 2B, the lipid binding groove binds to a lipid (PAM) mainly through hydrophobic interactions: residues Q75, F76, M125, and F130 stabilize the carboxylic group end of PAM, and residues P78, L79, V82, L124 and F128 stabilize the hydrocarbon chain of PAM. One skill in the art can identify the corresponding residues in other FZDs that constitute the lipid binding groove by aligning the amino acid sequences of different FZDs, e.g., using a sequence alignment software.

It was found unexpectedly that the binding of TcdB to a FZD-CRD is enhanced in the presence of a lipid in the lipid binding groove. However, binding of the lipid and/or TcdB to the lipid binding groove prevents the docking of the PAM on Wnt, which is added to Wnt by post-translational modification, in turn blocks Wnt from binding to FZD. Other agents can be designed to bind to the lipid binding groove of a FZD. In some embodiments, such agent blocks Wnt from binding to FZD and blocks Wnt signaling. Methods and tools for designing an agent that can bind to a binding site of known structure in a protein (e.g., the lipid binding groove of FZD) are available to those skilled in the art. For example, one skilled in the art can use a molecular design software that is capable of carrying themolecular modeling. Non-limiting examples of molecular designing software included: Abalone, AMBER, Ascalaph Designer, BOSS, DENEB, Discovery Studio, DOCK, Firefly, FoldX, HyperChem with HMHN and DSHC, Lead Finder, Ligand-Scout, Maestro, MAPS, Materials Studio, Molecular Operating Environment, SAMSON, Scigress, Spartan, Tinker, and Winmostar. Agents that bind to a binding site of known structure in a protein (e.g., the lipid binding groove of FZD) can be designed de novo, or be generated via modifying existing molecules. Such agents may be, without limitation, peptides, artificial proteins, antibodies, nucleic acids, or small molecules.

In some embodiments, the agent is an artificial protein. An "artificial protein," as used herein, refers to a protein that is not encoded by a naturally occurring genetic sequence. An artificial protein mimics the function and structure of true proteins. Further, while the building blocks of a naturally protein are amino acids, an artificial protein may contain amino acids, nucleotides, nucleotide analogs, and other chemical moieties. Different types of artificial proteins and their design have been described in the art, e.g., in Razeghifard et al., Curr Protein Pept Sci. 2007 Feb.; 8(1):3-18; and Lou et al., Nature Communications 7, Article number: 12294 2016, incorporated herein by reference.

In some embodiments, the agent is an antibody. An "antibody" or "immunoglobulin (Ig)" is a large, Y-shaped protein produced mainly by plasma cells that is used by the immune system to neutralize an exogenous substance (e.g., a pathogens such as bacteria and viruses). Antibodies are classified as IgA, IgD, IgE, IgG, and IgM. "Antibodies" and "antibody fragments" include whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. An antibody may be a polyclonal antibody or a monoclonal antibody.

The basic 4-chain antibody unit is a heterotetrameric glycoprotein composed of two identical L chains and two H chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the a and 7 chains and four CH domains for and F isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, (e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6, incorporated herein by reference).

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated a, δ, ε, γ and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, Md. (1991), incorporated herein by reference). The constant domains are not involved directly in binding an antibody to an antigen, but exhibit various effector functions, such as participation of the antibody in antibody dependent cellular cytotoxicity (ADCC).

Methods of producing antibodies (e.g., monoclonal antibodies or polyclonal antibodies) are known in the art. For example, a polyclonal antibody may be prepared by immunizing an animal, preferably a mammal, with an allergen of choice followed by the isolation of antibody-producing B-lymphocytes from blood, bone marrow, lymph nodes, or spleen. Alternatively, antibody-producing cells may be isolated from an animal and exposed to an allergen in vitro against which antibodies are to be raised. The antibody-producing cells may then be cultured to obtain a population of antibody-producing cells, optionally after fusion to an immortalized cell line such as a myeloma. In some embodiments, as a starting material B-lymphocytes may be isolated from the tissue of an allergic patient, in order to generate fully human polyclonal antibodies. Antibodies may be produced in mice, rats, pigs (swine), sheep, bovine material, or other animals transgenic for the human immunoglobulin genes, as starting material in order to generate fully human polyclonal antibodies. In some embodiments, mice or other animals transgenic for the human immunoglobulin genes (e.g. as disclosed in U.S. Pat. No. 5,939,598), the animals may be immunized to stimulate the in vivo generation of specific antibodies and antibody producing cells before preparation of the polyclonal antibodies from the animal by extraction of B lymphocytes or purification of polyclonal serum.

Monoclonal antibodies are typically made by cell culture that involves fusing myeloma cells with mouse spleen cells immunized with the desired antigen (i.e., hyrbidoma technology). The mixture of cells is diluted and clones are grown from single parent cells on microtitre wells. The antibodies secreted by the different clones are then assayed for their ability to bind to the antigen (with a test such as ELISA or Antigen Microarray Assay) or immuno-dot blot. The most productive and stable clone is then selected for future use.

In some embodiments, the antibodies described herein are "humanized" for use in human (e.g., as therapeutics). "Humanized" forms of non-human (e.g., rodent) antibodies are chimeric antibodies that contain minimal sequence derived from the non-human antibody. Humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In some embodiments, the agent is a small molecule. A "small molecule" refers to an organic compound, whether naturally-occurring or artificially created (e.g., via chemical synthesis) that has a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, small molecules are monomeric organic compounds that have a molecular weight of less than about 1500 g/mol. In some embodiments, the molecular weight of the small molecule is less than about 1000 g/mol or less than about 500 g/mol. In some embodiments, the small molecule is a drug, for example, a drug that has already been deemed safe and effective for use in humans or animals by the appropriate governmental agency or regulatory body. Nonlimiting examples of a small molecule include lipids, monosaccharides, second messengers, other natural products and metabolites, as well as drugs and other xenobiotics.

A "lipid" refers to a group of naturally occurring molecules that include fats, waxes, sterols, fat-soluble vitamins (such as vitamins A, D, E, and K), monoglycerides, diglycerides, triglycerides, phospholipids, and others. A "monosaccharide" refers to a class of sugars (e.g., glucose) that cannot be hydrolyzed to give a simpler sugar. Non-limiting examples of monosaccharides include glucose (dextrose), fructose (levulose) and galactose. A "second messenger" is a molecule that relay signals received at receptors on the cell surface (e.g., from protein hormones, growth factors, etc.) to target molecules in the cytosol and/or nucleus. Nonlimiting examples of second messenger molecules include cyclic AMP, cyclic GMP, inositol trisphosphate, diacylglycerol, and calcium. A "metabolite" is a molecule that forms as an intermediate produce of metabolism. Non-limiting examples of a metabolite include ethanol, glutamic acid, aspartic acid, 5' guanylic acid, Isoascorbic acid, acetic acid, lactic acid, glycerol, and vitamin B2. A "xenobiotic" is a foreign chemical substance found within an organism that is not normally naturally produced by or expected to be present within. Non-limiting examples of xenobiotics include drugs, antibiotics, carcinogens, environmental pollutants, food additives, hydrocarbons, and pesticides.

In some embodiments, the agent reduces binding of TcdB to FZD (e.g., by at least 20%), compared to without the agent. In some embodiments, the agent reduces binding of TcdB to FZD by at least 20%, at least 30%, at least 40%, at least 50%, at least 60%, at least 70%, at least 80%, at least 90%, at least 95%, at least 99%, or more, compared to without the agent. In some embodiments, the agent reduces binding of TcdB to FZD by 20%, 30%, 40%, 50%, 60%, 70%, 80%, 90%, 95%, 99%, or more, compared to without the agent.

In some embodiments, the agent reduces binding of Wnt to FZD (e.g., by at least 20%), compared to without of the agent. In some embodiments, the agent reduces binding of Wnt to FZD by at least 20%, at least 30%, at least 40%, at least 50%, at least 60%, at least 70%, at least 80%, at least 90%, at least 95%, at least 99%, or more, compared to without the agent. In some embodiments, the agent reduces binding of Wnt to FZD by 20%, 30%, 40%, 50%, 60%, 70%, 80%, 90%, 95%, 99%, or more, compared to without the agent.

In some embodiments, the agent reduces Wnt signaling (e.g., by at least 20%), compared to without the agent. In some embodiments, the agent reduces Wnt signaling by at least 20%, at least 30%, at least 40%, at least 50%, at least 60%, at least 70%, at least 80%, at least 90%, at least 95%, at least 99%, or more, compared to without the agent. In some embodiments, the agent Wnt signaling by 20%, 30%, 40%, 50%, 60%, 70%, 80%, 90%, 95%, 99%, or more, compared to without the agent.

In some embodiments, the agent that binds to the lipid binding groove of FZD is a polypeptide derived from TcdB. It was demonstrated herein that a short TcdB fragment, corresponding to amino acids 1285-1804 of full length, wild type TcdB (SEQ ID NO: 1), binds to the lipid binding groove of FZD. This fragment is designated TcdB$_{1285-1804}$ (also termed "sTcdB" or "TcdB-FBD" SEQ ID NO: 2). Several sTcB variants are also found to bind the lipid binding groove of FZD.

Accordingly, some aspects of the present disclosure provide isolated polypeptides that are at least 80% identical to the TcdB fragments described herein. In some embodiments, the isolated polypeptides are used as the agent that binds to the lipid binding groove of FDZ. "An isolated polypeptide," as used herein, refers to a polypeptide that is isolated from, or is otherwise substantially free of (e.g., at least 80%, 90%, 95%, 97%, 99%, or 99.5% free of), other protein(s) and/or other polypeptide(s) (e.g., TcdB polypeptide species). In some embodiments, the isolated polypeptides is 100% free of other protein(s) and/or other polypeptide(s) (e.g., TcdB polypeptide species).

In some embodiments, the isolated polypeptide comprises an amino acid sequence of any one of SEQ ID NOs: 2 and 19-25. In some embodiments, the isolated polypeptide does not comprise the amino acid of SEQ ID NO: 1. In some embodiments, the isolated polypeptide consists of the amino acid sequence of any one of SEQ ID NOs: 2 and 19-25. In some embodiments, the isolated polypeptide comprises an amino acid sequence that is at least 80% identical to any one of SEQ ID NOs: 2 and 19-25. For example, the isolated polypeptide may comprise an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NOs: 2 and 19-25. In some embodiments, the isolated polypeptide comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% identical to any one of SEQ ID NOs: 2 and 19-25.

In some embodiments, the isolated polypeptide comprises amino acid substitutions, compared to the native amino acid sequence of the sTcdB (SEQ ID NO: 2) or any of the TcdB variants that also binds to the lipid binding groove of FZD (e.g., any one of SEQ ID Nos: 19-25). In some embodiments, the amino acid substitution is a conservative amino acid substitution. A "conservative amino acid substitution", refers to an amino acid substitution that changes an amino acid to a different amino acid with similar biochemical properties (e.g. charge, hydrophobicity and size). Conservative substitutions of amino acids include, for example, substitutions made amongst amino acids within the following groups: (a) M, I, L, V; (b) F, Y, W; (c) K, R, H; (d) A, G; (e) S, T; (f) Q, N; and (g) E, D. Conservative amino acid substitutions do not alter the relative charge or size characteristics of the protein in which the amino acid substitutions are made. Conservative amino acid substitutions typically do not change the overall structure of the peptide and/or the type of amino acid side chains available for forming van der Waals bonds with a binding partner. In some embodiments, the isolated polypeptide may comprise 1-100 conservative amino acid substitutions, compared to SEQ ID NO: 2. For example, the isolated polypeptide may comprise 1-100, 1-95, 1-90, 1-85, 1-80, 1-75, 1-70, 1-65, 1-60, 1-55, 1-50, 1-45, 1-40, 1-35, 1-30, 1-25, 1-20, 1-15, 1-10, 1-5, 5-100, 5-95, 5-90, 5-85, 5-80, 5-75, 5-70, 5-65, 5-60, 5-55, 5-50, 5-45, 5-40, 5-35, 5-30, 5-25, 5-20, 5-15, 5-10, 10-100, 10-95, 10-90, 10-85, 10-80, 10-75, 10-70, 10-65, 10-60, 10-55, 10-50, 10-45, 10-40, 10-35, 10-30, 10-25, 10-20, 10-15, 15-100, 15-95, 15-90, 15-85, 15-80, 15-75, 15-70, 15-65, 15-60, 15-55, 15-50, 15-45, 15-40, 15-35, 15-30, 15-25, 15-20, 20-100, 20-95, 20-90, 20-85, 20-80, 20-75, 20-70, 20-65, 20-60, 20-55, 20-50, 20-45, 20-40, 20-35, 20-30, 20-25, 25-100, 25-95, 25-90, 25-85, 25-80, 25-75, 25-70, 25-65, 25-60, 25-55, 25-50, 25-45, 25-40, 25-35, 25-30, 30-100, 30-95, 30-90, 30-85, 30-80, 30-75, 30-70, 30-65, 30-60, 30-55, 30-50, 30-45, 30-40, 30-35, 35-100, 35-95, 35-90, 35-85, 35-80, 35-75, 35-70, 35-65, 35-60, 35-55, 35-50, 35-45, 35-40, 40-100, 40-95, 40-90, 40-85, 40-80, 40-75, 40-70, 40-65, 40-60, 40-55, 40-50, 40-45, 45-100, 45-95, 45-90, 45-85, 45-80, 45-75, 45-70, 45-65, 45-60, 45-55, 45-50, 50-100, 50-95, 50-90, 50-85, 50-80, 50-75, 50-70, 50-65, 50-60, 50-55, 55-100, 55-95, 55-90, 55-85, 55-80, 55-75, 55-70, 55-65, 55-60, 60-100, 60-95, 60-90, 60-85, 60-80, 60-75, 60-70, 60-65, 65-100, 65-95, 65-90, 65-85, 65-80, 65-75, 65-70, 70-100, 70-95, 70-90, 70-85, 70-80, 70-75, 75-100, 75-95, 75-90, 75-85, 75-80, 80-100, 80-95, 80-90, 80-85, 85-100, 85-95, 85-90, 90-100, 90-95, or 95-100 conservative amino acid substitutions, compared to SEQ ID NO: 2. In some embodiments, the isolated polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 conservative amino acid substitutions, compared to SEQ ID NO: 2. Amino acid substitution can be achieved during chemical synthesis of the peptide by adding the desired substitute amino acid at the appropriate sequence in the synthesis process. Alternatively, molecular biology methods (e.g., recombination DNA technology) can be used.

In some embodiments, the isolated polypeptides comprises modifications. Polypeptides comprising modifications have additional features other than amino acid contents. As used herein, a "modification" or "derivative" of a peptide results in a modified or derivatized polypeptide, which is a form of a given peptide that is chemically modified relative to the reference peptide, the modification including, but not limited to, oligomerization or polymerization, modifications of amino acid residues or peptide backbone, cross-linking, cyclization, conjugation, pegylation, glycosylation, acetylation, phosphorylation, acylation, carboxylation, lipidation, thioglycolic acid amidation, alkylation, methylation, polyglycylation, glycosylation, polysialylation, adenylylation, PEGylation, fusion to additional heterologous amino acid sequences, or other modifications that substantially alter the stability, solubility, or other properties of the peptide while substantially retaining the activity of the polypeptides described herein. The isolated polypeptides comprising such modifications, are cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combination thereof.

In some embodiments, the isolated polypeptide that contains a modification contains non-amino acid elements, such as polyethylene glycols, lipids, poly- or mono-saccharide, and phosphates. In some embodiments, the modification is at the C-terminus (e.g., C-terminal amidation) of the isolated polypeptide. In some embodiments, the modification is at the N-terminus (e.g., N-terminal acetylation) of the isolated polypeptide. In some embodiments, both the N-terminus and the C-terminus of the isolated polypeptide contain modifications. Terminal modifications are useful, and are well known, to reduce susceptibility to proteinase digestion, and therefore serve to prolong half-life of the polypeptides in solutions, particularly biological fluids where proteases may be present. In some embodiments, the isolated polypeptide is further modified within the sequence, such as, modification by terminal-NH2 acylation, e.g., acetylation, or thioglycolic acid amidation, by terminal-carboxylamidation, e.g., with ammonia, methylamine, and the like terminal modifications.

Amino terminus modifications include methylation (e.g., —NHCH3 or —N(CH3)2), acetylation (e.g., with acetic acid or a halogenated derivative thereof such as a-chloroacetic acid, a-bromoacetic acid, or a-iodoacetic acid), adding a benzyloxycarbonyl (Cbz) group, or blocking the amino terminus with any blocking group containing a carboxylate functionality defined by RCOO— or sulfonyl functionality defined by R—SO2—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the polypeptide. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; Muralidharan and Muir, 2006, Nat Methods, 3:429-38; and Lockless and Muir, 2009, Proc Natl Acad Sci USA. Jun 18, Epub. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

In some embodiments, the isolated polypeptide is phosphorylated. Phosphorylation can occur in a cell where the polypeptide is produced via post-translational modification mechanisms. Alternatively, one can phosphorylate a peptide in vitro (e.g., as described in Hruby, et al. (1990) Biochem J. 268:249-262, incorporated herein by reference). In some embodiments, the isolated polypeptide can be modified by replacing the naturally occurring side chains of the genetically encoded amino acids (or the stereoisomeric D amino acids) with other side chains, for instance with groups such as alkyl, lower (C1-C6) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocycles. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

In some embodiments, the isolated polypeptide is multimeric, e.g., a dimer, trimer, tetramer, or pentamer. In some embodiments, the molecular linker used for forming the oligomeric polypeptides is a peptide linker molecule. In some embodiments, the peptide linking molecule comprises at least one amino acid residue which links at least two peptides according to the disclosure. The peptide linker comprises, e.g., at least 2, 3, 4, 5, 6, 7, 8, 9, 10 or more amino acids residues. In some embodiments, the peptide linker is less than 50 amino acids residues. The peptide linking molecule can couple polypeptides or proteins covalently or non-covalently. Typical amino acid residues used for linking are glycine, tyrosine, cysteine, lysine, glutamic and aspartic acid, or the like. A peptide linker is attached on its amino-terminal end to one peptide, polypeptide or polypeptide domain (e.g., a C-peptide) and on its carboxyl-terminal end to another peptide, polypeptide or polypeptide domain (again, e.g., a C-peptide). Examples of useful linker peptides include, but are not limited to, glycine polymers ((G)n) including glycine-serine and glycine-alanine polymers (e.g., a (Gly4Ser)n repeat where n=1-8, preferably, n=3, 4, 5, or 6). Other examples of peptide linker molecules are described in U.S. Pat. No. 5,856,456 and are hereby incorporated by reference.

In some embodiments, the molecular linker is a chemical linker such as linkages by disulfide bonds between cysteine amino acid residues or by chemical bridges formed by amine crosslinkers, for example, glutaraldehyde, bis(imido ester), bis(succinimidyl esters), diisocyanates and diacid chlorides. Extensive data on chemical cross-linking agents can be found at INVITROGEN's Molecular Probe under section 5.2.

In some embodiments, the isolated peptide described herein are dimerized or multimerized by covalent attachment to at least one linker moiety. The linker moiety is preferably, although not necessarily, a C1-C12 linking moiety optionally terminated with one or two —NH— linkages and optionally substituted at one or more available carbon atoms with a lower alkyl substituent. In some embodiments, the linker comprises —NH—R—NH—wherein R is a lower (C1-C6) alkylene substituted with a functional group, such as a carboxyl group or an amino group, that enables binding to another molecular moiety (e.g., as may be present on the surface of a solid support during peptide synthesis or to a pharmacokinetic-modifying agent such as PEG). In certain embodiments the linker is a lysine residue. In some embodiments, the linker bridges the C-termini of two peptide monomers, by simultaneous attachment to the C-terminal amino acid of each monomer. In some embodiments, the linker bridges the peptides by attaching to the side chains of amino acids not at the C-termini. When the linker attaches to a side chain of an amino acid not at the C-termini of the peptides, the side chain preferably contains an amine, such as those found in lysine, and the linker contains two or more carboxy groups capable of forming an amide bond with the peptides.

In some embodiments, the isolated peptide (e.g., monomer, dimer, or multimer) is attached to one or more polymer moieties. In some embodiments, these polymers are covalently attached to the isolated polypeptides. In some embodiments, for therapeutic use of the end product preparation, the polymer is pharmaceutically acceptable. One skilled in the art will be able to select the desired polymer based on such considerations as whether the polymer-peptide conjugate will be used therapeutically, and if so, the desired dosage, circulation time, resistance to proteolysis, and other considerations.

Exemplary suitable polymers include, without limitation, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Such a polymer may or may not have its own biological activity. The polymers can be covalently or non-covalently conjugated to the polypeptide. Methods of conjugation for increasing serum half-life and for radiotherapy are known in the art, for example, in U.S. Pat. Nos. 5,180,816, 6,423,685, 6,884,780, and 7,022,673, which are hereby incorporated by reference in their entirety.

In some embodiments, the isolated peptide (e.g., monomer, dimer, or multimer) is attached to one or more water soluble polymer moieties. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl-pyrrolidone)polyethylene glycol, propropylene glycol homopolymers, polypropylene oxide/ethylene oxide copolymers, and polyoxyethylated polyols. In some embodiments, the water soluble polymer is PEG.

The polymer may be of any molecular weight, and may be branched or unbranched. The average molecular weight of the reactant PEG is preferably between about 3,000 and about 50,000 daltons (the term "about" indicating that in preparations of PEG, some molecules will weigh more, and some less, than the stated molecular weight). More preferably, the PEG has a molecular weight of from about 10 kDa to about 40 kDa, and even more preferably, the PEG has a molecular weight from 15 to 30 kDa. Other sizes may be used, depending on the desired therapeutic profile (e.g., duration of sustained release desired; effects, if any, on biological activity; ease in handling; degree or lack of antigenicity; and other effects of PEG on a therapeutic peptide known to one skilled in the art).

The number of polymer molecules attached may vary; for example, one, two, three, or more water-soluble polymers may be attached to a peptide of the disclosure. The multiple attached polymers may be the same or different chemical moieties (e.g., PEGs of different molecular weight).

In some embodiments, PEG may be attached to at least one terminus (N-terminus or C-terminus) of an isolated polypeptide. In other embodiments, PEG may be attached to a linker moiety of an isolated polypeptide dimer or multimer. In some embodiments, the linker contains more than one reactive amine capable of being derivatized with a suitably activated PEG species.

In some embodiments, the isolated polypeptide that is attached to a PEG polymer is termed to be "PEGylated". PEGylation is the process of covalent attachment of Polyethylene glycol polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins. PEGylation, by increasing the molecular weight of a molecule, can impart several significant pharmacological advantages over the unmodified form, such as: improved drug solubility, reduced dosage frequency, without diminished efficacy with potentially reduced toxicity, extended circulating life, increased drug stability, and enhanced protection from proteolytic degradation. In addition, PEGylated drugs are have wider opportunities for new delivery formats and dosing regimens. Methods of PEGylating molecules, proteins and peptides are well known in the art, e.g., as described in U.S. Pat. Nos. 5,766,897; 7,610,156; 7,256,258 and the International Application No. WO/1998/032466.

In some embodiments, the isolated polypeptide (with or without the modifications described herein) can be conjugated to other polymers in addition to polyethylene glycol (PEG). The polymer may or may not have its own biological activity. Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation to a polymer can improve serum half-life, among other effects. A variety of chelating agents can be used to conjugate the peptides described herein. These chelating agents include but are not limited to ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4, 7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et. al, 1978, Nature 271, 752-755; Harokopakis E., et. al., 1995, Journal of Immunological Methods, 185:31-42; S. F. Atkinson, et. al., 2001, J. Biol. Chem., 276:27930-27935; and U. S Pat. Nos.: 5,601,825, 5,180,816, 6,423,685, 6,706,252, 6,884,780, and 7,022,673, which are hereby incorporated by reference in their entirety.

In some embodiments, attaching the isolated polypeptide to a polymer (e.g., PEG) prolongs the serum half-life (e.g., by at least 20%, at least 30%, at least 40%, at least 50%, at least 60%, at least 70%, at least 80%, at least 90%, at least 100%, 2-fold, 5-fold, 10-fold, 100-fold, or more) of the isolated polypeptide, compared to an isolated polypeptide that is not attached to the polymer. In some embodiments, attaching the isolated polypeptide to a polymer (e.g., PEG) prolongs the shelf half-life (e.g., by at least 20%, at least 30%, at least 40%, at least 50%, at least 60%, at least 70%, at least 80%, at least 90%, at least 100%, 2-fold, 5-fold, 10-fold, 100-fold, or more) of the isolated polypeptide, compared to an isolated polypeptide that is not attached to the polymer. The "serum half-life" of an isolated polypeptide, as used herein, refers to the period of time required for the concentration or amount of the polypeptides in the body to be reduced by one-half. A polypeptide's serum half-life depends on how quickly it is eliminated from the serum. The longer the serum half-life is, the more stable the polypeptide is in the body. The "shelf-life", refers to the period of time, from the date of manufacture, that a product is expected to remain within its approved product specification while stored under defined conditions. It is desirable for a therapeutic agent, e.g., the isolated polypeptide of the present disclosure, to have a longer shelf-life.

Other methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., J. Am. Chem. Soc. 2000, 122, 11037-11038), which is incorporated herein by reference in its entirety. The polypeptides described herein can be conjugated or otherwise covalently attached to other molecules (e.g., using a chemical linker). One such form of attachment is through a non-amide linkage (e.g., a disulfide bond).

In some embodiments, the isolated polypeptide described herein further comprises a fusion domain. Well known examples of such fusion domains include, without limitation, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. In some embodiments, the isolated polypeptide is fused with a domain that stabilizes the isolated polypeptide fragment in vivo (a "stabilizer" domain). "Stabilizing", as used herein, means an increase in the serum or shelf half-life of the polypeptide in vivo, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains.

In some embodiments, the fusion domain is an antibody or a domain thereof suitable for enhancing the serum or shelf half-life of the molecule. In some embodiments, the isolated polypeptide is attached (e.g., covalently attached such as via a linker molecule) to the fusion domain. In some embodiments, the fusion domain comprises one or more constant domains in an immunoglobulin Fc region. As used herein, the term, "immunoglobulin Fc region" or simply "Fc domain" means the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In some embodiments, the immunoglobulin Fc region comprises at least an immunoglobulin hinge region a CH2 domain and a CH3 domain, and preferably lacks the CH1 domain.

In some embodiments, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. In some embodiments, the Fc domain from an IgG, IgA, IgM, IgD, or IgE. The portion of the DNA construct encoding the immunoglobulin Fc region, in some embodiments, comprises at least a portion of a hinge domain and/or at least a portion of a CH3 domain of Fc γ or the homologous domains in any of IgA, IgD, IgE, or IgM.

In some embodiments, the isolated polypeptides further comprises an Fc portion of human IgG. In some embodiments, the Fc domain comprises the amino acid sequence of SEQ ID NO: 7. In some embodiments, the Fc domain comprises an amino acid sequence that is at least 80% identical to SEQ ID NO: 7. For example, the Fc domain may comprise an amino acid sequence that is at least 80% at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to ID NO: 7. In some embodiments, the Fc domain comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% identical to SEQ ID NO: 7. In some embodiments, the Fc domain consists of the amino acid sequence of SEQ ID NO: 7.

In some embodiments, the isolated polypeptide comprising an Fc fusion domain comprises an amino acid sequence that is at least 80% identical to any one of SEQ ID NOs: 8, 9, and 26-39. For example, the isolated polypeptide comprising an Fc fusion domain may comprise an amino acid sequence that is at least 80% at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NOs: 8, 9, and 26-39. In some embodiments, the isolated polypeptide comprising an Fc fusion domain comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% identical to any one of SEQ ID NOs: 8, 9, and 26-39. In some embodiments, the isolated polypeptide comprises an Fc fusion domain comprises the amino acid sequence of SEQ ID NO: 8 or SEQ ID NO: 9. In some embodiments, the isolated polypeptide comprises an Fc fusion domain consists of the amino acid sequence of any one of SEQ ID NOs: 8, 9, and 26-39.

In some embodiments, the Fc domain may have one or more mutations at residues such as Asp-265, lysine 322, and Asn-434. In some embodiments, the mutant Fc domain having one or more of these mutations (e.g., Asp-265 mutation) has reduced ability of binding to the Fc receptor relative to a wildtype Fc domain. In some embodiments, the mutant Fc domain having one or more of these mutations (e.g., Asn-434 mutation) has increased ability of binding to the MHC class I-related Fc-receptor (FcRN) relative to a wildtype Fc domain.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

In some embodiments, the isolated polypeptide comprises a fusion domain that comprises a cysteine-rich domain (CRD) of Frizzled. In some embodiments, the CRD domain of FZD comprises the amino acid sequence of any one of SEQ ID NO: 3-6. In some embodiments, the CRD domain of FZD comprises an amino acid sequence that is at least 80% identical to any one of SEQ ID NO: 3-6. For example, the CRD domain of FZD may comprise an amino acid sequence that is at least 80% at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NO: 3-6. In some embodiments, the CRD domain of FZD comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% identical to any one of SEQ ID NO: 3-6. In some embodiments, the CRD domain of FZD consists of the amino acid sequence of any one of SEQ ID NO: 3-6.

In some embodiments, the isolated peptide comprising a fusion domain that is a CRD domain of FZD comprises the amino acid sequence of any one of SEQ ID NO: 10-17 and 40-95. In some embodiments, the isolated peptide comprising a fusion domain that is a CRD domain of FZD comprises an amino acid sequence that is at least 80% identical to any one of SEQ ID NO: 10-17 and 40-95. For example, the isolated peptide comprising a fusion domain that is a CRD domain of FZD may comprise an amino acid sequence that is at least 80% at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NO: 10-17 and 40-95. In some embodiments, the isolated peptide comprising a fusion domain that is a CRD domain of FZD comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% identical to any one of SEQ ID NO: 10-17. In some embodiments, the isolated peptide comprising a fusion domain that is a CRD domain of FZD consists of the amino acid sequence of any one of SEQ ID NO: 10-17 and 40-95.

In some embodiments, the isolated polypeptide is fused to a fusion domain that comprises a therapeutic agent (e.g., an anti-bacterial agent). In some embodiments, the therapeutic agent is an antibiotic. Classes of anti-bacterial agents that may be used in accordance with the present disclosure include, without limitation, aminoglycosides, ansamycins, carbacephems, carbapenems, cephalosporins, glycopeptides, lincosamides, lipopeptides, macrolides, monobactams, nitrofurans, oxazolidinones, penicillins, quinolones, sulfonamides, and tetracyclines.

In some embodiments, the therapeutic agent is an antibody for a FZD co-receptor. It is known in the art that to facilitate Wnt signaling, co-receptors may be required alongside the interaction between the Wnt protein and FZDs. Upon activation of the receptor, a signal is sent to the phosphoprotein Dishevelled (Dsh), which is located in the cytoplasm. Blocking of the Frizzled co-receptors via binding of an antibody also blocks Wnt signaling. Examples of Frizzled co-receptors include, without limitation, lipoprotein receptor-related protein (LRP)-5/6, receptor tyrosine kinase (RTK), and tyrosine-protein kinase transmembrane receptor (ROR2).

All combinations of the different modifications and derivatizations are envisioned for the isolated polypeptides described herein. Modifications, derivatives and methods of derivatizing polypeptides are described in Published International Application WO 2010/014616, the contents of which are incorporated herein by reference.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the isolated polypeptide or any of the variant or derivative described herein binds to FZD. In some embodiments, the isolated polypeptide or any of the variant or derivative described herein reduces Wnt signaling (e.g., by at least 20%), compared to in the absence of the isolated polypeptide. For example, the isolated polypeptide or any of the variant or derivative described herein may reduce Wnt signaling by at least 20%, at least 30%, at least 40%, at least 50%, at least 60%, at least 70%, at least 80%, at least 90%, at least 95%, at least 99%, or 100%, compared to in the absence of the isolated polypeptide. In some embodiments, the isolated polypeptide or any of the variant or derivative described herein reduces Wnt signaling by 20%, 30%, 40%, 50%, 60%, 70%, 80%, 90%, 95%, 99%, or 100%, compared to in the absence of the isolated polypeptide.

The isolated polypeptides comprising amino acid substitutions, modifications, or fusion domains will substantially retain the activity of the non-modified polypeptide. "Substantially retain" means one or more activity of the variant is at least 30% compared to the activity of the original polypeptide in a similar assay, under similar conditions; preferably the activity is at least 30%, at least 40%, at least 50%, at least 60%, at least 70%, at least 80%, at least 90%, at least 95%, at least 99%, at least 100%, at least 2-fold, at least 5-fold, at least 10-fold, at least 100-fold or higher activity compared to the un-modified polypeptide.

The isolated polypeptides of the present disclosure, will generally be produced by expression form recombinant nucleic acids in appropriate cells (e.g., *E. coli*, or insect cells) and isolated. The nucleic acids encoding the polypeptides described herein may be obtained, and the nucleotide sequence of the nucleic acids determined, by any method known in the art. Further provided herein are isolated and/or recombinant nucleic acids encoding any of the isolated polypeptide fragments disclosed herein. In some embodiments, the isolated nucleic acid molecule comprises a polynucleotide encoding a polypeptide comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical of any one of SEQ ID NO: 2, and 8-95. In some embodiments, the isolated nucleic acid molecule comprises a polynucleotide encoding a polypeptide comprising an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% identical to any one of SEQ ID NO: 2 and 8-95.

In some embodiments, the nucleic acid is comprised within a vector, such as an expression vector. In some embodiments, the vector comprises a promoter operably linked to the nucleic acid.

A variety of promoters can be used for expression of the polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the polypeptides described herein. In some embodiments, the expression of the polypeptides described herein is regulated by a constitutive, an inducible or a tissue-specific promoter.

The host cells used to express the isolated polypeptides described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667).

A variety of host-expression vector systems may be utilized to express the isolated polypeptides described herein. Such host-expression systems represent vehicles by which the coding sequences of the isolate d polypeptides described herein may be produced and subsequently purified, but also represent cells which may, when transformed or transfected with the appropriate nucleotide coding sequences, express the isolated polypeptides described herein in situ. These include, but are not limited to, microorganisms such as bacteria (e.g., *E. coli* and *B. subtilis*)

transformed with recombinant bacteriophage DNA, plasmid DNA or cosmid DNA expression vectors containing coding sequences for the isolated polypeptides described herein; yeast (e.g., *Saccharomyces pichia*) transformed with recombinant yeast expression vectors containing sequences encoding the isolated polypeptides described herein; insect cell systems infected with recombinant virus expression vectors (e.g., baclovirus) containing the sequences encoding the isolated polypeptides described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the isolated polypeptides described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the polypeptides being expressed. For example, when a large quantity of such a protein is to be produced, for the generation of pharmaceutical compositions of polypeptides described herein, vectors which direct the expression of high levels of fusion protein products that are readily purified may be desirable. Such vectors include, but are not limited, to the *E. coli* expression vector pUR278 (Ruther et al. (1983) "Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The lpp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544). In some embodiments, an expression vector is introduced into a host cell for transient expression of a product.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the polypeptides described herein may be expressed as a single gene product (e.g., as a single polypeptide chain, i.e., as a polyprotein precursor), requiring proteolytic cleavage by native or recombinant cellular mechanisms to form separate polypeptides described herein. The disclosure thus encompasses engineering a nucleic acid sequence to encode a polyprotein precursor molecule comprising the polypeptides described herein, which includes coding sequences capable of directing post translational cleavage of said polyprotein precursor. Post-translational cleavage of the polyprotein precursor results in the polypeptides described herein. The post translational cleavage of the precursor molecule comprising the polypeptides described herein may occur in vivo (i.e., within the host cell by native or recombinant cell systems/mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action). Purification and modification of recombinant proteins is well known in the art such that the design of the polyprotein precursor could include a number of embodiments readily appreciated by a skilled worker.

Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," Biotechnology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express polypeptides described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the polypeptides described herein. Such engineered cell lines may be particularly useful in screening and evaluation of polypeptides that interact directly or indirectly with the polypeptides described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150:1-14.

The expression levels of polypeptides described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a polypeptide described herein is amplifiable, increase in the level of inhibitor present in culture of host cell will increase the number of copies of the marker gene. Since the amplified region is associated with the nucleotide sequence of a polypeptide described herein or a polypeptide described herein, production of the polypeptide will also increase (Crouse et al. (1983) "Expression And Amplification Of Engineered Mouse Dihydrofolate Reductase Minigenes," Mol. Cell. Biol. 3:257-266).

Once a polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fc domain (or portion thereof)), and sizing column chromatography), centrifugation, differential solubility, or by any other standard technique for the purification of polypeptides or antibodies.

Other aspects of the present disclosure relate to a cell comprising a nucleic acid described herein or a vector described herein. The cell may be a prokaryotic or eukaryotic cell. In some embodiments, the cell in a mammalian cell. Exemplary cell types are described herein. The isolated polypeptide described herein may be produced recombinantly, by obtaining a cell comprising a nucleic acid encoding the isolated polypeptide, expressing nucleic acid the cell, and isolating and purifying the polypeptide.

Other aspects of the present disclosure provide compositions comprising the isolated polypeptide, or any variants and derivatives described herein. In some embodiments, the composition is a pharmaceutical composition. In some embodiments, the composition further comprises a pharmaceutically acceptable carrier. The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the polypeptide from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, an isolated polypeptide of the present disclosure in a composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the polypeptide of the disclosure does not absorb are used.

In other embodiments, the isolated polypeptides of the present disclosure are delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

Isolated polypeptides of the present disclosure can be administered as pharmaceutical compositions comprising a therapeutically effective amount of a binding agent and one or more pharmaceutically compatible ingredients.

In typical embodiments, the pharmaceutical composition is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. The polypeptides of the present disclosure can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethylsulfate, or "DOTAP," are particularly preferred for such lipid particles and vesicles. The preparation of such lipid particles is well known. See, e.g., U.S. Pat. Nos. 4,880,635; 4,906,477; 4,911,928; 4,917,951; 4,920,016; and 4,921,757.

The pharmaceutical compositions of the present disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

In some embodiments, the isolated polypeptides described herein may be conjugated to a therapeutic moiety, e.g., an antibiotic. Techniques for conjugating such therapeutic moieties to polypeptides, including e.g., Fc domains, are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al. (1982) "The Preparation And Cytotoxic Properties Of Antibody-Toxin Conjugates," Immunol. Rev., 62:119-158.

Further, the pharmaceutical composition can be provided as a pharmaceutical kit comprising (a) a container containing a polypeptide of the disclosure in lyophilized form and (b) a second container containing a pharmaceutically acceptable diluent (e.g., sterile water) for injection. The pharmaceutically acceptable diluent can be used for reconstitution or dilution of the lyophilized polypeptide of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an isolated polypeptide of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The isolated polypeptides, variants or derivatives, or compositions comprising such may be used to treat a variety of diseases. In some embodiments, the diseases are caused, at least in part, by the dysregulation of Wnt signaling pathways. In some embodiments, the disease is *Clostridium difficile* infection (CDI). Further provided herein are methods of treating CDI, the method comprising administering a therapeutically effective amount of the isolated polypeptide, a variant or derivative, or a composition comprising such to a subject in need thereof to treat the CDI. The sTcdB polypeptide, while being able to block the wild-type TcdB from entering the cells, still inhibits Wnt signaling due to its occupancy of the FZD receptors. Thus, agents that activate Wnt signaling downstream of the FZD receptors may afford additional therapeutic effects against CDI. Accordingly, in some embodiments, the method further comprises administering to the subject an effective of a second agent that induces Wnt signaling downstream of Frizzled in a cell. Agents that activate Wnt signaling downstream of the FZD receptors are known in the art. Non-limiting examples of such agents include GSK-3 inhibitors such as Lithium (LiCl) and CHIR99021. GSK-3 inhibits Wnt signaling downstream of the FZD receptors. Therefore, GSK-3 inhibitors are able to activate Wnt signaling downstream of the FZD receptors. Other non-limiting examples of agents that induce Wnt signaling include, without limitation, SB 216763 (Tocris Bioscience, catalog #1616), BIO (Tocris Bioscience, catalog #3194), TCS 2002 (Tocris Bioscience, catalog #3869), TC-G 24 (Tocris Bioscience, catalog #4353), TWS 119 (Tocris Bioscience, catalog #3835), SB 415286 (Tocris Bioscience, catalog #1617), A 1070722 (Tocris Bioscience, catalog #4431), AR-A 014418 (Tocris Bioscience, catalog #3966), L803-mts (Tocris Bioscience, catalog #2256). The activating of Wnt signaling occurs in a cell. In some embodiments, the cell is a colonic epithelial cell.

In some embodiments, the method of treating CDI further comprises administering to the subject a therapeutically effective amount of a third agent that inhibits the cysteine protease activity of TcdB in a cell. In some embodiments, the third agent is ebselen. Ebselen (also called PZ 51, DR3305, and SPI-1005), is a synthetic organoselenium drug molecule with anti-inflammatory, anti-oxidant and cytoprotective activity. It acts as a mimic of glutathione peroxidase and can also react with peroxynitrite. Ebselen is a potent scavenger of hydrogen peroxide as well as hydroperoxides including membrane bound phospholipid and cholesterylester hydroperoxides. Several ebselen analogues have been shown to scavenge hydrogen peroxide in the presence of thiols. Ebselen is known in the art to be inhibiting the cysteine protease activity of TcdB. Other non-limiting examples of cysteine protease inhibitors include serpins, stefins, and Inhibitors of apoptosis (IAPs).

In some embodiments, the method of treating CDI further comprises administering to the subject a therapeutically effective amount of a fourth agent that facilitate blocking TcdB binding to FZDs. Such agents may be, for example, an FZD antibody. It is to be understood that any agents that competes with TcdB for binding to FZD may be used.

In some embodiments, the disease caused by the dysregulation of Wnt signaling is cancer. The dysregulation of Wnt signaling pathway is a known cause of cancer and is a central mechanism in cancer biology. For example, Wnt overexpression could lead to malignant transformation of mouse mammary tissue. Therefore, the inhibition of Wnt signaling has been a focus for developing cancer therapeutics. As described herein, the isolated polypeptide, variants or derivatives, or compositions comprising such inhibits Wnt signaling. Thus, other aspects of the present disclosure provide methods of treating cancer, the methods administering to the subject in need thereof a therapeutically effective amount of the isolated polypeptide, a variant or derivative, or a compositions comprising such.

In some embodiments, the method of treating cancer further comprises administering to the subject a therapeutically effective amount of a second agent that blocks Wnt signaling. Non-limiting examples of agents that block Wnt signaling include Dkk family proteins, Secreted Frizzled Related Proteins (sFRP), Draxin, IGFBP-4, SOST/Sclerostin, USAG1, and WIF-1. In some embodiments, the agent that blocks Wnt signaling is an FZD antibody. The use of these agents in blocking Wnt signaling is known in the art. Many types of cancer are characterized with over-activated Wnt signaling and over-expression of Frizzled. For instance, >90% of colon cancers feature aberrant Wnt signaling. Recent study (Gujral et al, Cell, 2014, 159, 844-856) showed that Frizzled 2 is over expressed in metastatic liver, lung, colon and breast cancers. The expression is highly correlated with the markers of epithelial-mesenchymal transition.

In some embodiments, the method of treating cancer further comprises administering to the subject a therapeutically effective amount of an anti-cancer agent. In some embodiments, the anti-cancer agent is selected from the group consisting of: small molecules, oligonucleotides, polypeptides, and combinations thereof. In some embodiments, the anti-cancer agent is a chemotherapeutic agent. In some embodiments, the chemotherapeutic agent is selected from the group consisting of: Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. In some embodiments, the chemotherapeutic agent is Doxorubicin.

In some embodiments, the anti-cancer agent is an immune checkpoint inhibitor. An "immune checkpoint" is a protein in the immune system that either enhances an immune response signal (co-stimulatory molecules) or reduces an immune response signal. Many cancers protect themselves from the immune system by exploiting the inhibitory immune checkpoint proteins to inhibit the T cell signal. Exemplary inhibitory checkpoint proteins include, without limitation, Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GAL9), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3), and V-domain Ig suppressor of T cell activation (VISTA).

Some of these immune checkpoint proteins need their cognate binding partners, or ligands, for their immune inhibitory activity. For example, A2AR is the receptor of adenosine A2A and binding of A2A to A2AR activates a negative immune feedback loop. As another example, PD-1 associates with its two ligands, PD-L1 and PD-L2, to down regulate the immune system by preventing the activation of T-cells. PD-1 promotes the programmed cell death of antigen specific T-cells in lymph nodes and simultaneously reduces programmed cell death of suppressor T cells, thus achieving its immune inhibitory function. As yet another example, CTLA4 is present on the surface of T cells, and when bound to its binding partner CD80 or CD86 on the surface of antigen-present cells (APCs), it transmits an inhibitory signal to T cells, thereby reducing the immune response.

An "immune checkpoint inhibitor" is a molecule that prevents or weakens the activity of an immune checkpoint protein, For example, an immune checkpoint inhibitor may inhibit the binding of the immune checkpoint protein to its cognate binding partner, e.g., PD-1, CTLA-4, or A2aR. In some embodiments, the immune checkpoint inhibitor is a small molecule. In some embodiments, the immune checkpoint inhibitors is a nucleic acid aptamer (e.g., a siRNA targeting any one of the immune checkpoint proteins). In some embodiments, the immune checkpoint inhibitor is a recombinant protein. In some embodiments, the immune checkpoint inhibitor is an antibody. In some embodiments, the antibody comprises an anti-CTLA-4, anti-PD-1, anti-PD-L1, anti-TIM3, anti-LAG3, anti-B7-H3, anti-B7-H4, anti-BTLA, anti-GAL9, anti-Chk, anti-A2aR, anti-IDO, anti-KIR, anti-LAG3, anti-VISTA antibody, or a combination of any two or more of the foregoing antibodies. In some embodiments, the immune checkpoint inhibitor is a monoclonal antibody. In some embodiments, the immune checkpoint inhibitor comprises anti-PD1, anti-PD-L1, anti-CTLA-4, or a combination of any two or more of the foregoing antibodies. For example, the anti-PD-1 antibody is pembrolizumab (Keytruda®) or nivolumab (Opdivo®) and the anti-CTLA-4 antibody is ipilimumab (Yervoy®). Thus, in some embodiments, the immune checkpoint inhibitor comprises pembrolizumab, nivolumab, ipilimumab, or any combination of two or more of the foregoing antibodies. The examples described herein are not meant to be limiting and that any immune checkpoint inhibitors known in the art and any combinations thereof may be used in accordance with the present disclosure.

Types of cancer that may be treated using the methods disclosed herein include, without limitation, neoplasms, malignant tumors, metastases, or any disease or disorder characterized by uncontrolled cell growth such that it would be considered cancerous. The cancer may be a primary or metastatic cancer. Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In some embodiments, the methods of the present disclosure may be used to treat colon cancer, liver cancer, lung cancer, breast cancer. In some embodiments, the cancer is osteosarcoma. In some embodiments, the breast cancer is triple negative breast cancer. In some embodiments, the cancer cells are metastatic. It is to be understood that the examples are not meant to be limiting and that any types of cancer that shows hyperactive Wnt signaling or overexpression of Frizzled may be treated using the methods disclosed herein.

"A therapeutically effective amount" as used herein refers to the amount of each therapeutic agent of the present disclosure (e.g., the isolated polypeptide fragment, the additional isolated polypeptide fragment, and the agent that activates Wnt signaling) required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the polypeptide used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the polypeptide (such as the half-life of the polypeptide, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the polypeptide is administered for preventive or therapeutic purposes, previous therapy, the subject's clinical history and response to the antagonist, and the discretion of the attending physician. Typically the clinician will administer a polypeptide until a dosage is reached that achieves the desired result. Administration of one or more polypeptides can be continuous or intermittent, depending, for example, upon the recipient's physiological condition, whether the purpose of the administration is therapeutic or prophylactic, and other factors known to skilled practitioners. The administration of a polypeptide may be essentially continuous over a preselected period of time or may be in a series of spaced dose, e.g., either before, during, or after developing a disease.

As used herein, the term "treating" refers to the application or administration of a polypeptide or composition including the polypeptide to a subject in need thereof. "A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., rodent (e.g., mouse or rat), primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). The non-human animal may be a male or female at any stage of development. The non-human animal may be a transgenic animal or genetically engineered animal.

In some embodiments, the subject is a companion animal (a pet). "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a research animal. Non-limiting examples of research animals include: rodents (e.g., rats, mice, guinea pigs, and hamsters), rabbits, or non-human primates.

In some embodiments, a "subject in need thereof" refers to a subject that needs treatment of a disease described herein. In some embodiments, the subject has or is at risk of developing CDI. In some embodiments, the subject has or is at risk of cancer. In some embodiments, the subject has dysregulated Wnt signaling.

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3- , or 6-month depot injectable or biodegradable materials and methods.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

*C. difficile* is an opportunistic pathogen that colonizes the colon in humans when the normal gut microbiome is disrupted. The infection leads to disruption of the colonic epithelial barrier, resulting in diarrhea and pseudomembranous colitis[1-4,6]. The diseases associated with CDI are caused by two homologous exotoxins, *C. difficile* toxin A (TcdA) and toxin B (TcdB), which act as glucosyltransferases that inactivate small GTPases[3,7-9]. Of the two toxins, TcdB alone is capable of causing the full-spectrum of diseases in humans, as TcdA-TcdB+ strains have been clinically isolated[14-17]. Chondroitin sulfate proteoglycan 4 (CSPG4), poliovirus receptor-like 3 (PVRL3), and FZDs have been recently identified as TcdB receptors[10,18,19], whereas FZDs are believed to be the major receptors in the colonic epithelium[10,20]. FZDs are a family of transmembrane receptors for lipid-modified morphogen Wnt[21,22]. Binding of TcdB to FZDs not only mediates toxin entry, but also inhibits Wnt signaling that regulates self-renewal of colonic stem cells and differentiation of the colonic epithelium[10,23,24]. The mechanism by which TcdB specifically recognizes FZDs and inhibits Wnt signaling is unknown.

Figure 1B:
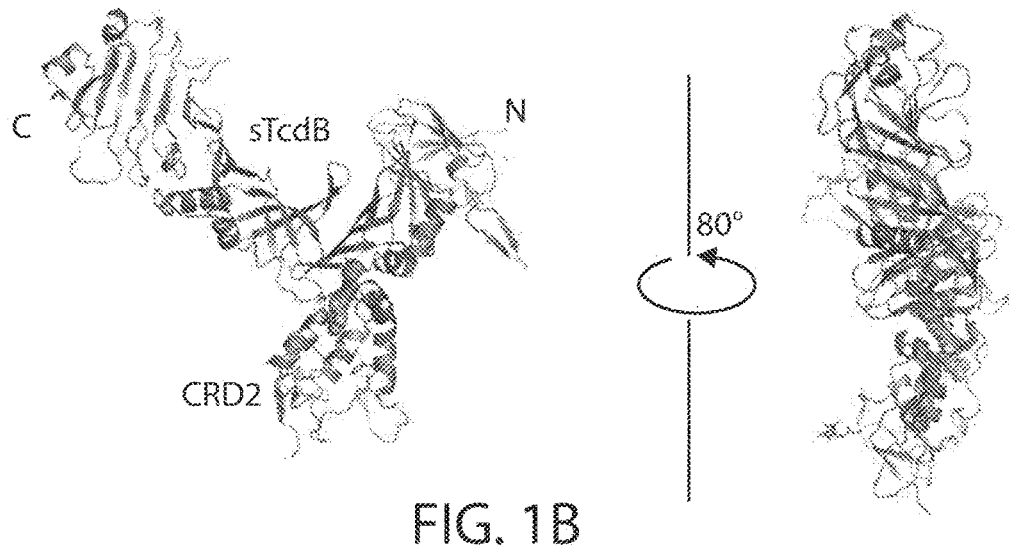
Figure 5A:
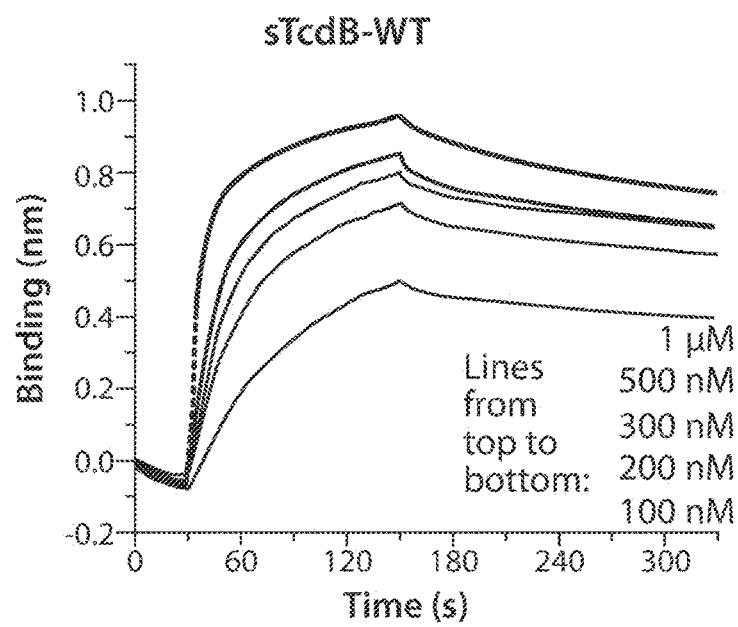
Figure 5B:
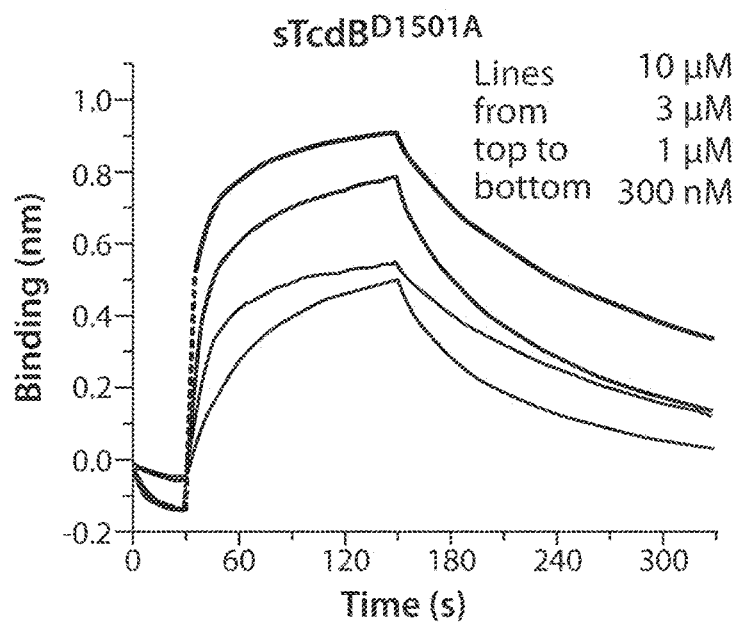
Figure 5C:
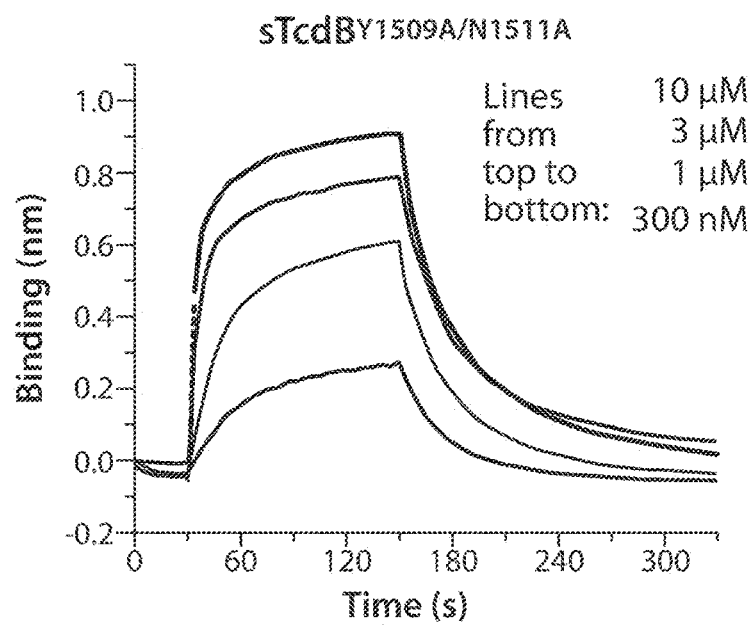
Figure 5D:
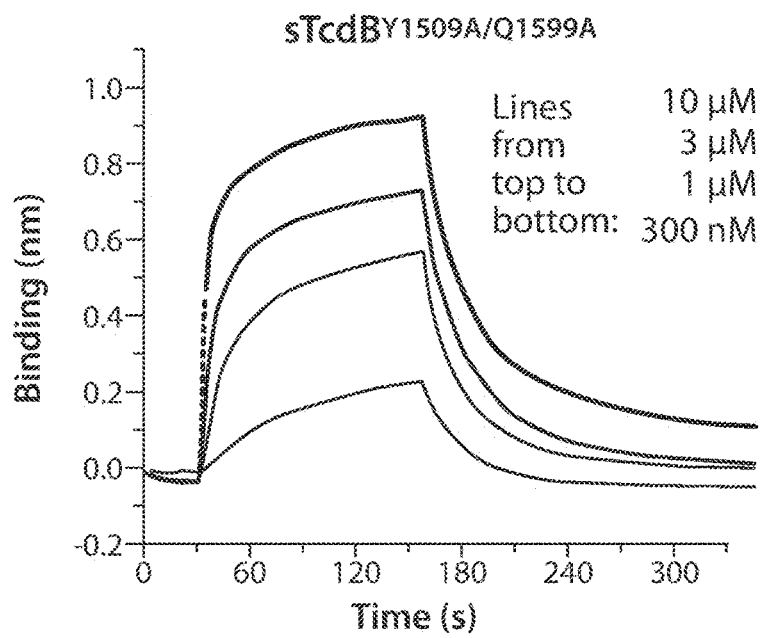
Figure 6A:
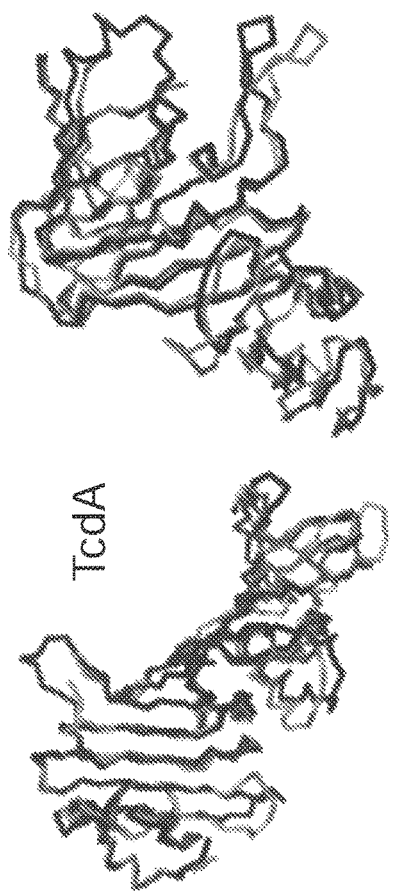
FIGS. 6A to 6C. Structural and sequence comparisons between sTcdB and the homologous fragment in TcdA.
Figure 6B:
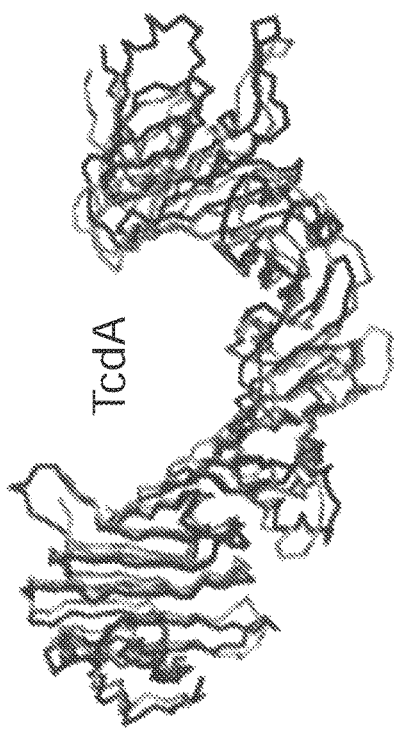
Figure 6C:
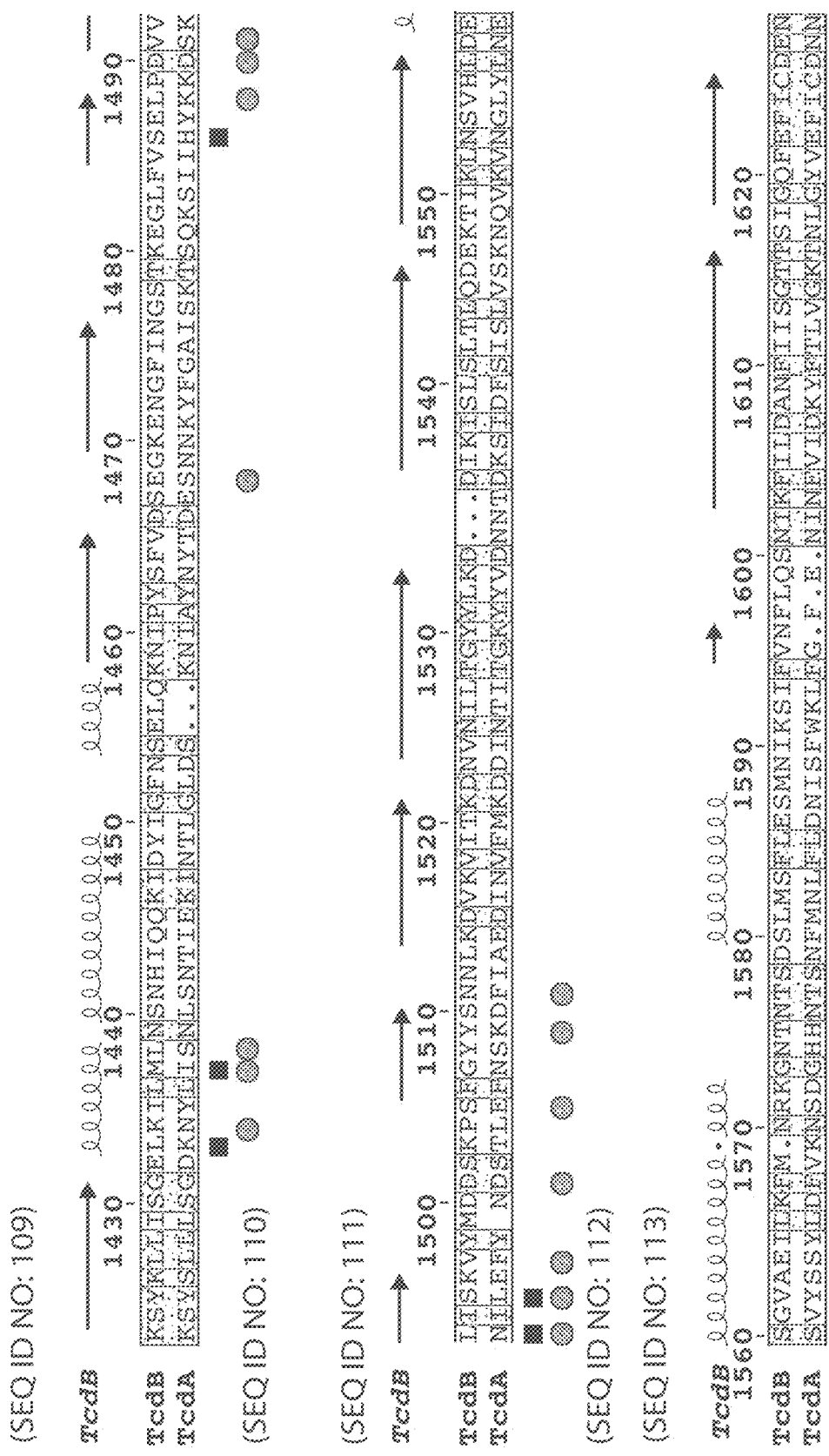

TcdB is a large multi-domain protein (~270 kDa) (FIG. 1A). A series of TcdB truncations were screened (Table 3) and finally narrowed down to a short TcdB fragment (residues 1285-1804, referred to as sTcdB) that contains the FZD-binding site. Bio-layer interferometry (BLI) analysis confirmed that sTcdB binds to CRD2 with an affinity (dissociation constant, $K_D$~13 nM) similar to that of full-length TcdB (FIGS. 5A, 5F)[10]. The co-crystal structure of sTcdB in complex with human CRD2 (residues 24-156) was determined at 2.5 Å resolution, which was composed of sTcdB produced in *E. coli* and CRD2 produced as a secreted protein from human embryonic kidney (HEK) cells. Coordinates and structure factors of the sTcdB-CRD2 complex have been deposited in the Protein Data Bank under accession code 6COB. The structure reveals one sTcdB-CRD2 complex in one asymmetric unit, which buried a total of ~1488 Å$^2$ of interface between them (FIG. 1B, Table 1). CRD2 adopts the conserved CRD folding with four α helices and two β strands stabilized by five 69 disulfide bridges. The comparison between CRD2 and FZD7-CRD (PDB: 5URV) and FZD8-CRD (PDB: 4F0A) yielded root-mean-square deviations of ~0.62 Å and ~1.13 Å, respectively[11,25]. sTcdB adopts an L-shape with its vertex bound by CRD2 (FIG. 1B). The overall structure of sTcdB is similar to the homologous region in TcdA (FIGS. 6A, 6B)[26].

TABLE I

Data collection, phasing and refinement statistics

|  | Native | Pt-SAD |
|---|---|---|
| Data collection |  |  |
| Space group | C222$_1$ | C222$_1$ |
| Cell dimensions |  |  |
| a, b, c (Å) | 74.6, 175.6, 174.4 | 73.3, 177.1, 174.6 |
| α, β, γ (°) | 90, 90, 90 | 90, 90, 90 |
| Wavelength (Å) | 0.9791 | 1.0717 |
| Resolution (Å) | 87.86-2.50 | 88.56-2.72 |
|  | (2.56-2.50)* | (2.82-2.72)* |
| R$_{merge}$ (%) | 4.68 (59.5) | 9.64 (>100) |
| R$_{pim}$ | 0.03 (0.35) | 0.04 (0.76) |
| Wilson B-factor (Å$^2$) | 56 | 68 |
| I/σI | 18.3 (1.8) | 15.7 (1.0) |
| CC$_{1/2}$ | 0.999 (0.849) | 0.999 (0.778) |
| Completeness (%) | 98.2 (99.0) | 93.4 (80.3) |
| Redundancy | 3.7 (3.6) | 6.5 (6.3) |
| Refinement |  |  |
| Resolution (Å) | 87.81-2.50 |  |
|  | (2.90-2.50)* |  |
| No. reflections | 39,324 |  |
| R$_{work}$/R$_{free}$ | 19.87/23.74 |  |

TABLE I-continued

Data collection, phasing and refinement statistics

|  | Native | Pt-SAD |
|---|---|---|
| No. atoms |  |  |
| Protein | 4,978 |  |
| Ligand/ion | 53 |  |
| Water | 37 |  |
| B-factors (Å$^2$) |  |  |
| Protein | 74 |  |
| Ligand/ion | 99 |  |
| Water | 68 |  |
| Ramachandran plot |  |  |
| Favored (%) | 94.5 |  |
| Allowed (%) | 5.5 |  |
| Outliers (%) | 0.0 |  |
| R.m.s deviations |  |  |
| Bond lengths (Å) | 0.008 |  |
| Bond angles (°) | 1.030 |  |

*Values in parenthesis are for highest-resolution shell. Each dataset was derived from a single crystal.

Figure 1C:
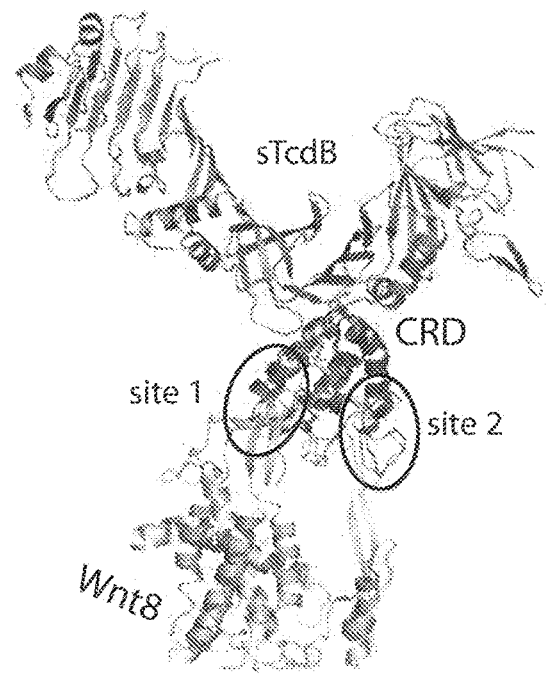
Figure 1D:
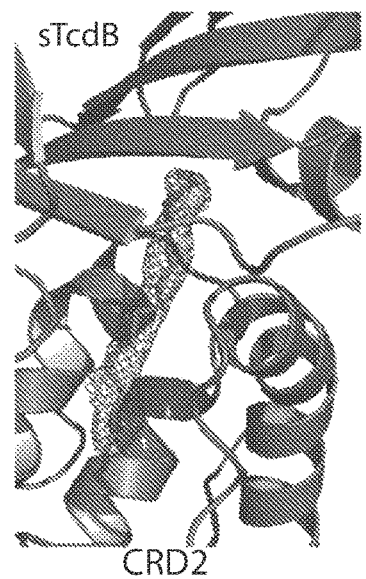

FZD-CRD contains the binding site for Wnt, which subsequently triggers downstream signaling pathways[11,21,24]. The crystal structure of a mouse FZD8-CRD (CRD8) in complex with *Xenopus* Wnt8 reveals that Wnt recognizes CRDs at two separated binding sites[11]. On one site, a palmitoleic acid (PAM) covalently linked to Wnt8-S187 is bound in a hydrophobic groove of CRD8, which is surrounded by protein-protein contacts between CRD8 and Wnt8. The other site is located at a distinct region in CRD8 and only involves protein-protein interactions (FIG. 1C). Comparing to the CRD8-Wnt8 complex, sTcdB engages CRD2 from the opposite side of the Wnt-binding interface (FIG. 1C). Therefore, there is no steric competition between sTcdB and the protein part of Wnt. But sTcdB covers a hydrophobic groove in CRD2 that is conserved in CRD8 and acts as the docking site for the Wnt PAM. Unexpectedly, a long cylinder-like electron density of ~16 Å in length was observed bound in this groove in CRD2 that is completely buried between sTcdB and CRD2 (FIG. 1D). This electron density is similar to the PAM moiety identified in the CRD8-Wnt8 complex and therefore assigned as a free PAM (FIGS. 1D, 1E)[11], although it could not unambiguously be determined whether it is palmitoleic or palmitic acid.

Figure 2A:
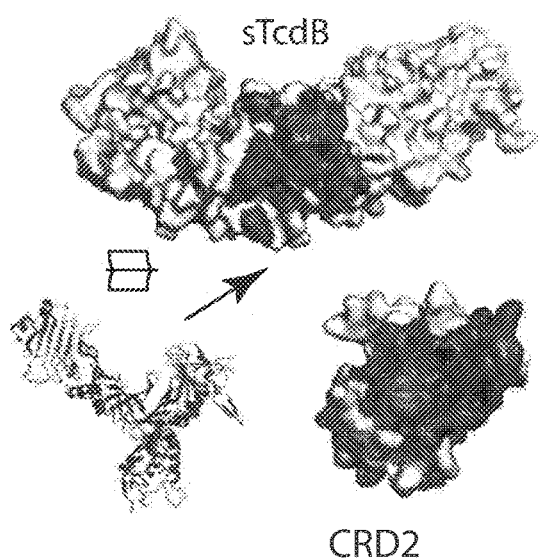
Figure 2B:
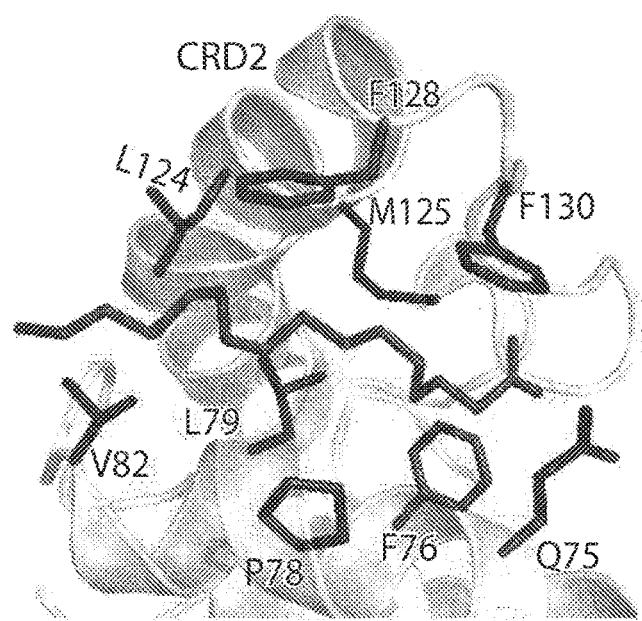
Figure 2C:
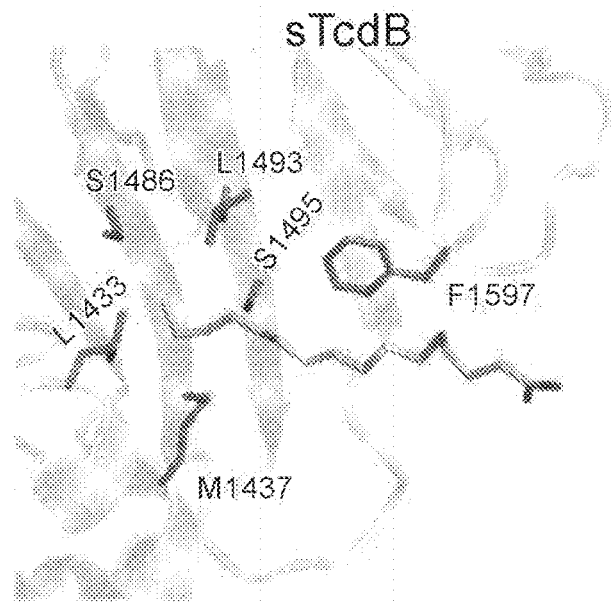

The free PAM is bound by both CRD2 and sTcdB, forming an intermediator within the complex (FIG. 2A). CRD2 binds to PAM mainly through hydrophobic interactions: residues Q75, F76, M125, and F130 stabilize the carboxylic group end of PAM, and residues P78, L79, V82, L124 and F128 stabilize the hydrocarbon chain of PAM (FIG. 2B). This binding mode is similar to how Wnt PAM is stabilized in CRD8[11]. However, this conserved lipid-binding mode found in CRD2 and CRD8 leaves the tail of the PAM acyl chain and some hydrophobic PAM-binding residues in CRD2 and CRD8 exposed to solvent, which are energetically unfavorable in aqueous environment. Interestingly, sTcdB forms a network of hydrophobic interactions that thoroughly shield PAM from the opposite side of CRD2. Specifically, F1597 in TcdB stabilizes the middle part of PAM, while residues L1433, M1437, S1486, L1493, and S1495 (together with V82 and L124 of CRD2) form a hydrophobic pocket to accommodate the PAM tail that protrudes from the CRD groove (FIG. 2B, 2C). Therefore, the free PAM is completely buried between CRD2 and sTcdB involving ~580 Å2 and ~320 Å2 of buried surface area with CRD2 and sTcdB, respectively.

Figure 2D:
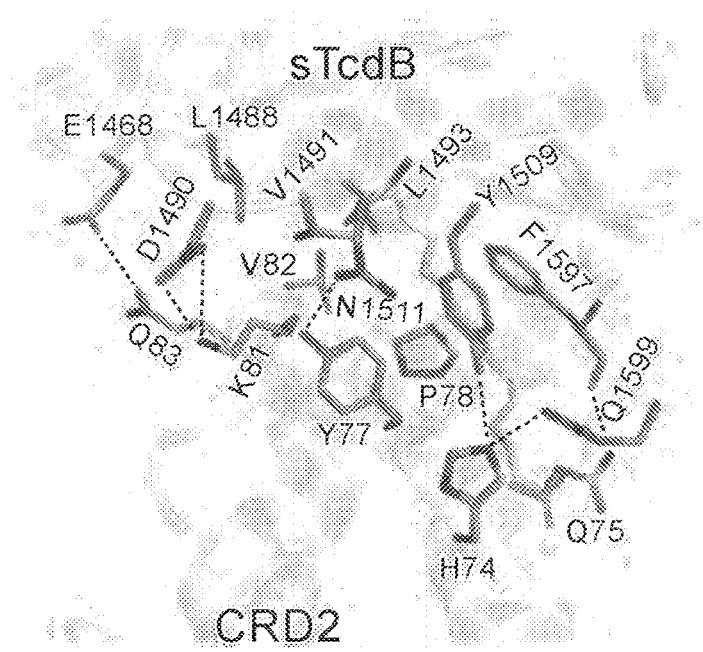

In addition to PAM-mediated interactions, sTcdB also recognizes CRD2 directly through a network of hydrogen bonds and hydrophobic interactions that surround the lipid-binding groove. Residues H74, Q75, Y77, P78, K81, V82, and Q83 in CRD2 interact with residues E1468, L1488, D1490, V1491, L1493, Y1509, N1511, Q1599, and F1597 in sTcdB on one side of the PAM, while residues V82, Q83, A123, L124, K127, F128, and F130 in CRD2 bind to residues K1434, M1437, L1438, S1495, V1497, D1501, S1505, F1597, and L1598 in sTcdB on the other side of PAM (FIGS. 2D, 2E, and Table 2). Many of these residues involved in protein-protein interactions also participate in PAM binding, suggesting that the binding between sTcdB and CRD is synergistically mediated by both proteins and PAM (FIG. 2F).

TABLE 2

Protein-protein and protein-lipid interactions in the sTcdB-CRD2 complex

Interactions between sTcdB and CRD

| CRD2 residue | sTcdB residue | Type of interaction |
| --- | --- | --- |
| H74 | Y1509 | Hydrogen bond (sc-sc) |
|  | Q1599 | Hydrogen bond (sc-sc) |
| Q75 | F1597 | Hydrogen bond (sc-mc) |
| Y77 | V1491 | vdW (sc-sc) |
|  | Y1509 | vdW (sc-sc) |
|  | N1511 | Hydrogen bond (sc-sc) |
| P78 | L1493 | vdW (sc-sc) |
|  | F1597 | vdW (sc-sc) |
|  | Y1509 | vdW (sc-sc) |
| K81 | L1488 | vdW (mc-sc) |
|  | D1490 | Salt bridge (sc-sc) |
| V82 | K1434 | Hydrogen bond (mc-sc) |
|  | L1493 | vdW (sc-sc) |
| Q83 | K1434 | Hydrogen bond (mc-sc) |
|  | E1468 | Hydrogen bond (sc-sc) |
| A123 | L1438 | vdW (sc-sc) |
| L124 | M1437 | vdW (sc-sc) |
|  | L1438 | vdW (sc-sc) |
| K127 | M1437 | Hydrogen bond (sc-mc) |
|  | D1501 | Salt bridge (sc-sc) |
|  | S1505 | Hydrogen bond (mc-mc) |
| F128 | M1437 | vdW (sc-sc) |
|  | S1495 | vdW (sc-sc) |
|  | V1497 | vdW (sc-sc) |
|  | S1505 | vdW (sc-sc) |
|  | S1505 | Hydrogen bond (mc-mc) |
|  | F1597 | vdW (sc-sc) |
| F130 | L1598 | vdW (sc-sc) |

PAM-mediated interactions between sTcdB and CDR2

| | CRD/sTcdB residue | Type of interaction |
| --- | --- | --- |
| PAM-CRD2 | Q75 | vdW |
|  | F76 | vdW |
|  | P78 | vdW |
|  | L79 | vdW |
|  | V82 | vdW |
|  | V124 | vdW |
|  | M125 | vdW |
|  | F128 | vdW |
|  | F130 | vdW |
| PAM-sTcdB | L1433 | vdW |
|  | M1437 | vdW |
|  | S1486 | vdW |
|  | L1493 | vdW |
|  | S1495 | vdW |
|  | F1597 | vdW |

*"vdW" stands for van der Waals interaction. "mc" and "Sc" indicates whether the contact was medicated by main-chain or side-chain atoms.

Figure 3A:
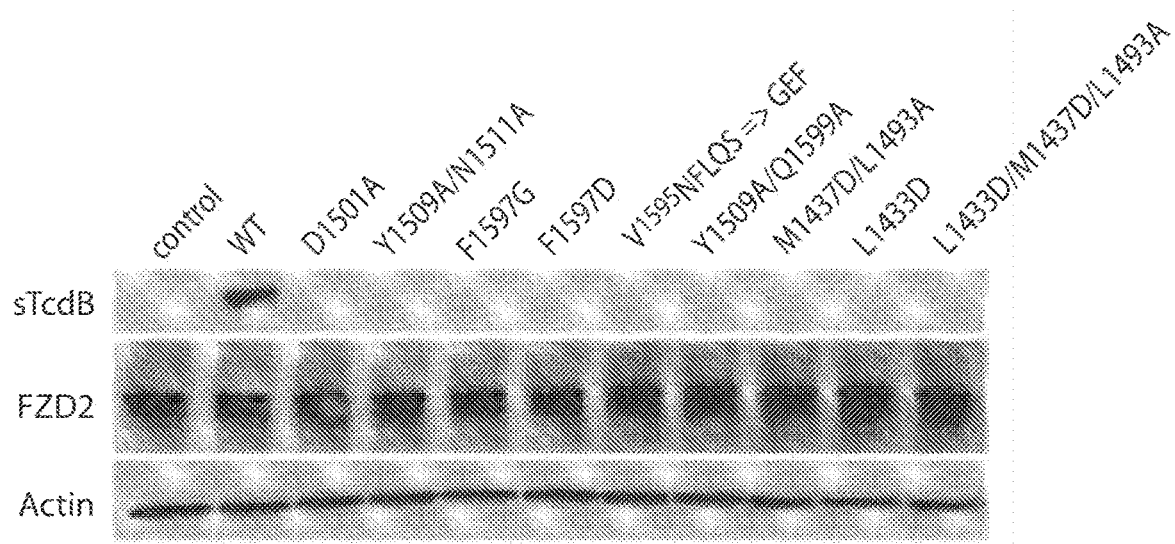
FIGS. 3A to 3F. Structure-based mutagenesis analyses of the interactions between TcdB and FZD2.
Figure 3B:
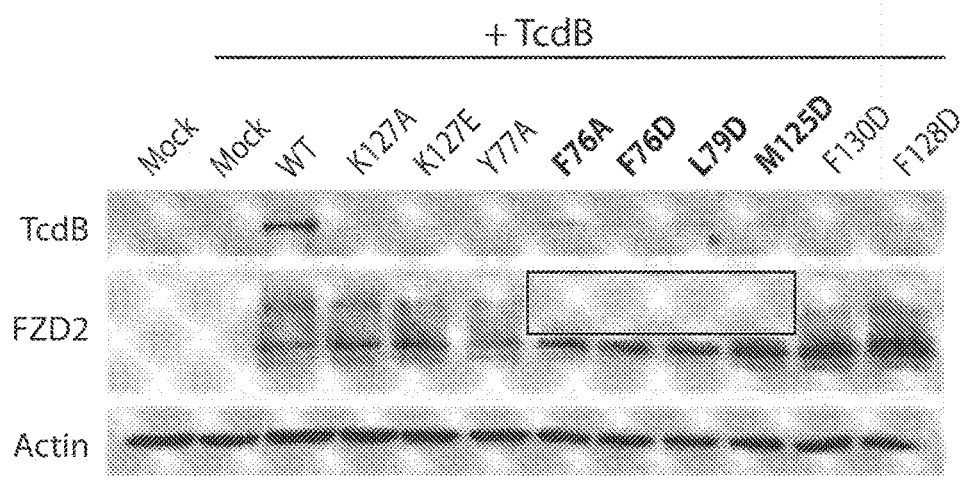
Figure 3C:
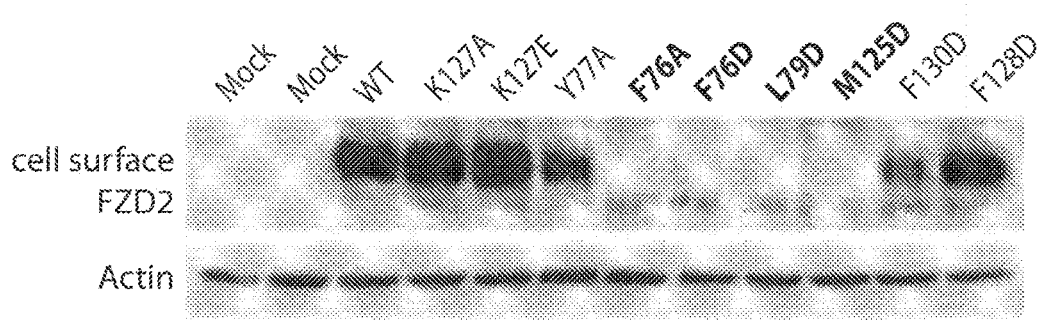
Figure 3D:
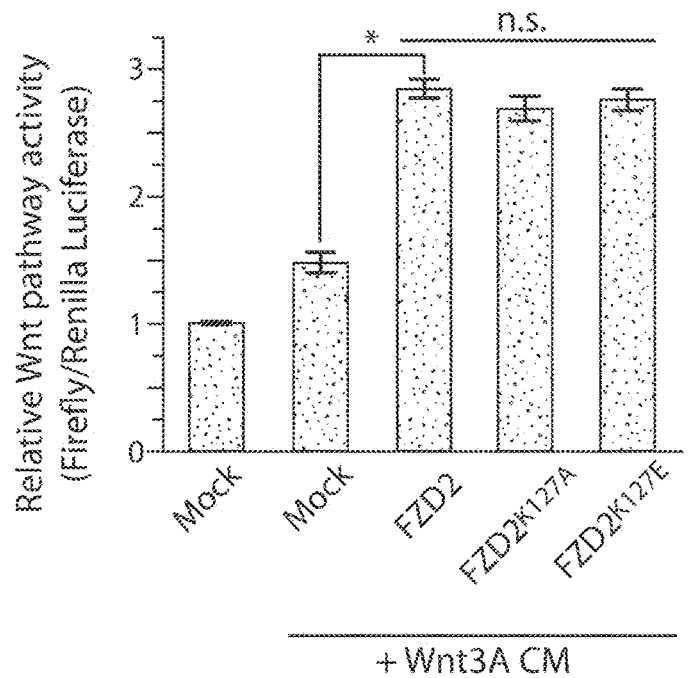
Figure 3E:
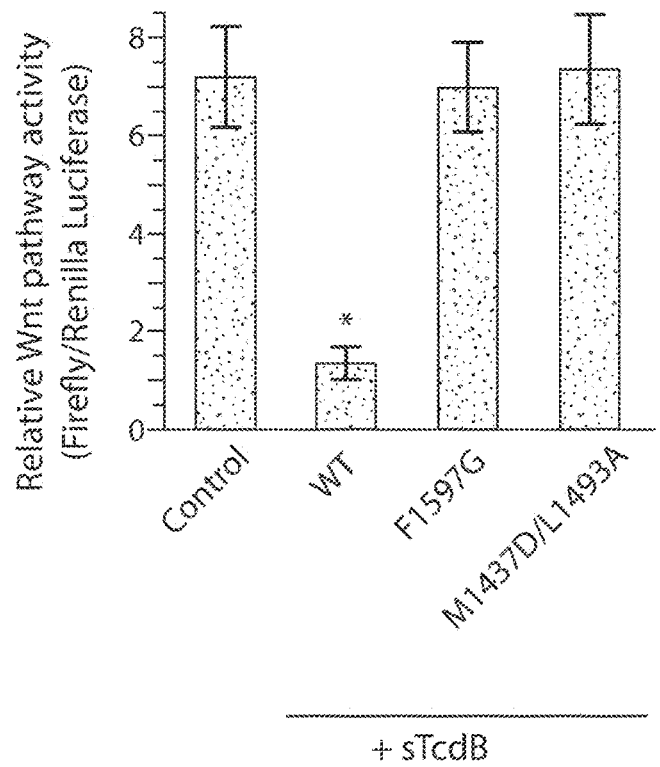
Figure 3F:
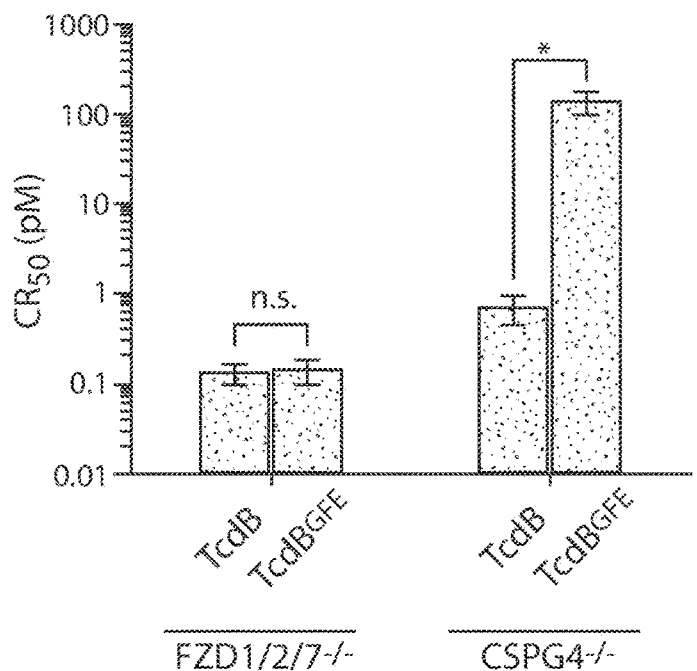
Figure 7:
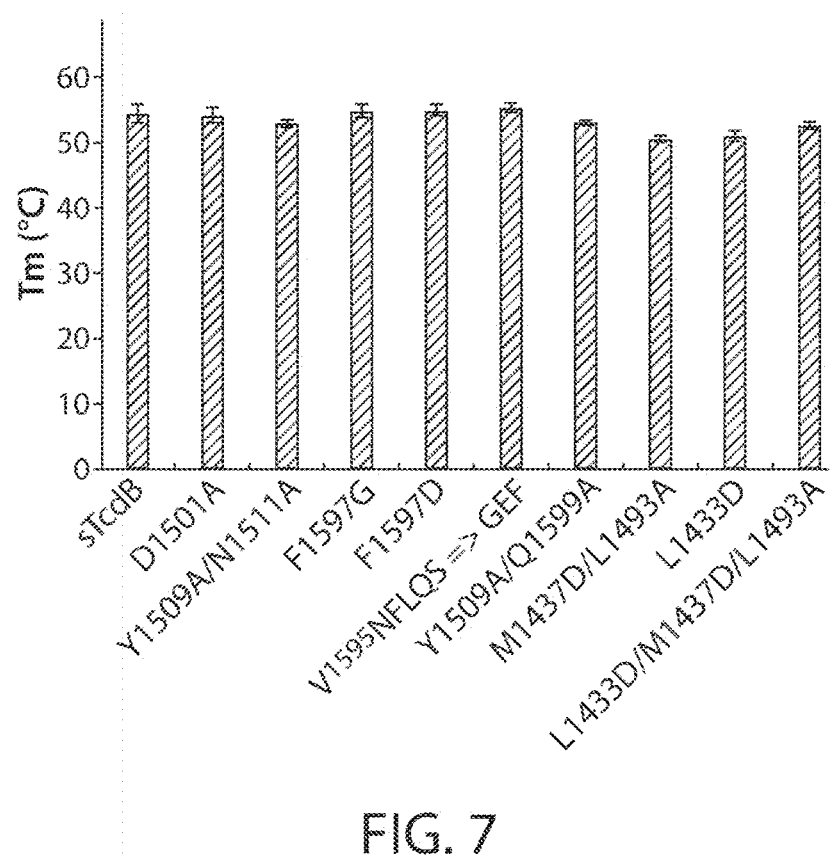
FIG. 7. sTcdB mutants adopt wild-type-like structures. The thermal stability of proteins was measured using a fluorescence-based thermal shift assay on a StepOne real-time PCR system (ThermoFisher). Protein melting was monitored using a hydrophobic dye, SYPRO Orange (Sigma-Aldrich), as the temperature was increased in a linear ramp from 25° C. to 95° C. The midpoint of the protein-melting curve (Tm) was determined using the software provided by the instrument manufacturer. The data are presented as mean±S.D.,n=3. All the sTcdB mutants showed Tm values comparable to the wild-type protein, indicating correct protein folding.
Figure 8A:
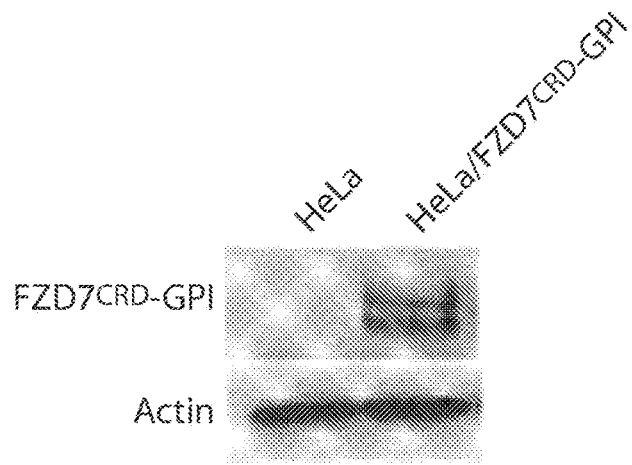
FIGS. 8A to 8C. Characterization of the binding of sTcdB variants to FZD7CRD-GPI on cell surface or to the His-tagged CRD2.
Figure 8B:
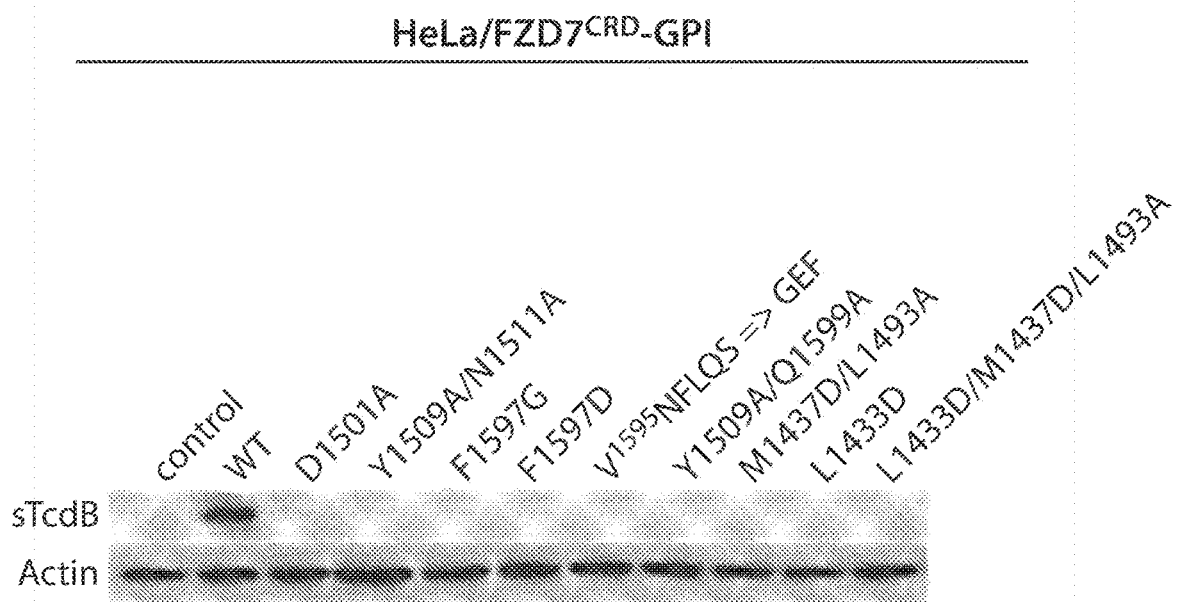
Figure 8C:
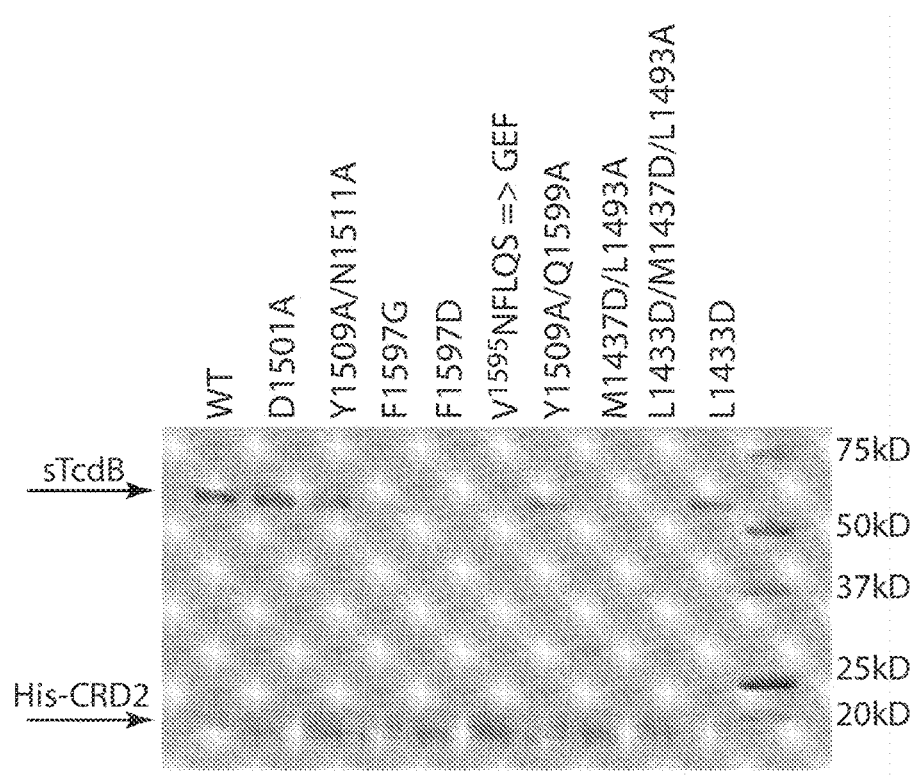

Next, a series of structure-guided mutations were designed in sTcdB to verify the structural findings. sTcdB-F1597G/D, M1437D/L1493 Å, and L1433D/M1437D/L1493A were selected to disrupt both sTcdB-PAM and sTcdB-CRD2 interactions, whereas L1433D would only effect the PAM binding. sTcdB-D1501 Å, Y1509 Å/N1511 Å, and Y1509 Å/Q1599A were selected to preferentially reduce protein-protein interactions with CRD2. None of these sTcdB mutants interfere with proper protein folding as verified by a thermal shift assay (FIG. 7). Binding of these sTcdB mutants was examined to HeLa cells transiently transfected with full-length FZD2 (FIG. 3A) or to a HeLa cell line that stably expressed GPI-anchored FZD7-CRD (FIGS. 8A, 8B). While both FZD2 and FZD7-CRD-GPI mediated robust binding of wild type (WT) sTcdB on cell surfaces, none of the sTcdB mutants showed detectable binding at the concentration used in the assay (50 nM). To further analyze the affinity and kinetics of binding, the binding of sTcdB mutants was examined to the immobilized His-tagged CRD2 using pull-down assays (FIG. 8C) and the immobilized Fc-tagged CRD2 using BLI assays (FIGS. 5A to 5F). sTcdB mutants with disrupted binding to both PAM and CRD2, e.g., F1597G/D, M1437D/L1493 Å, and L1433D/M1437D/L1493 Å, did not yield detectable binding in either pull-down assays or BLI assays ($K_D$>10 μM). Mutations at the protein-protein interface significantly weakened the sTcdB-CRD2 binding affinity by ~41-140 (or ~43-138) folds compared to WT sTcdB. A single point mutation (L1433D) disrupting a hydrophobic pocket on TcdB that accommodates the distal acyl tail of PAM also decreased the binding to CRD2 by ~35 (or ~37) folds. None of these TcdB-FBD variants interfere with protein folding as verified by a thermal shift assay (FIG. 7). The binding of TcdB-FBD variants to HeLa cells transiently transfected with full-length FZD2 (FIG. 3A) or stably expressed GPI-anchored FZD7-CRD were then examined (FIGS. 8A-8C). TcdB-FBD variants did not show detectable binding to FZD2 or FZD7-CRD-GPI at the concentration tested (50 nM), while WT TcdB-FBD bound robustly to these cells. The pull-down (FIG. 8A) and the BLI (FIG. 5) assays were more sensitive than the cell-based assays (FIG. 3A and FIG. 8B) in detecting weak interactions between CRD2 and TcdB-FBD variants, likely as a result of relatively low concentrations of FZD2/7 expressed on the cell surface. The mutagenesis studies thus verify the structural findings and suggest that TcdB exploits a free fatty acid as the co-receptor to engage FZDs.

The CRD2- or PAM-interacting residues in TcdB are not conserved in TcdA (FIG. 6C), explaining the unresponsiveness of FZDs to TcdA. Structure and sequence alignments revealed that TcdA and TcdB are very different in a small area containing three residues (F1597, L1598, and Q1599) that bind to PAM and CRD2 (FIG. 6C). When this region was replaced in TcdB ($^{1595}$VNFLQS) with the corresponding residues in TcdA ($^{1596}$GFE), this mutant could no longer bind CRD2. This finding confirms the importance of this region in TcdB for an effective receptor binding, and also explains the unresponsiveness of FZDs to TcdA[10].

A full length TcdB carrying the same mutations that abolish FZD binding (termed $TcdB^{GFE}$) and used it as a molecular tool to determine the physiological relevance of FZDs and lipids to the toxicity of TcdB. The activity of $TcdB^{GFE}$ was first validated using a cell-rounding assay (CR50) on FZD1/2/7 KO HeLa cells, which still express a high level of CSPG4 that could mediate toxin entry (13). As shown in FIG. 3F, $TcdB^{GFE}$ and WT TcdB displayed a similar toxicity on FZD1/2/7 KO HeLa cells, indicating that TcdBGFE was properly folded. To separate the contribution of CSPG4 and FZDs to toxin cell entry, the activity of TcdB$^{GFE}$ and WT TcdB on CSPG4 KO HeLa cells was further tested. Indeed, FZD-binding deficient TcdB$^{GFE}$ displayed a ~190 fold reduced toxicity compared to the WT toxin, demonstrating the functional role of FZDs in mediating TcdB binding and entry into cells (FIG. 3F).

Figure 9A:
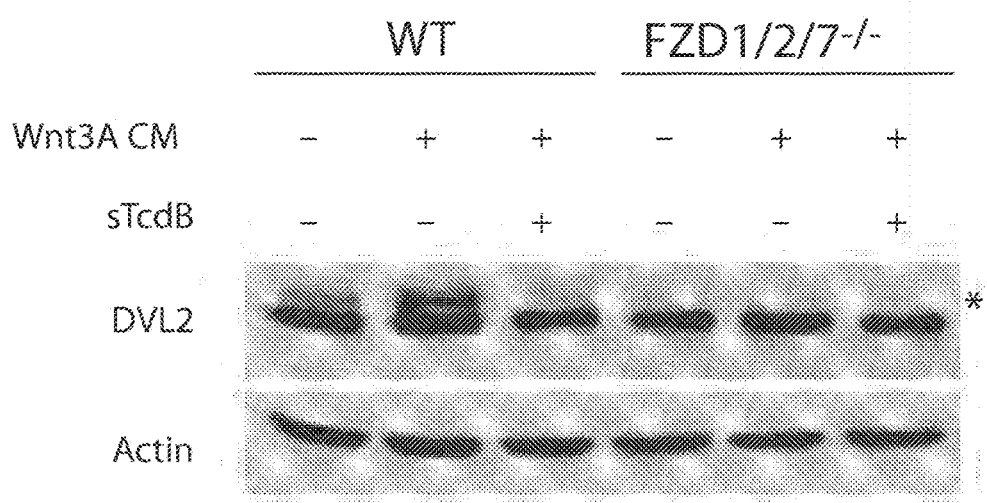
FIGS. 9A to 9D. Characterization of the selected sTcdB and FZD2 mutants by measuring Wnt-induced DVL2 phosphorylation.
Figure 9B:
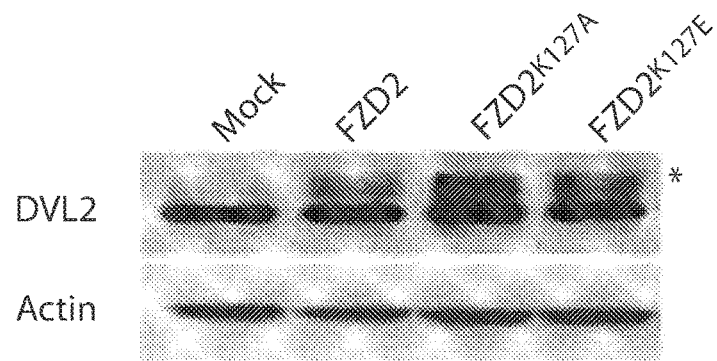

Complementary mutagenesis studies in CRD2 were then carried out. Based on the crystal structure, mutations K127 Å/E and Y77A were selected to preferentially disrupt protein-protein interactions between CRD2 and TcdB, while mutations F76 Å/D, L79D, M125D were designed to selectively disrupt the core of the lipid-binding groove in CRD2. Two residues on the CRD2 surface that partly interact with PAM and TcdB were also examined (F128D and F130D). Full-length mouse FZD2 containing these mutations were transfected in HeLa cells (residue numbering is based on human FZD2 sequence). FZDs are normally glycosylated, which is critical for its proper maturation and trafficking onto plasma membranes[27]. While all four mutations of FZD2 that have the disrupted lipid-binding groove in CRD2 (F76 Å/D, L79D, M125D) were expressed in cells, they lacked detectable levels of glycosylation (FIG. 3B). Surface biotinylation assays confirmed that these four mutants failed to reach the cell surface (FIG. 3C). These findings suggest that binding of an endogenous free fatty acids in the hydrophobic groove in CRD2 is probably critical for proper maturation and trafficking of FZD2. Mutations at the protein-protein interface (K127 Å/E, Y77 Å) or the two residues (F128D and F130D) that are solvent exposed in the absence of TcdB binding did not significantly alter glycosylation and surface expression of FZD2, but failed to mediate binding of full-length TcdB when expressed in CSPG4$^{-/-}$ HeLa cells (FIGS. 3B, 3C). Furthermore, it was confirmed that FZD2-K127 Å/E mediated similar levels of Wnt signaling as WT FZD2 in cells, demonstrating that they were correctly folded and selectively impaired TcdB binding without affecting Wnt signaling (FIG. 3D, FIGS. 9A, 9B). Taken together, the comprehensive structure-based mutagenesis studies discussed herein demonstrate that TcdB-FZD engagement is mediated by both lipid-protein and protein-protein interactions.

Figure 4A:
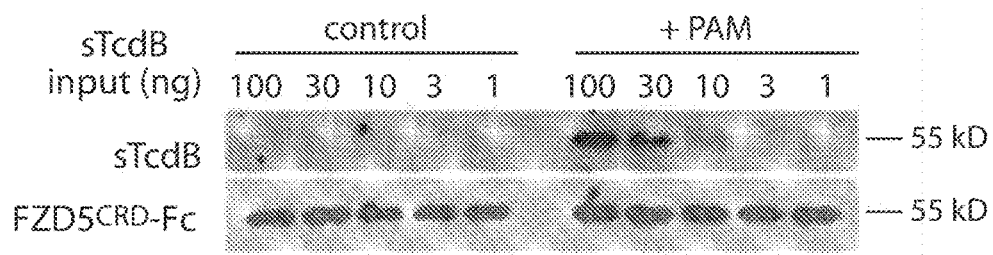
FIGS. 4A to 4H. PAM facilitates binding of TcdB to FZD-CRDs, which in turn prevents docking of the Wnt fatty acid.

The hydrophobic lipid-binding groove in CRD2 is largely conserved across all 10 members of human FZDs (FIG. 2F), although subtle residue differences in this region may influence how tight a fatty acid binds to a CRD. This pocket is also the docking site for Wnt PAM[28]. The lipid-binding grooves in CRDs of FZD1, 2, and 7 are identical. Consistently, it has been reported that a purified FZD7-CRD retained a free fatty acid in its hydrophobic groove that came from the expression host[25]. In addition, some unassigned electron densities were previously observed in this hydrophobic groove in crystal structures of mouse FZD8-CRD[29] and human FZD4-CRD[25,30,31], which could represent free fatty acids bound with low occupancy. These findings suggest that some CRDs may have weaker binding affinities to endogenous fatty acids, which may partly fall off during protein purification. Consistent with this notion, a recent study showed that the purified CRD5 does not contain free fatty acid, but it could bind an exogenous PAM in the conserved lipid-binding groove during co-crystallization[25]. It was found that CRD5 alone only weakly pulled down sTcdB, but pre-incubation of CRD5 with PAM significantly increased its binding to sTcdB (FIG. 4A). This "gain-of-function" for CRD5 to bind sTcdB caused by the free PAM further demonstrates that a CRD-bound fatty acid is critical for TcdB recognition.

Figure 1E:
Figure 4B:
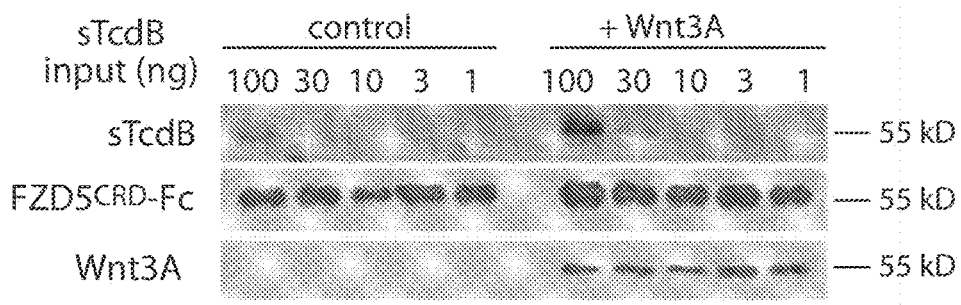
Figure 4C:
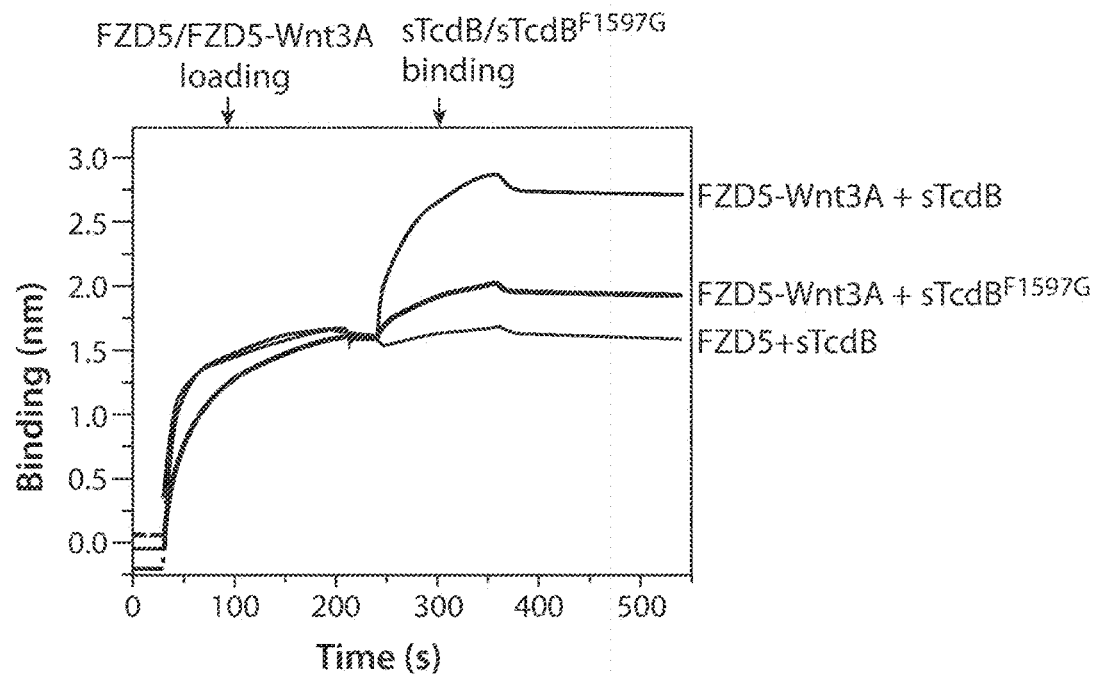
Figure 10A:
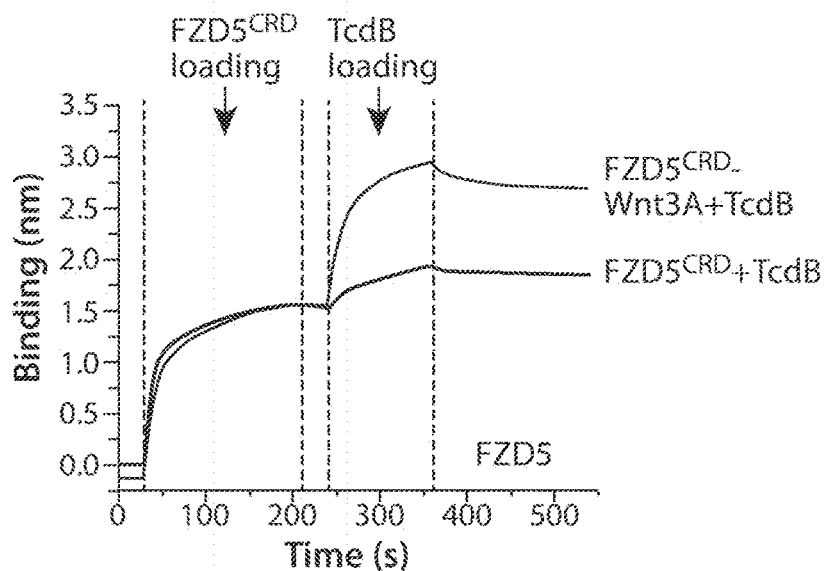
FIGS. 10A to 10D. Pre-loading Wnt3A enhanced binding of TcdB to various CRDs.
Figure 10B:
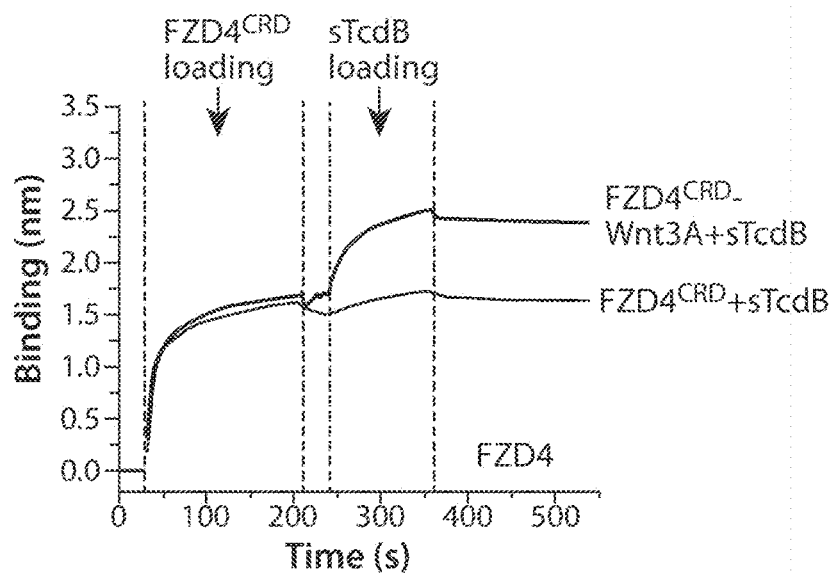
Figure 10C:
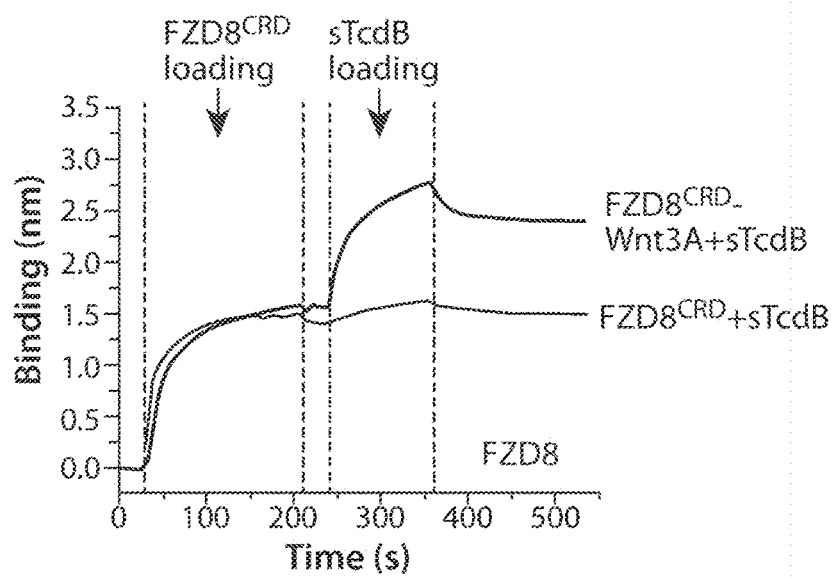
Figure 10D:
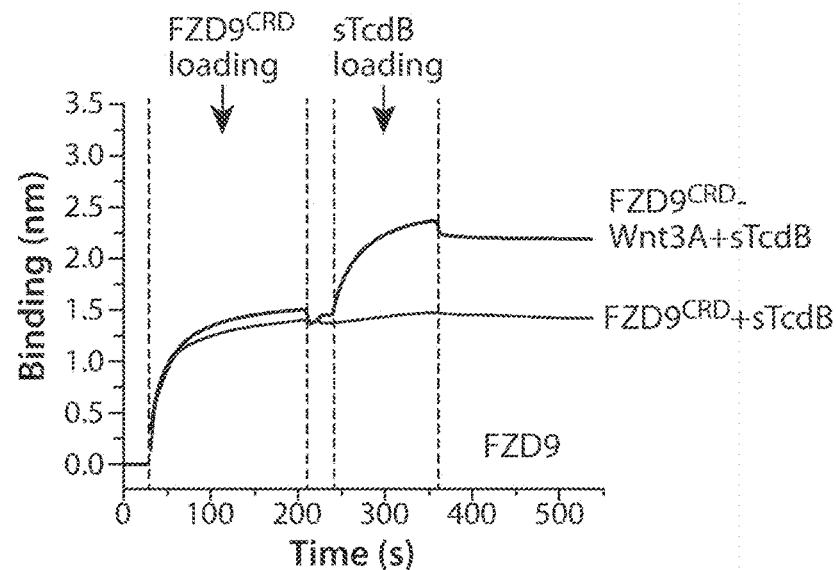

A structure comparison between the CRD2-sTcdB and CRD8-Wnt8 complexes suggests that the Wnt PAM could mimic the free fatty acid to facilitate TcdB binding, while the peptide moiety of Wnt does not interfere with TcdB binding (FIGS. 1C, 1E). Indeed, pre-incubation of Wnt3A with CRD5 enhanced binding of sTcdB to CRD5 in pull-down assays and BLI assays, whereas the enhancement was reduced for sTcdB-F1597G (FIGS. 4B, 4C). This Wnt-mediated enhancement was also observed for binding of full-length TcdB to CRD5 (FIG. 10A). Furthermore, sTcdB showed enhanced binding to three other CRDs (human FZD4, FZD8, and FZD9) examined in BLI assays when Wnt3A was pre-loaded onto these CRDs (FIGS. 10B, 10C, 10D). Taken together, these findings further support the structural model that a fatty acid in the hydrophobic groove of CRD strengthens binding of TcdB, and demonstrate that TcdB could take advantage of the Wnt PAM, a conserved Wnt posttranslational modification, to enhance its binding to CRDs.

Figure 9C:
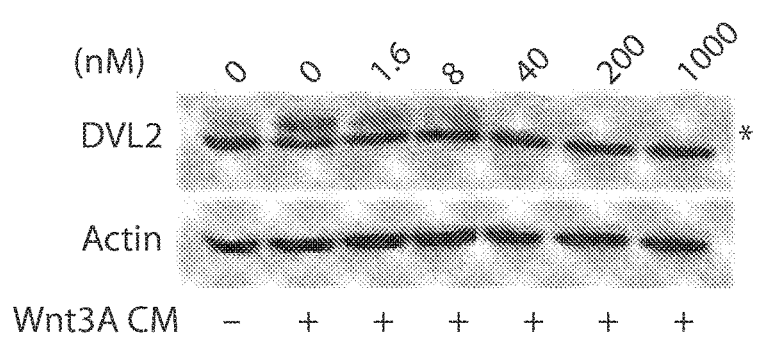
Figure 9D:
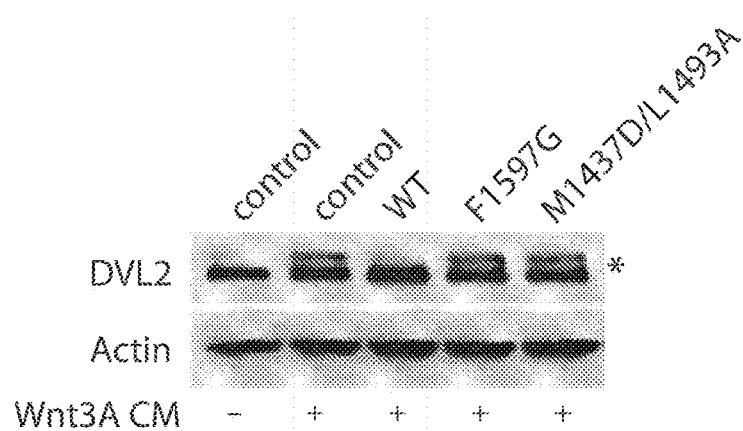

For the purified CRD2 that carries an endogenous fatty acid, pre-incubating it with Wnt3A did not affect its binding to sTcdB or full-length TcdB (FIG. 4D, FIG. 11A), indicating that the endogenous fatty acid bound in CRD2 is likely replaced by the Wnt PAM as both could support TcdB binding. In contrast, pre-incubation of sTcdB or full-length TcdB with CRD2 clearly impeded binding of Wnt3A to CRD2 (FIG. 4E, FIG. 11B). These findings suggest that TcdB may stabilize the binding of endogenous fatty acid in CRD2 that subsequently hampers its replacement by the Wnt PAM. This hypothesis is consistent with the observation that sTcdB was able to block Wnt3A-induced signaling in reporter cells, while the CRD-binding deficient sTcdB mutations did not (FIG. 3E, FIGS. 9C, 9D).

The co-crystal structure of the sTcdB-CRD2 complex reported here establishes the molecular mechanism underlying TcdB recognition of FZDs for host cell binding. It reveals an unexpected central role of an endogenous fatty acid, which is bound in a conserved hydrophobic groove in CRD, for TcdB binding. Although it remains to be determined whether all FZDs are associated with endogenous fatty acids in cells, TcdB exploits this fatty acid to enhance its binding capability to a broad range of FZD members. Among the 10 FZDs, FZD1, 2 and 7 are the high-affinity receptors for TcdB[10], which is likely a combination of their tight interactions with fatty acids, as well as their specific protein-protein interactions with TcdB. For instance, residues Y77, K81, V82, A123 and K127 of CRD2 that forms multiple charge and hydrophobic interactions with TcdB are only conserved in FZD1, 2, and 7 (FIG. 2F).

The crystal structure discussed herein also suggests a novel mechanism for inhibiting Wnt signaling. A direct competition with Wnt for FZD binding would be energy costly, because Wnt and FZD are tightly engaged with each other involving extensive protein-protein and protein-lipid interactions[11]. TcdB instead impedes the docking of the crucial fatty acid moiety of Wnt by jamming the lipid-binding groove of CRD with an endogenous fatty acid (FIG. 4G). In addition, recent studies suggested that Wnt PAM may contribute to CRD dimerization that subsequently activates the downstream signaling pathways, although the contribution of such FZD dimerization in Wnt signaling remains to be fully established[25,32]. Two different CRD dimer configurations have been reported[25,32]. Binding of TcdB, even just the sTcdB, would prevent CRD dimerization in either model, and may also contribute to Wnt signaling inhibition (FIG. 4F). Wnt signaling is critical for development and tissue homeostasis. Its mis-regulation plays important roles in many diseases including cancer[24,33].

It is well established that Wnt binds to FZD-CRD via the Wnt PAM as a major driving force. The Wnt PAM occupies the same hydrophobic groove in CRD as the free lipid (FIG. 1E). It was found that TcdB-FBD can bind to the Wnt-FZD complex using the Wnt PAM as a co-receptor, as TcdB-FBD engages CRD2 from the opposite side of the Wnt-binding interface without direct steric competition with Wnt (FIG. 4H). The ability to recognize Wnt-bound FZDs is perhaps particularly advantageous for TcdB to recognize certain FZDs that may have weaker affinities for free lipids. Indeed, we found that pre-incubation of Wnt3A with CRD5 enhanced binding of TcdB-FBD to CRD5 in pull-down and BLI assays, whereas the enhancement was dramatically reduced for TcdB-FBD-F1597G (FIGS. 4B and 4C). Similar Wnt-mediated enhancement was also observed for three other CRDs (human FZD4, FZD8, and FZD9) (FIGS. 10B-10D), and was further confirmed using full-length TcdB and CRD5 (FIG. 10A). Thus TcdB can use the Wnt PAM, a conserved Wnt posttranslational modification, as a co-receptor to recognize a broad range of FZDs despite their sequence variations.

Figure 4D:
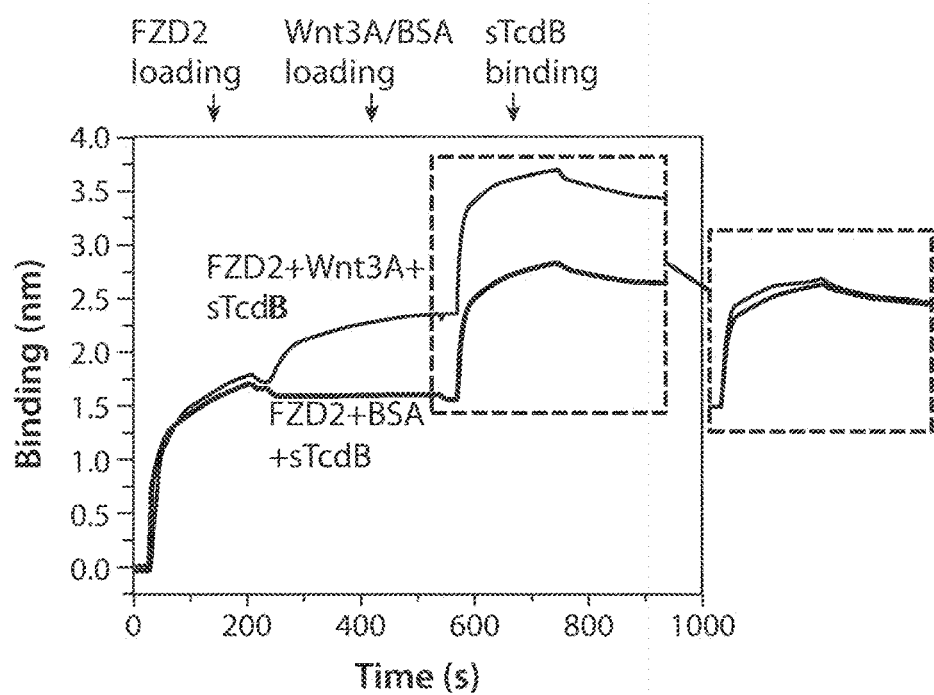
Figure 4E:
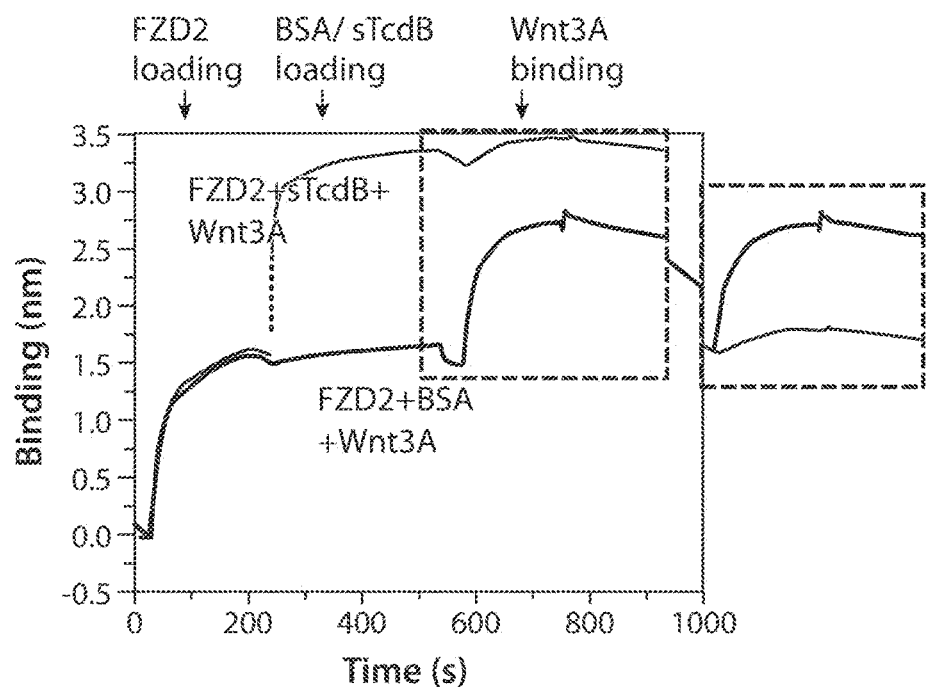
Figure 4F:
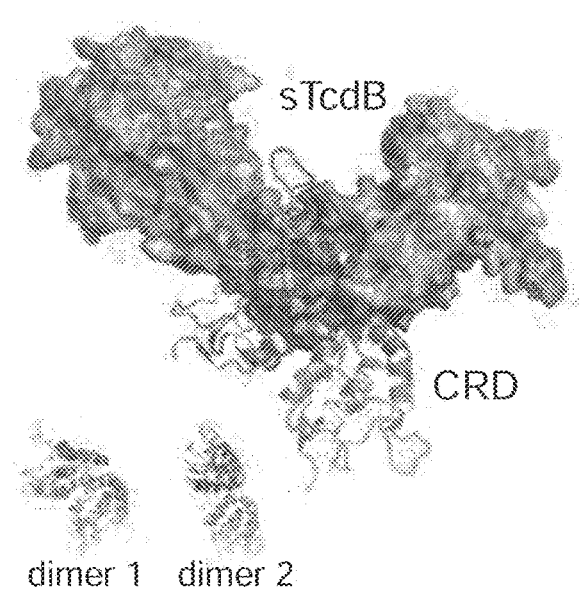
Figure 4G:
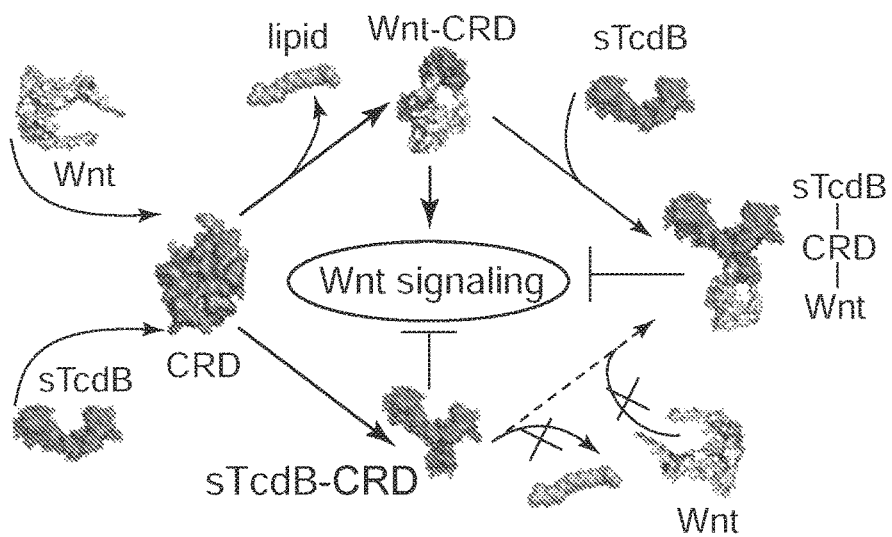
Figure 4H:
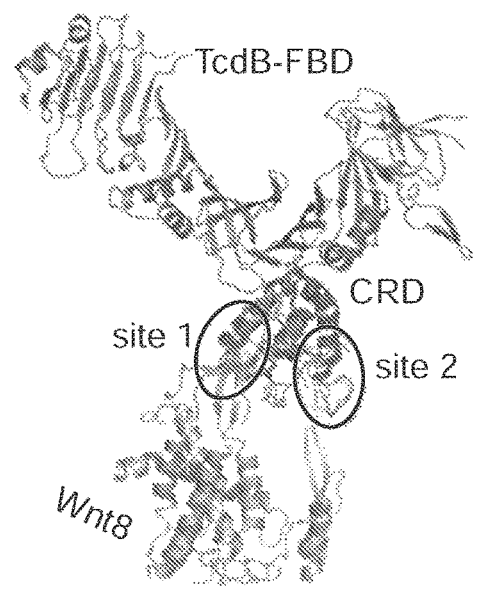
Figure 11A:
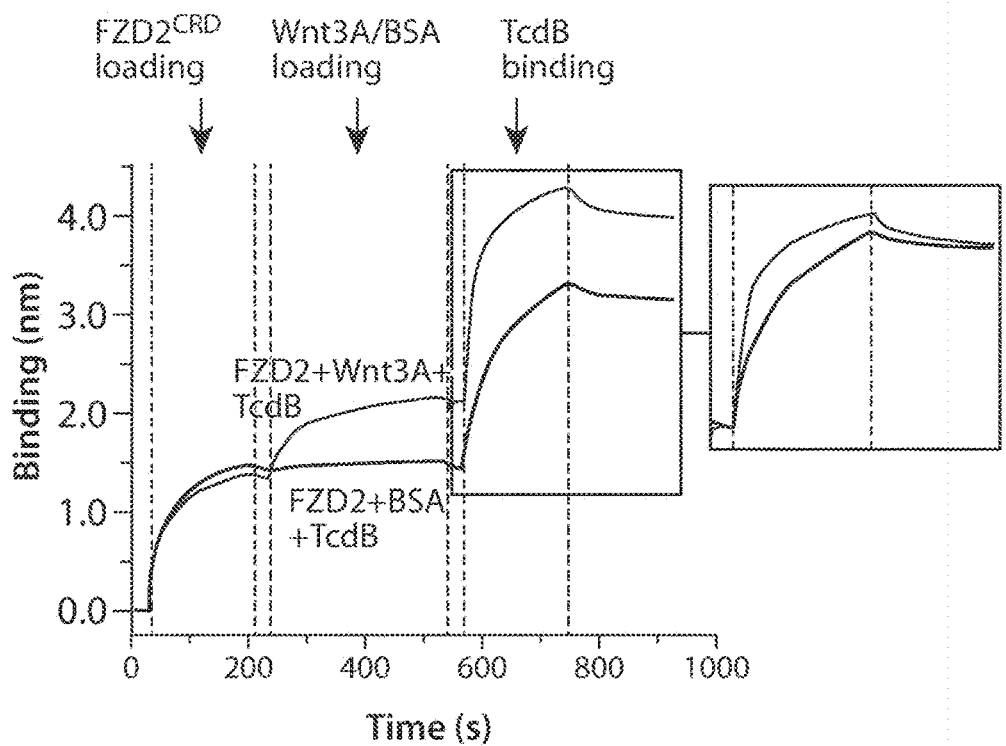
FIGS. 11A to 11B. Wnt3A did not impair the binding of full-length TcdB to CRD2, but TcdB impeded binding of Wnt3A to CRD2. The relationship between Wnt3A and full-length TcdB in terms of their binding to CRD2 was accessed via sequential protein loading in BLI assays. The binding of full-length TcdB to CRD2 was marginally changed when CRD2 was pre-bound with Wnt3A (FIG. 11A). In contrast, binding of TcdB to CRD2 blocked subsequent binding of Wnt3A (FIG. 11B). BSA (0.1 mg/ml) served as a control. Different loading steps are noted.
Figure 11B:
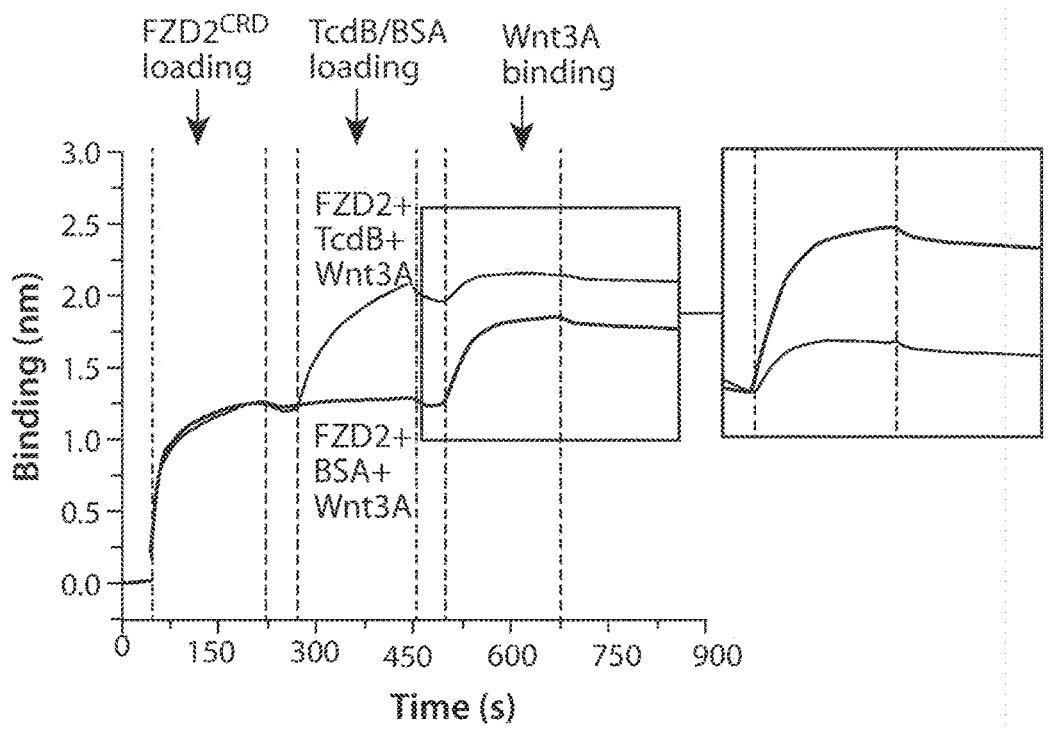
Figure 15A:
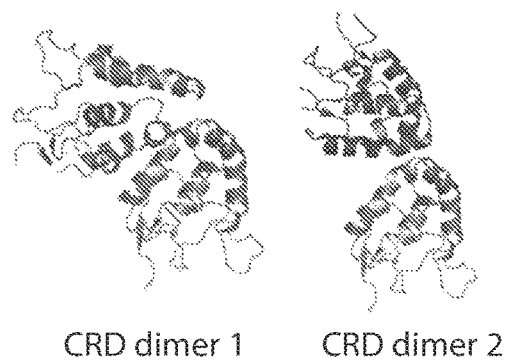
FIGS. 15A-15B. TcdB blocks CRD dimerization.
Figure 15B:
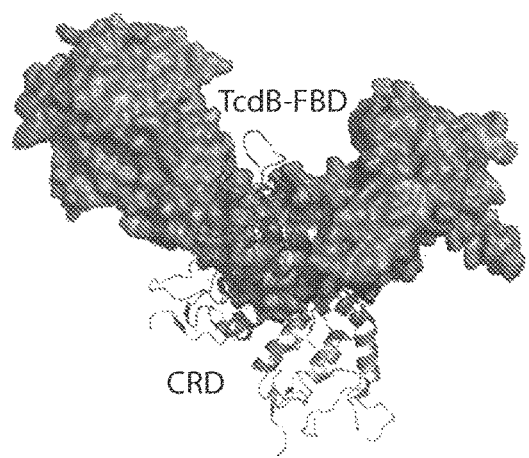

CRD2 and the pre-formed CRD2-Wnt3A complex were recognized equally well by TcdB-FBD or full-length TcdB (FIG. 4D and FIG. 11A). This suggests that either the free lipid or the Wnt PAM supports TcdB binding to CRD2. In contrast, upon binding to TcdB-FBD or full-length TcdB, CRD2 could no longer bind Wnt3A (FIG. 4E and FIG. 11B). This is likely because the Wnt PAM cannot displace the free fatty acid once it is locked in place by TcdB. This is consistent with the observation that TcdB-FBD blocked Wnt3 Å-induced signaling in cells, while the CRD-binding deficient TcdB-FBD variants did not (FIG. 3E, and FIGS. 9C and 9D). Recent studies suggested that Wnt PAM may contribute to CRD dimerization, although the contribution of such FZD dimerization to activate Wnt signaling remains to be fully established (25, 32). Two different CRD dimer configurations have been reported (FIG. 15A). Binding of TcdB, or TcdB-FBD, would prevent CRD dimerization in either configuration due to steric competitions, which may also contribute to Wnt signaling inhibition (FIG. 15B).

Figure 14A:
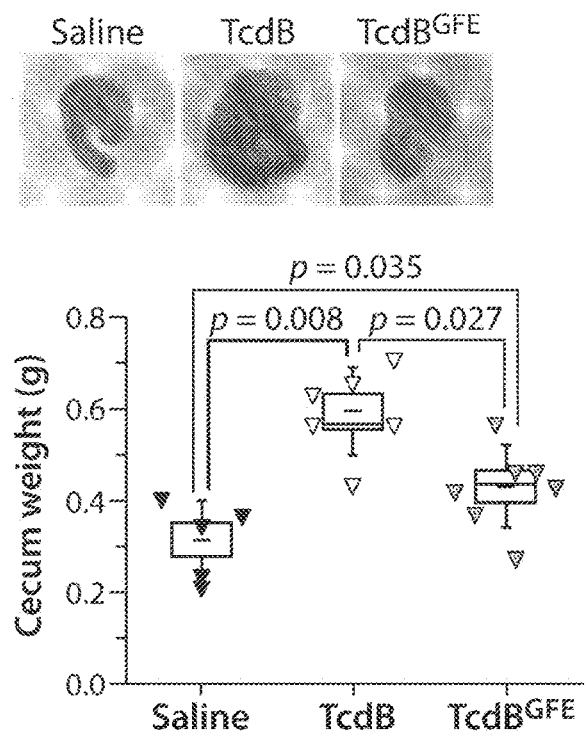
FIGS. 14A-14D. FZDs and the FZD-bound fatty acids are the major pathologically relevant receptors for TcdB in the colonic tissues.
Figure 14B:
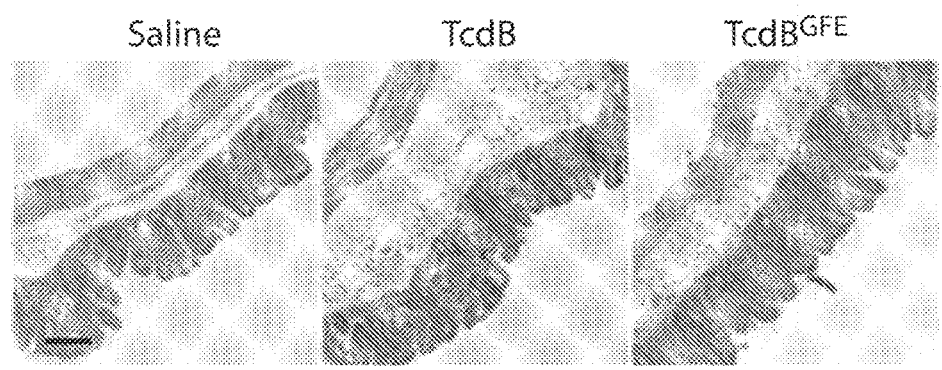
Figure 14C:
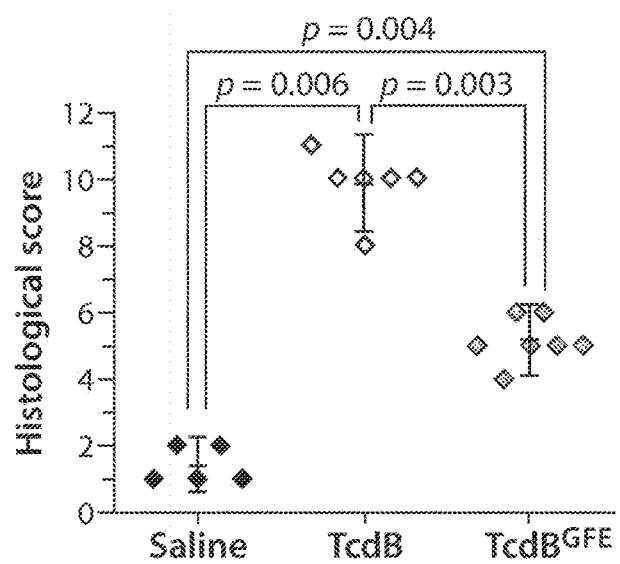
Figure 14D:
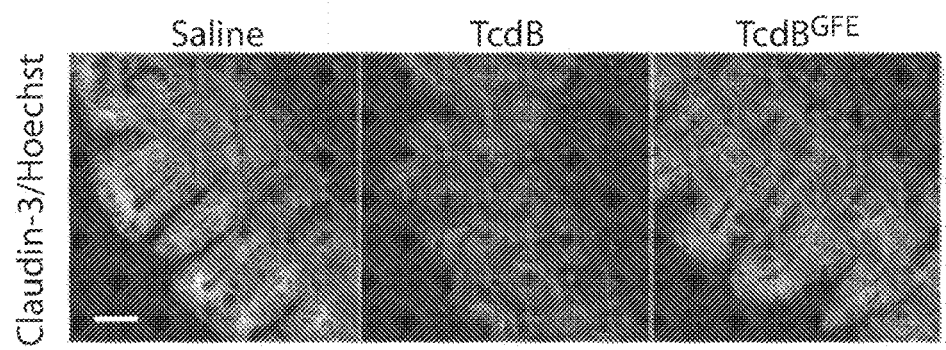

Given the extensive in vitro and ex vivo data demonstrating the role of FZDs and the FZD-bound fatty acids as TcdB receptors, it was sought to determine the physiological relevance of TcdB-lipid-FZD interactions to the toxicity of TcdB in vivo. Colonic tissues are the pathological relevant target tissue for TcdB. It has been shown that FZDs are major receptors in the colonic epithelium, while CSPG4 is not expressed in the colonic epithelium, but in the sub-epithelial myofibroblasts (10). Therefore, a murine cecum injection model was used, which has been previously utilized to assess TcdB-induced damage to colonic tissues (39, 40). Briefly, a full length FZD-binding deficient TcdB mutant, TcdBGFE (FIG. 3F), the WT TcdB, or the control saline solution was injected into cecum of WT mice. Mice were allowed to recover and cecum tissues were harvested 12 h later for analysis. WT TcdB induced severe bloody fluid accumulation and vesicular congestion in the cecum, resulting in drastic swelling as expected. In contrast, TcdBGFE induced much less fluid accumulation and no obvious vesicular congestion (FIG. 14A). To further examine the damage to tissues, histological analysis was carried out with paraffin embedded cecum tissue sections. These tissues were scored based on four histological criteria, including disruption of the epithelium, hemorrhagic congestion, mucosal edema, and inflammatory cell infiltration, on a scale of 0 to 3 (normal, mild, moderate, or severe). WT TcdB induced extensive disruption of the epithelium and inflammatory cell infiltration, as well as severe hemorrhagic congestion and mucosal edema, while TcdBGFE induced much less damage on all four criteria (FIGS. 14B and 14C). The integrity of epithelial tight junction was further assessed by immunofluorescent staining for tight junction marker Claudin-3. WT TcdB induced extensive loss of Claudin-3 in the epithelium, while the overall morphology of the epithelial tight junction was not changed after treatment with TcdB$^{GFE}$ (FIG. 14D). Taken together, these data further prove that FZDs are the major pathologically relevant receptors for TcdB in the colonic tissues.

Wnt signaling is critical for development, tissue homeostasis, stem cell biology, and many other processes, and its malfunction is implicated in diseases including a variety of human cancers and degenerative diseases (24, 33). The FZD-binding mechanism exploited by TcdB adds to the growing evidence that FZD-lipid binding is important for regulating FZD functions[25,32], and suggests novel pharmacological strategies to modulate Wnt signaling by targeting the lipid-binding groove in FZDs. The unexpected fatty acid-dependent binding between TcdB and FZDs also exposes a weakness of TcdB, which could be exploited to develop 2 novel antitoxins that block toxin-receptor recognition.

Figure 12:
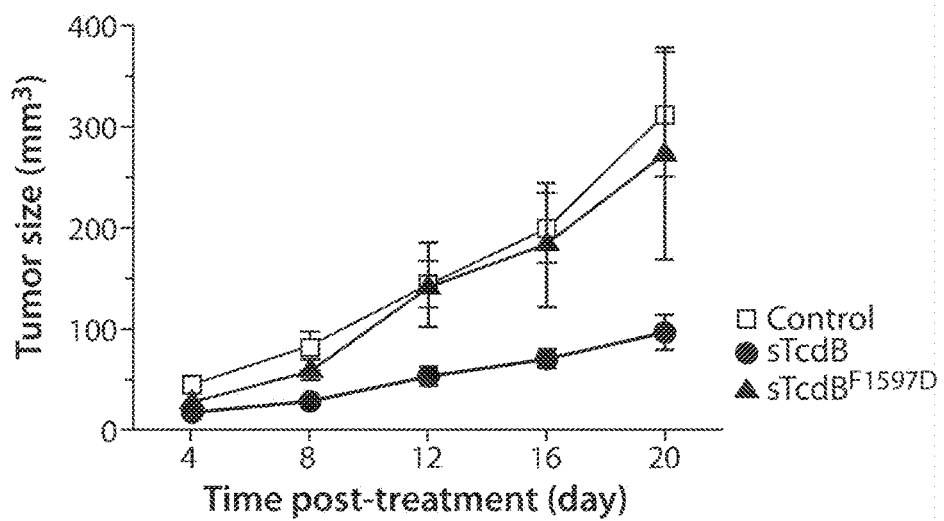
FIG. 12. Osteosarcoma cells treated with sTcdB form smaller tumors in vivo. U2OS cells were exposed to sTcdB (150 nM) or a sTcdB mutant (F1597D) for 6 hours in medium. Cells were then collected and injected subcutaneously into athymic nude mice (10 mice per group, 5×106 cells per site). Injected cells grow into solid tumor over time. The tumor size was measured every four days for 20 days.

Cancer cells treated with sTcdB Studies were carried out to examine whether sTcdB fragment might be able to inhibit growth of cancer cells. First, a list of cancer cell lines were screened and it was found that osteosarcoma cell lines exhibit high levels of Wnt activity. Thus, an osteosarcoma cell line U2OS was chosen as a model for proof-of-principal studies. Cells were first exposed to sTcdB in medium for 6 hours. sTcdB containing a point mutation that reduces FZD-binding (F1597D) served as a control. Treated cells were injected into nude mice and developed into tumors. As shown in FIG. 12, tumors formed by cells pre-exposed to sTcdB is smaller than tumor formed from control cells and cells that exposed to mutant sTcdB (F1597D), demonstrating that sTcdB inhibited the formation of tumor and/or tumor growth rate. This effect depends on binding of sTcdB to FZDs as the mutant sTcdB has no effect.

Figure 13A:
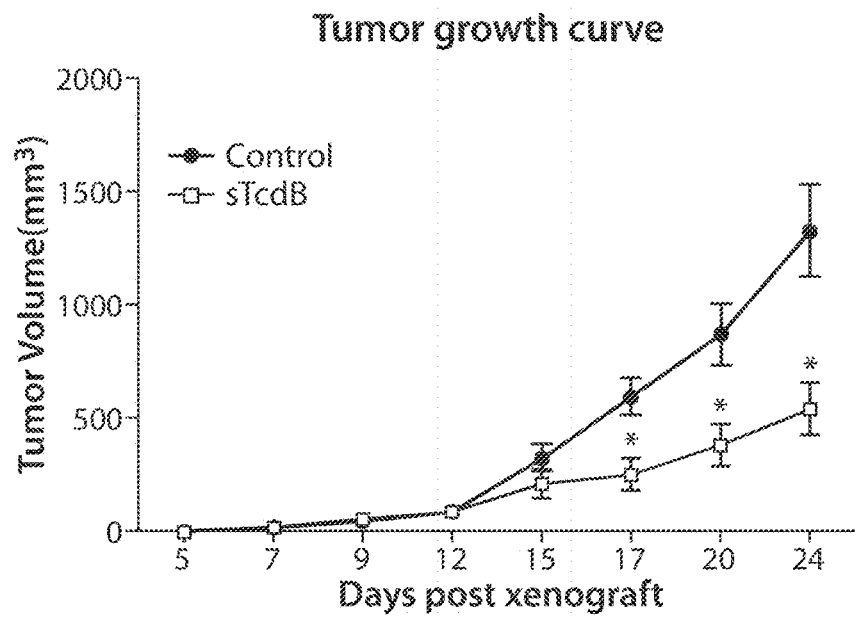
FIGS. 13A to 13B. sTcdB inhibits growth of triple negative breast cancer cells. Knocking out genes P53 and BRCA1 generates breast cancer in mouse models. These cancer tissues bear features of triple negative breast cancer in humans. The cancer tissue were isolated from knockout mice and grown as organoid models in vitro. Ten thousands organoid cells were subcutaneously injected into athymic nude mice, which grow into new cancers. sTcdB was injected via intraperitoneal route at 20 mg/kg dose at day 12, 14, 17, 20, and 23. Compared to the control group that injected with PBS, injecting sTcdB inhibited growth of these breast cancer cells in vivo. N=6, *p<0.05 (FIG. 13A). MDA-MB-231 is a widely used human breast cancer cell line that represents triple negative breast cancer cells. These cells grow as a sphere in vitro during culture (control). Adding sTcdB into culture medium blocked growth of these cells (FIG. 13B).
Figure 13B:
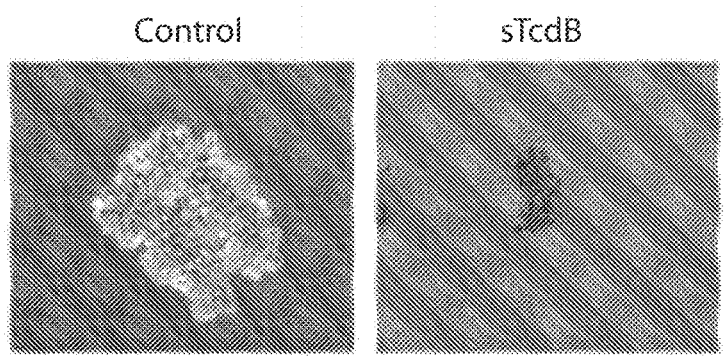

Whether sTcdB can inhibit growth of triple negative breast cancer cells was further examined. Knocking out genes P53 and BRCA1 generates breast cancer in mouse models. These cancer tissues bear features of triple negative breast cancer in humans. The cancer tissue were isolated from knockout mice and grown as organoid models in vitro. Ten thousands organoid cells were subcutaneously injected into athymic nude mice, which grow into new cancers. sTcdB was injected via intraperitoneal route at 20 mg/kg dose at day 12, 14, 17, 20, and 23. Compared to the control group that injected with PBS, injecting sTcdB TD3 inhibited growth of these breast cancer cells in vivo. N=6, *p<0.05 (FIG. 13A). MDA-MB-231 is a widely used human breast cancer cell line that represents triple negative breast cancer cells. These cells grow as a sphere in vitro during culture (control). Adding sTcdB into culture medium blocked growth of these cells (FIG. 13B).

Methods

Cloning, Expression, and Purification of Recombinant Proteins

The gene encoding sTcdB (residues 1285-1804) was cloned into a modified pET28a vector with a 6×His/SUMO (*Saccharomyces cerevisiae* Smt3p) tag introduced to its N-terminus. A second sTcdB construct was made by adding an additional HA tag to the C terminus, which was used for BLI, pull down, and cell surface binding assays. The CRD of human Frizzled 2 (residues 24-156) was cloned into a modified pcDNA vector for mammalian cell expression, and a human IL2 signal sequence (MYRMQLLSCIALSLA-LVTNS (SEQ ID NO: 18)), a 9×His tag, and a human rhinovirus 3C protease cleavage site were added to its N-terminus. All sTcdB mutants were generated by two-step PCR and verified by DNA sequencing.

sTcdB was expressed in *E. coli* strain BL21-Star (DE3) (Invitrogen). Bacteria were cultured at 37° C. in LB medium containing kanamycin. The temperature was reduced to 16° C. when $OD_{600}$ reached ~0.8. Expression was induced with 1 mM IPTG (isopropyl-b-D-thiogalactopyranoside) and continued at 16° C. overnight. The cells were harvested by centrifugation and stored at −80° C. until use.

The His-tagged sTcdB (WT and the mutants) was purified using $Ni^{2+}$-NTA (nitrilotriacetic acid, Qiagen) affinity resins in a buffer containing 50 mM Tris, pH 8.0, 400 mM NaCl, and 40 mM imidazole. The proteins were eluted with a high-imidazole buffer (50 mM Tris, pH 8.0, 400 mM NaCl, and 300 mM imidazole) and then dialyzed at 4° C. against a buffer containing 20 mM HEPES, pH 7.5, and 150 mM NaCl. After cleaving the His-SUMO tag by SUMO protease, sTcdB was further purified by MonoQ ion-exchange (20 mM Tris, pH 8.5) and Superdex-200 size-exclusion chromatography (GE Healthcare, 20 mM Tris, pH 8.0, and 100 mM NaCl).

His-tagged CRD2 was expressed and secreted from Free-Style HEK 293 cells (ThermoFisher) and purified directly from cell culture medium using $Ni^{2+}$-NTA resins. The sTcdB-CRD2 complex was prepared by mixing the purified sTcdB and CRD2 at a molar ratio of ~1:3 for 2 hours on ice, and the complex was further purified using a MonoQ ion-exchange column (20 mm Tris, pH 8.5). The complex was concentrated to ~10 mg/ml for crystallization.

Crystallization

Initial crystallization screens were carried out at 20° C. using a Gryphon crystallization robot (Art Robbins Instruments) with high-throughput crystallization screening kits (Hampton Research and Qiagen). The best crystals of sTcdB-CRD2 complex suitable for X-ray diffraction were obtained using hanging-drop vapor diffusion in a reservoir containing 0.1 M sodium acetate (pH 5.0) and 1 M ammonium sulfate. For cryo-protection, the reservoir solution was supplemented with additional 2.2 M sodium malonate. Crystals of the platinum-derived sTcdB-CRD2 complex were obtained by soaking native crystals in 100 mM potassium tetracyanoplatinate (II) for 5 minutes and cryoprotected similarly as native crystals.

Data Collection and Structure Determination

The X-ray diffraction data were collected at 100 K at the NE-CAT beamline 24-ID-C, Advanced Photon Source (APS). The data were processed with XDS as implemented in RAPD (github.com/RAPD/RAPD)[34]. For the Pt-soaked sTcdB-CRD2 complex, 0.2 degree, 0.2 second exposure fine phi-sliced data using a PILATUS 6MF was collected at the Platinum LIII peak above the absorption edge (1.0717 Å) using one crystal. A native 2.5 Å dataset was collected using 0.2 degree, 0.2 second exposure at 0.9791 Å wavelength using one crystal. The single wavelength anomalous dispersion dataset of the sTcdB-CRD2 complex was sufficient to calculate the initial phase using PHENIX.AutoSol[35]. The phase information was used to build an initial model using PHENIX.AutoBuild[35], which was improved through multiple cycles of manual model building in COOT[36] and refinement in Phenix[35]. This partially refined structure was then used as a search model in molecular replacement on the native 2.5 Å dataset using PHENIX.Phaser[35]. Further structural modeling and refinement were carried out iteratively using COOT[36] and Phenix.Refinement[35]. All the refinement progress was monitored with the free R value using a 5% randomly selected test set[37]. The structures were validated through the MolProbity[38]. Data collection and structural refinement statistics are listed in Table 1. All structure figures were prepared with Pymol (DeLano Scientific).

Protein Melting Assay

The thermal stability of sTcdB variants was measured using a fluorescence-based thermal shift assay on a StepOne real-time PCR machine (Life Technologies). Each protein (~0.1 mg/ml) was mixed with the fluorescent dye SYPRO Orange (Sigma-Aldrich) and heated from 25° C. to 95° C. in a linear ramp. The midpoint of the protein-melting curve (Tm) was determined using the analysis software provided by the instrument manufacturer. Data obtained from three independent experiments were averaged to generate the bar graph.

Cell Lines, Antibodies and Constructs

HeLa (H1, #CRL-1958), 293T (#CRL-3216), L cells (#CRL-2648), and L/Wnt3A (#CRL-2647) cells were originally obtained from ATCC. They tested negative for mycoplasma contamination, but have not been authenticated. HeLa-Cas9, HeLa-Cas9 FZD1/2/7$^{-/-}$, and HeLa-Cas9 CSPG4$^{-/-}$ cells were generated in-house and have been described previously[10]. Stable HeLa-FZD7$^{CRD}$-Myc-GPI cells were generated by lentiviral transduction of HeLa H1 cells with a construct expressing FZD7$^{CRD}$-Myc-GPI (pLEX_307 vector, #41392, Addgene), followed by selection with 5 μg/ml puromycin. The following mouse monoclonal antibodies were purchased from the indicated vendors: 1D4 tag (MA1-722, ThermoFisher Scientific), HA tag (16B12, Covance), β-actin (AC-15, Sigma), Myc tag (9E10, ThermoFisher Scientific). Rabbit monoclonal antibodies against DVL2 (30D2, #3224) and Wnt3a (#2391) was purchased from Cell Signaling. Rabbit polyclonal antibody against Claudin-3 (ab15102) was purchased from Abcam. Chicken polyclonal IgY (#754 Å) against TcdB was purchased from List Biological Labs. Antibody validation is available on the manufacturers' websites. pRK5-FZD2-1D4 was originally generated in J. Nathans' laboratory (Baltimore, MD) and were obtained from Addgene (#42254). Full-length FZD2-1D4 mutants were generated from pRK5-FZD2-1D4 by site-directed mutagenesis (Agilent Technologies, CA).

TcdB, Frizzled and Other Recombinant Proteins

Recombinant full length TcdB (from *C. difficile* strain VPI 10463) was expressed in *Bacillus megaterium* as previously described[10,39] and purified as a 6×His-tagged protein. Recombinant human proteins were purchased from R&D Systems (FZD2$^{CRD}$-Fc, FZD8$^{CRD}$-Fc, and FZD9$^{CRD}$-Fc), Sino Biologics (FZD4$^{CRD}$-Fc and FZD5$^{CRD}$-Fc), and StemRD (Wnt3 Å).

TcdB Binding to Cells and Immunoblot Analysis

Transient transfection of HeLa cells was carried out using PolyJet (SignaGen). Binding of TcdB to cells was analyzed by exposing cells to TcdB (10 nM) or HA-tagged sTcdB (100 nM) for 10 minutes at room temperature. Cells were washed three times with PBS and then harvested with RIPA buffer (50 mM Tris, 1% NP40, 150 mM NaCl, 0.5% sodium deoxycholate, 0.1% SDS, plus a protease inhibitor cocktail (Sigma-Aldrich)). Cell lysates were centrifuged and supernatants were subjected to SDS-PAGE and immunoblot analysis. Cell surface proteins biotinylation and isolation were carried out using Pierce™ Cell surface Protein Isolation Kit (#89881, ThermoFisher Scientific) following the manufacturer's instruction.

Cytopathic Assay

The cytopathic effect (cell rounding) of TcdB was analysed using standard cell-rounding assay. Briefly, cells were exposed to a gradient of TcdB and TcdBGFE for 24 hours. Phase-contrast images of cells were taken (Olympus IX51, ×10-20 objectives). The numbers of round shaped and normal shaped cells were counted manually. The percentage of round shaped cells was plotted and fitted using the Origin software. CR50 is defined as the toxin concentration that induces 50% of cells to become round in 24 hours.

Pull-Down Assays

The pull-down assays between the His-tagged CRD2 and sTcdB variants were performed using $Ni^{2+}$-NTA resins in 1 ml binding buffer containing 50 mM Tris, pH 8.5, 400 mM NaCl, 10 mM imidazole, and 0.1% Tween-20. His-tagged CRD2 served as the bait and sTcdB variants (WT and mutants) were the preys. CRD2 was pre-incubated with $Ni^{2+}$-NTA resins at room temperature for 30 minutes, and the unbound protein was washed away using the binding buffer. The resins were then divided into small aliquots and mixed with sTcdB variants (~1.5 µM, ~2.5-fold molar excess over CRD2). Pull-down assays were carried out at room temperature for 30 minutes. The resins were then washed twice, and the bound proteins were released from the resins with 400 mM imidazole.

For the assays between $FZD5^{CRD}$ and sTcdB, 100 ng of $FZD5^{CRD}$-Fc protein premixed with or without 100 ng Wnt3A was immobilized on 30 µl of Protein G agarose beads (#20398, ThermoFisher Scientific) by incubation for 30 minutes at 4° C. followed by washing with PBS. sTcdB diluted in the indicated buffer was added and incubated for 30 min at 4° C. The beads were then washed, pelleted, boiled in SDS sample buffer, and subjected to immunoblot analysis. The palmitoleic acid (#P9417, Sigma-Aldrich) saturated PBS was generated as described previously[25]. Briefly, 100 µl of palmitoleic acid stock (10 mg/ml in DMSO) was added into 10 ml of PBS, followed by incubation at room temperature with vigorous vortex for 2 hours. Palmitoleic acid suspension was then centrifuged at 14,000 rpm for 20 minutes, and the central part was taken as saturated buffer. DMSO was kept constant at 1% in both palmitoleic acid saturated and the control buffer.

Bio-Layer Interferometry (BLI) Assays

The binding affinities between sTcdB variants and $FZD2^{CRD}$ were measured by BLI assay using the Blitz system (ForteBio). Briefly, $FZD2^{CRD}$-Fc (20 µg/ml) were immobilized onto capture biosensors (Dip and Read Anti-hIgG-Fc, ForteBio) and balanced with PBS. The biosensors were then exposed to different concentrations of sTcdB or its mutants, followed by the dissociation in PBS. Binding affinities ($K_D$) were calculated using the Blitz system software (ForteBio). To analyze binding of TcdB to CRD-Wnt complex, Fc-tagged CRDs of FZD5, 4, 8, and 9 (20 µg/ml) were pre-mixed with or without Wnt3A (20 µg/ml) and incubated on ice for 30 minutes. The proteins were then immobilized onto capture biosensors and balanced with PBS. 5 µM sTcdB or 1 µM TcdB were then applied to the loaded biosensors, followed by wash with PBS. To analyze sequential binding of Wnt3A and TcdB to CRD2, $FZD2^{CRD}$-Fc (20 µg/ml) were immobilized onto capture biosensors and balanced with PBS. The loaded biosensors were first exposed to 20 µg/ml Wnt3 Å, balanced again with PBS, and then exposed to 5 µM sTcdB or 1 µM TcdB. Alternatively, the biosensors were first exposed to 5 µM sTcdB or 1 µM TcdB, balanced with PBS, and then exposed to 20 µg/ml Wnt3A. All biosensors were then washed with PBS for the dissociation.

Wnt Signaling Assay

The TOPFLASH/TK-Renilla dual luciferase reporter assay was used to detect Wnt signalling. Briefly, HeLa or 293T cells in 24-well plates were co-transfected with TOPFLASH (50 ng/well), TK-Renilla (internal control, 10 ng/well), and pcDNA3 (200 ng/well). Wnt3A conditional medium (CM) was generated from L/Wnt3a cell cultures. Culture medium from L cells served as the control medium. After 24 hours, cells were exposed to either Wnt3A CM or control medium with or without sTcdB (200 nM, unless otherwise noted) for 6 hours. Cell lysates were harvested and subjected to either Firefly/Renilla dual luciferase assay or immunoblot analysis for detecting phosphorylated DVL2. Wnt signalling activates expression of TOPFLASH luciferase reporter (firefly luciferase). Co-transfected Renilla luciferase serves as an internal control. The ability of $FZD2^{K127A/E}$ mutants to mediate Wnt signalling was examined using FZD1/2/7$^{-/-}$ HeLa cells, by co-transfection of TOPFLASH (100 ng/well), TK-Renilla (internal control, 20 ng/well), and WT or FZD2 mutants (500 ng/well). After 24 hours, cells were exposed to either Wnt3A CM or control medium for additional 6 hours. Cell lysates were harvested and subjected to either Firefly/Renilla dual luciferase assay or immunoblot analysis for detecting phosphorylated DVL2.

Cecum Toxin Injection Assay

Mice (CD1, 6-8 weeks, both male and female, from Envigo) were anesthetized following overnight fasting. A midline laparotomy was performed to locate the cecum. 100 µl of saline or toxin (15 µg) was injected into the connection part between ileum and cecum via insulin syringe (29G1/2), followed by closing the wounds with stitches. Mice were allowed to recover and were euthanized 12 hours later to harvest the cecum tissue. It was noted that a small number of mice died within a few hours after the surgery (<5 hours, 4 of 10 for TcdB and 3 of 10 for TcdBGEF) for unknown reasons. These mice were not included in the analysis study. The cecum tissues were then fixed, paraffin-embedded, sectioned, and subjected to either hematoxylin and eosin (H&E) staining for histological score analysis or immunofluorescent staining for Claudin-3.

Histological Analysis and Immunofluorescence Staining

The cecum tissues were washed with PBS for three times, followed by fixing in 10% phosphate buffered formalin for 24 hours. The tissues were embedded in paraffin and sectioned 5 µm each. Histology analysis was carried out with H&E staining. Stained sections were scored by observers blinded to experimental groups, based on 4 criteria including disruption of the epithelia, hemorrhagic congestion, mucosal edema, and inflammatory cell infiltration, on a scale of 0 to 3 (normal, mild, moderate, or severe). Immunofluorescence analysis of claudin-3 was carried out using rabbit anti-Claudin-3 (1:100) polyclonal antibody. Confocal images were captured with the Ultraview Vox Spinning Disk Confocal System.

Treating Triple Negative Breast Cancer with sTcdB Ten thousand of p53−/− Brca1−/− breast cancer derived organoid cells were subcutaneously injected in athymic nude mice, which give rise to new tumors. When the size of tumors reaches around 85 mm3, TD3 was given by intraperitoneal injection at 20 mg/kg at day 12, 14,17,20 and 23. The tumor size was determined every 2-3 days after tumor formed. The tumor volume was calculated by the formula: $V=(W2\times L)/2$ for caliper measurements, where V is tumor volume, W is tumor width, L is tumor length. Mice were sacrificed and tumors were weighted at day 24.

TABLE 3

Additional TcdB fragments and their activity

| Fragment boundaries | Expression | Biochemical behavior | Pull down by His-CRD2 |
|---|---|---|---|
| 792-1835 | Yes | Poor | N/A |
| 1024-1804 | Yes | Good | Yes |
| 1028-1835 | Yes | Good | Yes |
| 1071-1512 | Yes | Good | No |
| 1114-1835 | Yes | Good | Yes |
| 1114-2101 | Yes | Good | Yes |
| 1133-1835 | Yes | Poor | N/A |
| 1285-1608 | No | N/A | N/A |
| 1285-1640 | No | N/A | N/A |
| 1285-1660 | No | N/A | N/A |
| 1285-1804 (sTcdB) | Yes | Good | Yes |
| 1294-1835 | Yes | Poor | N/A |
| 1313-1616 | No | N/A | N/A |
| 1340-1616 | No | N/A | N/A |
| 1365-1804 | Yes | Poor | N/A |
| 1394-1835 | Yes | Poor | N/A |
| 1400-1804 | Yes | Poor | N/A |
| 1401-1835 | Yes | Poor | N/A |
| 1430-1804 | Yes | Good | No |
| 1454-1804 | Yes | Good | No |
| 1501-1835 | Yes | Poor | N/A |
| 1510-1688 | Yes | Good | No |
| 1510-1804 | Yes | Good | No |
| 1688-1835 | Yes | Good | No |

TABLE 4

Amino Acid Sequences

| Polypeptide | Amino Acid Sequence | SEQ ID NO |
|---|---|---|
| Full-length TcdB | MSLVNRKQLEKMANVRFRTQEDEYVAILDALEEYHNMSENTVVEKYLKLKDIN SLTDIYIDTYKKSGRNKALKKFKEYLVTEVLELKNNNLTPVEKNLHFVWIGGQI NDTAINYINQWKDVNSDYNVNVFYDSNAFLINTLKKTVVESAINDTLESFRENL NDPRFDYNKFFRKRMEIIYDKQKNFINYYKAQREENPELIIDDIVKTYLSNEYSKE IDELNTYIEESLNKITQNSGNDVRNFEEFKNGESFNLYEQELVERWNLAAASDIL RISALKEIGGMYLDVDMLPGIQPDLFESIEKPSSVTVDFWEMTKLEAIMKYKEYI PEYTSEHFDMLDEEVQSSFESVLASKSDKSEIFSSLGDMEASPLEVKIAFNSKGIIN QGLISVKDSYCSNLIVKQIENRYKILNNSLNPAISEDNDFNTTTNTFIDSIMAEANA DNGRFMMELGKYLRVGFFPDVKTTINLSGPEAYAAAYQDLLMFKEGSMNIHLIE ADLRNFEISKTNISQSTEQEMASLWSFDDARAKAQFEEYKRNYFEGSLGEDDNL DFSQNIVVDKEYLLEKISSLARSSERGYIHYIVQLQGDKISYEAACNLFAKTPYDS VLFQKNIEDSEIAYYYNPGDGEIQEIDKYKIPSIISDRPKIKLTFIGHGKDEFNTDIF AGFDVDSLSTEIEAAIDLAKEDISPKSIEINLLGCNMFSYSINVEETYPGKLLLKVK DKISELMPSISQDSIIVSANQYEVRINSEGRRELLDHSGEWINKEESIIKDISSKEYIS FNPKENKITVKSKNLPELSTLLQEIRNNSNSSDIELEEKVMLTECEINVISNIDTQIV EERIEEAKNLTSDSINYIKDEFKLIESISDALCDLKQQNELEDSHFISFEDISETDEG FSIRFINKETGESIFVETEKTIFSEYANHITEEISKIKGTIFDTVNGKLVKKVNLDTT HEVNTLNAAFFIQSLIEYNSSKESLSNLSVAMKVQVYAQLFSTGLNTITDAAKVV ELVSTALDETIDLLPTLSEGLPIIATIIDGVSLGAAIKELSETSDPLLRQEIEAKIGIM AVNLTTATTAIITSSLGIASGFSILLVPLAGISAGIPSLVNNELVLRDKATKVVDYF KHVSLVETEGVFTLLDDKIMMPQDDLVISEIDFNNNSIVLGKCEIWRMEGGSGHT VTDDIDHFFSAPSITYREPHLSIYDVLEVQKEELDLSKDLMVLPNAPNRVFAWET GWTPGLRSLENDGTKLLDRIRDNYEGEFYWRYFAFIADALITTLKPRYEDTNIRI NLDSNTRSFIVPIITTEYIREKLSYSFYGSGGTYALSLSQYNMGINIELSESDVWIID VDNVVRDVTIESDKIKKGDLIEGILSTLSIEENKIILNSHEINFSGEVNGSNGFVSLT FSILEGINAIIEVDLLSKSYKLLISGELKILMLNSNHIQQKIDYIGFNSELQKNIPYSF VDSEGKENGFINGSTKEGLFVSELPDVVLISKVYMDDSKPSFGYYSNNLKDVKVI TKDNVNILTGYYLKDDIKISLSLTLQDEKTIKLNSVHLDESGVAEILKFMNRKGN TNTSDSLMSFLESMNIKSIFVNFLQSNIKFILDANFIISGTTSIGQFEFICDENDNIQP YFIKFNTLETNYTLYVGNRQNMIVEPNYDLDDSGDISSTVINFSQKYLYGIDSCV NKVVISPNIYTDEINITPVYETNNTYPEVIVLDANYINEKINVNINDLSIRYVWSND GNDFILMSTSEENKVSQVKIRFVNVFKDKTLANKLSFNFSDKQDVPVSEIILSFTP SYYEDGLIGYDLGLVSLYYNEKFYINNFGMMVSGLIYINDSLYYFKPPVNNLITGF VTVGDDKYYFNPINGGAASIGETIIDDKNYYFNQSGVLQTGVFSTEDGFKYFAPA NTLDENLEGEAIDFTGKLIIDENIYYFDDNYRGAVEWKELDGEMHYFSPETGKA FKGLNQIGDYKYYFNSDGVMQKGFVSINDNKHYFDDSGVMKVGYTEIDGKHFY FAENGEMQIGVFNTEDGFKYFAHHNEDLGNEEGEEISYSGILNFNNKIYYFDDSF TAVVGWKDLEDGSKYYFDEDTAEAYIGLSLINDGQYYFNDDGIMQVGFVTIND KVFYFSDSGIIESGVQNIDDNYFYIDDNGIVQIGVFDTSDGYKYFAPANTVNDNIY GQAVEYSGLVRVGEDVYYFGETYTIETGWIYDMENESDKYYFNPETKKACKGI NLIDDIKYYFDEKGIMRTGLISFENNNYYFNENGEMQFGYINIEDKMFYFGEDGV MQIGVFNTPDGFKYFAHQNTLDENFEGESINYTGWLDLDEKRYYFTDEYIAATG SVIIDGEEYYFDPDTAQLVISE | 1 |
| TcdB$_{1285-1804}$ or sTcdB | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY | 2 |

TABLE 4-continued

Amino Acid Sequences

| Polypeptide | Amino Acid Sequence | SEQ ID NO |
|---|---|---|
| | GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYY | |
| FZD1-CRD | YNGERGISVPDHGYCQPISIPLCTDIAYNQTIMPNLLGHTNQEDAGLEVHQFYPL VKVQCSAELKFFLCSMYAPVCTVLEQALPPCRSLCERARQGCEALMNKFGFQW PDTLKCEKFPVHGAGELCVGQNTSDK | 3 |
| FZD2-CRD | YNGERGISVPDHGYCQPISIPLCTDIAYNQTIMPNLLGHTNQEDAGLEVHQFYPL VKVQCSAELKFFLCSMYAPVCTVLEQALPPCRSLCERARQGCEALMNKFGFQW PDTLKCEKFPVHGAGELCVGQNTSDK | 4 |
| FZD3-CRD | YNGERGISVPDHGYCQPISIPLCTDIAYNQTIMPNLLGHTNQEDAGLEVHQFYPL VKVQCSAELKFFLCSMYAPVCTVLEQALPPCRSLCERARQGCEALMNKFGFQW PDTLKCEKFPVHGAGELCVGQNTSDK | 5 |
| FZD8-CRD | AKELACQEITVPLCKGIGYNYTYMPNQFNHDTQDEAGLEVHQFWPLVEIQCSPD LKFFLCSMYTPICLEDYKKPLPPCRSVCERAKAGCAPLMRQYGFAWPDRMRCD RLPEQGNPDTLCMDY | 6 |
| Fc portion of human IgG1 | THTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALP VPIEKTISKAKGQPREPQVYTLPPSREEMTKNQVSLTCLVKGFYPSDIAVEWESN GQPENNYKTTPPVLDSDGPFFLYSKLTVDKSRWQQGNVFSCSVMHEALHNHYT QKSLSLSPGK | 7 |
| TcdB$_{1285-1804}$-Fc fusion | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKC KVSNKALPVPIEKTISKAKGQPREPQVYTLPPSREEMTKNQVSLTCLVKGFYPSDI AVEWESNGQPENNYKTTPPVLDSDGPFFLYSKLTVDKSRWQQGNVFSCSVMHE ALHNHYTQKSLSLSPGK | 8 |
| Fc fusion-TcdB$_{1285-1804}$ | THTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALP VPIEKTISKAKGQPREPQVYTLPPSREEMTKNQVSLTCLVKGFYPSDIAVEWESN GQPENNYKTTPPVLDSDGPFFLYSKLTVDKSRWQQGNVFSCSVMHEALHNHYT QKSLSLSPGKTNIRINLDSNTRSFIVPIITTEYIREKLSYSFYGSGGTYALSLSQYNM GINIELSESDVWIIDVDNVVRDVTIESDKIKKGDLIEGILSTLSIEENKIILNSHEINF SGEVNGSNGFVSLTFSILEGINAIIEVDLLSKSYKLLISGELKILMLNSNHIQQKIDY IGFNSELQKNIPYSFVDSEGKENGFINGSTKEGLFVSELPDVVLISKVYMDDSKPS FGYYSNNLKDVKVITKDNVNILTGYYLKDDIKISLSLTLQDEKTIKLNSVHLDES GVAEILKFMNRKGNTNTSDSLMSFLESMNIKSIFVNFLQSNIKFILDANFIISGTTSI GQFEFICDENDNIQPYFIKFNTLETNYTLYVGNRQNMIVEPNYDLDDSGDISSTVI NFSQKYLYGIDSCVNKVVISPNIYTDEINITPVYETNNTYPEVIVLDANYINEKINV NINDLSIRYVWSNDGNDFILMSTSEENKVSQVKIRFVNVFKDKTLANKLSFNFSD KQDVPVSEIILSFTPSYY | 9 |
| FZD1-CRD-TcdB$_{1285-1804}$ | YNGERGISVPDHGYCQPISIPLCTDIAYNQTIMPNLLGHTNQEDAGLEVHQFYPL VKVQCSAELKFFLCSMYAPVCTVLEQALPPCRSLCERARQGCEALMNKFGFQW PDTLKCEKFPVHGAGELCVGQNTSDKTNIRINLDSNTRSFIVPIITTEYIREKLSYS FYGSGGTYALSLSQYNMGINIELSESDVWIIDVDNVVRDVTIESDKIKKGDLIEGI LSTLSIEENKIILNSHEINFSGEVNGSNGFVSLTFSILEGINAIIEVDLLSKSYKLLISG ELKILMLNSNHIQQKIDYIGFNSELQKNIPYSFVDSEGKENGFINGSTKEGLFVSEL PDVVLISKVYMDDSKPSFGYYSNNLKDVKVITKDNVNILTGYYLKDDIKISLSLT LQDEKTIKLNSVHLDESGVAEILKFMNRKGNTNTSDSLMSFLESMNIKSIFVNFL QSNIKFILDANFIISGTTSIGQFEFICDENDNIQPYFIKFNTLETNYTLYVGNRQNMI VEPNYDLDDSGDISSTVINFSQKYLYGIDSCVNKVVISPNIYTDEINITPVYETNNT YPEVIVLDANYINEKINVNINDLSIRYVWSNDGNDFILMSTSEENKVSQVKIRFVN VFKDKTLANKLSFNFSDKQDVPVSEIILSFTPSYY | 10 |
| FZD2-CRD-TcdB$_{1285-1804}$ | YNGERGISVPDHGYCQPISIPLCTDIAYNQTIMPNLLGHTNQ TABLE 4-continued Amino Acid Sequences

| Polypeptide | Amino Acid Sequence | SEQ ID NO |
|---|---|---|
| | PDVVLISKVYMDDSKPSFGYYSNNLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | |
| FZD3-CRD-<br>TcdB$_{1285-1804}$ | YNGERGISVPDHGYCQPISIPLCTDIAYNQTIMPNLLGHTNQEDAGLE TABLE 4-continued Amino Acid Sequences

| Polypeptide | Amino Acid Sequence | SEQ ID NO |
|---|---|---|
| | NIPYSFVDSEGKENGFINGSTKEGLFVSELPDVVLISKVYMDDSKPSFGYYSNNL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYAKELACQEITVPLCKGIGYNYTYMPNQFNHDTQDEAGLEVHQFWP<br>LVEIQCSPDLKFFLCSMYTPICLEDYKKPLPPCRSVCERAKAGCAPLMRQYGFA<br>WPDRMRCDRLPEQGNPDTLCMDY | |
| TcdB<sub>1285-1804</sub> D1501A | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMASKPSFGYYSNNL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYY | 19 |
| TcdB<sub>1285-1804</sub> Y1509A | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYASNNL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYY | 20 |
| TcdB<sub>1285-1804</sub> N1511A | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYYSANL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYY | 21 |
| TcdB<sub>1285-1804</sub> Q1599A | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYYSNNL<br>KDVKVITKDNVNILTGYYLKDDIKISLSLTLQDEKTIKLNSVHLDESGVAEILKFM<br>NRKGNTNTSDSLMSFLESMNIKSIFVNFLASNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYY | 22 |
| TcdB<sub>1285-1804</sub> Y1509A/N1511A | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYASANL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYY | 23 |
| TcdB<sub>1285-1804</sub> Y1509A/Q1599A | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYASNNL<br>KDVKVITKDNVNILTGYYLKDDIKISLSLTLQDEKTIKLNSVHLDESGVAEILKFM<br>NRKGNTNTSDSLMSFLESMNIKSIFVNFLASNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYY | 24 |

TABLE 4-continued

Amino Acid Sequences

| Polypeptide | Amino Acid Sequence | SEQ ID NO |
|---|---|---|
| L1433D | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGEDKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYY | 25 |
| TcdB$_{1285-1804}$ D1501A-Fc fusion | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDASKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKC KVSNKALPVPIEKTISKAKGQPREPQVYTLPPSREEMTKNQVSLTCLVKGFYPSDI AVEWESNGQPENNYKTTPPVLDSDGPFFLYSKLTVDKSRWQQGNVFSCSVMHE ALHNHYTQKSLSLSPGK | 26 |
| TcdB$_{1285-1804}$ Y1509A-Fc fusion | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKC KVSNKALPVPIEKTISKAKGQPREPQVYTLPPSREEMTKNQVSLTCLVKGFYPSDI AVEWESNGQPENNYKTTPPVLDSDGPFFLYSKLTVDKSRWQQGNVFSCSVMHE ALHNHYTQKSLSLSPGK | 27 |
| TcdB$_{1285-1804}$ N1511A-Fc fusion | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSANL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKC KVSNKALPVPIEKTISKAKGQPREPQVYTLPPSREEMTKNQVSLTCLVKGFYPSDI AVEWESNGQPENNYKTTPPVLDSDGPFFLYSKLTVDKSRWQQGNVFSCSVMHE ALHNHYTQKSLSLSPGK | 28 |
| TcdB$_{1285-1804}$ Q1599A-Fc fusion | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLASNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKC KVSNKALPVPIEKTISKAKGQPREPQVYTLPPSREEMTKNQVSLTCLVKGFYPSDI AVEWESNGQPENNYKTTPPVLDSDGPFFLYSKLTVDKSRWQQGNVFSCSVMHE ALHNHYTQKSLSLSPGK | 29 |
| TcdB$_{1285-1804}$ Y1509A/N1511A-Fc fusion | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK | 30 |

TABLE 4-continued

Amino Acid Sequences

| Polypeptide | Amino Acid Sequence | SEQ ID NO |
|---|---|---|
| | NIPYSFVDSEGKENGFINGSTKEGLFVSELPDVVLISKVYMDDSKPSFGYASANL<br>KDVKVITKDNVNILTGYYLKDDIKISLSLTLQDEKTIKLNSVHLDESGVAE<u>I</u>LKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKC<br>KVSNKALPVPIEKTISKAKGQPREPQVYTLPPSREEMTKNQVSLTCLVKGFYPSDI<br>AVEWESNGQPENNYKTTPPVLDSDGPFFLYSKLTVDKSRWQQGNVFSCSVMHE<br>ALHNHYTQKSLSLSPGK | |
| TcdB$_{1285-1804}$<br>Y1509A/Q1599A-<br>Fc fusion | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYASNNL<br>KDVKVITKDNVNILTGYYLKDDIKISLSLTLQDEKTIKLNSVHLDESGVAE<u>I</u>LKFM<br>NRKGNTNTSDSLMSFLESMNIKSIFVNFLASNIKFILDANFIISGTTSIGQFEFICDE<br>NDNIQPYFIKFNTLETNYTLYVGNRQNMI<u>V</u>EPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKC<br>KVSNKALPVPIEKTISKAKGQPREPQVYTLPPSREEMTKNQVSLTCLVKGFYPSDI<br>AVEWESNGQPENNYKTTPPVLDSDGPFFLYSKLTVDKSRWQQGNVFSCSVMHE<br>ALHNHYTQKSLSLSPGK | 31 |
| L1433D-Fc<br>fusion | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGE<u>D</u>KILMLNSNHIQQKIDYIGFNSELQK<br>NIPYSFVDSEGKENGFINGSTKEGLFVSELPD<u>V</u>VLISKVYMDDSKPSFGYYSNNL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKC<br>KVSNKALPVPIEKTISKAKGQPREPQVYTLPPSREEMTKNQVSLTCLVKGFYPSDI<br>AVEWESNGQPENNYKTTPPVLDSDGPFFLYSKLTVDKSRWQQGNVFSCSVMHE<br>ALHNHYTQKSLSLSPGK | 32 |
| Fc fusion-<br>TcdB$_{1285-1804}$<br>D1501A | THTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALP<br>VPIEKTISKAKGQPREPQVYTLPPSREEMTKNQVSLTCLVKGFYPSDIAVEWESN<br>GQPENNYKTTPPVLDSDGPFFLYSKLTVDKSRWQQGNVFSCSVMHEALHNHYT<br>QKSLSLSPGKTNIRINLDSNTRSFIVPIITTEYIREKLSYSFYGSGGTYALSLSQYNM<br>GINIELSESDVWIIDVDNVVRDVTIESDKIKKGDLIEGILSTLSIEENKIILNSHEINF<br>SGEVNGSNGFVSLTFSILEGINAIIEVDLLSKSYKLLISGELKILMLNSNHIQQKIDY<br>IGFNSELQKNIPYSFVDSEGKENGFINGSTKEGLFVSELPDVVLISKVYMDASKPS<br>FGYYSNNLKDVKVITKDNVNILTGYYLKDDIKISLSLTLQDEKTIKLNSVHLDES<br>GVAEILKFMNRKGNTNTSDSLMSFLESMNIKSIFVNFLQSNIKFILDANFIISGTTSI<br>GQFEFICDENDNIQPYFIKFNTLETNYTLYVGNRQNMIVEPNYDLDDSGDISSTVI<br>NFSQKYLYGIDSCVNKVVISPNIYTDEINITPVYETNNTYPEVIVLDANYINEKINV<br>NINDLSIRYVWSNDGNDFILMSTSEENKVSQVKIRFVNVFKDKTLANKLSFNFSD<br>KQDVPVSEIILSFTPSYY | 33 |
| Fc fusion-<br>TcdB$_{1285-1804}$<br>Y1509A | THTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALP<br>VPIEKTISKAKGQPREPQVYTLPPSREEMTKNQVSLTCLVKGFYPSDIAVEWESN<br>GQPENNYKTTPPVLDSDGPFFLYSKLTVDKSRWQQGNVFSCSVMHEALHNHYT<br>QKSLSLSPGKTNIRINLDSNTRSFIVPIITTEYIREKLSYSFYGSGGTYALSLSQYNM<br>GINIELSESDVWIIDVDNVVRDVTIESDKIKKGDLIEGILSTLSIEENKIILNSHEINF<br>SGEVNGSNGFVSLTFSILEGINAIIEVDLLSKSYKLLISGELKILMLNSNHIQQKIDY<br>IGFNSELQKNIPYSFVDSEGKENGFINGSTKEGLFVSELPDVVLISKVYMDDSKPS<br>FGYASNNLKDVKVITKDNVNILTGYYLKDDIKISLSLTLQDEKTIKLNSVHLDES<br>GVAE<u>I</u>LKFMNRKGNTNTSDSLMSFLESMNIKSIFVNFLQSNIKFILDANFIISGTTSI<br>GQFEFICDENDNIQPYFIKFNTLETNYTLYVGNRQNMIVEPNYDLDDSGDISSTVI<br>NFSQKYLYGIDSCVNKVVISPNIYTDEINITPVYETNNTYPEVIVLDANYINEKINV<br>NINDLSIRYVWSNDGNDFILMSTSEENKVSQVKIRFVNVFKDKTLANKLSFNFSD<br>KQDVPVSEIILSFTPSYY | 34 |
| Fc fusion-<br>TcdB$_{1285-1804}$<br>N1511A | THTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALP<br>VPIEKTISKAKGQPREPQVYTLPPSREEMTKNQVSLTCLVKGFYPSDIAVEWESN | 35 |

TABLE 4-continued

Amino Acid Sequences

| Polypeptide | Amino Acid Sequence | SEQ ID NO |
|---|---|---|
| | GQPENNYKTTPPVLDSDGPFFLYSKLTVDKSRWQQGNVFSCSVMHEALHNHYT<br>QKSLSLSPGKTNIRINLDSNTRSFIVPIITTEYIREKLSYSFYGSGGTYALSLSQYNM<br>GINIELSESDVWIIDVDNVVRDVTIESDKIKKGDLIEGILSTLSIEENKIILNSHEINF<br>SGEVNGSNGFVSLTFSILEGINAIIEVDLLSKSYKLLISGELKILMLNSNHIQQKIDY<br>IGFNSELQKNIPYSFVDSEGKENGFINGSTKEGLFVSELPDVVLISKVYMDDSKPS<br>FGYYSANLKDVKVITKDNVNILTGYYLKDDIKISLSLTLQDEKTIKLNSVHLDES<br>GVAEILKFMNRKGNTNTSDSLMSFLESMNIKSIFVNFLQSNIKFILDANFIISGTTSI<br>GQFEFICDENDNIQPYFIKFNTLETNYTLYVGNRQNMIVEPNYDLDDSGDISSTVI<br>NFSQKYLYGIDSCVNKVVISPNIYTDEINITPVYETNNTYPEVIVLDANYINEKINV<br>NINDLSIRYVWSNDGNDFILMSTSEENKVSQVKIRFVNVFKDKTLANKLSFNFSD<br>KQDVPVSEIILSFTPSYY | |
| Fc fusion-<br>TcdB$_{1285\text{-}1804}$<br>Q1599A | THTCPPCPAPEL TABLE 4-continued Amino Acid Sequences

| Polypeptide | Amino Acid Sequence | SEQ ID NO |
|---|---|---|
| | FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDASKPSFGYYSNNLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | |
| FZD1-CRD-<br>TcdB$_{1285-1804}$<br>Y1509A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASNNLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 41 |
| FZD1-CRD-<br>TcdB$_{1285-1804}$<br>N1511A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYYSANLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 42 |
| FZD1-CRD-<br>TcdB$_{1285-1804}$<br>Q1599A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYYSNNLKDVKVITKDNVNILTGYYLKDDIKISLSLT<br>LQDEKTIKLNSVHLDESGVAEILKFMNRKGNTNTSDSLMSFLESMNIKSIFVNFL<br>ASNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 43 |
| FZD1-CRD-<br>TcdB$_{1285-1804}$<br>Y1509A/N1511A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASANLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 44 |
| FZD1-CRD-<br>TcdB$_{1285-1804}$<br>Y1509A/Q1599A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASNNLKDVKVITKDNVNILTGYYLKDDIKISLSLT<br>LQDEKTIKLNSVHLDESGVAEILKFMNRKGNTNTSDSLMSFLESMNIKSIFVNFL<br>ASNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 45 |

TABLE 4-continued

Amino Acid Sequences

| Polypeptide | Amino Acid Sequence | SEQ ID NO |
|---|---|---|
| FZD1-CRD-L1433D | YNGERGISVPDHGYCQPISIPLCTDIAYNQTIMPNLLGHTNQEDAGLEVHQFYPL VKVQCSAELKFFLCSMYAPVCTVLEQALPPCRSLCERARQGCEALMNKFGFQW PDTLKCEKFPVHGAGELCVGQNTSDKTNIRINLDSNTRSFIVPIITTEYIREKLSYS FYGSGGTYALSLSQYNMGINIELSESDVWIIDVDNVVRDVTIESDKIKKGDLIEGI LSTLSIEENKIILNSHEINFSGEVNGSNGFVSLTFSILEGINAIIEVDLLSKSYKLLISG EDKILMLNSNHIQQKIDYIGFNSELQKNIPYSFVDSEGKENGFINGSTKEGLFVSE LPDVVLISKVYMDDSKPSFGYYSNNLKDVKVITKDNVNILTGYYLKDDIKISLSL TLQDEKTIKLNSVHLDESGVAEILKFMNRKGNTNTSDSLMSFLESMNIKSIFVNF LQSNIKFILDANFIISGTTSIGQFEFICDENDNIQPYFIKFNTLETNYTLYVGNRQN MIVEPNYDLDDSGDISSTVINFSQKYLYGIDSCVNKVVISPNIYTDEINITPVYETN NTYPEVIVLDANYINEKINVNINDLSIRYVWSNDGNDFILMSTSEENKVSQVKIRF VNVFKDKTLANKLSFNFSDKQDVPVSEIILSFTPSYY | 46 |
| TcdB$_{1285-1804}$ D1501A-FZD1-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDASKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 47 |
| TcdB$_{1285-1804}$ Y1509A-FZD1-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 48 |
| TcdB$_{1285-1804}$ N1511A-FZD1-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSANL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 49 |
| TcdB$_{1285-1804}$ Q1599A-FZD1-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLASNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 50 |
| TcdB$_{1285-1804}$ Y1509A/N1511A-FZD1-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASANL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL | 51 |

TABLE 4-continued

Amino Acid Sequences

| Polypeptide | Amino Acid Sequence | SEQ ID NO |
|---|---|---|
| | EVHQFYPLVKVQCSAELKFFLCSMYAPVCTVLEQALPPCRSLCERARQGCEALM<br>NKFGFQWPDTLKCEKFPVHGAGELCVGQNTSDK | |
| TcdB$_{1285-1804}$<br>Y1509A/Q1599A-<br>FZD1-CRD | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYASNNL<br>KDVKVITKDNVNILTGYYLKDDIKISLSLTLQDEKTIKLNSVHLDESGVAEILKFM<br>NRKGNTNTSDSLMSFLESMNIKSIFVNFLASNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYYNGERGISVPDHGYCQPISIPLCTDIAYNQTIMPNLLGHTNQEDAGL<br>EVHQFYPLVKVQCSAELKFFLCSMYAPVCTVLEQALPPCRSLCERARQGCEALM<br>NKFGFQWPDTLKCEKFPVHGAGELCVGQNTSDK | 52 |
| L1433D-<br>FZD1-CRD | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGEDKILMLNSNHIQQKIDYIGFNSELQK<br>NIPYSFVDSEGKENGFINGSTKEGLFVSELPDVVLISKVYMDDSKPSFGYYSNNL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYYNGERGISVPDHGYCQPISIPLCTDIAYNQTIMPNLLGHTNQEDAGL<br>EVHQFYPLVKVQCSAELKFFLCSMYAPVCTVLEQALPPCRSLCERARQGCEALM<br>NKFGFQWPDTLKCEKFPVHGAGELCVGQNTSDK | 53 |
| FZD2-CRD-<br>TcdB$_{1285-1804}$<br>D1501A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDASKPSFGYYSNNLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 54 |
| FZD2-CRD-<br>TcdB$_{1285-1804}$<br>Y1509A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASNNLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 55 |
| FZD2-CRD-<br>TcdB$_{1285-1804}$<br>N1511A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYYSANLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 56 |
| FZD2-CRD-<br>TcdB$_{1285-1804}$<br>Q1599A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYYSNNLKDVKVITKDNVNILTGYYLKDDIKISLSLT | 57 |

TABLE 4-continued

Amino Acid Sequences

| Polypeptide | Amino Acid Sequence | SEQ ID NO |
|---|---|---|
| | LQDEKTIKLNSVHLDESGVAEILKFMNRKGNTNTSDSLMSFLESMNIKSIFVNFL<br>ASNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | |
| FZD2-CRD -<br>TcdB₁₂₈₅₋₁₈₀₄<br>Y1509A/N1511A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASANLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 58 |
| FZD2-CRD-<br>TcdB₁₂₈₅₋₁₈₀₄<br>Y1509A/Q1599A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASNNLKDVKVITKDNVNILTGYYLKDDIKISLSLT<br>LQDEKTIKLNSVHLDESGVAEILKFMNRKGNTNTSDSLMSFLESMNIKSIFVNFL<br>ASNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 59 |
| FZD2-CRD-<br>L1433D | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>EDKILMLNSNHIQQKIDYIGFNSELQKNIPYSFVDSEGKENGFINGSTKEGLFVSE<br>LPDVVLISKVYMDDSKPSFGYYSNNLKDVKVITKDNVNILTGYYLKDDIKISLSL<br>TLQDEKTIKLNSVHLDESGVAEILKFMNRKGNTNTSDSLMSFLESMNIKSIFVNF<br>LQSNIKFILDANFIISGTTSIGQFEFICDENDNIQPYFIKFNTLETNYTLYVGNRQN<br>MIVEPNYDLDDSGDISSTVINFSQKYLYGIDSCVNKVVISPNIYTDEINITPVYETN<br>NTYPEVIVLDANYINEKINVNINDLSIRYVWSNDGNDFILMSTSEENKVSQVKIRF<br>VNVFKDKTLANKLSFNFSDKQDVPVSEIILSFTPSYY | 60 |
| TcdB₁₂₈₅₋₁₈₀₄<br>D1501A-<br>FZD2-CRD | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDASKPSFGYYSNNL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYYNGERGISVPDHGYCQPISIPLCTDIAYNQTIMPNLLGHTNQEDAGL<br>EVHQFYPLVKVQCSAELKFFLCSMYAPVCTVLEQALPPCRSLCERARQGCEALM<br>NKFGFQWPDTLKCEKFPVHGAGELCVGQNTSDK | 61 |
| TcdB₁₂₈₅₋₁₈₀₄<br>Y1509A-<br>FZD2-CRD | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK<br>NIPYSFVDSEGKENGFINGSTKEGLFVSELPDVVLISKVYMDDSKPSFGYASNNL<br>KDVKVITKDNVNILTGYYLKDDIKISLSLTLQDEKTIKLNSVHLDESGVAEILKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYYNGERGISVPDHGYCQPISIPLCTDIAYNQTIMPNLLGHTNQEDAGL<br>EVHQFYPLVKVQCSAELKFFLCSMYAPVCTVLEQALPPCRSLCERARQGCEALM<br>NKFGFQWPDTLKCEKFPVHGAGELCVGQNTSDK | 62 |
| TcdB₁₂₈₅₋₁₈₀₄<br>N1511A-<br>FZD2-CRD | TNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQK | 63 |

TABLE 4-continued

Amino Acid Sequences

| Polypeptide | Amino Acid Sequence | SEQ ID NO |
|---|---|---|
| | NIPYSFVDSEGKENGFINGSTKEGLFVSELPDVVLISKVYMDDSKPSFGYYS<u>A</u>NL<br>KDVKVITKDNVNILTGYYLKDDIKISLSLTLQDEKTIKLNSVHLDESGVAE<u>I</u>LKFM<br>NRKGNTNTSDSLMSFLESMNIKSIFVNFLQSNIKFILDANFIISGTTSIGQFEFICDE<br>NDNIQPYFIKFNTLETNYTLYVGNRQNMIVEPNYDLDDSGDISSTVINFSQKYLY<br>GIDSCVNKVVISPNIYTDEINITPVYETNNTYPEVIVLDANYINEKINVNINDLSIRY<br>VWSNDGNDFILMSTSEENKVSQVKIRFVNVFKDKTLANKLSFNFSDKQDVPVSE<br>IILSFTPSYYYNGERGISVPDHGYCQPISIPLCTDIAYNQTIMPNLLGHTNQEDAGL<br>EVHQFYPLVKVQCSAELKFFLCSMYAPVCTVLEQALPPCRSLCERARQGCEALM<br>NKFGFQWPDTLKCEKFPVHGAGELCVGQNTSDK | |
| TcdB<sub>1285-1804</sub><br>Q1599A-<br>FZD2-CRD | TNIRINLDSN TABLE 4-continued Amino Acid Sequences

| Polypeptide | Amino Acid Sequence | SEQ ID NO |
|---|---|---|
| FZD3-CRD-TcdB$_{1285-1804}$ Y1509A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASNNLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLD ANYINEKINVNINDLSIRYVWSNDGNDFILMSTSEENKVSQVKIRFVN<br>VFKDKTLANKLSFNFSDKQDVPVSEIILSFTPSYY | 69 |
| FZD3-CRD-TcdB$_{1285-1804}$ N1511A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYYSANLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 70 |
| FZD3-CRD-TcdB$_{1285-1804}$ Q1599A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYYSNNLKDVKVITKDNVNILTGYYLKDDIKISLSLT<br>LQDEKTIKLNSVHLDESGVAEILKFMNRKGNTNTSDSLMSFLESMNIKSIFVNFL<br>ASNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 71 |
| FZD3-CRD-TcdB$_{1285-1804}$ Y1509A/N1511A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASANLKDVKVITKDNVNILTGYYLKDDIKISLSLT<br>LQDEKTIKLNSVHLDESGVAEILKFMNRKGNTNTSDSLMSFLESMNIKSIFVNFL<br>QSNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 72 |
| FZD3-CRD-TcdB$_{1285-1804}$ Y1509A/Q1599A | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>ELKILMLNSNHIQQKIDYIGFNSELQKNIPYSFVDSEGKENGFINGSTKEGLFVSEL<br>PDVVLISKVYMDDSKPSFGYASNNLKDVKVITKDNVNILTGYYLKDDIKISLSLT<br>LQDEKTIKLNSVHLDESGVAEILKFMNRKGNTNTSDSLMSFLESMNIKSIFVNFL<br>ASNIKFILDANFIISGTTSIGQFEFICDENDNIQPYFIKFNTLETNYTLYVGNRQNMI<br>VEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYY | 73 |
| FZD3-CRD-L1433D | YNGERGISVPDHGYCQPISIPLCTDIAYNQTIMPNLLGHTNQEDAGLEVHQFYPL<br>VKVQCSAELKFFLCSMYAPVCTVLEQALPPCRSLCERARQGCEALMNKFGFQW<br>PDTLKCEKFPVHGAGELCVGQNTSDKTNIRINLDSNTRSFIVPIITTEYIREKLSYS<br>FYGSGGTYALSLSQYNMGINIELSESDVWIIDVDNVVRDVTIESDKIKKGDLIEGI<br>LSTLSIEENKIILNSHEINFSGEVNGSNGFVSLTFSILEGINAIIEVDLLSKSYKLLISG<br>EDKILMLNSNHIQQKIDYIGFNSELQKNIPYSFVDSEGKENGFINGSTKEGLFVSE<br>LPDVVLISKVYMDDSKPSFGYYSNNLKDVKVITKDNVNILTGYYLKDDIKISLSL<br>TLQDEKTIKLNSVHLDESGVAEILKFMNRKGNTNTSDSLMSFLESMNIKSIFVNF<br>LQSNIKFILDANFIISGTTSIGQFEFICDENDNIQPYFIKFNTLETNYTLYVGNRQN<br>MIVEPNYDLDDSGDISSTVINFSQKYLYGIDSCVNKVVISPNIYTDEINITPVYETN | 74 |

TABLE 4-continued

Amino Acid Sequences

| Polypeptide | Amino Acid Sequence | SEQ ID NO |
|---|---|---|
| | NTYPEVIVLDANYINEKINVNINDLSIRYVWSNDGNDFILMSTSEENKVSQVKIRF VNVFKDKTLANKLSFNFSDKQDVPVSEIILSFTPSYY | |
| TcdB$_{1285-1804}$ D1501A-FZD3-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDASKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 75 |
| TcdB$_{1285-1804}$ Y1509A-FZD3-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 76 |
| TcdB$_{1285-1804}$ N1511A-FZD3-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSANL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 77 |
| TcdB$_{1285-1804}$ Q1599A-FZD3-CRD | TNIRINLDSNTRSFIVPIITTEYIREKLSYSFYGSGGTYALSLSQYNMGINIELSESD VWIIDVDNVVRDVTIESDKIKKGD LIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLASNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 78 |
| TcdB$_{1285-1804}$ Y1509A/N1511A-FZD3-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASANL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 79 |
| TcdB$_{1285-1804}$ Y1509A/Q1599A-FZD3-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASNNL KDVKVITKDNVNILTGYYLKDDIKISLSLTLQDEKTIKLNSVHLDESGVAEILKFM NRKGNTNTSDSLMSFLESMNIKSIFVNFLASNIKFILDANFIISGTTSIGQFEFICDE NDNIQPYFIKFNTLETNYTLYVGNRQNMIVEPNYDLDDSGDISSTVINFSQKYLY | 80 |

TABLE 4-continued

Amino Acid Sequences

| Polypeptide | Amino Acid Sequence | SEQ ID NO |
|---|---|---|
| | GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | |
| L1433D-FZD3-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGEDKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYYNGERGISVPDHGYCQPISIPLCTDIAYNQTIMPNLLGHTNQEDAGL EVHQFYPLVKVQCSAELKFFLCSMYAPVCTVLEQALPPCRSLCERARQGCEALM NKFGFQWPDTLKCEKFPVHGAGELCVGQNTSDK | 81 |
| FZD8-CRD-TcdB$_{1285-1804}$ D1501A | AKELACQEITVPLCKGIGYNYTYMPNQFNHDTQDEAGLEVHQFWPLVEIQCSPD LKFFLCSMYTPICLEDYKKPLPPCRSVCERAKAGCAPLMRQYGFAWPDRMRCD RLPEQGNPDTLCMDYTNIRINLDSNTRSFIVPIITTEYIREKLSYSFYGSGGTYALS LSQYNMGINIELSESDVWIIDVDNVVRDVTIESDKIKKGDLIEGILSTLSIEENKIIL NSHEINFSGEVNGSNGFVSLTFSILEGINAIIEVDLLSKSYKLLISGELKILMLNSNH IQQKIDYIGFNSELQKNIPYSFVDSEGKENGFINGSTKEGLFVSELPDVVLISKVY MDASKPSFGYYSNNLKDVKVITKDNVNILTGYYLKDDIKISLSLTLQDEKTIKLN SVHLDESGVAEILKFMNRKGNTNTSDSLMSFLESMNIKSIFVNFLQSNIKFILDAN FITSGTTSIGQFEFICDENDNIQPYFIKFNTLETNYTLYVGNRQNMIVEPNYDLDDS GDISSTVINFSQKYLYGIDSCVNKVVISPNIYTDEINITPVYETNNTYPEVIVLDAN YINEKINVNINDLSIRYVWSNDGNDFILMSTSEENKVSQVKIRFVNVFKDKTLAN KLSFNFSDKQDVPVSEIILSFTPSYY | 82 |
| FZD8-CRD-TcdB$_{1285-1804}$ Y1509A | AKELACQEITVPLCKGIGYNYTYMPNQFNHDTQDEAGLEVHQFWPLVEIQCSPD LKFFLCSMYTPICLEDYKKPLPPCRSVCERAKAGCAPLMRQYGFAWPDRMRCD RLPEQGNPDTLCMDYTNIRINLDSNTRSFIVPIITTEYIREKLSYSFYGSGGTYALS LSQYNMGINIELSESDVWIIDVDNVVRDVTIESDKIKKGDLIEGILSTLSIEENKIIL NSHEINFSGEVNGSNGFVSLTFSILEGINAIIEVDLLSKSYKLLISGELKILMLNSNH IQQKIDYIGFNSELQKNIPYSFVDSEGKENGFINGSTKEGLFVSELPDVVLISKVY MDDSKPSFGYASNNLKDVKVITKDNVNILTGYYLKDDIKISLSLTLQDEKTIKLN SVHLDESGVAEILKFMNRKGNTNTSDSLMSFLESMNIKSIFVNFLQSNIKFILDAN FITSGTTSIGQFEFICDENDNIQPYFIKFNTLETNYTLYVGNRQNMIVEPNYDLDDS GDISSTVINFSQKYLYGIDSCVNKVVISPNIYTDEINITPVYETNNTYPEVIVLDAN YINEKINVNINDLSIRYVWSNDGNDFILMSTSEENKVSQVKIRFVNVFKDKTLAN KLSFNFSDKQDVPVSEIILSFTPSYY | 83 |
| FZD8-CRD-TcdB$_{1285-1804}$ N1511A | AKELACQEITVPLCKGIGYNYTYMPNQFNHDTQDEAGLEVHQFWPLVEIQCSPD LKFFLCSMYTPICLEDYKKPLPPCRSVCERAKAGCAPLMRQYGFAWPDRMRCD RLPEQGNPDTLCMDYTNIRINLDSNTRSFIVPIITTEYIREKLSYSFYGSGGTYALS LSQYNMGINIELSESDVWIIDVDNVVRDVTIESDKIKKGDLIEGILSTLSIEENKIIL NSHEINFSGEVNGSNGFVSLTFSILEGINAIIEVDLLSKSYKLLISGELKILMLNSNH IQQKIDYIGFNSELQKNIPYSFVDSEGKENGFINGSTKEGLFVSELPDVVLISKVY MDDSKPSFGYYSANLKDVKVITKDNVNILTGYYLKDDIKISLSLTLQDEKTIKLN SVHLDESGVAEILKFMNRKGNTNTSDSLMSFLESMNIKSIFVNFLQSNIKFILDAN FITSGTTSIGQFEFICDENDNIQPYFIKFNTLETNYTLYVGNRQNMIVEPNYDLDDS GDISSTVINFSQKYLYGIDSCVNKVVISPNIYTDEINITPVYETNNTYPEVIVLDAN YINEKINVNINDLSIRYVWSNDGNDFILMSTSEENKVSQVKIRFVNVFKDKTLAN KLSFNFSDKQDVPVSEIILSFTPSYY | 84 |
| FZD8-CRD-TcdB$_{1285-1804}$ Q1599A | AKELACQEITVPLCKGIGYNYTYMPNQFNHDTQDEAGLEVHQFWPLVEIQCSPD LKFFLCSMYTPICLEDYKKPLPPCRSVCERAKAGCAPLMRQYGFAWPDRMRCD RLPEQGNPDTLCMDYTNIRINLDSNTRSFIVPIITTEYIREKLSYSFYGSGGTYALS LSQYNMGINIELSESDVWIIDVDNVVRDVTIESDKIKKGDLIEGILSTLSIEENKIIL NSHEINFSGEVNGSNGFVSLTFSILEGINAIIEVDLLSKSYKLLISGELKILMLNSNH IQQKIDYIGFNSELQKNIPYSFVDSEGKENGFINGSTKEGLFVSELPDVVLISKVY MDDSKPSFGYYSNNLKDVKVITKDNVNILTGYYLKDDIKISLSLTLQDEKTIKLN SVHLDESGVAEILKFMNRKGNTNTSDSLMSFLESMNIKSIFVNFLASNIKFILDAN FITSGTTSIGQFEFICDENDNIQPYFIKFNTLETNYTLYVGNRQNMIVEPNYDLDDS GDISSTVINFSQKYLYGIDSCVNKVVISPNIYTDEINITPVYETNNTYPEVIVLDAN YINEKINVNINDLSIRYVWSNDGNDFILMSTSEENKVSQVKIRFVNVFKDKTLAN KLSFNFSDKQDVPVSEIILSFTPSYY | 85 |
| FZD8-CRD-TcdB$_{1285-1804}$ Y1509A/N1511A | AKELACQEITVPLCKGIGYNYTYMPNQFNHDTQDEAGLEVHQFWPLVEIQCSPD LKFFLCSMYTPICLEDYKKPLPPCRSVCERAKAGCAPLMRQYGFAWPDRMRCD RLPEQGNPDTLCMDYTNIRINLDSNTRSFIVPIITTEYIREKLSYSFYGSGGTYALS LSQYNMGINIELSESDVWIIDVDNVVRDVTIESDKIKKGDLIEGILSTLSIEENKIIL | 86 |

TABLE 4-continued

Amino Acid Sequences

| Polypeptide | Amino Acid Sequence | SEQ ID NO |
|---|---|---|
| | NSHEINFSGEVNGSNGFVSLTFSILEGINAIIEVDLLSKSYKLLISGELKILMLNSNH<br>IQQKIDYIGFNSELQKNIPYSFVDSEGKENGFINGSTKEGLFVSELPDVVLISKVY<br>MDDSKPSFGYASA NLKDVKVITKDNVNILTGYYLKDDIKISLSLTLQDEKTIKLN<br>SVHLDESGVAEILKFMNRKGNTNTSDSLMSFLESMNIKSIFVNFLQSNIKFILDAN<br>FITSGTTSIGQFEFICDENDNIQPYFIKFNTLETNYTLYVGNRQNMIVEPNYDLDDS<br>GDISSTVINFSQKYLYGIDSCVNKVVISPNIYTDEINITPVYETNNTYPEVIVLDAN<br>YINEKINVNINDLSIRYVWSNDGNDFILMSTSEENKVSQVKIRFVNVFKDKTLAN<br>KLSFNFSDKQDVPVSEIILSFTPSYY | |
| FZD8-CRD-<br>TcdB$_{1285-1804}$<br>Y1509A/Q1599A | AKELACQEITVPLCKGIGYNYTYMPNQFNHDTQ TABLE 4-continued Amino Acid Sequences

| Polypeptide | Amino Acid Sequence | SEQ ID NO |
|---|---|---|
| TcdB$_{1285-1804}$ Q1599A-FZD8-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLASNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYAKELACQEITVPLCKGIGYNYTYMPNQFNHDTQDEAGLEVHQFWP LVEIQCSPDLKFFLCSMYTPICLEDYKKPLPPCRSVCERAKAGCAPLMRQYGFA WPDRMRCDRLPEQGNPDTLCMDY | 92 |
| TcdB$_{1285-1804}$ Y1509A/N1511A-FZD8-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASANL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYAKELACQEITVPLCKGIGYNYTYMPNQFNHDTQDEAGLEVHQFWP LVEIQCSPDLKFFLCSMYTPICLEDYKKPLPPCRSVCERAKAGCAPLMRQYGFA WPDRMRCDRLPEQGNPDTLCMDY | 93 |
| TcdB$_{1285-1804}$ Y1509A/Q1599A-FZD8-CRD CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGELKILMLNSNHIQQKIDYIGFNSELQK NIPYSFVDSEGKENGFINGSTKEGLFVSELPDVVLISKVYMDDSKPSFGYASNNL KDVKVITKDNVNILTGYYLKDDIKISLSLTLQDEKTIKLNSVHLDESGVAEILKFM NRKGNTNTSDSLMSFLESMNIKSIFVNFLASNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYAKELACQEITVPLCKGIGYNYTYMPNQFNHDTQDEAGLEVHQFWP LVEIQCSPDLKFFLCSMYTPICLEDYKKPLPPCRSVCERAKAGCAPLMRQYGFA WPDRMRCDRLPEQGNPDTLCMDY | 94 |
| L1433D-FZD8-CRD | TNIRINLDSNTRSFIVPIITTEYIREKLSYSFYGSGGTYALSLSQYNMGINIELSESD VWIIDVDNVVRDVTIESDKIKKGDLIEGILSTLSIEENKIILNSHEINFSGEVNGSNG FVSLTFSILEGINAIIEVDLLSKSYKLLISGEDKILMLNSNHIQQKIDYIGFNSELQK NIPYSFVDSEGKENGFINGSTKEGLFVSELPDVVLISKVYMDDSKPSFGYYSNNL KDVKVITKDNVNILTGYYLKDDIKISLSLTLQDEKTIKLNSVHLDESGVAEILKFM NRKGNTNTSDSLMSFLESMNIKSIFVNFLQSNIKFILDANFIISGTTSIGQFEFICDE NDNIQPYFIKFNTLETNYTLYVGNRQNMIVEPNYDLDDSGDISSTVINFSQKYLY GIDSCVNKVVISPNIYTDEINITPVYETNNTYPEVIVLDANYINEKINVNINDLSIRY VWSNDGNDFILMSTSEENKVSQVKIRFVNVFKDKTLANKLSFNFSDKQDVPVSE IILSFTPSYYAKELACQEITVPLCKGIGYNYTYMPNQFNHDTQDEAGLEVHQFWP LVEIQCSPDLKFFLCSMYTPICLEDYKKPLPPCRSVCERAKAGCAPLMRQYGFA WPDRMRCDRLPEQGNPDTLCMDY | 95 |

*mutation positions are corresponding to the amino acid position in full-length, wild-type TcdB (SEQ ID NO: 1).

REFERENCES

1. Rupnik, M., Wilcox, M. H. & Gerding, D. N. Clostridium difficile infection: new developments in epidemiology and pathogenesis. Nat Rev Microbiol 7, 526-536 (2009).
2. Heinlen, L. & Ballard, J. D. Clostridium difficile infection. Am J Med Sci 340, 247-252 (2010).
3. Voth, D. E. & Ballard, J. D. Clostridium difficile toxins: mechanism of action and role in disease. Clin Microbiol Rev 18, 247-263 (2005).
4. Hunt, J. J. & Ballard, J. D. Variations in virulence and molecular biology among emerging strains of Clostridium difficile. Microbiol Mol Biol Rev 77, 567-581 (2013).
5. Lessa, F. C., et al. Burden of Clostridium difficile infection in the United States. N Engl J Med 372, 825-834 (2015).
6. Smits, W. K., Lyras, D., Lacy, D. B., Wilcox, M. H. & Kuijper, E. J. Clostridium difficile infection. Nat Rev Dis Primers 2, 16020 (2016).
7. Jank, T. & Aktories, K. Structure and mode of action of clostridial glucosylating toxins: the ABCD model. Trends Microbiol 16, 222-229 (2008).
8. Sun, X., Savidge, T. & Feng, H. The enterotoxicity of Clostridium difficile toxins. Toxins (Basel) 2, 1848-1880 (2010).
9. Pruitt, R. N. & Lacy, D. B. Toward a structural understanding of Clostridium difficile toxins A and B. Front Cell Infect Microbiol 2, 28 (2012).
10. Tao, L., et al. Frizzled proteins are colonic epithelial receptors for C. difficile toxin B. Nature 538, 350-355 (2016).

11. Janda, C. Y., Waghray, D., Levin, A. M., Thomas, C. & Garcia, K. C. Structural basis of Wnt recognition by Frizzled. Science 337, 59-64 (2012).
12. Takada, R., et al. Monounsaturated fatty acid modification of Wnt protein: its role in Wnt secretion. Dev Cell 11, 791-801 (2006).
13. Willert, K., et al. Wnt proteins are lipid-modified and can act as stem cell growth factors. Nature 423, 448-452 (2003).
14. Drudy, D., Fanning, S. & Kyne, L. Toxin A-negative, toxin B-positive Clostridium difficile. Int J Infect Dis 11, 5-10 (2007).
15. Lyras, D., et al. Toxin B is essential for virulence of Clostridium difficile. Nature 458, 1176-1179 (2009).
16. Kuehne, S. A., et al. The role of toxin A and toxin B in Clostridium difficile infection. Nature (2010).
17. Carter, G. P., et al. Defining the Roles of TcdA and TcdB in Localized Gastrointestinal Disease, Systemic Organ Damage, and the Host Response during Clostridium difficile Infections. MBio 6, e00551 (2015).
18. Yuan, P., et al. Chondroitin sulfate proteoglycan 4 functions as the cellular receptor for Clostridium difficile toxin B. Cell Res 25, 157-168 (2015).
19. LaFrance, M. E., et al. Identification of an epithelial cell receptor responsible for Clostridium difficile TcdB-induced cytotoxicity. Proc Natl Acad Sci USA 112, 7073-7078 (2015).
20. Terada, N., et al. Immunohistochemical study of NG2 chondroitin sulfate proteoglycan expression in the small and large intestines. Histochem Cell Biol 126, 483-490 (2006).
21. MacDonald, B. T. & He, X. Frizzled and LRP5/6 receptors for Wnt/beta-catenin signaling. Cold Spring Harb Perspect Biol 4(2012).
22. Wang, Y., Chang, H., Rattner, A. & Nathans, J. Frizzled Receptors in Development and Disease. Curr Top Dev Biol 117, 113-139 (2016).
23. Gregorieff, A. & Clevers, H. Wnt signaling in the intestinal epithelium: from endoderm to cancer. Genes Dev 19, 877-890 (2005).
24. Nusse, R. & Clevers, H. Wnt/beta-Catenin Signaling, Disease, and Emerging Therapeutic Modalities. Cell 169, 985-999 (2017).
25. Nile, A. H., Mukund, S., Stanger, K., Wang, W. & Hannoush, R. N. Unsaturated fatty acyl recognition by Frizzled receptors mediates dimerization upon Wnt ligand binding. Proc Natl Acad Sci USA 114, 4147-4152 (2017).
26. Chumbler, N. M., et al. Crystal structure of Clostridium difficile toxin A. Nat Microbiol 1, 15002 (2016).
27. Yamamoto, A., Nagano, T., Takehara, S., Hibi, M. & Aizawa, S. Shisa promotes head formation through the inhibition of receptor protein maturation for the caudalizing factors, Wnt and FGF. Cell 120, 223-235 (2005).
28. Bazan, J. F., Janda, C. Y. & Garcia, K. C. Structural architecture and functional evolution of Wnts. Dev Cell 23, 227-232 (2012).
29. Dann, C. E., et al. Insights into Wnt binding and signalling from the structures of two Frizzled cysteine-rich domains. Nature 412, 86-90 (2001).
30. Shen, G., et al. Structural basis of the Norrin-Frizzled 4 interaction. Cell Res 25, 1078-1081 (2015).
31. Chang, T. H., et al. Structure and functional properties of Norrin mimic Wnt for signalling with Frizzled4, Lrp5/6, and proteoglycan. Elife 4(2015).
32. DeBruine, Z. J., et al. Wnt5a promotes Frizzled-4 signalosome assembly by stabilizing cysteine-rich domain dimerization. Genes Dev 31, 916-926 (2017).
33. Steinhart, Z., et al. Genome-wide CRISPR screens reveal a Wnt-FZD5 signaling circuit as a druggable vulnerability of RNF43-mutant pancreatic tumors. Nature medicine 23, 60-68 (2017). Kabsch, W. Xds. Acta Crystallogr D Biol Crystallogr 66, 125-132 (2010).
34. Adams, P. D., et al. PHENIX: a comprehensive Python-based system for macromolecular structure solution. Acta Crystallogr D Biol Crystallogr 66, 213-221 (2010).
35. Emsley, P., Lohkamp, B., Scott, W. G. & Cowtan, K. Features and development of Coot. Acta Crystallogr D Biol Crystallogr 66, 486-501 (2010).
36. Brunger, A. T. Free R value: a novel statistical quantity for assessing the accuracy of crystal structures. Nature 355, 472-475 (1992).
37. Chen, V. B., et al. MolProbity: all-atom structure validation for macromolecular crystallography. Acta Crystallogr D Biol Crystallogr 66, 12-21 (2010).
38. Yang, G., et al. Expression of recombinant Clostridium difficile toxin A and B in Bacillus megaterium. BMC Microbiol 8, 192 (2008).
39. Y. Zhang et al., Anaerobe 48, 249-256 (2017).
40. K. M. D'Auria et al., Infect Immun 81, 3814-3824 (2013)
41. P. Gupta et al., J Biol Chem 292, 17290-17301 (2017)

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim.

Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A method of reducing Wnt signaling, the method comprising administering to a subject in need thereof, a therapeutically effective amount of an isolated polypeptide comprising a TcdB fragment consisting of the amino acid sequence of SEQ ID NO: 2, wherein the isolated polypeptide does not comprise an amino acid sequence that is 100% identical to amino acids 1114-1835 of SEQ ID NO: 1.

2. The method of claim 1, further comprising administering to the subject an effective amount of a second agent that blocks Wnt signaling.

3. The method of claim 2, wherein the second agent is a Dkk family protein, a Secreted Frizzled Related Protein (sFRP), Draxin, IGFBP-4, SOST/Sclerostin, USAG1, WIF-1, or a Frizzled antibody.

4. The method of claim 1, wherein the subject has cancer that is associated with dysregulated Wnt signaling or over-expression of frizzled.

5. The method of claim 4, further comprising administering to the subject a therapeutically effective amount of an anti-cancer agent.

6. The method of claim 4, wherein the cancer is metastatic cancer.

7. The method of claim 4, wherein the cancer is osteosarcoma.

8. The method of claim 4, wherein the cancer is breast cancer, stomach cancer, pancreatic cancer, or prostate cancer.

9. The method of claim 8, wherein the breast cancer is triple negative breast cancer.

* * * * *

UNITED STATES PATENT AND TRADEMARK OFFICE
CERTIFICATE OF CORRECTION

PATENT NO. : 12,252,515 B2
APPLICATION NO. : 16/962338
DATED : March 18, 2025
INVENTOR(S) : Min Dong et al.

Page 1 of 1

It is certified that error appears in the above-identified patent and that said Letters Patent is hereby corrected as shown below:

In the Specification

At Column 1, Line 17, please replace the paragraph titled GOVERNMENT SUPPORT with the following paragraph:
FEDERALLY SPONSORED RESEARCH
This invention was made with government support under Grant Numbers AI091823, AI125704, AI123920, NS080833, and AI132387, awarded by the National Institutes of Health. The Government has certain rights in the invention.

Signed and Sealed this
Sixth Day of May, 2025

Coke Morgan Stewart
*Acting Director of the United States Patent and Trademark Office*